(12) United States Patent
Graham et al.

(10) Patent No.: US 9,707,234 B2
(45) Date of Patent: Jul. 18, 2017

(54) SPIROCYCLIC HETERCYCLE COMPOUNDS USEFUL AS HIV INTEGRASE INHIBITORS

(71) Applicant: MERCK SHARP & DOHME CORP., Rahway, NJ (US)

(72) Inventors: Thomas H. Graham, Scotch Plains, NJ (US); Wensheng Liu, Edison, NJ (US); Tao Yu, Edison, NJ (US); Yonglian Zhang, Metuchen, NJ (US); Sherman T. Waddell, Westfield, NJ (US); John S. Wai, Harleysville, PA (US); Paul J. Coleman, Harleysville, PA (US); John M. Sanders, Hatfield, PA (US); Mark W. Embrey, Harleysville, PA (US); Abbas M. Walji, Lansdale, PA (US); Ronald Dale Ferguson, II, Westfield, NJ (US); Christine Ng Di Marco, Conshohocken, PA (US); Thomas G. Steele, Schwenksville, PA (US); Lihong Hu, Shanghai (CN); Xuanjia Peng, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/105,376

(22) PCT Filed: Dec. 17, 2014

(86) PCT No.: PCT/US2014/070712
§ 371 (c)(1),
(2) Date: Jun. 16, 2016

(87) PCT Pub. No.: WO2015/095258
PCT Pub. Date: Jun. 25, 2015

(65) Prior Publication Data
US 2016/0317543 A1 Nov. 3, 2016

(30) Foreign Application Priority Data
Dec. 20, 2013 (WO) ................ PCT/CN2013/090156

(51) Int. Cl.
| | | |
|---|---|---|
| C07D 471/20 | (2006.01) |
| C07D 471/22 | (2006.01) |
| C07D 491/20 | (2006.01) |
| A61K 31/53 | (2006.01) |
| A61K 31/499 | (2006.01) |
| A61K 31/675 | (2006.01) |
| A61K 45/06 | (2006.01) |
| A61K 31/55 | (2006.01) |
| A61K 31/427 | (2006.01) |
| A61K 31/513 | (2006.01) |
| A61K 31/52 | (2006.01) |

(Continued)

(52) U.S. Cl.
CPC ............ *A61K 31/53* (2013.01); *A61K 31/427* (2013.01); *A61K 31/499* (2013.01); *A61K 31/513* (2013.01); *A61K 31/52* (2013.01); *A61K 31/55* (2013.01); *A61K 31/675* (2013.01); *A61K 45/06* (2013.01); *C07D 471/20* (2013.01); *C07D 471/22* (2013.01); *C07D 475/10* (2013.01); *C07D 491/10* (2013.01); *C07D 491/20* (2013.01); *C07D 495/10* (2013.01); *C07D 495/20* (2013.01); *C07F 9/65616* (2013.01)

(58) Field of Classification Search
CPC .. C07D 471/20; C07D 471/22; C07D 491/20; A61K 31/53; A61K 45/06; A61K 31/499; A61K 31/675
See application file for complete search history.

(56) References Cited

U.S. PATENT DOCUMENTS

| | | |
|---|---|---|
| 2009/0143356 A1 | 6/2009 | Yoshida et al. |
| 2009/0253681 A1 | 10/2009 | Summa et al. |

(Continued)

FOREIGN PATENT DOCUMENTS

| | | | |
|---|---|---|---|
| JP | WO 2011105590 A1 * | 9/2011 | ......... A61K 31/4985 |
| WO | 2005087766 A1 | 9/2005 | |

(Continued)

OTHER PUBLICATIONS

International Search Report and Written Opinion for PCT/US2014/070712 mailed Mar. 18, 2016, 10 pages.

*Primary Examiner* — Kahsay Habte
(74) *Attorney, Agent, or Firm* — Nicole M. Beeler; Catherine D. Fitch

(57) ABSTRACT

The present invention relates to Spirocyclic Heterocycle Compounds of Formula (I): and pharmaceutically acceptable salts thereof, wherein A, B, X, Y, $R^1$, $R^2$ and $R^{11}$ are as defined herein. The present invention also relates to compositions comprising at least one Spirocyclic Heterocycle Compound, and methods of using the Spirocyclic Heterocycle Compounds for treating or preventing HIV infection in a subject.

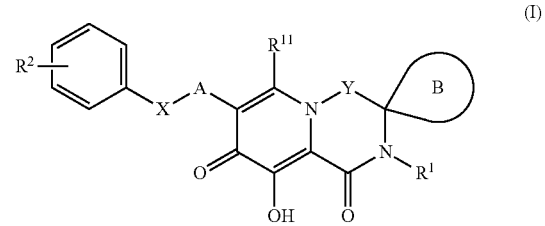

(I)

19 Claims, No Drawings

(51) Int. Cl.
*C07D 475/10* (2006.01)
*C07D 491/10* (2006.01)
*C07D 495/10* (2006.01)
*C07D 495/20* (2006.01)
*C07F 9/6561* (2006.01)

(56) References Cited

U.S. PATENT DOCUMENTS

2009/0318421 A1    12/2009    Johns et al.
2012/0108564 A1*    5/2012    Miyazaki ............ A61K 31/4985
                                                                    514/210.18

FOREIGN PATENT DOCUMENTS

| WO | 2006066414 A1 | 6/2006 |
| WO | 2014099586 A1 | 6/2014 |
| WO | 2015048363 A1 | 4/2015 |

\* cited by examiner

SPIROCYCLIC HETERCYCLE COMPOUNDS USEFUL AS HIV INTEGRASE INHIBITORS

CROSS REFERENCE TO RELATED APPLICATIONS

This application is a U.S. National Phase application under 35 U.S.C. §371 of PCT Application No. PCT/US14/070712 filed Dec. 17, 2014, which claims priority from PCT Application No. PCT/CN13/090156, filed Dec. 20, 2013.

FIELD OF THE INVENTION

The present invention relates to Spirocyclic Heterocycle Compounds, compositions comprising at least one Spirocyclic Heterocycle Compound, and methods of using the Spirocyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Tohours, hours. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

SUMMARY OF THE INVENTION

In one aspect, the present invention provides Compounds of Formula (I):

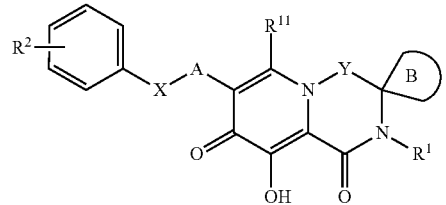

or a pharmaceutically acceptable salt or prodrug thereof, wherein:

A is —NHC(O)— or 5 or 6-membered monocyclic heteroaryl;

B is a 3 to 8-membered heterocycloalkyl or an 8 to 14 membered bicyclic heterocycloalkyl, each of which can be optionally be substituted with one or more groups, each independently selected from $R^7$;

X is $C_1$-$C_3$ alkylene;

Y is —C($R^3$)$_2$— or —N($R^4$)—;

$R^1$ is selected from H, $C_1$-$C_6$ alkyl, $C_3$-$C_7$ cycloalkyl, —($C_1$-$C_4$ alkylene)-O—($C_1$-$C_6$ alkyl), —($C_1$-$C_4$ alkylene)-S—($C_1$-$C_6$ alkyl), —($C_1$-$C_4$ alkylene)-SO$_2$—($C_1$-$C_6$ alkyl), —($C_1$-$C_4$ alkylene)-N—($C_1$-$C_6$ alkyl)$_2$, —($C_1$-$C_6$ alkylene)$_p$-P(O)(—OR$^{10}$)$_2$, $C_1$-$C_6$ haloalkyl, $C_1$-$C_6$ hydroxyalkyl, phenyl, 3 to 8-membered monocyclic heterocycloalkyl and 5 or 6-membered monocyclic heteroaryl;

$R^2$ represents up to 3 optional substitutents, each independently selected from halo, $C_1$-$C_6$ alkyl, —O—($C_1$-$C_6$ alkyl) and $C_1$-$C_6$ haloalkyl;

each occurrence of $R^3$ is independently selected from H, $C_1$-$C_6$ alkyl, $C_1$-$C_6$ haloalkyl, —($C_1$-$C_4$ alkylene)$_p$-(5 or 6-membered monocyclic heteroaryl), ($C_1$-$C_4$ alkylene)$_p$-(phenyl), $C_3$-$C_7$ cycloalkyl, —($C_1$-$C_6$ alkylene)$_p$-P(O)(—OR$^{10}$)$_2$, —($C_1$-$C_4$ alkylene)-S—($C_1$-$C_6$ alkyl), —($C_1$-$C_4$ alkylene)-SO$_2$—($C_1$-$C_6$ alkyl), —N($R^6$)C(O)R$^5$, —($C_1$-$C_4$ alkylene)-N—($C_1$-$C_6$ alkyl)$_2$ and 3 to 8-membered monocyclic heterocycloalkyl;

$R^4$ is selected from H, $C_1$-$C_6$ alkyl, $C_1$-$C_6$ haloalkyl, $C_1$-$C_6$ hydroxyalkyl, —SO$_2$R$^5$, —C(O)R$^5$, —($C_1$-$C_6$ alkylene)$_p$-C(O)N(R$^6$)$_2$, —($C_1$-$C_6$ alkylene)$_p$-P(O)(—OR$^{10}$)$_2$, —N(R$^6$)C(O)R$^5$, —($C_2$-$C_4$ alkylene)-O—($C_1$-$C_6$ alkyl), —($C_2$-$C_4$ alkylene)-S—($C_1$-$C_6$ alkyl), —($C_2$-$C_4$ alkylene)-SO$_2$—($C_1$-$C_6$ alkyl), —($C_2$-$C_4$ alkylene)-N—($C_1$-$C_6$ alkyl)$_2$, —($C_1$-$C_6$ alkylene)$_p$-($C_3$-$C_7$ cycloalkyl), —($C_1$-$C_4$ alkylene)$_p$-(5 or 6-membered monocyclic heteroaryl), —($C_1$-$C_4$ alkylene)$_p$-(8 to 10-membered bicyclic heteroaryl), —($C_1$-$C_4$ alkylene)$_p$-(phenyl) and 4 to 8-membered monocyclic heterocycloalkyl;

each occurrence of $R^5$ is independently selected from $C_1$-$C_6$ alkyl, $C_1$-$C_6$ haloalkyl, $C_3$-$C_7$ cycloalkyl, phenyl, 3 to 8-membered monocyclic heterocycloalkyl or 6-membered monocyclic heteroaryl and 8 to 10-membered bicyclic heteroaryl, wherein said $C_3$-$C_7$ cycloalkyl group, said phenyl group, said 5 or 6-membered monocyclic heteroaryl group and said 8 to 10-membered bicyclic heteroaryl group can be optionally substituted with one or more groups, each independently selected from $R^7$;

each occurrence of $R^6$ is independently selected from H, $C_1$-$C_6$ alkyl, $C_3$-$C_7$ cycloalkyl, —($C_1$-$C_6$ alkylene)-N(R$^8$)$_2$, $C_1$-$C_6$ haloalkyl, —C(O)O($C_1$-$C_6$ alkyl), —($C_1$-$C_6$ alkylene)$_p$-R$^9$ and —($C_1$-$C_6$ alkylene)-O—($C_1$-$C_6$ alkyl);

each occurrence of $R^7$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, 5 or 6-membered monocyclic heteroaryl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —$NH_2$, —NH($C_1$-$C_6$ alkyl), —N($C_1$-$C_6$ alkyl)$_2$, —S(O)$_2$($C_1$-$C_6$ alkyl), —NHS(O)$_2$—($C_1$-$C_6$ alkyl), —S(O)$_2$NH—($C_1$-$C_6$ alkyl), —S(O)$_2$N($C_1$-$C_6$ alkyl)$_2$, —OC(O)—($C_1$-$C_6$ haloalkyl), —C(O)O-benzyl, —($C_1$-$C_6$ alkylene)$_p$-C(O)O—($C_1$-$C_6$ alkyl), —($C_1$-$C_6$ alkylene)$_p$-C(O)—($C_1$-$C_6$ alkyl), —($C_1$-$C_6$ alkylene)$_p$-C(O)N($R^8$)$_2$, $C_1$-$C_6$ hydroxyalkyl, —P(O)(O$R^{10}$)$_2$, and —CN;

each occurrence of $R^8$ is independently selected from H, $C_1$-$C_6$ alkyl, $C_3$-$C_7$ cycloalkyl, $C_1$-$C_6$ haloalkyl, —C(O)O ($C_1$-$C_6$ alkyl), —($C_1$-$C_6$ alkylene)$_p$-$R^9$ and —($C_1$-$C_6$ alkylene)-O—($C_1$-$C_6$ alkyl);

each occurrence of $R^9$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^{10}$ is independently selected from H and $C_1$-$C_6$ alkyl; $R^{11}$ is selected from H, $C_1$-$C_6$ alkyl, $C_1$-$C_6$ hydroxyalkyl, —O—($C_1$-$C_6$ alkyl), $C_3$-$C_7$ cycloalkyl and —($C_1$-$C_4$ alkylene)-O—($C_1$-$C_6$ alkyl); and each occurrence of p is independently 0 or 1.

The Compounds of Formula (I) (also referred to herein as the "Spirocyclic Heterocycle Compounds") and pharmaceutically acceptable salts thereof, may be useful, for example, for inhibiting HIV viral replication or replicon activity, and for treating or preventing HIV infection in a subject. Without being bound by any specific theory, it is believed that the Spirocyclic Heterocycle Compounds may inhibit HIV viral replication by inhibiting HIV Integrase.

Accordingly, the present invention provides methods for treating or preventing HIV infection in a subject, comprising administering to the subject an effective amount of at least one Spirocyclic Heterocycle Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Spirocyclic Heterocycle Compounds, compositions comprising at least one Spirocyclic Heterocycle Compound, and methods of using the Spirocyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Spirocyclic Heterocycle Compound and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C (O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_4$ alkylene" refers to an alkylene group having from 1 to 4 carbon atoms. The term "C$_2$-C$_4$ alkylene" refers to an alkylene group having from 2 to 4 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —CH$_2$CH=CH—, —CH$_2$CH=CHCH$_2$—, —CH=CHCH$_2$CH$_2$—, —CH$_2$CH$_2$CH=CH— and —CH(CH$_3$)CH=CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkenylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

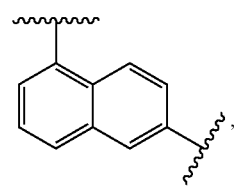 [SMILES: *c1ccc2c(*)cccc2c1]

is understood to represent both:

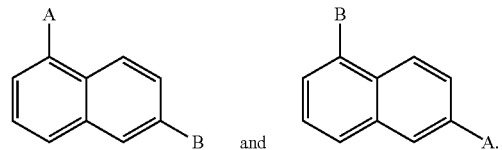

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

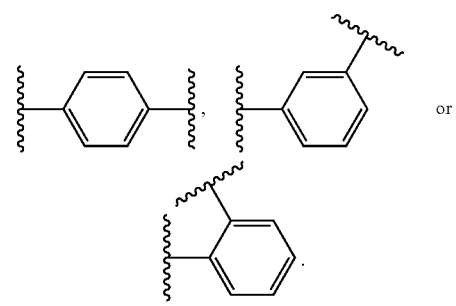

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

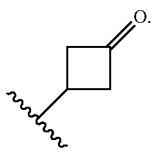

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

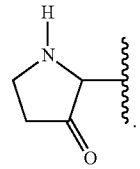

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

Examples of "ring system substituents," include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O—haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S—alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)—cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

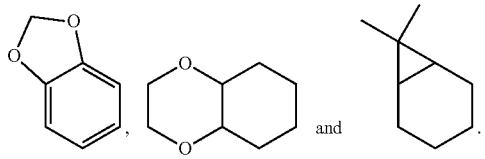

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^1$, R$^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design,* (1987) Edward B. Roche, ed., American Pharmaceutical Association and Pergamon Press. The term "prodrug" means a compound (e.g., a drug precursor) that is transformed in vivo to provide a Spirocyclic Heterocycle Compound or a pharmaceutically acceptable salt of the compound. The transformation may occur by various mechanisms (e.g., by metabolic or chemical processes), such as, for example, through hydrolysis in blood. For example, if a Spirocyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as (β-dimethylaminoethyl), carbamoyl-(C$_1$-C$_2$)alkyl, N,N-di (C$_1$-C$_2$)alkylcarbamoyl-(C$_1$-C$_2$)alkyl and piperidino-, pyrrolidino- or morpholino(C$_2$-C$_3$)alkyl, and the like.

Similarly, if a Spirocyclic Heterocycle Compound contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino(C$_1$-C$_4$)alkyl, α-amino (C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Spirocyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently (C$_1$-C$_{10}$)alkyl, (C$_3$-C$_7$) cycloalkyl, benzyl, a natural α-aminoacyl, —C(OH)C(O)OY$^1$ wherein Y$^1$ is H, (C$_1$-C$_6$) alkyl or benzyl, —C(OY$^2$)Y$^3$ wherein Y$^2$ is (C$_1$-C$_4$) alkyl and Y$^3$ is (C$_1$-C$_6$)alkyl; carboxy (C$_1$-C$_6$)alkyl; amino(C$_1$-C$_4$)alkyl or mono-N— or di-N,N—(C$_1$-C$_6$)alkylaminoalkyl; —C(Y$^4$)Y$^5$ wherein Y$^4$ is H or methyl and Y$^5$ is mono-N— or di-N,N—(C$_1$-C$_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted withours, for example, halogen, C$_{1-4}$alkyl, —O—(C$_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a C$_{1-20}$ alcohol or reactive derivative thereof, or by a 2,3-di (C$_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Spirocyclic Heterocycle Compounds can form salts which are also within the scope of this invention. Reference to a Spirocyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Spirocyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Spirocyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Spirocyclic Heterocycle Compounds may be atropisomers (e.g., substituted biaryls) and are considered as part of this invention. Enantiomers can also be directly separated using chiral chromatographic techniques.

It is also possible that the Spirocyclic Heterocycle Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Spirocyclic Heterocycle Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Spirocyclic Heterocycle Compounds may be useful in human and veterinary medicine for treating or preventing HIV infection in a subject. In one embodiment, the Spirocyclic Heterocycle Compounds can be inhibitors of HIV viral replication. In a specific embodiment, the Spirocyclic Heterocycle Compounds are inhibitors of HIV-1. Accordingly, the Spirocyclic Heterocycle Compounds may be useful for treating HIV infections and AIDS. In accordance with the invention, the Spirocyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Spirocyclic Heterocycle Compound or a pharmaceutically acceptable salt thereof. In a specific embodiment, the present invention provides methods for treating AIDS in a subject comprising administering to the subject an effective amount of at least one Spirocyclic Heterocycle Compound or a pharmaceutically acceptable salt thereof.

LIST OF ABBREVIATIONS

Anal.=analytical
n-BuLi=n-butyl lithium
m-CPBA=3-chloroperoxybenzoic acid
DCM=dichloromethane
DEA=diethylamine
DIEA=N,N-diisopropylethylamine
DMF=dimethylformamide
ESI=electrospray ionization
EtOAc=ethyl acetate
EtOH=ethanol
HPLC=high-pressure liquid chromatography
IPA=iso-propyl alcohol
IPAc=iso-propyl acetate
KF=Karl-Fischer titration (to determine water content)
KOt-Bu=potassium tert-butoxide
LCMS=liquid chromatography-mass spectrometry
LiHMDS=lithum hexamethyl silazane
MeCN=acetonitrile
MeOH=methanol
MPa=milipascal
MS=mass spectroscopy
MTBE=methyl tert-butyl ether
n/a=not applicable
NHS=normal human serum
NMR=nuclear magnetic resonance spectroscopy
Piv=pivalate, 2,2-dimethylpropanoyl
Pd/C=palladium on carbon
rt=room temperature
SFC=supercritical fluid chromatography
TFA=trifluoroacetic acid
TLC=thin-layer chromatography
p-TsOH=para-toluene sulfonic acid
THF=tetrahydrofuran The Compounds of Formula (I)

The present invention provides Spirocyclic Heterocycle Compounds of Formula

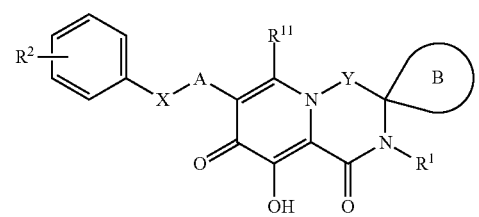

(I)

and pharmaceutically acceptable salts thereof, wherein A, B, X, Y, $R^1$, $R^2$ and $R^{11}$ are defined above for the Compounds of Formula (I).

In one embodiment, A is 5 or 6-membered monocyclic heterocycle.

In another embodiment, A is 5-membered monocyclic heterocycle.

In one embodiment, X is —$CH_2$—.
In another embodiment, X is —$CH(CH_3)$—.
In one embodiment, $R^4$ is H.
In another embodiment, $R^4$ is $C_1$-$C_6$ alkyl.

In another embodiment, $R^4$ is other than H.
In one embodiment, $R^{11}$ is H.
In another embodiment, $R^{11}$ is $C_3$-$C_7$ cycloalkyl.
In another embodiment, $R^{11}$ is —($C_1$-$C_4$ alkylene)-O—($C_1$-$C_6$ alkyl).
In another embodiment, $R^{11}$ is —$CH_2OCH_3$.
In one embodiment, the compounds of formula (I) have the formula (Ia):

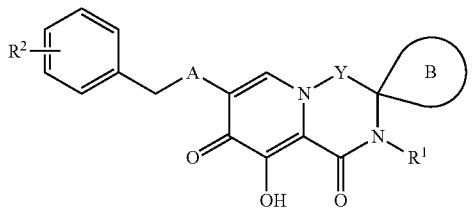

(Ia)

or a pharmaceutically acceptable salt or prodrug thereof, wherein:

A is: —NHC(O)— or:

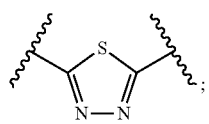 [SMILES: *c1nnc(*)s1]

;

B is a 5 or 6-membered heterocycloalkyl;
Y is —$CH_2$— or —N($CH_3$)—;
$R^1$ is selected from $C_1$-$C_6$ alkyl and —($C_2$-$C_4$ alkylene)-O—($C_1$-$C_6$ alkyl);
$R^2$ represents up to 3 optional substituents, each independently selected from halo.

In one embodiment, for the compounds of formula (I) or (Ia), A is —NHC(O)—.
In another embodiment, embodiment, for the compounds of formula (I) or (Ia), A is:

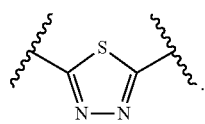 [SMILES: *c1nnc(*)s1]

.

In one embodiment, for the compounds of formula (I) or (Ia), B is 5-membered heterocycloalkyl.
In another embodiment, for the compounds of formula (I) or (Ia), B is 6-membered heterocycloalkyl.
In another embodiment, for the compounds of formula (I) or (Ia), B is tetrahydrofuranyl.
In still another embodiment, for the compounds of formula (I) or (Ia), B is tetrahydropyranyl.
In another embodiment, for the compounds of formula (I) or (Ia), B is piperidinyl, optionally substituted on the ring nitrogen atom with —C(O)$OR^5$, —C(O)$R^5$, —S(O)$_2$—($C_1$-$C_6$ alkyl) or —S(O)$_2$NH—($C_1$-$C_6$ alkyl).
In one embodiment, for the compounds of formula (I) or (Ia), Y is —$CH_2$—.
In another embodiment, for the compounds of formula (I) or (Ia), Y is —N($CH_3$)—.
In one embodiment, for the compounds of formula (I) or (Ia), $R^1$ is $C_1$-$C_6$ alkyl.

In another embodiment, for the compounds of formula (I) or (Ia), $R^1$ is —($C_2$-$C_4$ alkylene)-O—($C_1$-$C_6$ alkyl).
In another embodiment, for the compounds of formula (I) or (Ia), $R^1$ is selected from methyl, ethyl and n-propyl.
In still another embodiment, for the compounds of formula (I) or (Ia), $R^1$ is —$CH_2CH_2OCH_3$.
In one embodiment, for the compounds of formula (I) or (Ia), each occurrence of $R^2$ is halo.
In another embodiment, for the compounds of formula (I) or (Ia), $R^2$ represents 2 fluoro groups.
In another embodiment, for the compounds of formula (I) or (Ia), $R^2$ represents 2 fluoro groups in the ortho and para positions.
In one embodiment, the compounds of formula (I) have the formula (Ib):

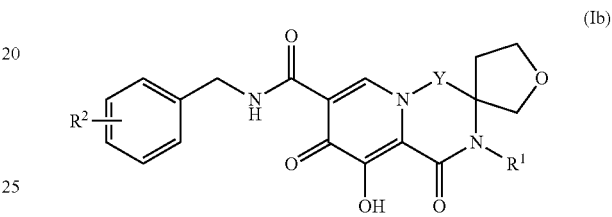

(Ib)

or a pharmaceutically acceptable salt or prodrug thereof, wherein:

Y is —$CH_2$— or —N($CH_3$)—;
$R^1$ is selected from $C_1$-$C_6$ alkyl and —($C_2$-$C_4$ alkylene)-O—($C_1$-$C_6$ alkyl);
$R^2$ represents up to 3 optional substituents, each independently selected from halo.

In one embodiment, for the compounds of formula (I), (Ia) or (Ib), Y is —$CH_2$—.
In another embodiment, for the compounds of formula (I), (Ia) or (Ib), Y is —N($CH_3$)—.
In one embodiment, for the compounds of formula (I), (Ia) or (Ib), $R^1$ is $C_1$-$C_6$ alkyl.
In another embodiment, for the compounds of formula (I), (Ia) or (Ib), $R^1$ is —($C_2$-$C_4$ alkylene)-O—($C_1$-$C_6$ alkyl).
In another embodiment, for the compounds of formula (I), (Ia) or (Ib), $R^1$ is selected from methyl, ethyl and n-propyl.
In another embodiment, for the compounds of formula (I), (Ia) or (Ib), $R^1$ is methyl.
In still another embodiment, for the compounds of formula (I), (Ia) or (Ib), $R^1$ is —$CH_2CH_2OCH_3$.
In one embodiment, for the compounds of formula (I), (Ia) or (Ib), each occurrence of $R^2$ is independently F or Cl.
In another embodiment, for the compounds of formula (I), (Ia) or (Ib), $R^2$ represents 2 fluoro groups.
In another embodiment, for the compounds of formula (I), (Ia) or (Ib), $R^2$ represents 2 fluoro groups in the ortho and para positions.
In one embodiment, for the compounds of formula (I), (Ia) or (Ib), Y is —N($CH_3$)— and $R^1$ is $C_1$-$C_6$ alkyl.
In another embodiment, for the compounds of formula (I), (Ia) or (Ib), Y is —N($CH_3$)— and $R^1$ is methyl.
In one embodiment, for the compounds of formula (I), (Ia) or (Ib), Y is —N($CH_3$)—; $R^1$ is $C_1$-$C_6$ alkyl; and each occurrence of $R^2$ is independently F or Cl.
In another embodiment, for the compounds of formula (I), (Ia) or (Ib), Y is —N($CH_3$)—; $R^1$ is methyl; and $R^2$ represents 2 fluoro groups.

In one embodiment, variables A, B, X, Y, $R^1$, $R^2$ and $R^{11}$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 5-173 as set forth in the table below, and pharmaceutically acceptable salts thereof. An embodiment of the invention includes a compound selected from compounds 5-173 of the Examples.

| Compound | Structure |
|---|---|
| 5 | 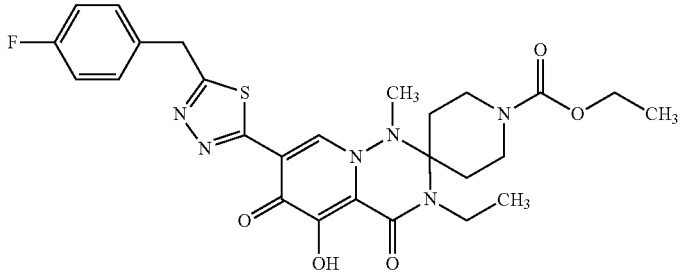 [SMILES: CCOC(=O)N1CCC2(CC1)N(CC)C(=O)c1c(O)c(=O)c(-c3nnc(Cc4ccc(F)cc4)s3)cn1N2C] |

| Compound | Structure |
|---|---|
| 6 | 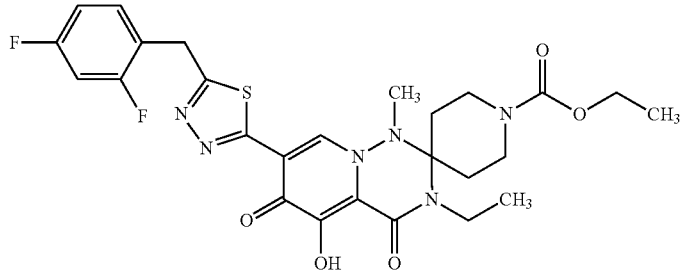 [SMILES: CCOC(=O)N1CCC2(CC1)N(CC)C(=O)c1c(O)c(=O)c(-c3nnc(Cc4ccc(F)cc4F)s3)cn1N2C] |
| 7 | 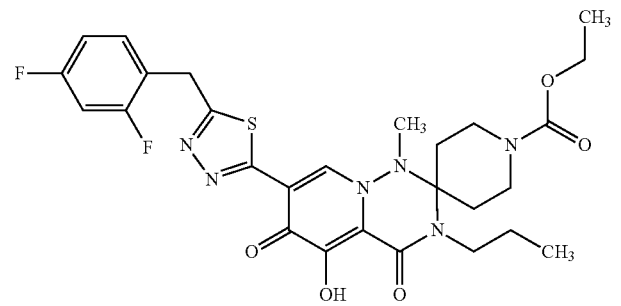 [SMILES: CCCN1C(=O)c2c(O)c(=O)c(-c3nnc(Cc4ccc(F)cc4F)s3)cn2N(C)C12CCN(C(=O)OCC)CC2] |
| 8 | 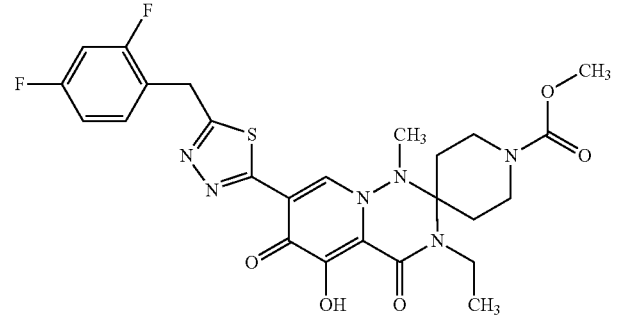 [SMILES: CCN1C(=O)c2c(O)c(=O)c(-c3nnc(Cc4ccc(F)cc4F)s3)cn2N(C)C12CCN(C(=O)OC)CC2] |
| 9 | 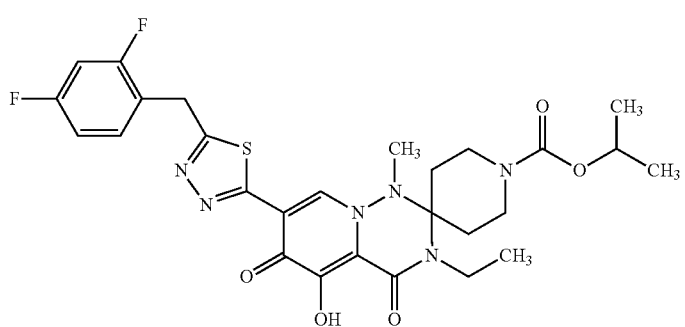 [SMILES: CCN1C(=O)c2c(O)c(=O)c(-c3nnc(Cc4ccc(F)cc4F)s3)cn2N(C)C12CCN(C(=O)OC(C)C)CC2] |
| 10 | 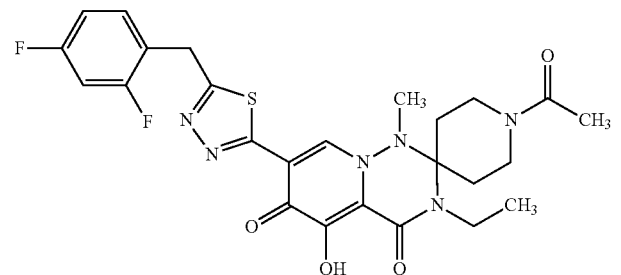 [SMILES: CCN1C(=O)c2c(O)c(=O)c(-c3nnc(Cc4ccc(F)cc4F)s3)cn2N(C)C12CCN(C(C)=O)CC2] |

| Compound | Structure |
|---|---|
| 11 | 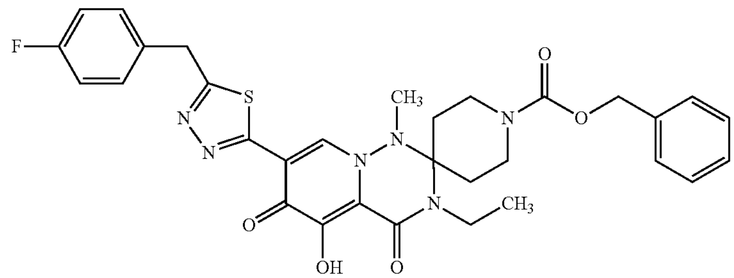 [SMILES: CCN1C(=O)c2c(O)c(=O)c(-c3nnc(Cc4ccc(F)cc4)s3)cn2N(C)C12CCN(C(=O)OCc1ccccc1)CC2] |
| 12 | 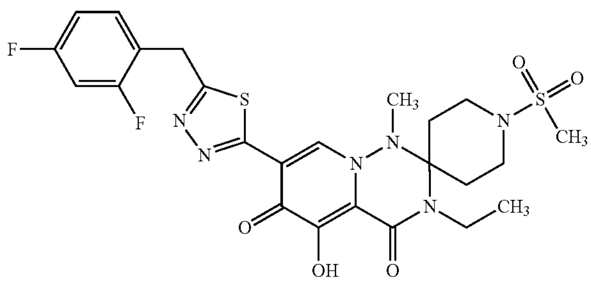 [SMILES: CCN1C(=O)c2c(O)c(=O)c(-c3nnc(Cc4ccc(F)cc4F)s3)cn2N(C)C12CCN(S(C)(=O)=O)CC2] |
| 13 | 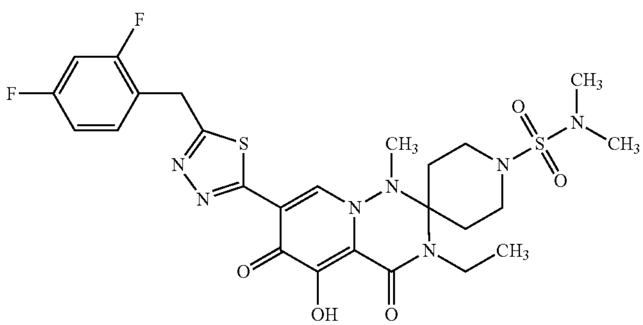 [SMILES: CCN1C(=O)c2c(O)c(=O)c(-c3nnc(Cc4ccc(F)cc4F)s3)cn2N(C)C12CCN(S(=O)(=O)N(C)C)CC2] |
| 14 | 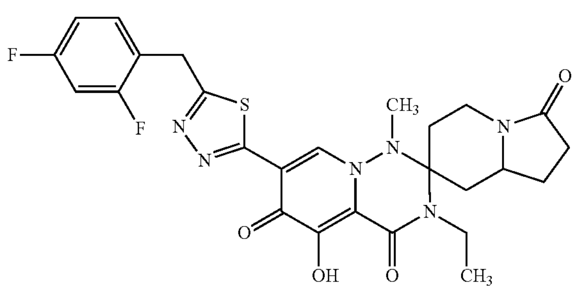 [SMILES: CCN1C(=O)c2c(O)c(=O)c(-c3nnc(Cc4ccc(F)cc4F)s3)cn2N(C)C12CCN1C(=O)CCC1C2] |
| 15 | 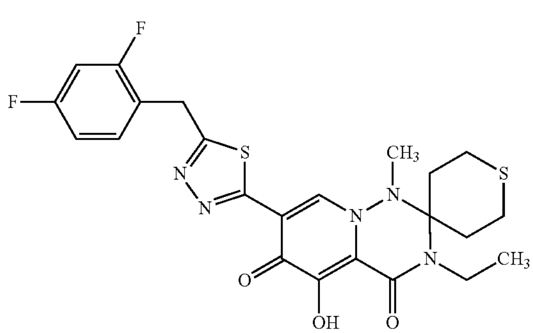 [SMILES: CCN1C(=O)c2c(O)c(=O)c(-c3nnc(Cc4ccc(F)cc4F)s3)cn2N(C)C12CCSCC2] |

-continued
| Compound | Structure |
|---|---|
| 16 | 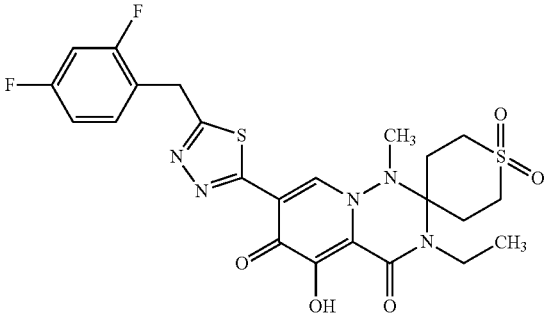 [SMILES: CCN1C(=O)c2c(O)c(=O)c(-c3nnc(Cc4ccc(F)cc4F)s3)cn2N(C)C12CCS(=O)(=O)CC2] |
| 17 | 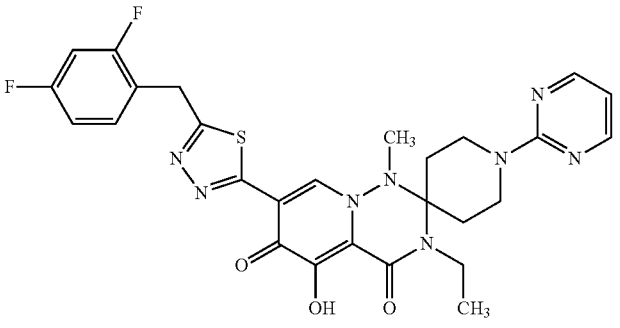 [SMILES: CCN1C(=O)c2c(O)c(=O)c(-c3nnc(Cc4ccc(F)cc4F)s3)cn2N(C)C12CCN(c1ncccn1)CC2] |
| 18 | 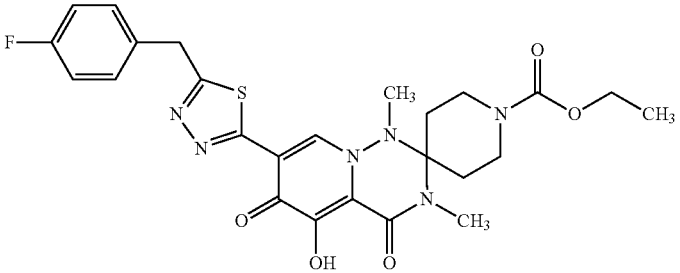 [SMILES: CCOC(=O)N1CCC2(CC1)N(C)C(=O)c1c(O)c(=O)c(-c3nnc(Cc4ccc(F)cc4)s3)cn1N2C] |
| 19 | 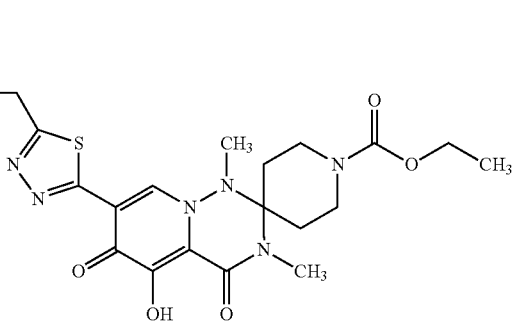 |
| 20 | 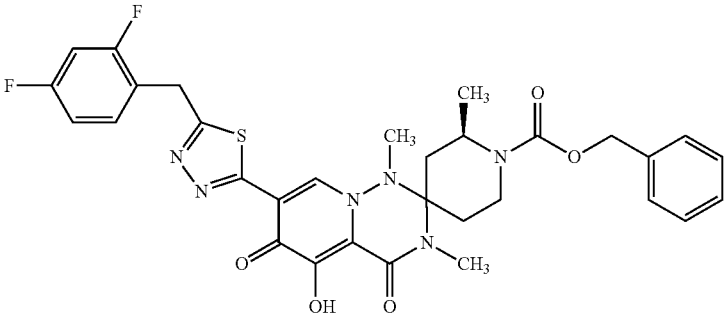 [SMILES: C[C@@H]1CC2(CCN1C(=O)OCc1ccccc1)N(C)C(=O)c1c(O)c(=O)c(-c3nnc(Cc4ccc(F)cc4F)s3)cn1N2C] |

| Compound | Structure |
|---|---|
| 21 | 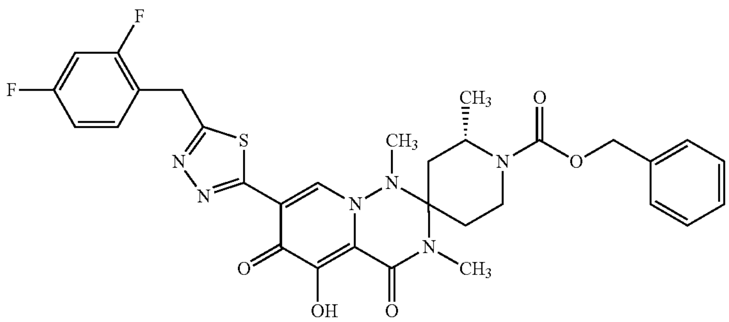 [SMILES: C[C@H]1CC2(CCN1C(=O)OCc1ccccc1)N(C)C(=O)c1c(O)c(=O)c(-c3nnc(Cc4ccc(F)cc4F)s3)cn1N2C] |
| 22 | 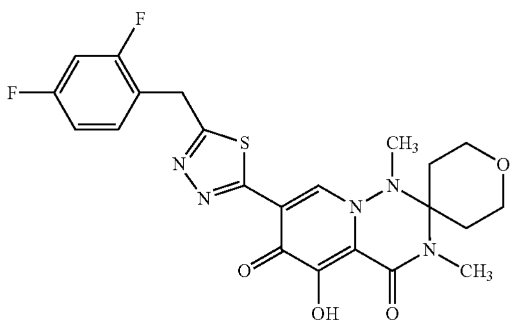 [SMILES: CN1C(=O)c2c(O)c(=O)c(-c3nnc(Cc4ccc(F)cc4F)s3)cn2N(C)C12CCOCC2] |
| 23 | 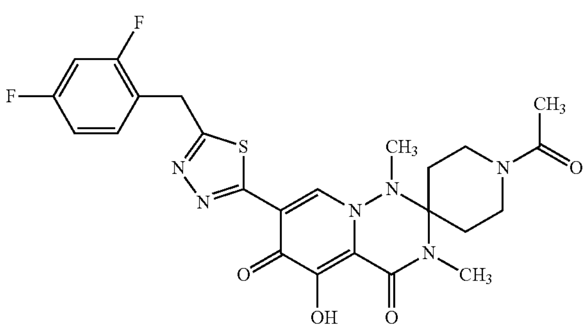 [SMILES: CC(=O)N1CCC2(CC1)N(C)C(=O)c1c(O)c(=O)c(-c3nnc(Cc4ccc(F)cc4F)s3)cn1N2C] |
| 24 | 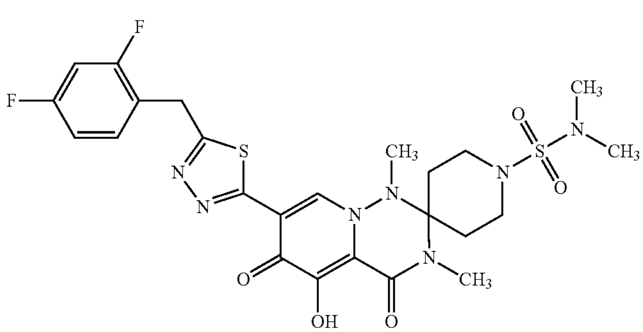 [SMILES: CN1C(=O)c2c(O)c(=O)c(-c3nnc(Cc4ccc(F)cc4F)s3)cn2N(C)C12CCN(S(=O)(=O)N(C)C)CC2] |

-continued

| Compound | Structure |
|---|---|
| 25 | 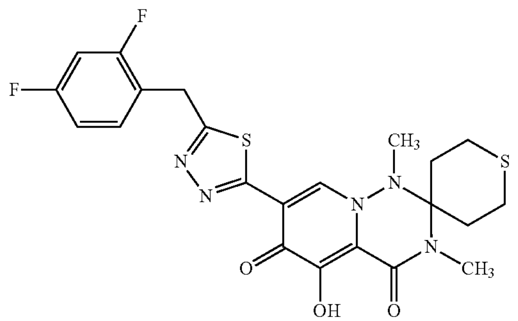 |
| 26 | 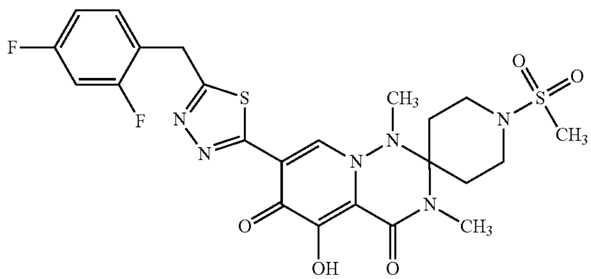 [SMILES: CN1C(=O)c2c(O)c(=O)c(-c3nnc(Cc4ccc(F)cc4F)s3)cn2N(C)C12CCN(S(C)(=O)=O)CC2] |
| 27 | 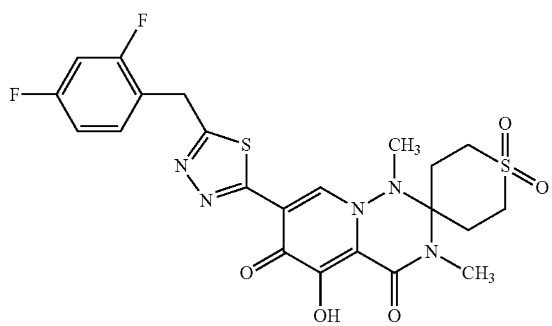 [SMILES: CN1C(=O)c2c(O)c(=O)c(-c3nnc(Cc4ccc(F)cc4F)s3)cn2N(C)C12CCS(=O)(=O)CC2] |
| 28 | 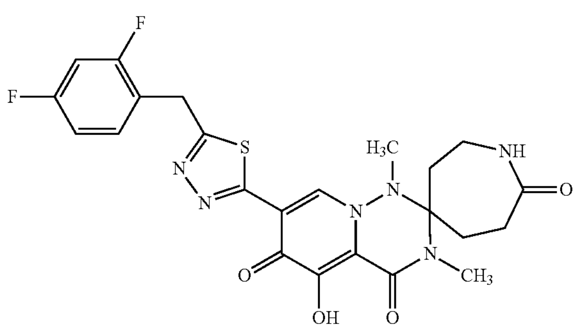 [SMILES: CN1C(=O)c2c(O)c(=O)c(-c3nnc(Cc4ccc(F)cc4F)s3)cn2N(C)C12CCNC(=O)CC2] |
| 29 | 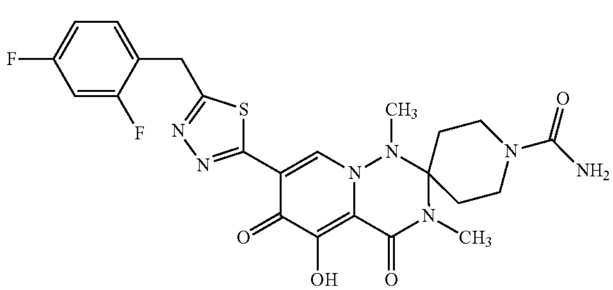 [SMILES: CN1C(=O)c2c(O)c(=O)c(-c3nnc(Cc4ccc(F)cc4F)s3)cn2N(C)C12CCN(C(N)=O)CC2] |

| Compound | Structure |
|---|---|
| 30 | 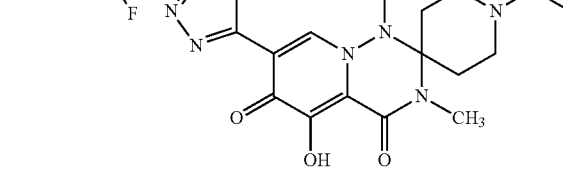 |
| 31 | 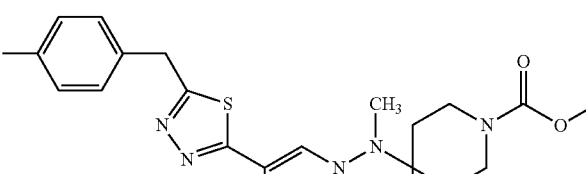 |
| 32 | 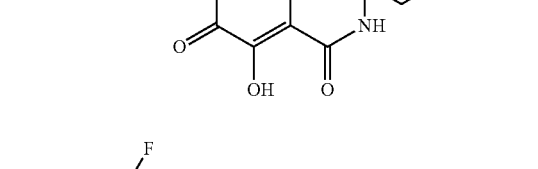 |
| 33 | 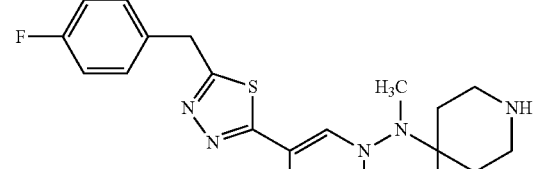 |
| 34 | 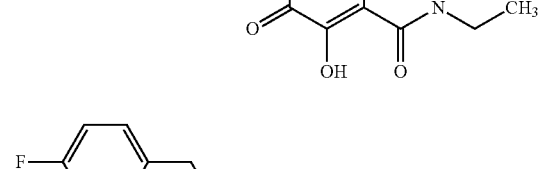 |

| Compound | Structure |
|---|---|
| 35 | 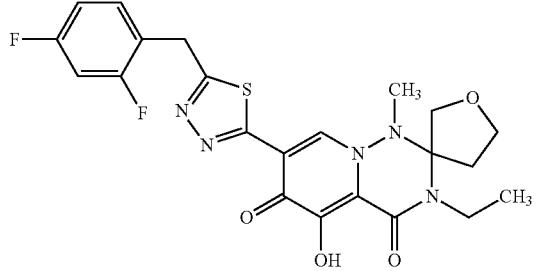<br>Enantiomer A |
| 36 | 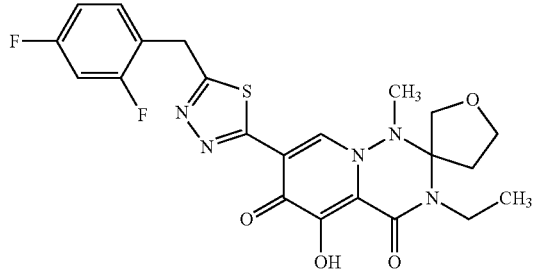<br>Enantiomer B |
| 37 | 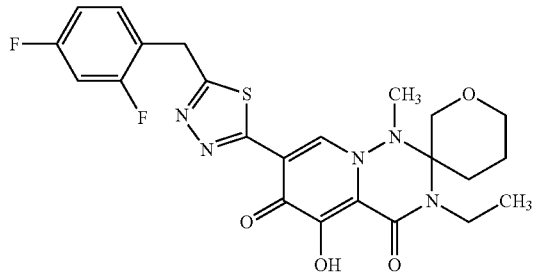 [SMILES: CCN1C(=O)c2c(O)c(=O)c(-c3nnc(Cc4ccc(F)cc4F)s3)cn2N(C)C12CCCOC2] |
| 38 | 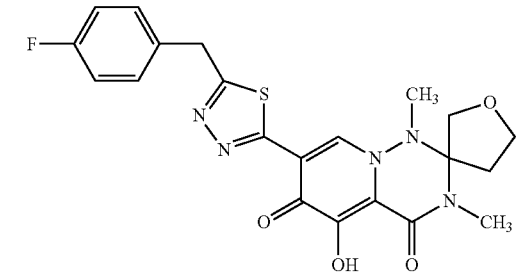 [SMILES: CN1C(=O)c2c(O)c(=O)c(-c3nnc(Cc4ccc(F)cc4)s3)cn2N(C)C12CCOC2] |
| 39 | 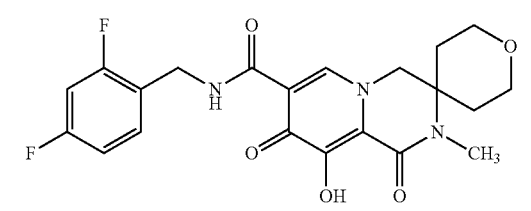 [SMILES: CN1C(=O)c2c(O)c(=O)c(C(=O)NCc3ccc(F)cc3F)cn2CC12CCOCC2] |

| Compound | Structure |
|---|---|
| 40 | (structure) |
| 41 | (structure) |
| 42 | (structure) |
| 43 | (structure) |
| 44 | (structure) |
| 45 | (structure) |
| 46 | (structure) |

| Compound | Structure |
|---|---|
| 47 | (structure with 2,4-difluorobenzyl carboxamide, pyridone core with OH, spiro tetrahydropyran, N-(4,4,4-trifluorobutyl) chain) |
| 48 | (structure with 2,4-difluorobenzyl carboxamide, CH₂OCH₃ substituent, pyridone core with OH, spiro tetrahydrofuran, N-CH₃) |
| 49 | (structure with 2,4-difluorobenzyl carboxamide, pyridone core with OH, spiro tetrahydrofuran, N-CH₂CH₂OCH₃) Enantiomer A |
| 50 | (structure with 2,4-difluorobenzyl carboxamide, pyridone core with OH, spiro tetrahydrofuran, N-CH₂CH₂OCH₃) Enantiomer B |
| 51 | (structure with 4-fluorobenzyl carboxamide, pyridone core with OH, spiro tetrahydrofuran, N-CH₂CH₂OCH₃) Enantiomer A |
| 52 | (structure with 3-chloro-4-fluorobenzyl carboxamide, pyridone core with OH, spiro tetrahydrofuran, N-CH₂CH₂OCH₃) Enantiomer A |

| Compound | Structure |
|---|---|
| 53 | 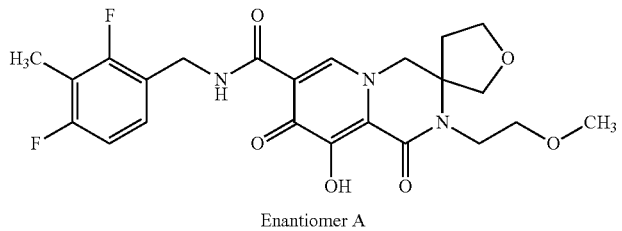 [SMILES: COCCN1C(=O)c2c(O)c(=O)c(C(=O)NCc3ccc(F)c(C)c3F)cn2CC12CCOC2]<br>Enantiomer A |
| 54 | 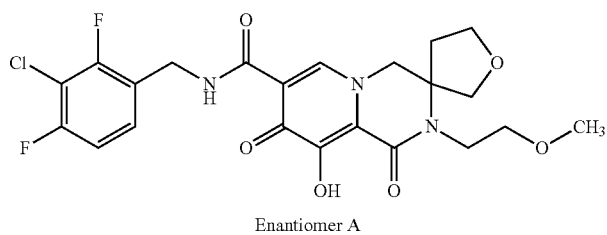 [SMILES: COCCN1C(=O)c2c(O)c(=O)c(C(=O)NCc3ccc(F)c(Cl)c3F)cn2CC12CCOC2]<br>Enantiomer A |
| 55 | 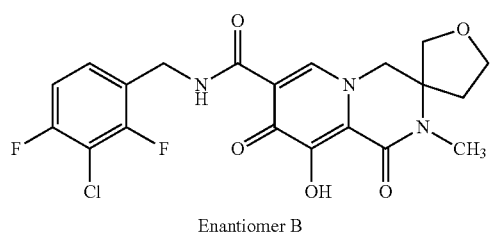 [SMILES: CN1C(=O)c2c(O)c(=O)c(C(=O)NCc3ccc(F)c(Cl)c3F)cn2CC12CCOC2]<br>Enantiomer B |
| 56 | 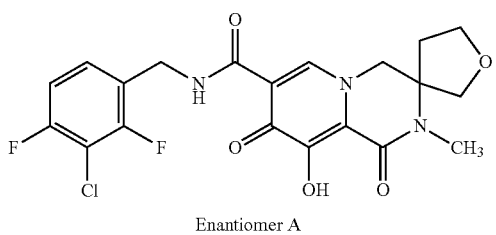 [SMILES: CN1C(=O)c2c(O)c(=O)c(C(=O)NCc3ccc(F)c(Cl)c3F)cn2CC12CCOC2]<br>Enantiomer A |
| 57 | 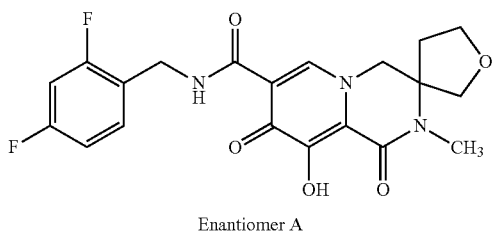 [SMILES: CN1C(=O)c2c(O)c(=O)c(C(=O)NCc3ccc(F)cc3F)cn2CC12CCOC2]<br>Enantiomer A |
| 58 | 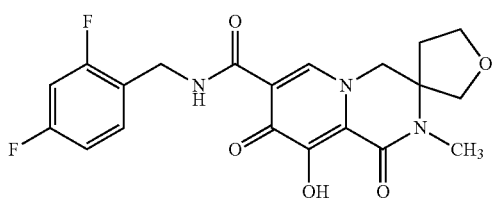 [SMILES: CN1C(=O)c2c(O)c(=O)c(C(=O)NCc3ccc(F)cc3F)cn2CC12CCOC2] |

| Compound | Structure |
|---|---|
| 59 | 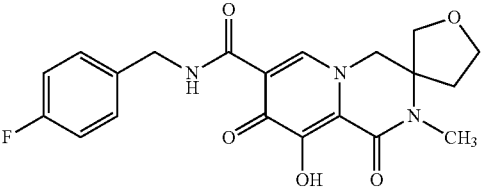 [SMILES: CN1C(=O)c2c(O)c(=O)c(C(=O)NCc3ccc(F)cc3)cn2CC12CCOC2]<br>Enantiomer A |
| 60 | 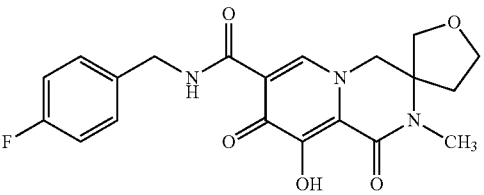 |
| 61 | 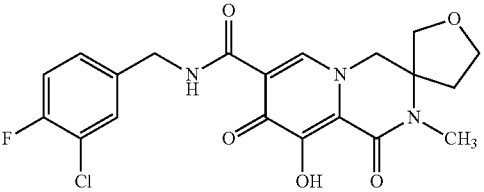<br>Enantiomer A |
| 62 | 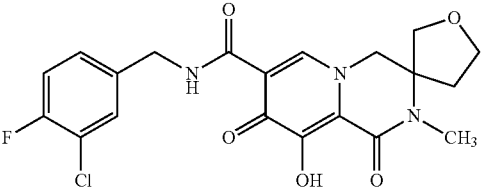<br>Enantiomer B |
| 63 | 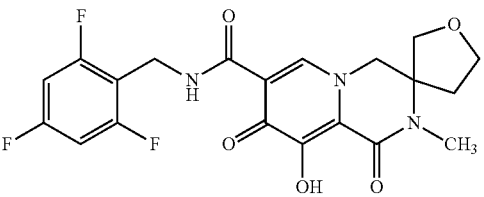<br>Enantiomer A |
| 64 | 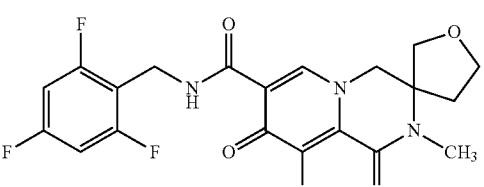<br>Enantiomer B |

-continued
| Compound | Structure |
|---|---|
| 65 | 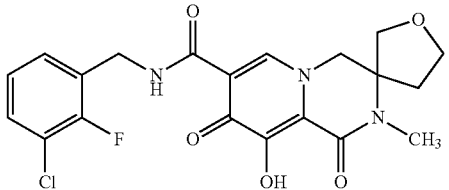<br>Enantiomer A |
| 66 | 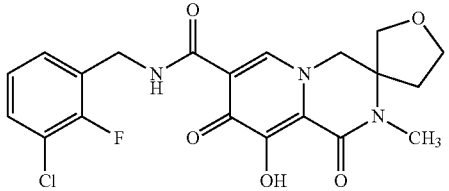<br>Enantiomer B |
| 67 | 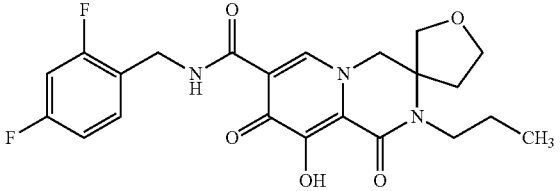<br>racemic |
| 68 | 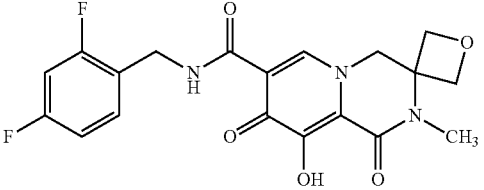 [SMILES: CN1C(=O)c2c(O)c(=O)c(C(=O)NCc3ccc(F)cc3F)cn2CC12COC2] |
| 69 | 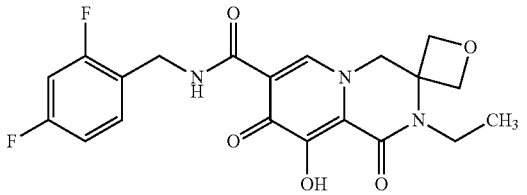 [SMILES: CCN1C(=O)c2c(O)c(=O)c(C(=O)NCc3ccc(F)cc3F)cn2CC12COC2] |
| 70 | 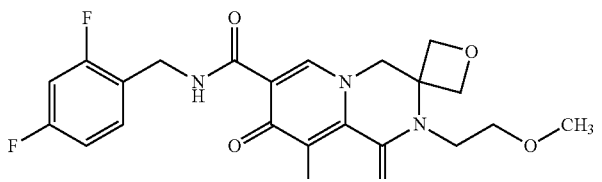 |
| 71 | 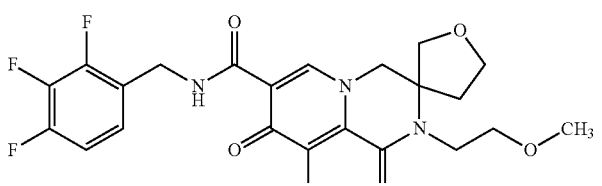<br>Enantiomer A |

| Compound | Structure |
|---|---|
| 72 | 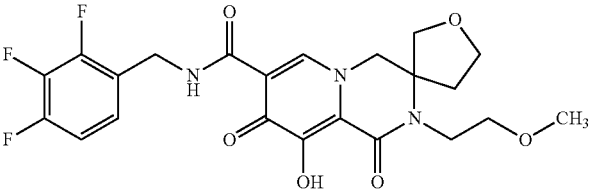<br>Enantiomer B |
| 73 | 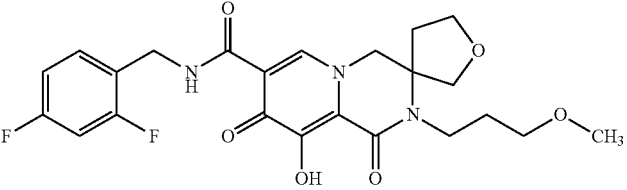<br>Enantiomer A |
| 74 | 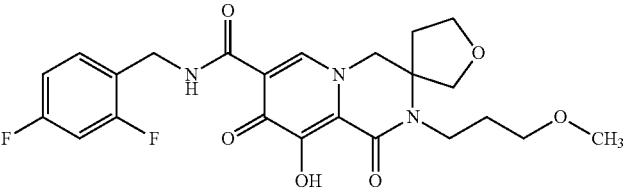<br>Enantiomer B |
| 75 | 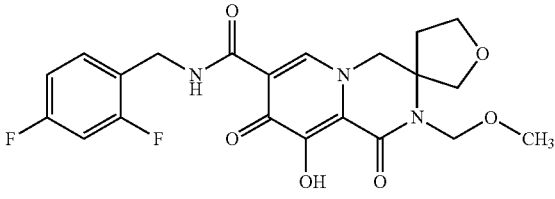<br>Enantiomer A |
| 76 | 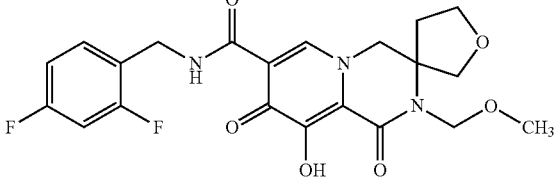<br>Enantiomer B |
| 77 | 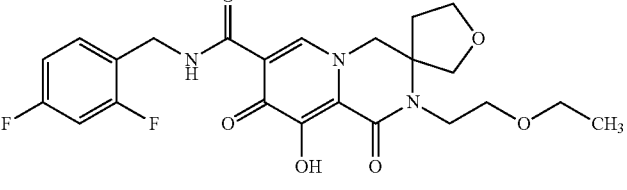<br>Enantiomer A |

-continued
| Compound | Structure |
|---|---|
| 78 | 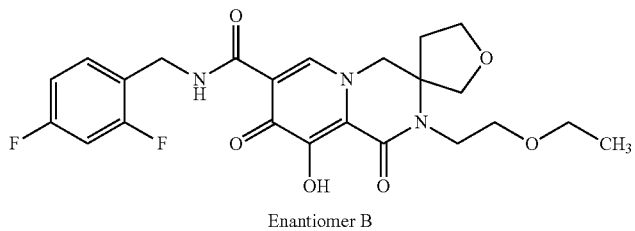 [SMILES: CCOCCN1C(=O)c2c(O)c(=O)c(C(=O)NCc3ccc(F)cc3F)cn2CC12CCOC2]<br>Enantiomer B |
| 79 | 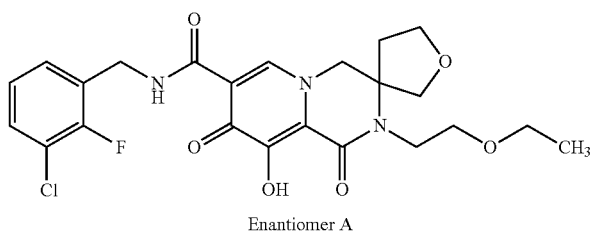 [SMILES: CCOCCN1C(=O)c2c(O)c(=O)c(C(=O)NCc3cccc(Cl)c3F)cn2CC12CCOC2]<br>Enantiomer A |
| 80 | 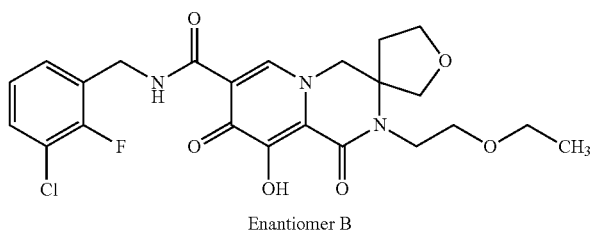 [SMILES: CCOCCN1C(=O)c2c(O)c(=O)c(C(=O)NCc3cccc(Cl)c3F)cn2CC12CCOC2]<br>Enantiomer B |
| 81 | 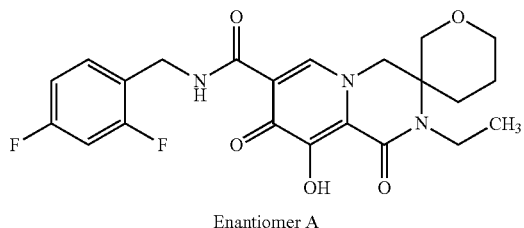 [SMILES: CCN1C(=O)c2c(O)c(=O)c(C(=O)NCc3ccc(F)cc3F)cn2CC12CCCOC2]<br>Enantiomer A |
| 82 | 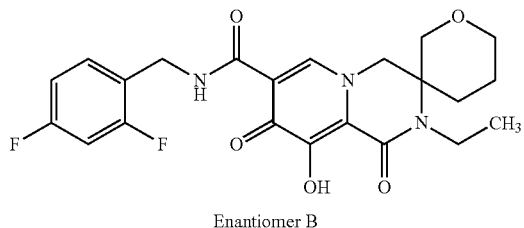 [SMILES: CCN1C(=O)c2c(O)c(=O)c(C(=O)NCc3ccc(F)cc3F)cn2CC12CCCOC2]<br>Enantiomer B |
| 83 | 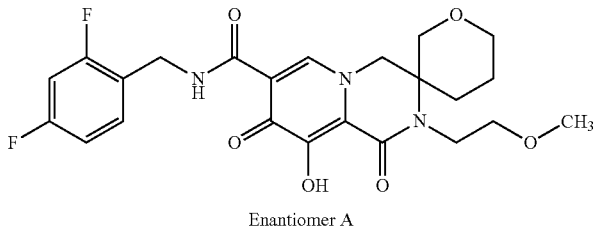 [SMILES: COCCN1C(=O)c2c(O)c(=O)c(C(=O)NCc3ccc(F)cc3F)cn2CC12CCCOC2]<br>Enantiomer A |

| Compound | Structure |
|---|---|
| 84 | 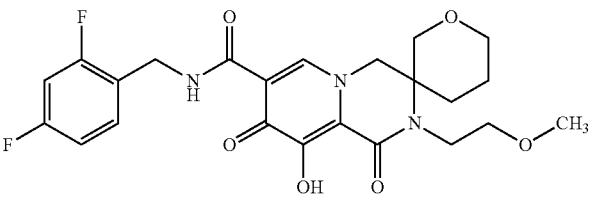<br>Enantiomer B |
| 85 | 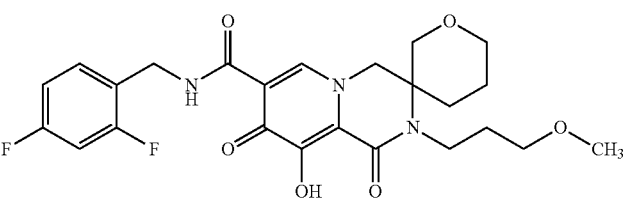<br>Enantiomer A |
| 86 | 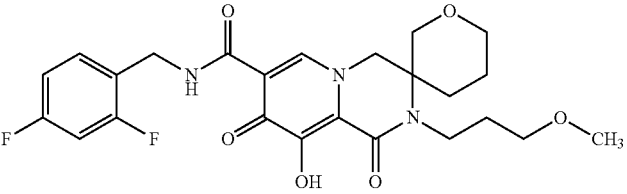<br>Enantiomer B |
| 87 | 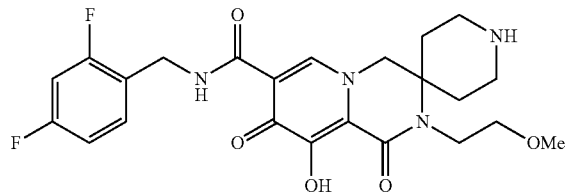 [SMILES: COCCN1C(=O)c2c(O)c(=O)c(C(=O)NCc3ccc(F)cc3F)cn2CC12CCNCC2] |
| 88 | 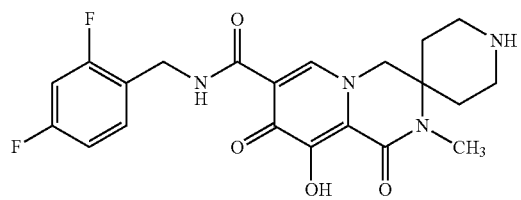 [SMILES: CN1C(=O)c2c(O)c(=O)c(C(=O)NCc3ccc(F)cc3F)cn2CC12CCNCC2] |
| 89 | 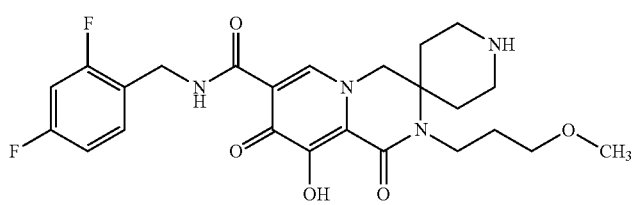 [SMILES: COCCCN1C(=O)c2c(O)c(=O)c(C(=O)NCc3ccc(F)cc3F)cn2CC12CCNCC2] |

-continued
| Compound | Structure |
|---|---|
| 90 | 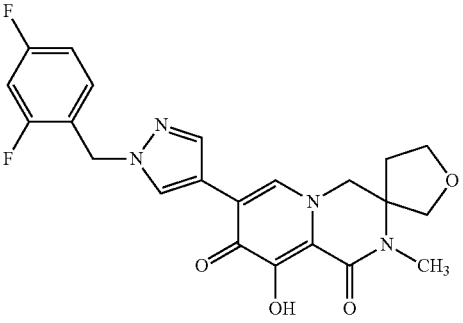 [SMILES: CN1C(=O)c2c(O)c(=O)c(-c3cnn(Cc4ccc(F)cc4F)c3)cn2CC12CCOC2] |
| 91 | 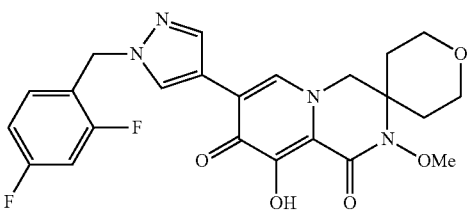 [SMILES: CON1C(=O)c2c(O)c(=O)c(-c3cnn(Cc4ccc(F)cc4F)c3)cn2CC12CCOCC2] |
| 92 | 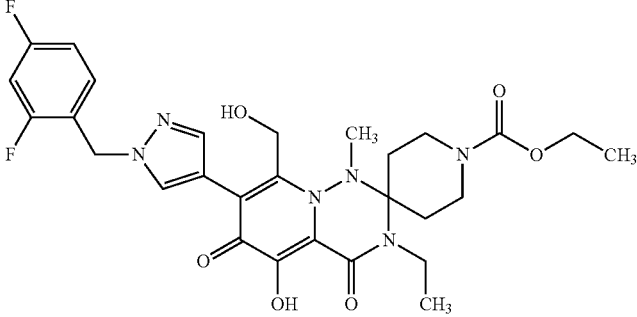 [SMILES: CCOC(=O)N1CCC2(CC1)N(CC)C(=O)c1c(O)c(=O)c(-c3cnn(Cc4ccc(F)cc4F)c3)c(CO)n1N2C] |
| 93 | 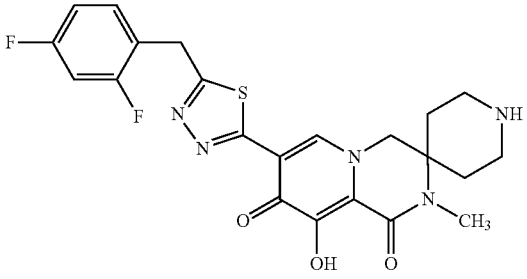 [SMILES: CN1C(=O)c2c(O)c(=O)c(-c3nnc(Cc4ccc(F)cc4F)s3)cn2CC12CCNCC2] |
| 94 | 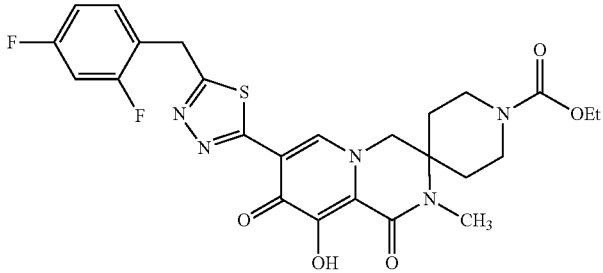 [SMILES: CCOC(=O)N1CCC2(CC1)Cn1cc(-c3nnc(Cc4ccc(F)cc4F)s3)c(=O)c(O)c1C(=O)N2C] |

-continued
| Compound | Structure |
|---|---|
| 95 | 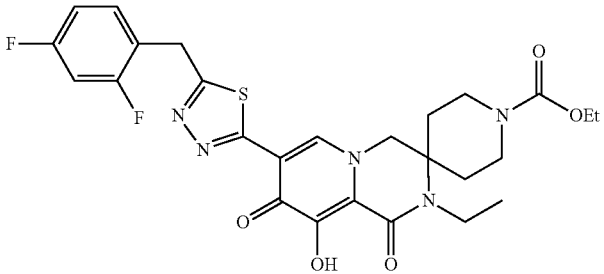 [SMILES: CCOC(=O)N1CCC2(CC1)Cn1cc(-c3nnc(Cc4ccc(F)cc4F)s3)c(=O)c(O)c1C(=O)N2CC] |
| 96 | 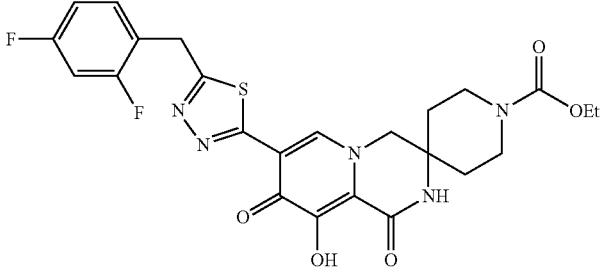 [SMILES: CCOC(=O)N1CCC2(CC1)Cn1cc(-c3nnc(Cc4ccc(F)cc4F)s3)c(=O)c(O)c1C(=O)N2] |
| 97 | 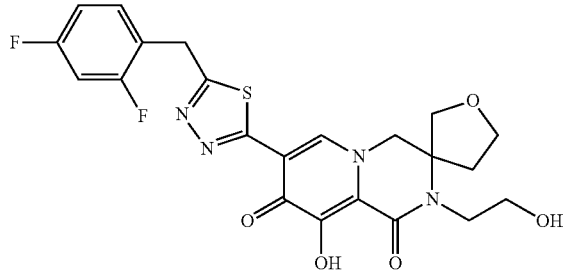 [SMILES: O=C1c2c(O)c(=O)c(-c3nnc(Cc4ccc(F)cc4F)s3)cn2CC2(CCOC2)N1CCO] |
| 98 | 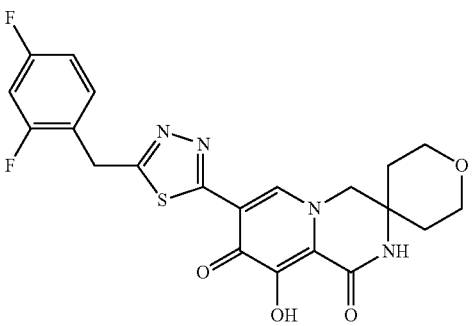 [SMILES: O=C1NC2(CCOCC2)Cn2cc(-c3nnc(Cc4ccc(F)cc4F)s3)c(=O)c(O)c21] |
| 99 | 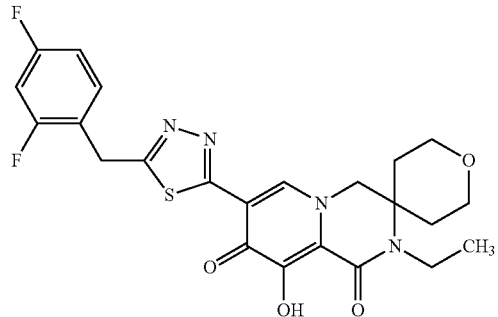 [SMILES: CCN1C(=O)c2c(O)c(=O)c(-c3nnc(Cc4ccc(F)cc4F)s3)cn2CC12CCOCC2] |

| Compound | Structure |
|---|---|
| 100 | (structure: 2,4-difluorophenyl-CH(CH2CH3)- linked to 1,3,4-thiadiazole connected to pyridinone-spiro-tetrahydropyran with N-ethyl) |
| 101 | (structure: 2,4-difluorobenzyl linked to 1,3,4-thiadiazole connected to pyridinone-spiro-tetrahydrofuran with N-CH3) |
| 102 | (structure: 2,4-difluorophenyl-CH(CH3)- linked to 1,3,4-thiadiazole connected to pyridinone-spiro-tetrahydrofuran with N-CH3) |
| 103 | (structure: 2,4-difluorobenzyl-NH-C(O)- linked to pyridazinone-spiro-tetrahydrofuran with N-CH3, N-CH3) Enantiomer A |
| 104 | (structure: 2,4-difluorobenzyl-NH-C(O)- linked to pyridazinone-spiro-tetrahydrofuran with N-CH3, N-CH3) Enantiomer B |

-continued
| Compound | Structure |
|---|---|
| 105 | 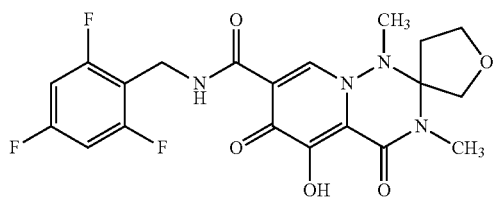<br>Enantiomer A |
| 106 | 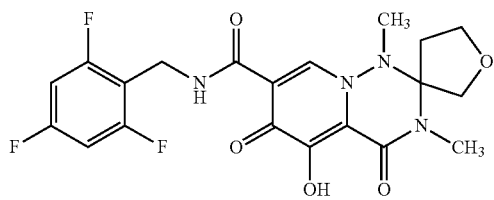<br>Enantiomer B |
| 107 | 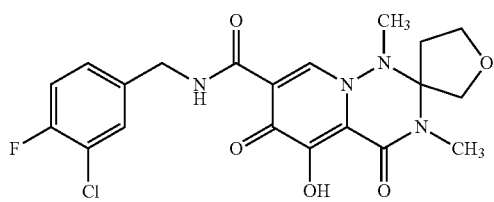<br>Enantiomer A |
| 108 | 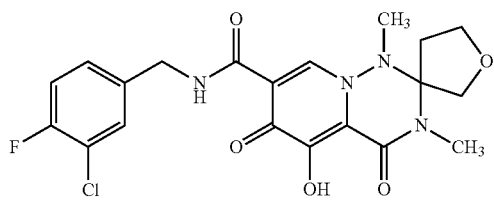<br>Enantiomer B |
| 109 | 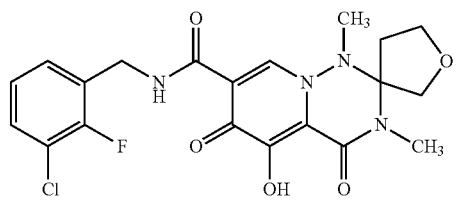<br>Enantiomer A |
| 110 | 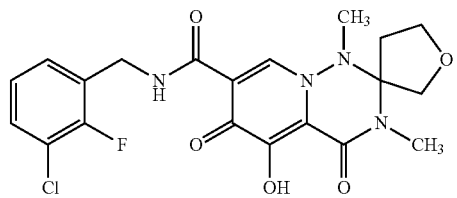<br>Enantiomer B |

| Compound | Structure |
|---|---|
| 111 | 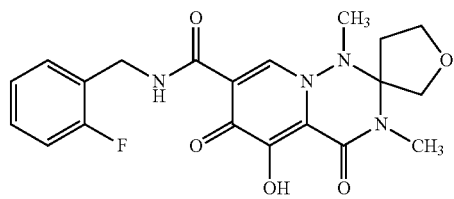<br>Enantiomer A |
| 112 | 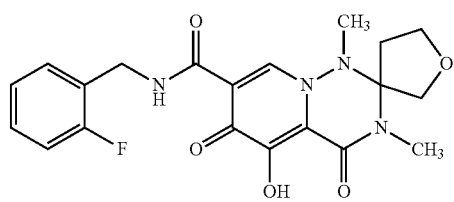<br>Enantiomer B |
| 113 | 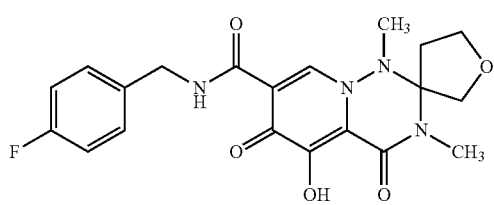<br>Enantiomer A |
| 114 | 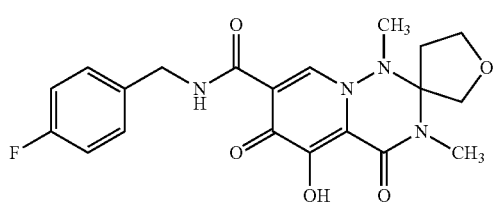<br>Enantiomer B |
| 115 | 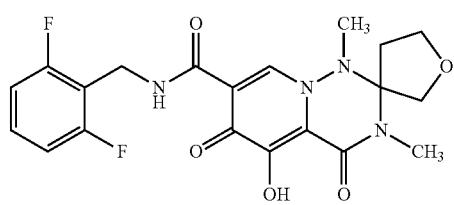<br>Enantiomer A |
| 116 | 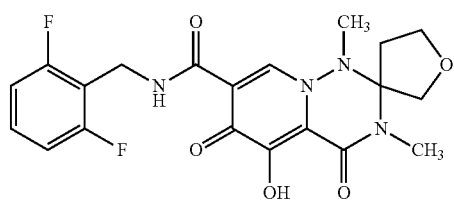<br>Enantiomer B |

| Compound | Structure |
|---|---|
| 117 | 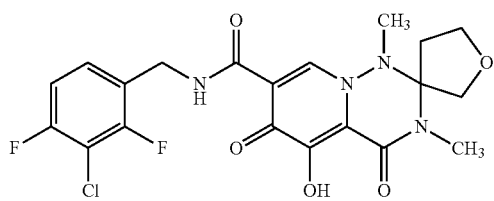<br>Enantiomer A |
| 118 | 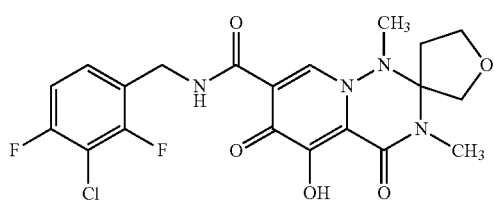<br>Enantiomer B |
| 119 | 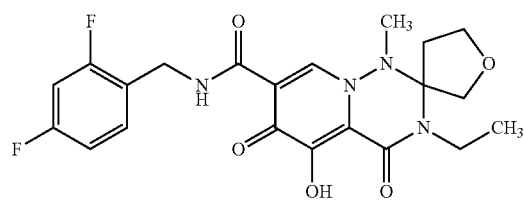<br>Enantiomer A |
| 120 | 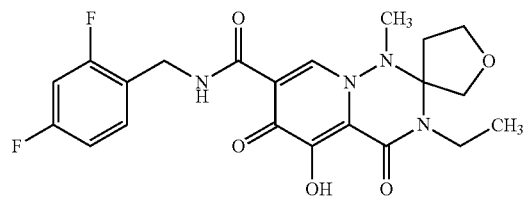<br>Enantiomer B |
| 121 | 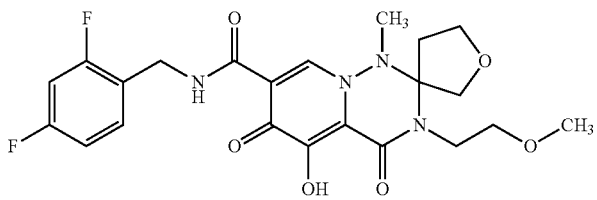<br>Enantiomer A |
| 122 | 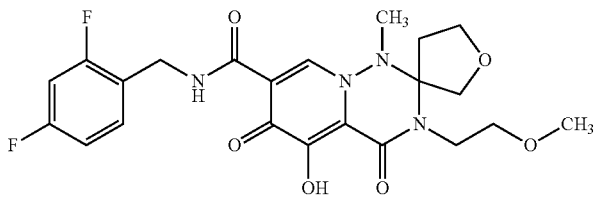<br>Enantiomer B |

| Compound | Structure |
|---|---|
| 123 | 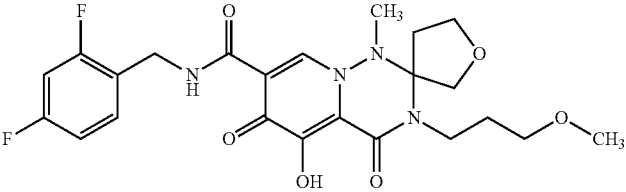<br>Enantiomer A |
| 124 | 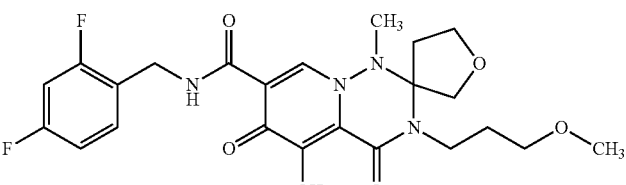<br>Enantiomer B |
| 125 | 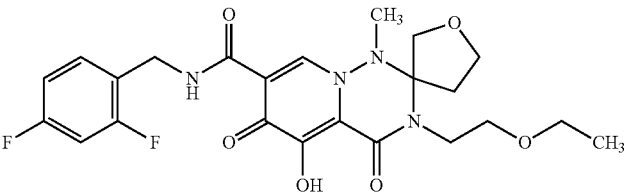<br>Enantiomer A |
| 126 | 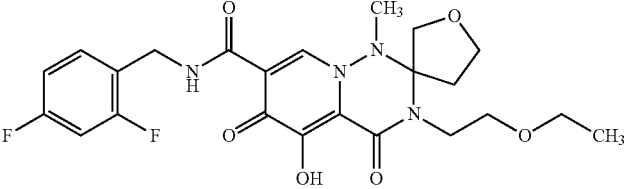<br>Enantiomer B |
| 127 | 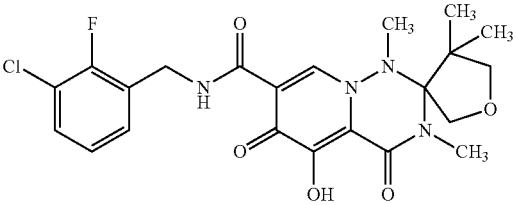<br>Enantiomer A |
| 128 | 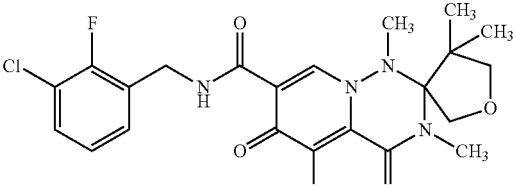<br>Enantiomer B |

| Compound | Structure |
|---|---|
| 129 | 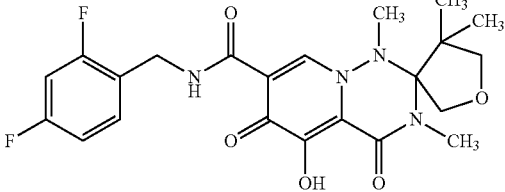<br>Enantiomer A |
| 130 | 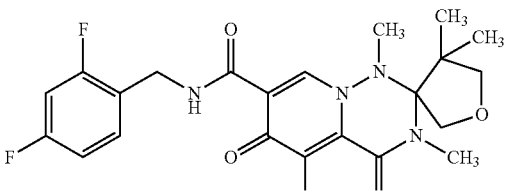<br>Enantiomer B |
| 131 | 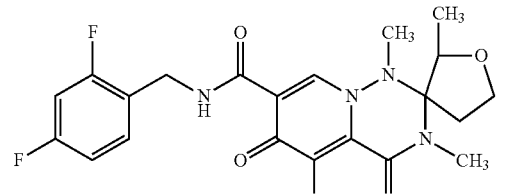<br>Enantiomer A |
| 132 | 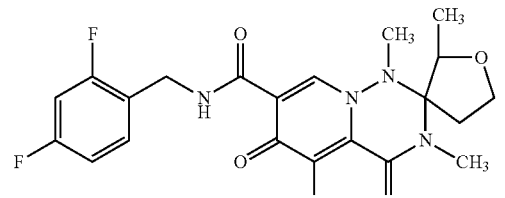<br>Enantiomer B |
| 133 | 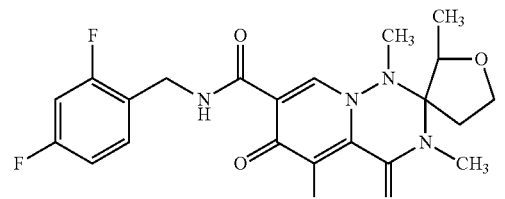<br>Enantiomer A |
| 134 | 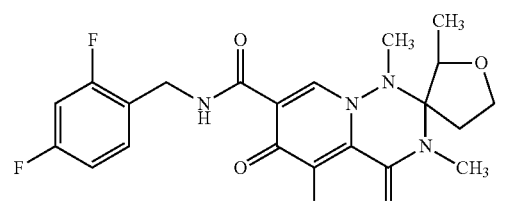<br>Enantiomer B |

| Compound | Structure |
|---|---|
| 135 | 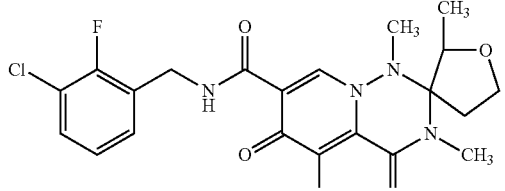
Enantiomer A |
| 136 | 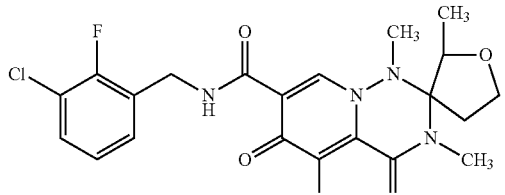
Enantiomer B |
| 137 | 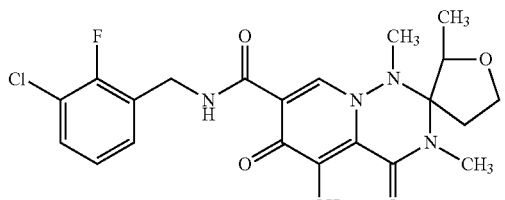
Enantiomer A |
| 138 | 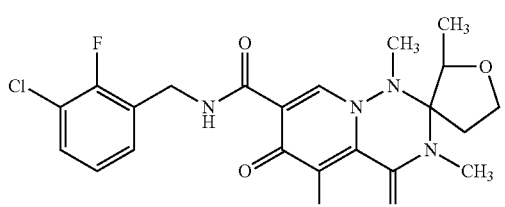
Enantiomer B |
| 139 | 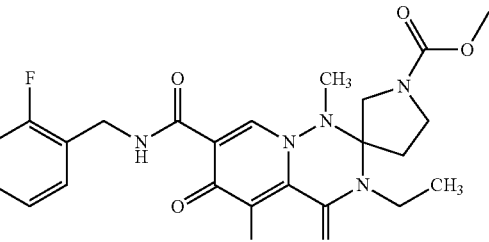
Enantiomer A |

US 9,707,234 B2
| Compound | Structure |
|---|---|
| 140 | 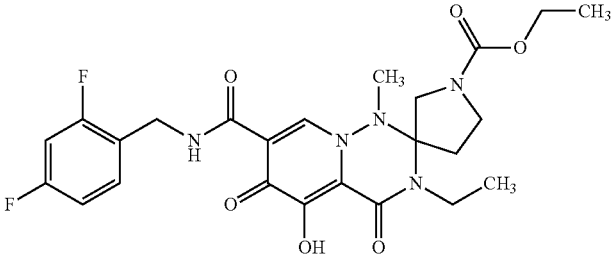
Enantiomer B |
| 141 | 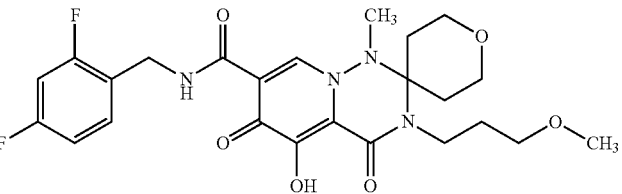 |
| 142 | 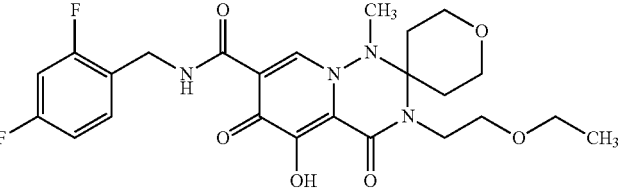 |
| 143 | 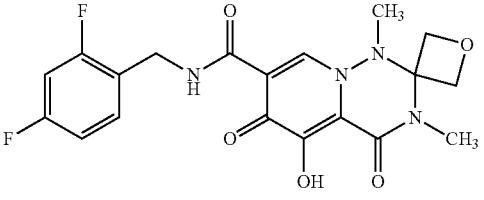 [SMILES: CN1C(=O)c2c(O)c(=O)c(C(=O)NCc3ccc(F)cc3F)cn2N(C)C12COC2] |
| 144 | 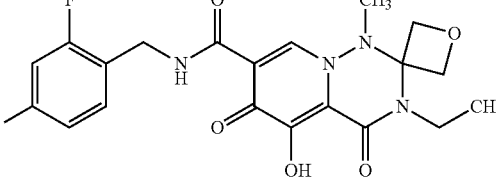 |
| 145 | 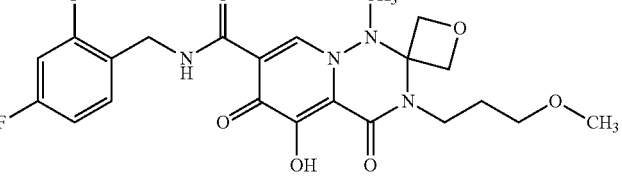 |
| 146 | 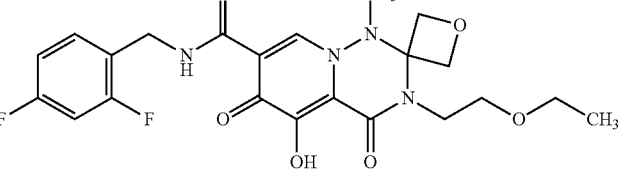 |

| Compound | Structure |
|---|---|
| 147 | 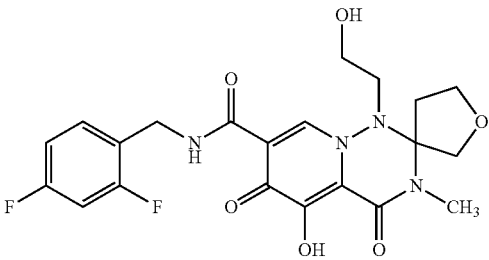<br>Enantiomer A |
| 148 | 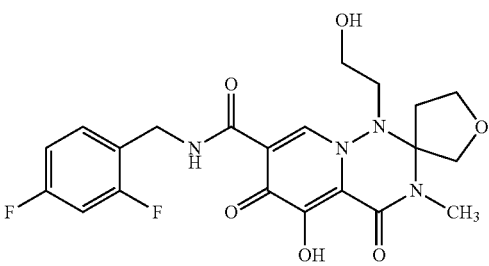<br>Enantiomer B |
| 149 | 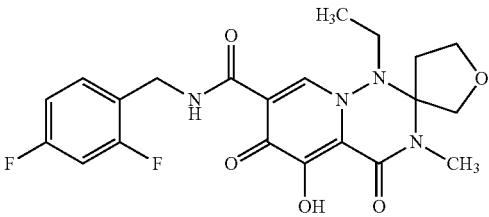<br>Enantiomer A |
| 150 | 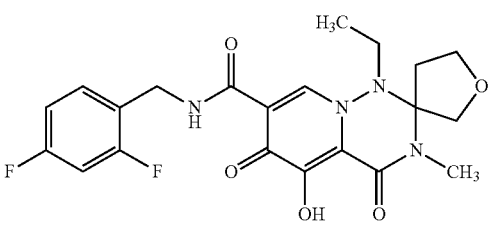<br>Enantiomer B |
| 151 | 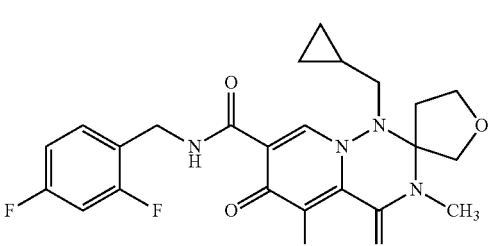<br>Enantiomer A |

| Compound | Structure |
|---|---|
| 152 | 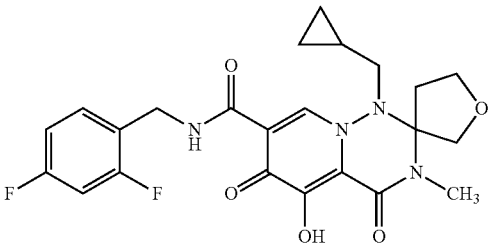<br>Enantiomer B |
| 153 | 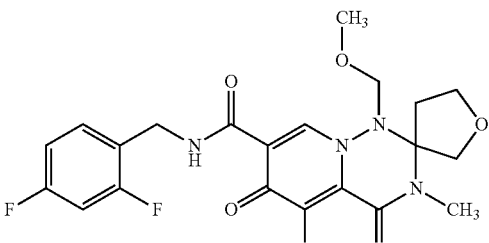<br>Enantiomer A |
| 154 | 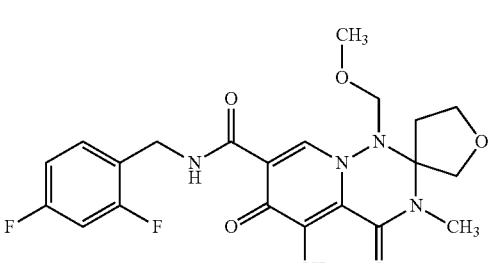<br>Enantiomer B |
| 155 | 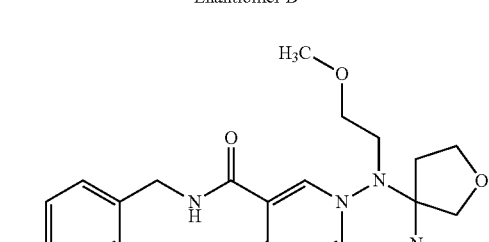<br>Enantiomer A |
| 156 | 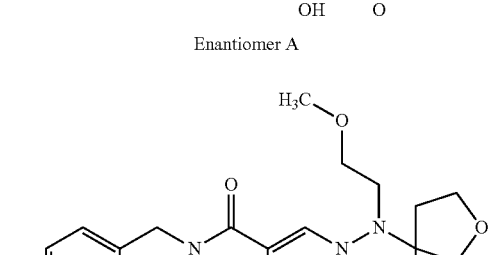<br>Enantiomer B |

| Compound | Structure |
|---|---|
| 157 | 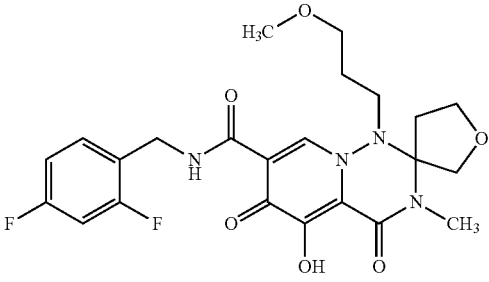<br>Enantiomer A |
| 158 | 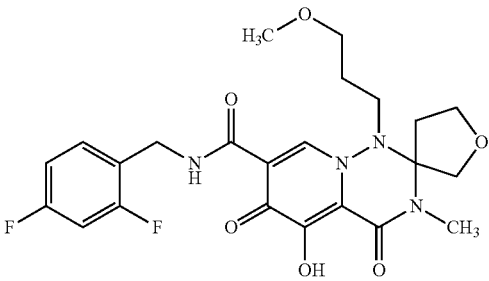<br>Enantiomer B |
| 159 | 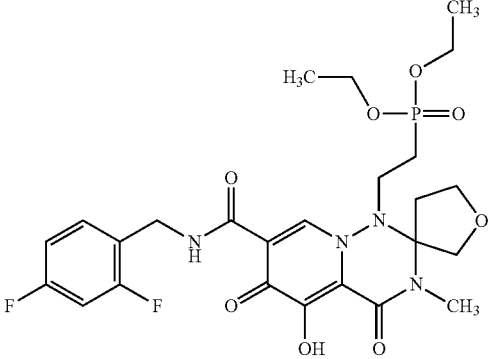<br>Enantiomer A |
| 160 | 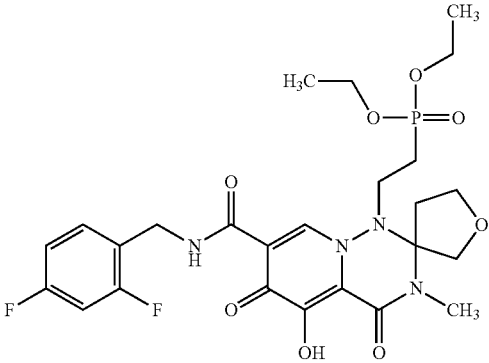<br>Enantiomer B |

| Compound | Structure |
|---|---|
| 161 | 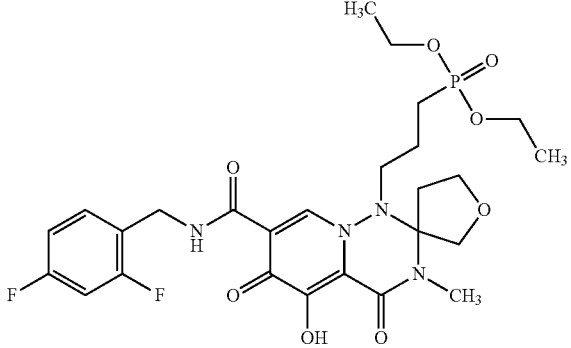 [SMILES: CCOP(=O)(CCCN1n2cc(C(=O)NCc3ccc(F)cc3F)c(=O)c(O)c2C(=O)N(C)C12CCOC2)OCC] |
| 162 | 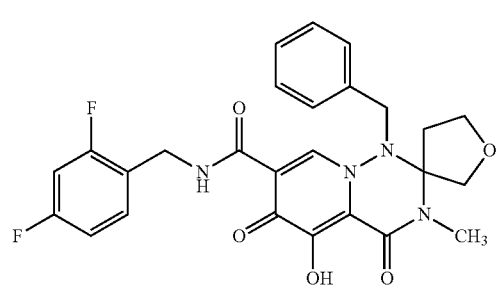<br>Enantiomer A |
| 163 | 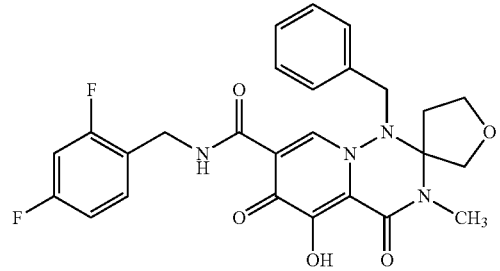<br>Enantiomer B |
| 164 | 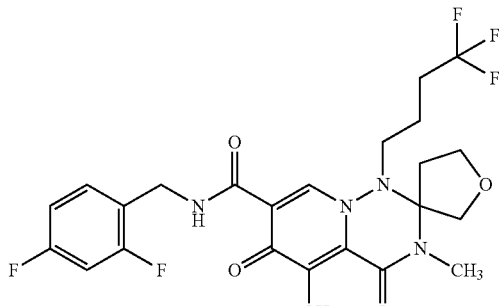<br>Enantiomer A |

| Compound | Structure |
|---|---|
| 165 | 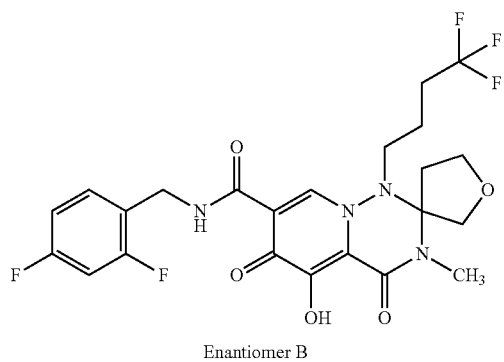 [SMILES: CN1C(=O)c2c(O)c(=O)c(C(=O)NCc3ccc(F)cc3F)cn2N(CCCC(F)(F)F)C12CCOC2]<br>Enantiomer B |
| 166 | 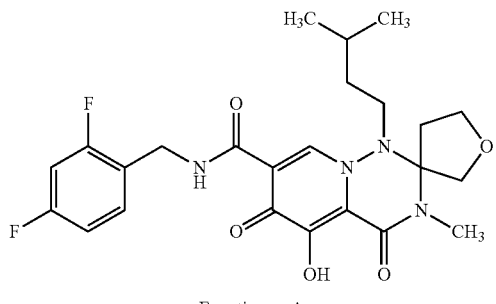<br>Enantiomer A |
| 167 | 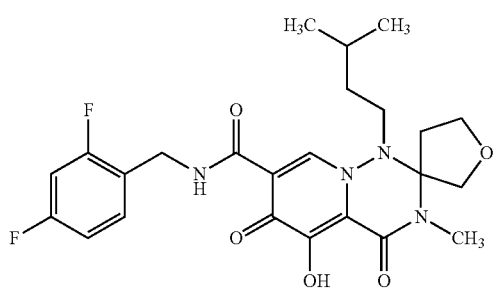<br>Enantiomer B |
| 168 | 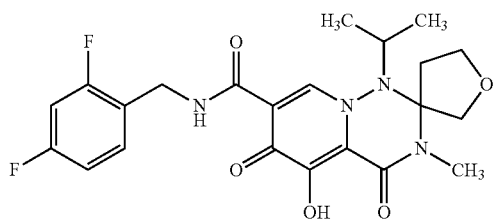 [SMILES: CC(C)N1n2cc(C(=O)NCc3ccc(F)cc3F)c(=O)c(O)c2C(=O)N(C)C12CCOC2] |
| 169 | 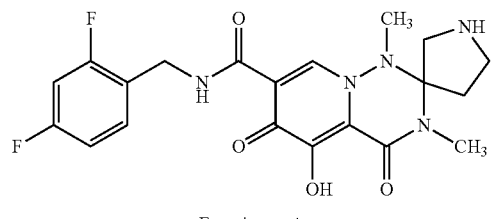<br>Enantiomer A |

| Compound | Structure |
|---|---|
| 170 | Enantiomer B |
| 171 | 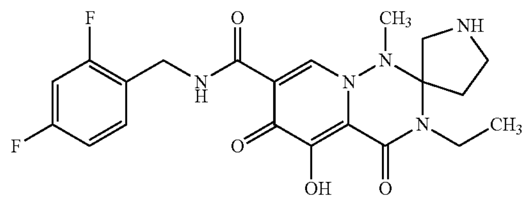 [SMILES: CCN1C(=O)c2c(O)c(=O)c(C(=O)NCc3ccc(F)cc3F)cn2N(C)C12CCNC2] |
| 172 | 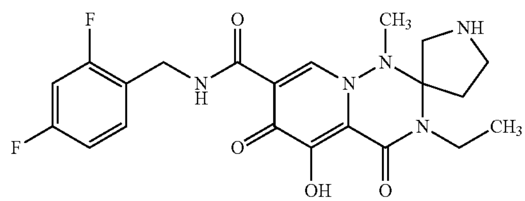 [SMILES: CCN1C(=O)c2c(O)c(=O)c(C(=O)NCc3ccc(F)cc3F)cn2N(C)C12CCNC2] |
| 173 | 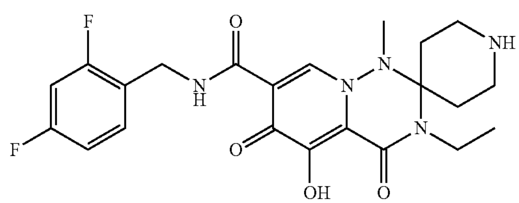 [SMILES: CCN1C(=O)c2c(O)c(=O)c(C(=O)NCc3ccc(F)cc3F)cn2N(C)C12CCNCC2] |

Treatment or Prevention of HIV Infection

The Spirocyclic Heterocycle Compounds may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Spirocyclic Heterocycle Compounds may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Spirocyclic Heterocycle Compound or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Spirocyclic Heterocycle Compounds are also useful in the preparation and execution of screening assays for antiviral compounds. For example the Spirocyclic Heterocycle Compounds may be useful for identifying resistant HIV cell lines harboring mutations, which are excellent screening tools for more powerful antiviral compounds. Furthermore, the Spirocyclic Heterocycle Compounds may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Spirocyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Spirocyclic Heterocycle Compound (which may include two or more different Spirocyclic Heterocycle Compounds), or a pharmaceutically acceptable salt thereof, and (ii) at least one additional therapeutic agent that is other than a Spirocyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Spirocyclic Heterocycle Compound and an additional therapeutic agent may be present in fixed amounts (dosage amounts) in a single dosage unit (e.g., a capsule, a tablet and the like).

In one embodiment, the at least one Spirocyclic Heterocycle Compound is administered during a time when the additional therapeutic agent(s) exert their prophylactic or therapeutic effect, or vice versa.

In another embodiment, the at least one Spirocyclic Heterocycle Compound and the additional therapeutic agent(s) are administered in doses commonly employed when such agents are used as monotherapy for treating a viral infection.

In another embodiment, the at least one Spirocyclic Heterocycle Compound and the additional therapeutic agent(s) are administered in doses lower than the doses commonly employed when such agents are used as monotherapy for treating a viral infection.

In still another embodiment, the at least one Spirocyclic Heterocycle Compound and the additional therapeutic agent(s) act synergistically and are administered in doses lower than the doses commonly employed when such agents are used as monotherapy for treating a viral infection.

In one embodiment, the at least one Spirocyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Spirocyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Spirocyclic Heterocycle Compound and the additional therapeutic agent(s) may inhibit the resistance of a viral infection to these agents.

As noted above, the present invention is also directed to use of a compound of

Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | InI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Spirocyclic Heterocycle Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

When administered to a subject, the Spirocyclic Heterocycle Compounds can be administered as a component of a composition that comprises a pharmaceutically acceptable carrier or vehicle. The present invention provides pharmaceutical compositions comprising an effective amount of at least one Spirocyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starchours, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methyl-cellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Spirocyclic Heterocycle Compounds are administered orally.

In another embodiment, the one or more Spirocyclic Heterocycle Compounds are administered intravenously.

In one embodiment, a pharmaceutical preparation comprising at least one Spirocyclic Heterocycle Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Spirocyclic Heterocycle Compound(s) by weight or volume. In various embodiments, the present compositions can contain, in one embodiment, from about 1% to about 70% or from about 5% to about 60% of the Spirocyclic Heterocycle Compound(s) by weight or volume.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general healthours, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Spirocyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Spirocyclic Heterocycle Compound, or a pharmaceutically acceptable salt or prodrug of said compound and a pharmaceutically acceptable carrier, vehicle or diluent.

In another aspect the present invention provides a kit comprising an amount of at least one Spirocyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Spirocyclic Heterocycle Compounds and the one or more additional therapeutic agents are provided in the same container. In one embodiment, the one or more Spirocyclic Heterocycle Compounds and the one or more additional therapeutic agents are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Scheme 1 below. Alternative synthetic pathways and analogous structures will be apparent to those skilled in the art of organic synthesis.

The following schemes describe general methods for preparing the compounds of formula (I), which correspond to the 4-pyridotriazines compounds of Formula (I).

Scheme 1

A → (H₂N—Y, B, Step 1) → C → (hydrolysis, Step 2) → D → (E, NH₂R¹, amide coupling, Step 3) → F → (G, acid catalysis, Step 4) → H

A pyranone compound of formula A is reacted with an amine of formula B to provide dihydropyridine compounds of formula C. Base promoted hydrolysis of the ester moiety of C to provide carboxylic acids of formula D, followed by amide coupling of D with an amine compound of formula E provides cyclization precursors of formula F. Acid catalyzed deprotection of the benzyl protecting group, followed by condensation with an aldehyde or ketone of formula G provides the product hours.

Scheme 2

A → (H₂N—CR²R³—NH₂, B, Step 1) → C → (Step 2) →

-continued

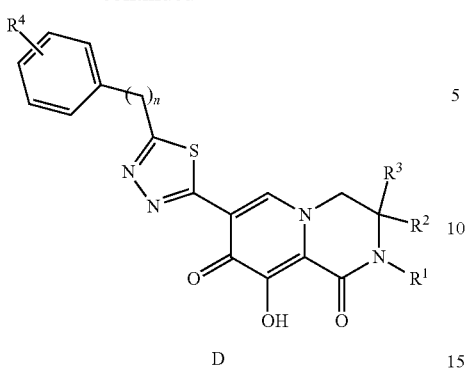

A pyranone compound of formula A is reacted with an amine of formula B under a variety of conditions to provide either a compound of formula C or to directly provide a compound of formula D. Compounds of formula C can also be converted to a compound of formula D.

Scheme 3

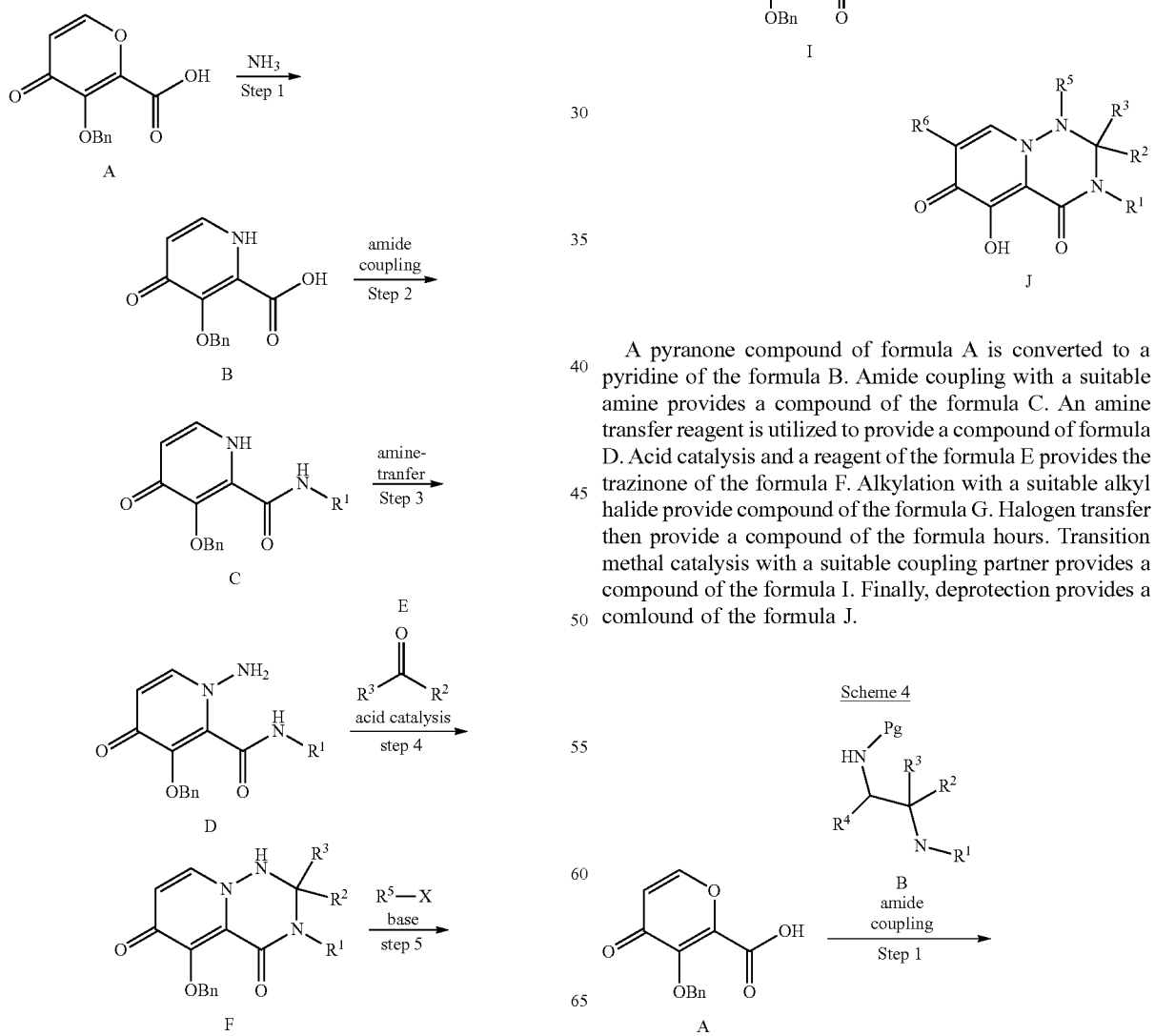

-continued

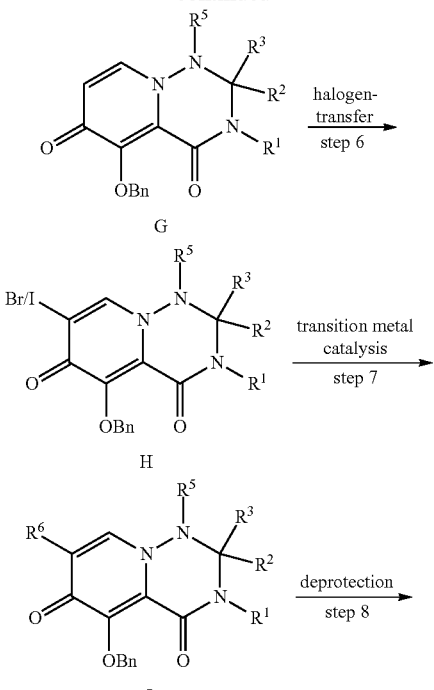

A pyranone compound of formula A is converted to a pyridine of the formula B. Amide coupling with a suitable amine provides a compound of the formula C. An amine transfer reagent is utilized to provide a compound of formula D. Acid catalysis and a reagent of the formula E provides the trazinone of the formula F. Alkylation with a suitable alkyl halide provide compound of the formula G. Halogen transfer then provide a compound of the formula hours. Transition methal catalysis with a suitable coupling partner provides a compound of the formula I. Finally, deprotection provides a comlound of the formula J.

Scheme 4

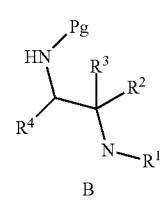

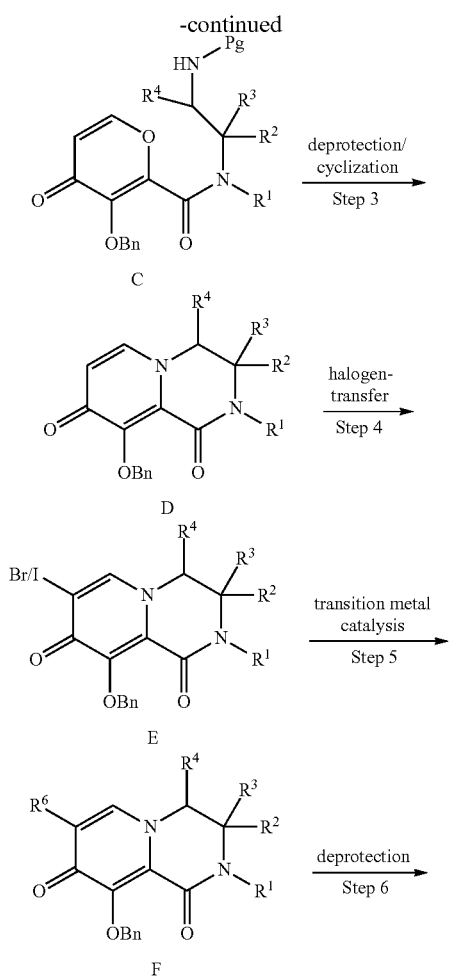

A pyranone compound of formula A is coupled to a suitably functionalized amine B for provide a compound of the general formula C. Amine deprotection and subsequent cyclization provides a compound of the general structure D. Halogen transfer provides a compound of the general structure E. Transition methal catalysis with a suitable coupling partner provides a compound of the formula F. Finally, deprotection provides a comlound of the formula G.

EXAMPLES

General Methods

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. Concentration refers to the removal of the volatile components at reduced pressure (e.g. rotary evaporation) unless otherwise noted. All temperatures are degrees Celsius unless otherwise noted. Mass spectra (MS) were measured by electrospray ion-mass spectroscopy (ESI) in positive ion detection mode and m/z refers to the [M+H]$^+$ ion unless otherwise noted. $^1$H NMR spectra were recorded at 400-500 MHz at ambient temparature unless otherwise noted. RP-HPLC refers to reverse-phase HPLC on C18-functionalized preparative or semi-preparative columns with gradient elution using acetonitrile and water modified with trifluoroacetic acid as eluents and fractions were lyophylized or concentrated by rotary evaporation unless otherwise noted. RP-MPLC refers to reverse phase medium pressure liquid chromatography using a flash chromatography system (e.g. ISCO or Biotage) and commercial pre-packed C18-functionalized silica gel columns with gradient elution using acetonitrile and water modified with trifluoroacetic acid as eluents and fractions were lyophylized or concentrated by rotary evaporation unless otherwise noted. Compounds described herein were synthesized as the racemates unless otherwise noted in the experimental procedures and compound tables. For stereoisomers, enantiomer A refers to the earlier eluting enantiomer and enantiomer B refers to the later eluting enantiomer at the point of chiral resolution and this nomenclature is maintained through the remainder of a synthetic sequence for a given enantiomeric series regardless of the possibility that subsequent intermediates and final compounds may have the same or opposite orders of elution.

Example 1

Preparation of Intermediate Compound 1-1

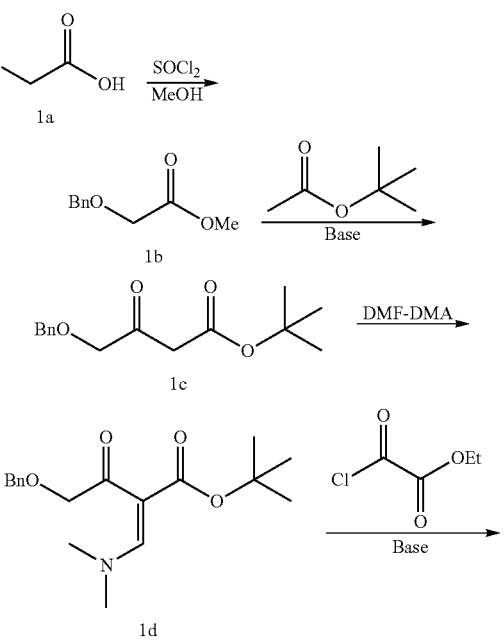

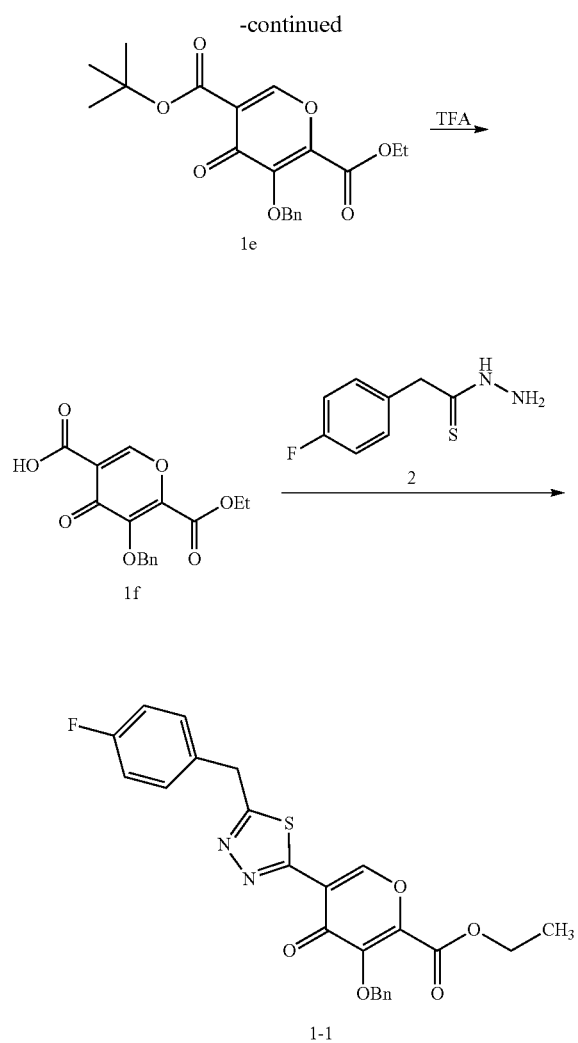

Step A—Synthesis of Intermediate Compound 1b

To a solution of compound 1a (200 g, 1.2 mol) in dry methanol (2 L) was added $SOCl_2$ (424 g, 3.6 mol) under $N_2$ at 0° C., then heated under reflux for 6 hours. The reaction mixture was concentrated in vacuo and the resulting residue was dissolved in Ethyl acetate (3 L). The organic phase was washed with $NaHCO_3$ (2 L×2), brine, dried over $Na_2SO_4$ and concentrated in vacuo to provide compound 1b as an oil.

Step B—Synthesis of Intermediate Compound 1c

To a solution of compound 1b (322 g, 2.78 mol) in dry THF (2.8 L) was added LiHMDS (2.78 L, 2.78 mol) at −70° C. under $N_2$. After stirred at −70° C. for 1 hours, then compound 2 (250 g, 1.39 mol) was added and the mixture was allowed to stir at −70° C. for 1.5 hours. The reaction was quenched with water (2 L) and extracted with Ethyl acetate (8 L×3). The combined organic phase was washed with brine, dried over $Na_2SO_4$, and concentrated in vacuo to provide compound 1c as an oil.

Step C—Synthesis of Intermediate Compound 1d

A mixture of compound 1c (85 g, 0.32 mol) and DMF-DMA (76 g, 0.64 mol) in DMF (200 mL) was heated to 100° C. for 6 hours. The reaction was concentrated in vacuo and the resulting residue was purified using column chromatography on silica gel (PE:EA=50:1 to 1:1) to provide compound 1d.

Step D—Synthesis of Intermediate Compound 1e

To a solution of compound 1d (50 g, 0.16 mol) in THF (300 mL) was added LiHMDS (190 mL, 0.19 mmol) at −70° C. under $N_2$. After stirring at −70° C. for 0.5 hours, ethyl 2-chloro-2-oxoacetate (25.8 g, 0.19 mol) was added and the mixture was allowed to stir at −70° C. for 1 hour. TLC(PE: EA=1:1) showed the reaction was complete. The reaction was quenched with sat. aq. $KHSO_4$ (250 mL) and extracted with Ethyl acetate (500 mL×3). The combined organic phase was washed with brine, dried over $Na_2SO_4$ and concentrated in vacuo to provide the crude product. The resulting residue was diluted with toluene and concentrated, then toluene (500 mL) and triethylamine (50 mL) were added and the mixture was allowed to stir at room temperature for 1 hour. The mixture was concentrated in vacuo and the crude product was purified using column chromatography on silica gel (PE:EA=1:0 to 40:1) to provide compound 1e.

Step E—Synthesis of Intermediate Compound 1f

To a stirring solution of the compound 1e (85 g, 0.23 mol) in ethyl acetate (100 mL) was added HCl/Ethyl acetate (4 N, 920 mL) at 0° C. and the resulting mixture was allowed to stir at room temperature for 1 hour. TLC (PE:EA=5:1) showed the reaction was complete. The reaction was concentrated in vacuo and to the resulting residue was added hexane (1 L). The mixture was allowed to stir for 1 hour and filtered to provide 1f.

Steps F—Synthesis of Compound 1-1

To a stirring solution of the compound 1f (3.3 g, 10.3 mmol) in toluene (70 mL) was added oxalyl chloride (20.6 mL) and DMF (0.2 mL) at 0° C. under $N_2$ and the resulting mixture was allowed to stir at room temperature for 2 hours. The mixture was concentrated in vacuo and to the resulting residue was added $CHCl_3$ (100 mL) and compound 2e (2.84 g, 15.45 mmol). The resulting mixture was allowed to stir at room temperature overnight. TLC ($CH_2Cl_2$:methanol=10:1) showed the starting material was consumed. To the reaction mixture was added HCl (4M, 10 mL in MTBE) the mixture was allowed to stir at room temperature for 2 h. To the mixture was added 5% aq. $KHSO_4$ (200 mL) and extracted with $CHCl_2$ twice. The organic layer was washed with brine, dried over $Na_2SO_4$ and concentrated in vacuo. The crude product was purified using silica gel column (PE:EA=50:1 to 1:1) to provide 1-1. $^1H$ NMR ($CDCl_3$, 400 MHz) 9.07 (s, 1H), 7.45 (m, 2H), 7.35-7.25 (m, 5H), 7.03 (m, 2H). 5.34 (s, 2H), 4.39-4.37 (q, 2H), 1.36-1.32 (t, 3H) LCMS (M+H)= 467.

The intermediate compound set forth in the table below was made using the methods described in the Example above and substituting the appropriate reactants and reagents:

| Compound | Structure | Exact Mass [M + H]+ |
|---|---|---|
| 1-2 | 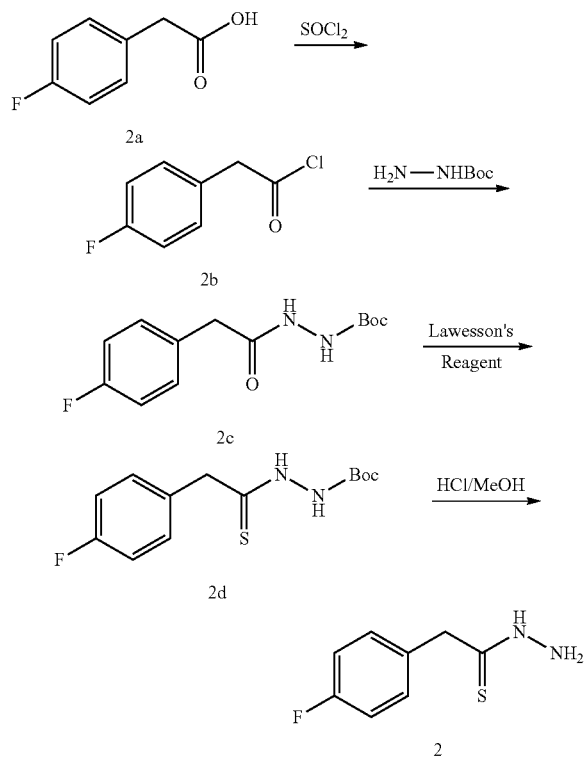 | 485 |

Example 2

Preparation of Intermediate Compound 2

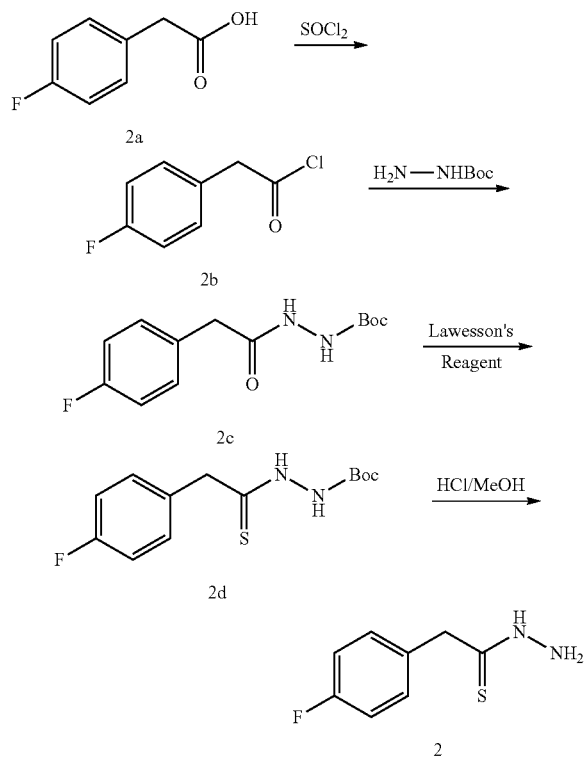

Step A—Synthesis of Intermediate Compound 2b

To a solution of compound 2a (100 g, 0.65 mol) in anhydrous dichloromethane (1 L) was added $SOCl_2$ (200 mL) dropwise at 0° C. under a drying tube charged with $CaCl_2$. After the addition, the mixture was heated to reflux and stirred overnight. The reaction was done in 2 batches, which were combined and concentrated in vacuo to provide crude compound 2b as an oil that was used without further purification.

Step B—Synthesis of Intermediate Compound 2c

To a solution of $BocNHNH_2$ (102.9 g, 0.78 mol) and triethylamine (135.4 mL, 0.97 mol) in anhydrous dichloromethane (800 mL) was added a solution of compound 2b (138 g) in anhydrous dichloromethane (500 mL) at 0° C. under drying tube charging with $CaCl_2$. The mixture was warmed up to room temperature and stirred for 2 hours. The mixture was quenched with water (1 L). The reaction was done in two batches which were combined. The two phases were separated and the aqueous layer was extracted with dichloromethane (1 L×2). The organic layer was washed with water (1 L×4), then brine, dried over $Na_2SO_4$, and concentrated in vacuo to provide compound 2c.

Step C—Synthesis of Intermediate Compound 2d

A mixture of compound 2c (50 g, 186.4 mmol) and Lawesson's reagent (75.4 g, 186.4 mmol) in THF (600 mL) was allowed to stir at 60° C. overnight. The mixture was poured into 10% $Na_2CO_3$ (1000 mL) and stirred at room temperature for 1 hour. The reaction was done in two batches which were combined, and the mixture was extracted with Ethyl acetate (1 L×3). The organic layer was washed with brine, dried over $Na_2SO_4$, and concentrated in vacuo to provide compound 2d.

Step D—Synthesis of Intermediate Compound 2

A suspension of compound 2d (240 g, 186.4 mmol, crude) in HCl/methanol (1.2 L, 4N) was allowed to stir at room temperature for 1 hour. The mixture was filtered and the filtrate was concentrated in vacuo to provide the HCl salt of compound 2, which was dissolved into water. The aqueous layer was basified with 10% $Na_2CO_3$ until pH=8 and extracted with ethyl acetate (1 L×4). The organic layer was washed with brine, dried over $Na_2SO_4$, concentrated in vacuo to provide Intermediate Compound 2. $^1$H NMR ($CDCl_3$, 400 MHz) 8.44 (br, 1H), 7.26-7.21 (m, 2H), 7.07-7.02 (m, 2H), 4.83 (br, 2H), 4.05 (s, 2H) LCMS (M+H)=185.0

Example 3

Preparation of Intermediate Compound 3

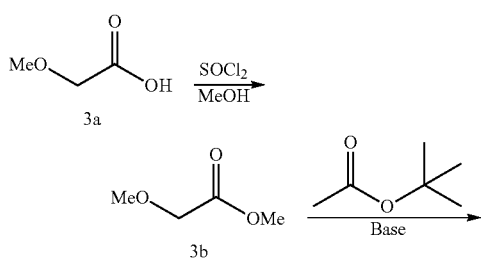

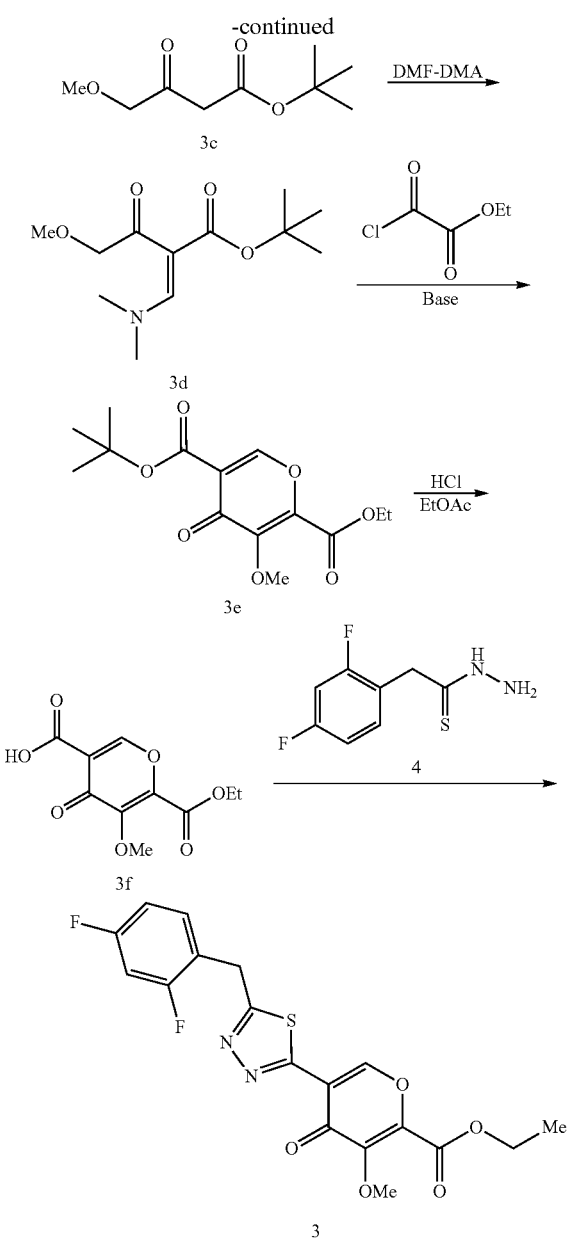

Step A—Synthesis of Intermediate Compound 3b

To the solution of compound 3a (200 g, 2.2 mol) in dry methanol (2 L) was added SOCl$_2$ (778 g, 6.6 mol) under N$_2$ at 0° C., then heated to reflux for 6 hours. The reaction mixture was concentrated, the resulting residue was dissolved in ethyl acetate (3 L) and washed with NaHCO$_3$ (2 L×2), the organic phase was washed with brine, dried over anhydrous Na$_2$SO$_4$ and concentrated in vacuo to provide compound 3b as an oil that was used without further purification.

Step B—Synthesis of Intermediate Compound 3c

A 10 L three-necked round bottom flask equipped with a mechanic stirrer and thermometer was charged with a solution of tert-butyl acetate (1612, 13.9 mol) in dry THF (14 L) and cooled to −70° C. under N$_2$. A solution of LiHMDS (13.9 L, 13.9 mol) in THF was added at −70° C. and the mixture was allowed to stir at −70° C. for 1 hour. A solution of 3b (723 g, 6.95 mol) in THF (1 L) was added to the reaction and stirred at −70° C. for 0.5 hours. The reaction was quenched by the addition of water (10 L) and the mixture was extracted with ethyl acetate. The combined the organic phase was washed with brine, dried over Na$_2$SO$_4$ and concentrated in vacuo to provide 3c as oil. $^1$H NMR (400 MHz, CDCl$_3$) δ 4.09 (s, 2H), 3.43 (s, 2H), 3.42 (s, 2H), 1.47 (s, 9H).

Step C—Synthesis of Intermediate Compound 3d

A mixture of 3c (564 g, 3 mol) and DMF-DMA (696 g, 6 mol) in toluene (1380 L) was heated to 80° C. for 2 hours. The reaction was concentrated to provide 3d as solid that was used without further purification. $^1$H NMR (400 MHz, CDCl$_3$) δ 7.65 (s, 1H), 4.35 (s, 2H), 3.40 (s, 2H), 3.36-2.87 (m, 6H), 1.48 (s, 9H).

Step D—Synthesis of Intermediate Compound 3e

A solution of 3d (600 g, 2469 mmol) in dry THF (3600 mL) was cooled to −70° C. under N$_2$, and treated dropwise over 0.5 hours with a solution of LiHMDS (3 L, 3 mol) in THF. The resulting mixture was then treated at −70° C. with ethyl 2-chloro-2-oxoacetate (403 g, 2962 mmol) and mixture was aged at −70° C. for 1 hour. The reaction was quenched with saturated aqueous KHSO$_4$ and extracted with ethyl acetate. The combined organic phase was washed with brine, dried over anhydrous Na$_2$SO$_4$ and concentrated in vacuo to provide the crude product. The resulting residue was diluted with toluene and concentrated in vacuo. Toluene (6 L) and triethylamine (600 mL) were were added and the mixture was allowed to stir at r.t for 1 hour and then concentrated in vacuo. The crude product was purified using column chromatography on silica gel column (PE:EA=100:1 to 10:1) to provide 3e. $^1$H NMR (400 MHz, CDCl$_3$) δ 8.41 (s, 1H), 4.43-4.42 (m, 2H), 4.03 (s, 2H), 1.57 (s, 9H), 1.43-1.39 (t, J=7.2, 3H).

Step E—Synthesis of Intermediate Compound 3f

To a stirred solution of the 3e (140 g, 469 mmol) in ethyl acetate (140 mL) at 0° C. was added HCl/ethyl acetate (4 N, 1400 mL). The resulting mixture was allowed to stir at r.t for 1 hour and then concentrated in vacuo. To the resulting residue was added to hexane (1.4 L). The resulting mixture was allowed to stir at room temperature to provide a precipitate. The mixture was filtered and the solid was collected and dried in vacuo to provide 3f.

Steps F—Synthesis of Intermediate Compound 3

To a stirred solution of the 3f (10 g, 41.3 mmol) in toluene (200 mL) was added oxalyl chloride (60 mL) and DMF (0.6 mL) at 0° C. under N$_2$. The resulting mixture was allowed to stir at r.t for 2 hours and then the mixture was concentrated in vacuo. The resulting residue was dissolved in CHCl$_3$ (300 mL), treated with 4 (12.5 g, 61.9 mmol) and aged at room temperature for 16 hours. The crude product was recystallization with petroleum ether and EA to provide Intermediate Compound 3. $^1$H NMR (400 MHz, CDCl$_3$) δ 9.08 (s, 1H), 7.33-7.27 (m, 1H), 6.89-6.84 (m, 2H), 4.49-4.44 (m, 4H), 4.08 (s, 3H), 1.45-1.42 (t, J=7.2, 3H).

Example 4

Preparation of Intermediate Compound 4

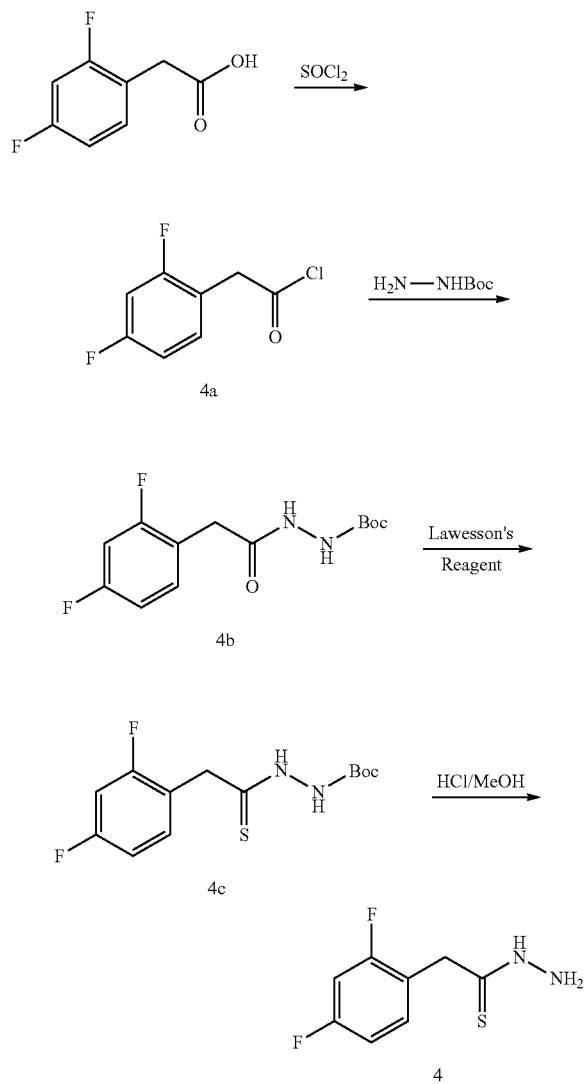

Step A—Synthesis of Intermediate Compound 4a

To a solution of 2-(2,4-difluorophenyl)acetic acid (100 g, 0.58 mol) in anhydrous dichloromethane (1000 mL) was added thionyl chloride (200 mL) at 0° C. After addition was complete, the mixture was heated at reflux and stirred overnight. The solution was concentrated in vacuo to provide the crude compound 4b as an oil that was used without further purification.

Step B—Synthesis of Intermediate Compound 4b

To a solution of BocNHNH2 (48 g, 0.64 mol) and triethylamine (110 mL, 0.72 mol) in anhydrous dichloromethane (600 mL) was added a solution of crude 4b (100 g, 0.53 mol) in anhydrous dichloromethane (1000 mL) at 0° C. After addition was complete, the mixture was warmed up to room temperature and stirred for 2 hrs. The mixture was quenched by the addition of water (500 mL). The two phases were separated and the aqueous layer was extracted with dichloromethane (500 mL×2). The organic layer was washed with water (500 mL×4), brine, dried over anhydrous $Na_2SO_4$, and concentrated in vacuo to provide 4c.

Step C—Synthesis of Intermediate Compound 4d

A mixture of compound 4c (50 g, 0.19 mol) and Lawesson's reagent (105 g, 0.25 mol) in THF (600 mL) was allowed to stir at 50° C. for 2 hours. The mixture was then poured into 10% aqueous $Na_2CO_3$ (1 L) and extracted with ethyl acetate (1 L×3). The combined organic extracts was washed with brine (500 mL), dried over anhydrous $Na_2SO_4$ and concentrated in vacuo to provide compound 4d.

Step D—Synthesis of Intermediate Compound 4

The suspension of 4d (70 g, 23 mmol) in HCl/methanol (500 mL, 4N) was allowed to stir at room temperature for 1 hour. The mixture was filtered and the filtrate was concentrated in vacuo to provide 3e as the HCl salt. The solid was dissolved in water and the aqueous layer was adjusted to pH=10 with 10% of aqueous $Na_2CO_3$. The solution was extracted with ethyl acetate (200 mL×6). The combined organic phase was washed with brine (500 mL), dried over $Na_2SO_4$, and concentrated in vacuo to provide Intermediate Compound 4. $^1$H NMR (400 MHz, $CDCl_3$) d 8.51 (br, 1H), 7.35-7.37 (d, 1H), 6.84-6.91 (m, 2H), 4.2 (br, 2H), 4.0 (s, 2H).

Example 5

Preparation of Compound 5

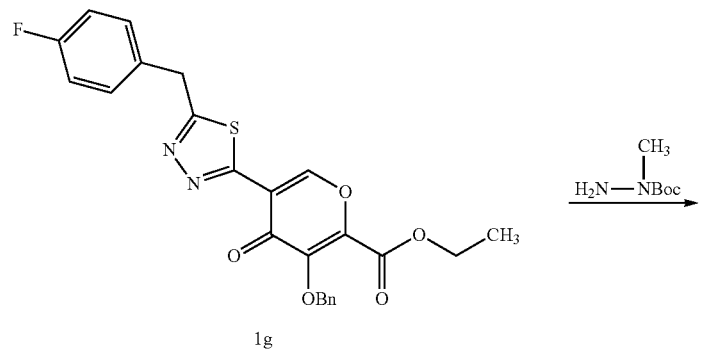

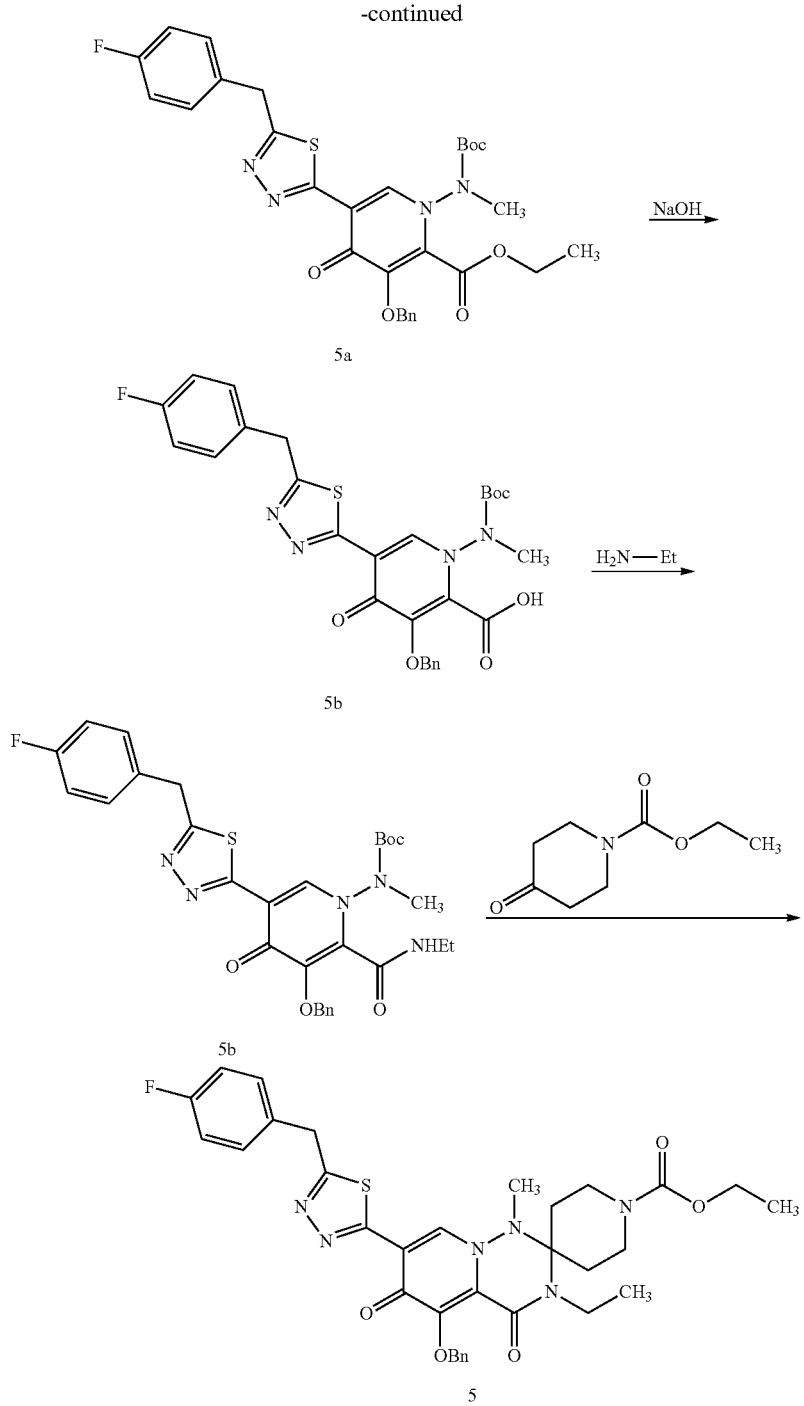

Step A—Synthesis of Intermediate Compound 5a

Compound 1g (3.00 g, 6.43 mmol) in N-methylimidazole (15.0 mL) was treated with tert-butyl 1-methylhydrazinecarboxylate (1.43 mL, 9.65 mmol) at room temperature. The mixture was heated at 70° C. for 6 hours and then cooled to room temperature and poured into ethyl acetate (50 mL). The combined organic extracts were washed with aqueous citric acid (1 M, 2×25 mL), water and brine. The organic layer was dried (Na$_2$SO$_4$), filtered and the filtrate was concentrated in vacuo. Purification using column chromatography on silica gel (0 to 100% Ethyl acetate/hexanes) provided compound 5a. $^1$H NMR (CDCl$_3$, 400 MHz) 8.67 (s, 1H), 7.43-7.40 (m, 2H), 7.36-7.30 (m, 5H), 7.05-7.00 (m, 2H), 5.42-5.35 (bs, 1H), 5.31-5.26 (bs, 1H), 4.45 (s, 2H), 4.31-4.28 (m, 2H), 3.38 (s, 3H), 1.40 (s, 9H), 1.25 (t, 3H) LCMS (M+H)=595

Step B—Synthesis of Intermediate Compound 5b

Compound 5a (0.10 g, 0.17 mmol) in THF (0.50 mL)/Water (0.17 mL)/methanol (0.17 mL) was added sodium hydroxide (0.21 mL, 0.42 mmol) and stirred for 16 hours at 25° C. Neutralize with 2N HCl (0.21 mL) and concentrate. The solid was taken up in CH$_2$Cl$_2$/methanol and filtered. The filtrate was concentrated in vacuo and purified using preparative RP-HPLC to provide 5b. $^1$H NMR (CDCl$_3$, 400 MHz) 8.78 (s, 1H), 7.43-7.41 (m, 2H), 7.34-7.28 (m, 5H), 7.04-7.00 (m, 2H), 5.45 (s, 2H), 4.45 (s, 2H), 3.39 (s, 3H), 1.41 (s, 9H), LCMS (M+H)=567

Step C—Synthesis of Intermediate Compound 5c 3-(benzyloxy)-1-((tert-butoxycarbonyl)(methyl)amino)-5-(5-(4-fluorobenzyl)-1,3,4-thiadiazol-2-yl)-4-oxo-1,4-dihydropyridine-2-carboxylic acid 5b (0.16 g, 0.29 mmol) in CH$_2$Cl$_2$ (1.4 mL) was added 1-(chloror-1-pyrrolidinylmethylene)pyrrolidinium hexafluorophosphate (0.096 g, 0.29 mmol) followed by ethylamine (0.15 mL, 0.29 mmol) and N,N-diisopropylethylamine (0.20 mL, 1.2 mmol). The reaction was allowed to stir for 30 minutes and was added another equivalent of PyClu and ethylamine After stirring for an additional 1 hour, the solution was extracted with CH$_2$Cl$_2$ and washed with saturated NaHCO$_3$. The organic layer was dried, concentrated in vacuo, and purified using preparative RP-HPLC to provide 5c. $^1$H NMR (CDCl$_3$, 400 MHz) 8.68 (s, 1H), 7.38-7.29 (m, 7H), 7.04-7.00 (m, 2H), 5.85 (bs, 1H), 5.57 (d, 1H), 5.11 (d, 1H), 4.45 (s, 2H), 3.43 (s, 3H), 3.27-3.20 (m, 2H), 1.45 (s, 9H), 1.02 (t, 3H) LCMS (M+H)=594

Step D—Synthesis of Compound 5

Compound 5c (101 mg, 0.170 mmol) and N-carbethoxy-4-piperidone (146 mg, 0.851 mmol) were dissolved in dichloroacetic acid (0.5 mL). The mixture was heated at 95° C. for 8 hours. The mixture was cooled to room temperature, diluted with DMSO (3 mL) and directly purified using preparative RP-HPLC to provide compound 5. LCMS (M+H)=557; $^1$H NMR (500 MHz, acetone): δ 8.82 (s; 1 H); 7.44 (dd; J=8.35; 5.43 Hz; 2 H); 7.11 (t; J=8.73 Hz; 2 H); 4.47 (s; 2 H); 4.21 (br s; 2 H); 4.08 (d; J=8.13 Hz; 2 H); 3.97 (br s; 2 H); 3.83 (dq; J=14.5; 7.1 Hz; 1 H); 3.65 (dq; J=14.5; 7.1 Hz; 1 H); 3.29 (br s; 3 H); 2.98 (s; 3 H); 1.88-1.94 (m; 1 H); 1.29 (t; J=7.12 Hz; 3 H); 1.21 (s; 3 H).

The following compounds of the present invention were made using the methods described in the Example above and substituting the appropriate reactants and reagents.

| Compound | Structure | Exact Mass [M + H]+ |
|---|---|---|
| 6 | 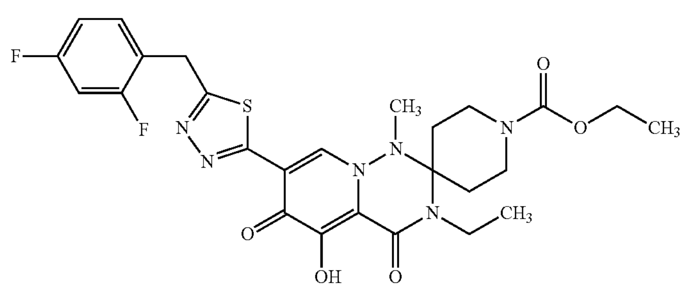 [SMILES: CCOC(=O)N1CCC2(CC1)N(CC)C(=O)c1c(O)c(=O)c(-c3nnc(Cc4ccc(F)cc4F)s3)cn1N2C] | 575 |
| 7 | 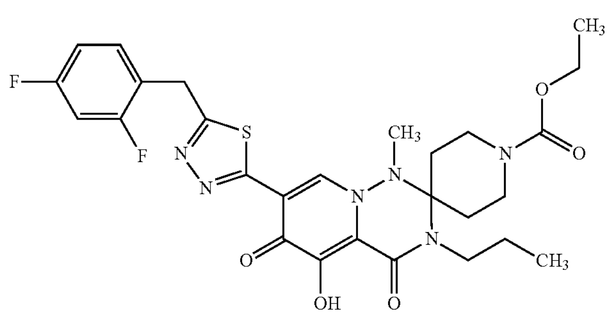 [SMILES: CCCN1C(=O)c2c(O)c(=O)c(-c3nnc(Cc4ccc(F)cc4F)s3)cn2N(C)C12CCN(C(=O)OCC)CC2] | 589 |
| 8 | 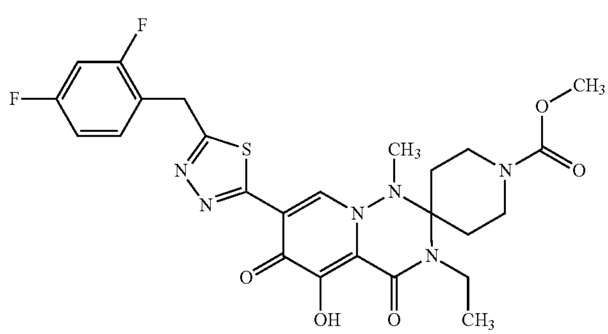 [SMILES: CCN1C(=O)c2c(O)c(=O)c(-c3nnc(Cc4ccc(F)cc4F)s3)cn2N(C)C12CCN(C(=O)OC)CC2] | 561 |

-continued

| Compound | Structure | Exact Mass [M + H]+ |
|---|---|---|
| 9 | 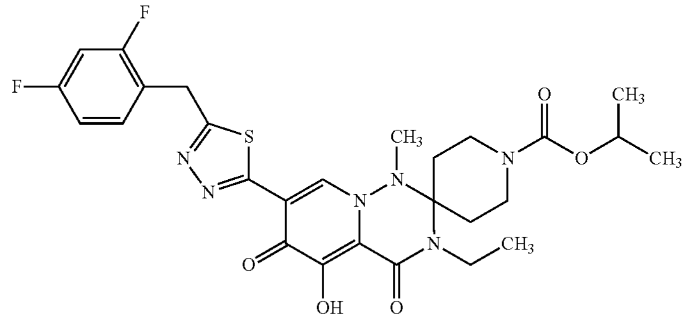 [SMILES: CCN1C(=O)c2c(O)c(=O)c(-c3nnc(Cc4ccc(F)cc4F)s3)cn2N(C)C12CCN(C(=O)OC(C)C)CC2] | 589 |
| 10 | 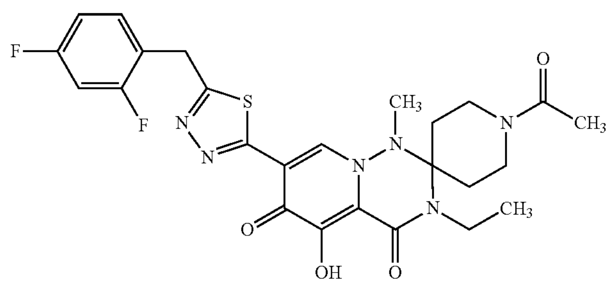 [SMILES: CCN1C(=O)c2c(O)c(=O)c(-c3nnc(Cc4ccc(F)cc4F)s3)cn2N(C)C12CCN(C(C)=O)CC2] | 545 |
| 11 | 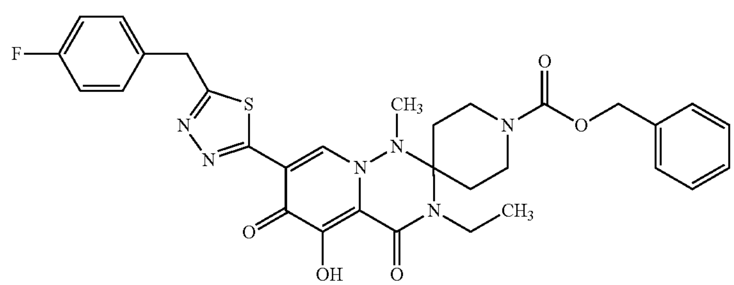 [SMILES: CCN1C(=O)c2c(O)c(=O)c(-c3nnc(Cc4ccc(F)cc4)s3)cn2N(C)C12CCN(C(=O)OCc1ccccc1)CC2] | 619 |
| 12 | 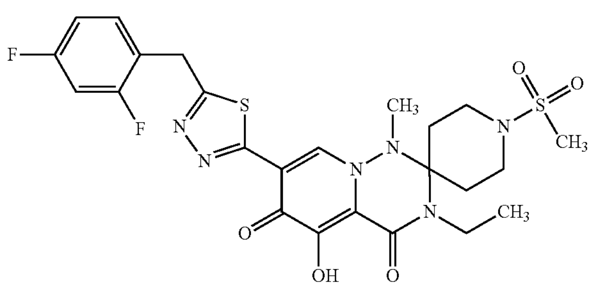 [SMILES: CCN1C(=O)c2c(O)c(=O)c(-c3nnc(Cc4ccc(F)cc4F)s3)cn2N(C)C12CCN(S(C)(=O)=O)CC2] | 581 |
| 13 | 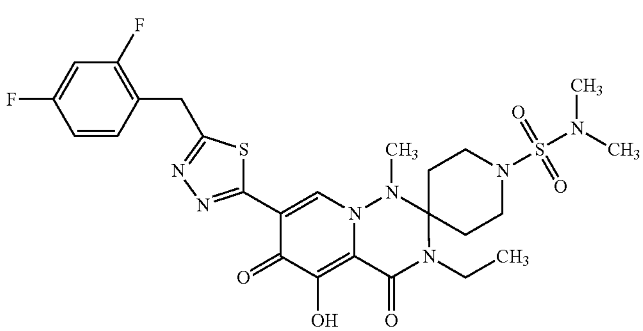 [SMILES: CCN1C(=O)c2c(O)c(=O)c(-c3nnc(Cc4ccc(F)cc4F)s3)cn2N(C)C12CCN(S(=O)(=O)N(C)C)CC2] | 610 |

-continued

| Compound | Structure | Exact Mass [M + H]+ |
|---|---|---|
| 14 | 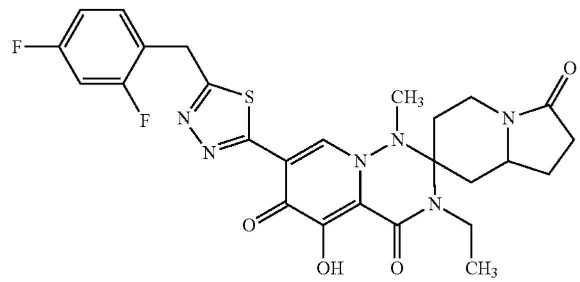 [SMILES: CCN1C(=O)c2c(O)c(=O)c(-c3nnc(Cc4ccc(F)cc4F)s3)cn2N(C)C12CCN1C(=O)CCC1C2] | 557 |
| 15 | 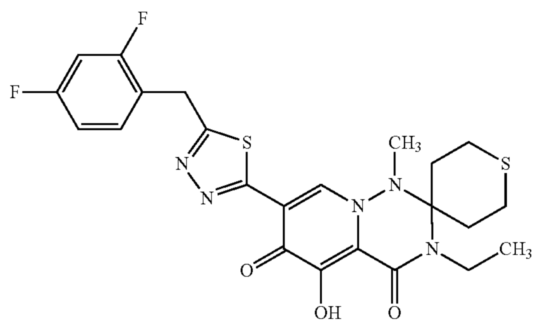 [SMILES: CCN1C(=O)c2c(O)c(=O)c(-c3nnc(Cc4ccc(F)cc4F)s3)cn2N(C)C12CCSCC2] | 520 |
| 16 | 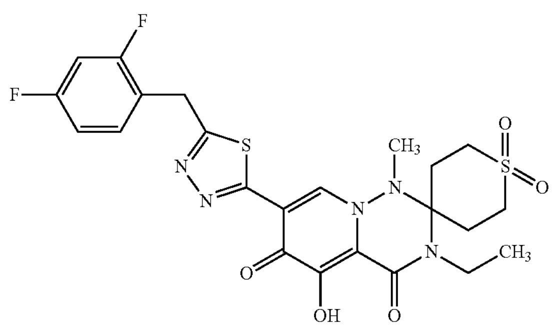 [SMILES: CCN1C(=O)c2c(O)c(=O)c(-c3nnc(Cc4ccc(F)cc4F)s3)cn2N(C)C12CCS(=O)(=O)CC2] | 552 |
| 17 | 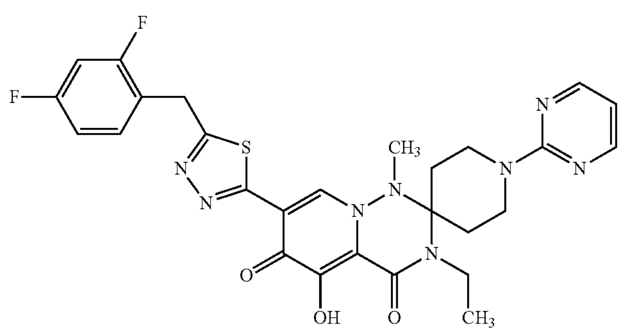 [SMILES: CCN1C(=O)c2c(O)c(=O)c(-c3nnc(Cc4ccc(F)cc4F)s3)cn2N(C)C12CCN(c1ncccn1)CC2] | 581 |
| 18 | 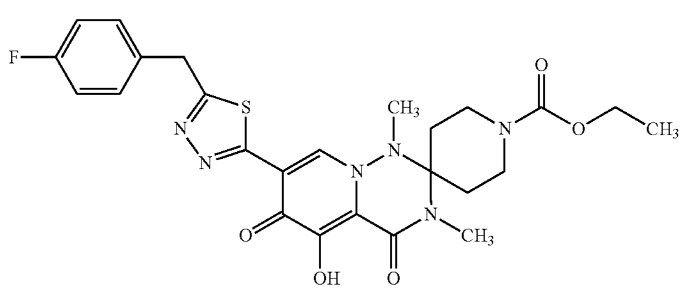 [SMILES: CCOC(=O)N1CCC2(CC1)N(C)C(=O)c1c(O)c(=O)c(-c3nnc(Cc4ccc(F)cc4)s3)cn1N2C] | 543 |

-continued

| Compound | Structure | Exact Mass [M + H]+ |
|---|---|---|
| 19 | 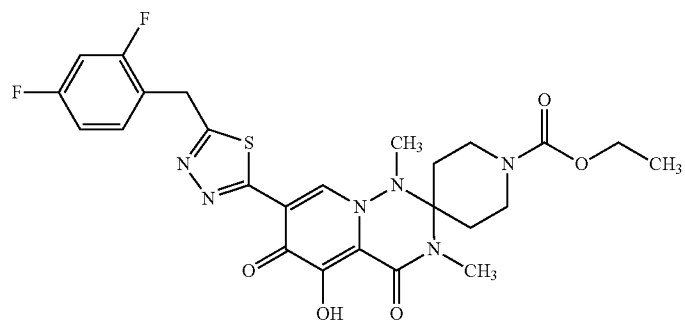 [SMILES: CCOC(=O)N1CCC2(CC1)N(C)C(=O)c1c(O)c(=O)c(-c3nnc(Cc4ccc(F)cc4F)s3)cn1N2C] | 561 |
| 20 | 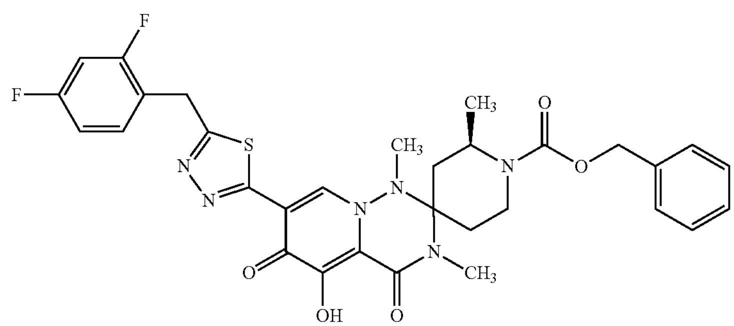 [SMILES: C[C@@H]1CC2(CCN1C(=O)OCc1ccccc1)N(C)C(=O)c1c(O)c(=O)c(-c3nnc(Cc4ccc(F)cc4F)s3)cn1N2C] | 637 |
| 21 | 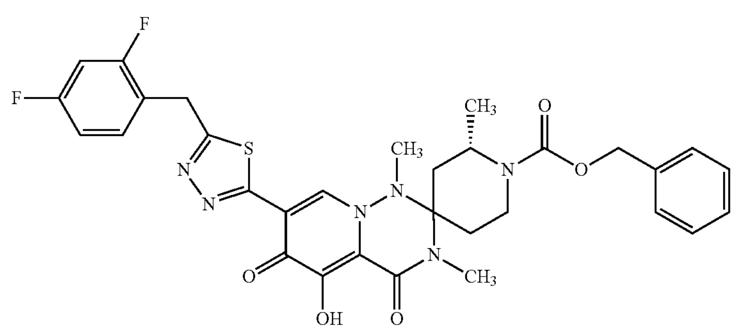 [SMILES: C[C@H]1CC2(CCN1C(=O)OCc1ccccc1)N(C)C(=O)c1c(O)c(=O)c(-c3nnc(Cc4ccc(F)cc4F)s3)cn1N2C] | 637 |
| 22 | 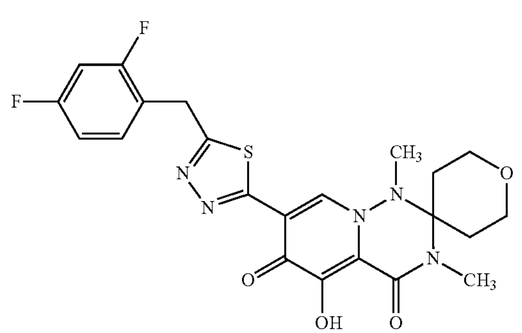 [SMILES: CN1C(=O)c2c(O)c(=O)c(-c3nnc(Cc4ccc(F)cc4F)s3)cn2N(C)C12CCOCC2] | 490 |

-continued

| Compound | Structure | Exact Mass [M + H]+ |
|---|---|---|
| 23 | 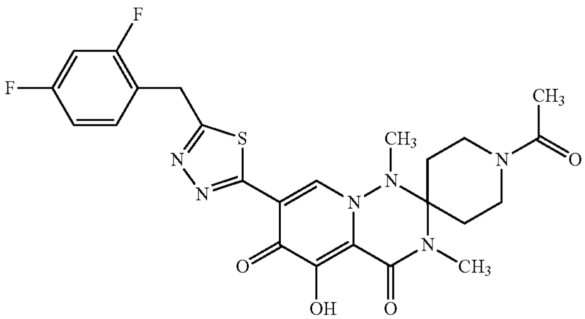 [SMILES: CC(=O)N1CCC2(CC1)N(C)C(=O)c1c(O)c(=O)c(-c3nnc(Cc4ccc(F)cc4F)s3)cn1N2C] | 531 |
| 24 | 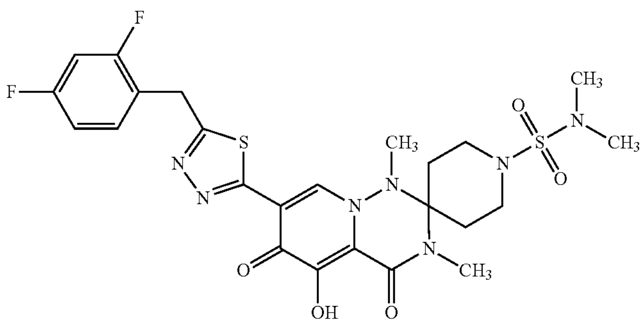 [SMILES: CN1C(=O)c2c(O)c(=O)c(-c3nnc(Cc4ccc(F)cc4F)s3)cn2N(C)C12CCN(S(=O)(=O)N(C)C)CC2] | 596 |
| 25 | 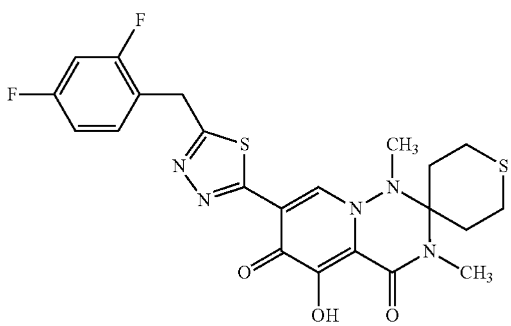 | 506 |
| 26 | 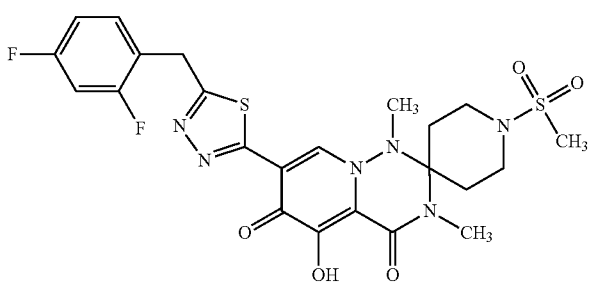 [SMILES: CN1C(=O)c2c(O)c(=O)c(-c3nnc(Cc4ccc(F)cc4F)s3)cn2N(C)C12CCN(S(C)(=O)=O)CC2] | 567 |
| 27 | 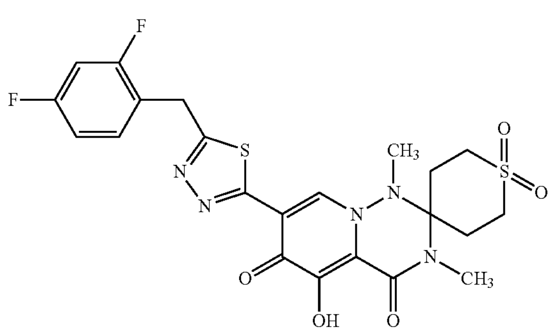 [SMILES: CN1C(=O)c2c(O)c(=O)c(-c3nnc(Cc4ccc(F)cc4F)s3)cn2N(C)C12CCS(=O)(=O)CC2] | 538 |

-continued

| Compound | Structure | Exact Mass [M + H]+ |
|---|---|---|
| 28 | 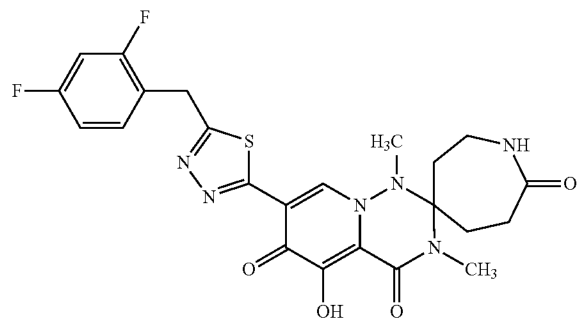 [SMILES: CN1C(=O)c2c(O)c(=O)c(-c3nnc(Cc4ccc(F)cc4F)s3)cn2N(C)C12CCNC(=O)CC2] | 517 |
| 29 | 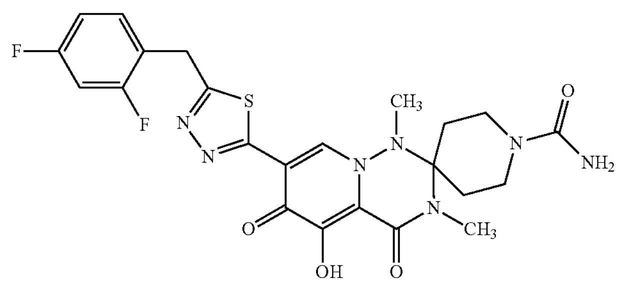 [SMILES: CN1C(=O)c2c(O)c(=O)c(-c3nnc(Cc4ccc(F)cc4F)s3)cn2N(C)C12CCN(C(N)=O)CC2] | 532 |
| 30 | 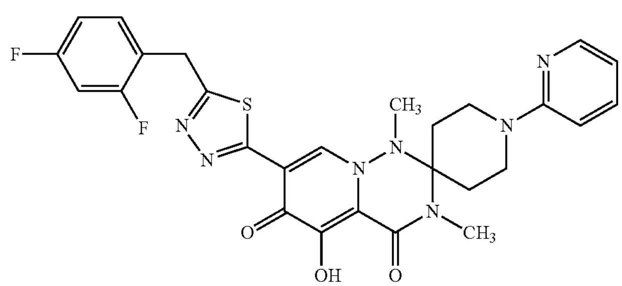 [SMILES: CN1C(=O)c2c(O)c(=O)c(-c3nnc(Cc4ccc(F)cc4F)s3)cn2N(C)C12CCN(c1ccccn1)CC2] | 566 |
| 31 | 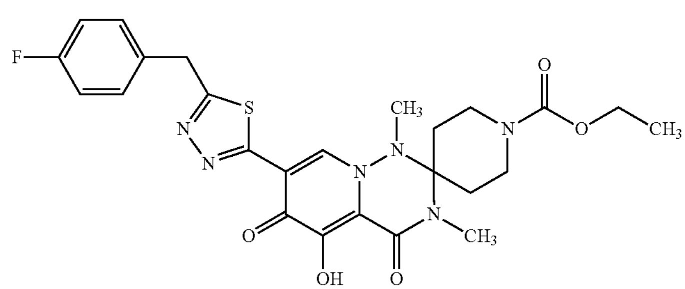 [SMILES: CCOC(=O)N1CCC2(CC1)N(C)C(=O)c1c(O)c(=O)c(-c3nnc(Cc4ccc(F)cc4)s3)cn1N2C] | 529 |

Example 6
Preparation of Compound 32
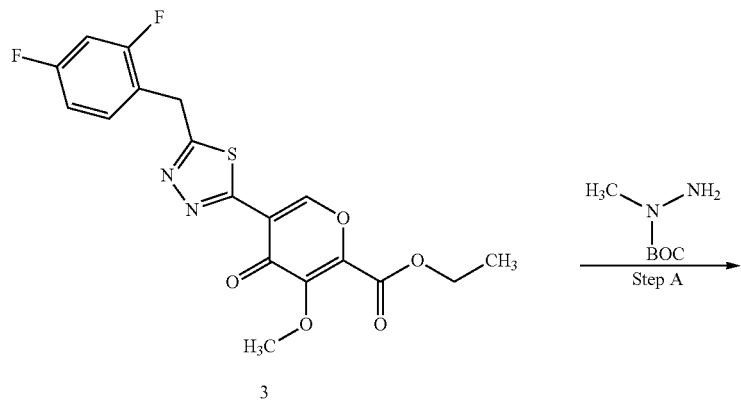
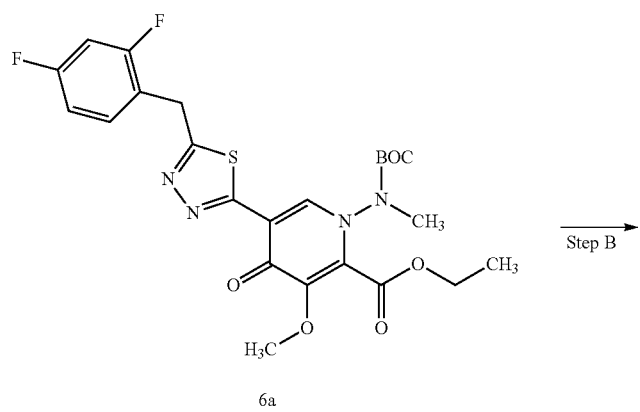
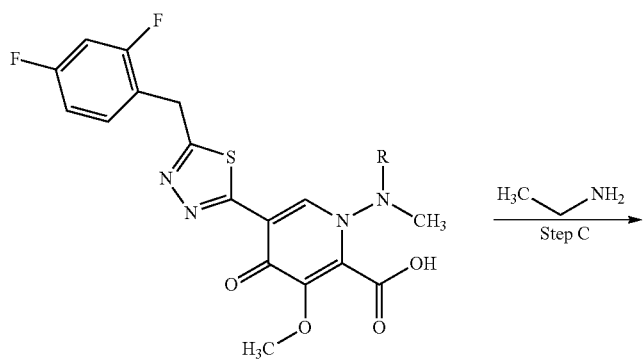

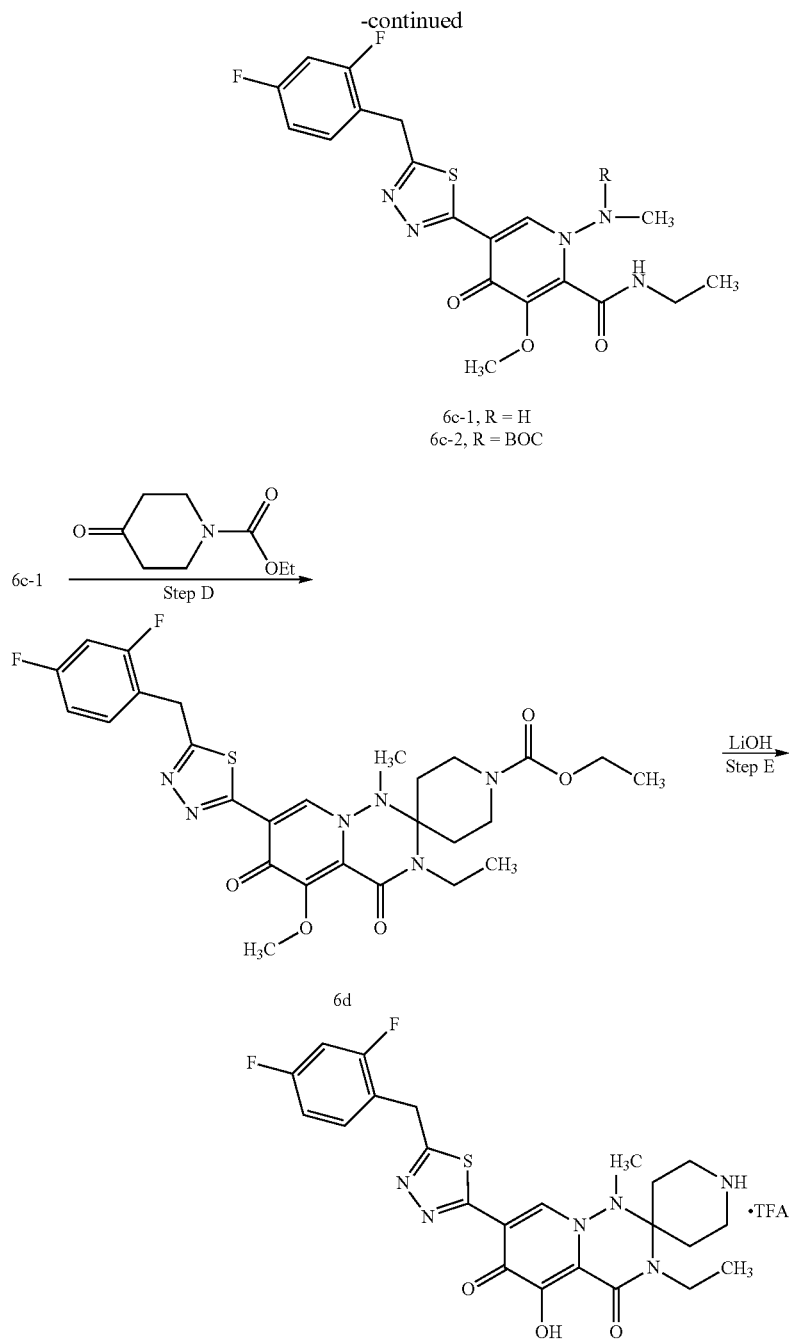

6c-1, R = H
6c-2, R = BOC

6d

32

Step A—Synthesis of Intermediate Compound 6a

Compound 3 (1.00 g, 2.45 mmol) in N-methylimidazole (6.0 mL) was treated with tert-butyl 1-methylhydrazinecarboxylate (0.363 mL, 2.45 mmol) and the mixture was allowed to stir at 60° C. for 20 hours, cooled to room temperature and diluted with DMSO (30 mL) and acetic acid (10 mL). Direct purification using preparative RP-MPLC provided intermediate compound 6a that was used without further purification. LCMS (M+H)=537, $^1$H NMR (500 MHz, CDCl$_3$): δ 8.73 (s; 1 H); 7.34-7.29 (m, 1 H); 6.83-6.87 (m; 2 H); 4.44-4.48 (m; 3 H); 4.39 (dd; J=10.8; 7.0 Hz; 1 H); 4.02 (s; 3 H); 3.41 (s; 3 H); 1.37-1.43 (m; 12 H).

Step B—Synthesis of Intermediate Compounds 6b-1 and 6b-2

Compound 6a (1.03 g, 1.920 mmol) in ethanol (10 mL) treated at room temperature with LiOH (2 M aqueous) (0.960 mL, 1.920 mmol). The mixture was allowed to stir at room temperature for 20 hours and then neutralized with glacial acetic acid and concentrated to remove a majority of the ethanol. The resulting residue was purified using RP-MPLC to separately provide intermediate compound 6b-1 and intermediate compound 6b-2. 6b-1: LCMS (M+H)=409; $^1$H NMR (500 MHz, DMSO) δ 8.92 (s; 1 H); 7.50-7.55 (m; 1 H); 7.28 (td; J=9.8; 2.5 Hz; 1 H); 7.11 (td; J=8.5; 2.7 Hz; 2 H); 4.48 (s; 2 H); 3.82 (s; 3 H); 2.80 (s; 3 H); 6b-2: LCMS (M+H)=509; ¹H NMR (500 MHz, CDCl₃) δ 8.75 (s; 1 H); 7.31-7.34 (m; 1 H); 6.82-6.87 (m; 2 H); 4.47-4.48 (m; 2 H); 4.04 (s; 3 H); 3.46 (s; 3 H); 1.42 (s; 9 H).

Step C—Synthesis of Intermediate Compound 6c-1

Compound 6b-1 (950 mg, 2.326 mmol) in DMF (4.0 mL) treated at 0° C. with PyClock (1549 mg, 2.79 mmol) and ethylamine (2 M in THF) (2.56 mL, 5.12 mmol). Stirred at room temperature for 6 hours. Quenched with water (1.0 mL). Neutralized with glacial acetic acid. Purification using preparative RP-HPLC provided a solid after lyophilization. The solid was suspended in acetonitrile (50 mL) and gently heated until dissolved. Water (50 mL) was added. The mixture was aged in at −20° C. for 15 minutes. The resulting flocculant precipitate was filtered and washed with 50% aqueous acetonitrile (2×10 mL) to provide intermediate compound 6c-1. LCMS (M+H)=436; 1H NMR (500 MHz, DMSO): δ 8.89 (s; 1 H); 8.67 (t; J=5.6 Hz; 1 H); 7.51-7.56 (m; 1 H); 7.29 (td; J=9.8; 2.6 Hz; 1 H); 7.11 (td; J=8.5; 2.5 Hz; 1 H); 6.92-6.95 (m; 1 H); 4.48 (s; 2 H); 3.80 (s; 3 H); 3.25 (p; J=6.7 Hz; 2 H); 2.79 (d; J=5.8 Hz; 3 H); 1.10 (t; J=7.2 Hz; 3 H).

Step C—Synthesis of Intermediate Compound 6c-2

Compound 6b-2 (2.654 g, 5.22 mmol) and PyClock (3.48 g, 6.26 mmol) in N,N-dimethylformamide (5 mL) was treated at room temperature with ethylamine (2 M in THF) (5.74 mL, 11.48 mmol). The misture was allowed to stir at room temperature for 16 hours and then quenched by the addition of water (0.5 mL) and neutralized with glacial acetic acid. Purification using RP-MPLC (C18, 150 g ISCO, 10 to 95% MeCN/water+0.1% TFA, 10CV) provided intermediate compound 6c-2. LCMS (M+H)=536; ¹H NMR (500 MHz, DMSO) δ 9.18 (s; 1 H); 8.78 (s; 1 H); 7.52-7.57 (m; 1 H); 7.27-7.31 (m; 1 H); 7.11 (td; J=8.5; 2.5 Hz; 1 H); 4.50 (s; 2 H); 3.84 (s; 3 H); 3.32 (s; 3 H); 3.22 (t; J=7.3 Hz; 2 H); 1.40 (br s; 9 H); 1.07 (t; J=7.2 Hz; 3 H).

Step D—Synthesis of Intermediate Compound 6d

Compound 6c-1 (100 mg, 0.230 mmol) and ethyl 4-oxopiperidine-1-carboxylate (197 mg, 1.148 mmol) in dichloroacetic acid (1 mL) was heated at 100° C. for 8 hours, cooled to room temperature and diluted with acetonitrile. Direct purification using preparative RP-HPLC provided intermediate compound 6d. LCMS (M+H)=575, ¹H NMR (500 MHz, CDCl₃): δ 8.88 (s; 1 H); 7.28-7.33 (m; 1 H); 6.83-6.87 (m; 2 H); 4.50 (s; 2 H); 4.29 (br t; J=18.32 Hz; 1 H); 4.15 (s; 3 H); 3.98 (br s; 1 H); 3.58-3.69 (m; 2 H); 3.10 (br s; 2 H); 2.87 (s; 3 H); 2.09-2.20 (m; 2 H); 1.73-1.79 (m; 1 H); 1.66 (d; J=13.75 Hz; 1 H); 1.24-1.29 (m; 6 H).

Step E—Synthesis of Compound 32

Compound 6d was dissolved in dioxane and treated with 1M aqueous LiOH at room temperature and then heated to 100° C. and allowed to stir at this temperature for 16 hours. The mixture was cooled to room temperature and neutralized with glacial acetic acid. Direct purification using preparative RP-HPLC provided compound 32 as the TFA salt. LCMS (M+H)=503, ¹H NMR (500 MHz, CD₃OD): δ 8.97 (s; 1 H); 7.43-7.48 (m; 1 H); 6.97-7.03 (m; 2 H); 4.49 (s; 2 H); 3.76-3.83 (m; 1 H); 3.67 (dq; J=14.7; 7.2 Hz; 1 H); 3.40-3.56 (m; 3 H); 3.30-3.31 (m; 3 H); 2.92 (s; 3 H); 2.59-2.61 (m; 2 H); 2.15-2.17 (m; 2 H); 1.32 (t; J=7.1 Hz; 3 H).

The following compound of the present invention was made using the methods described in the Example above and substituting the appropriate reactants and reagents.

| Compound | Structure | Exact Mass [M + H]+ |
|---|---|---|
| 33 | 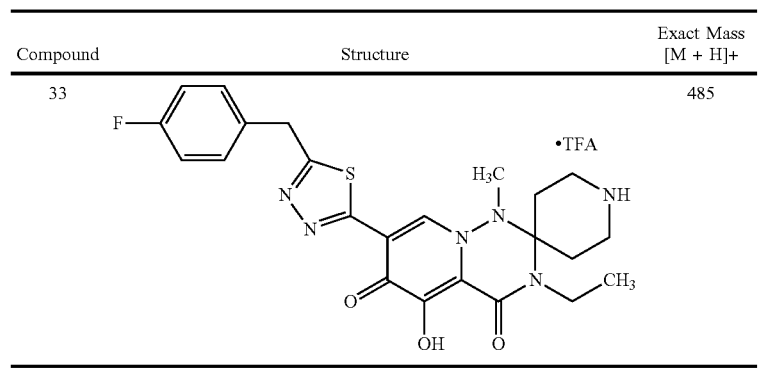 | 485 |

Example 7

Preparation of Compound 34

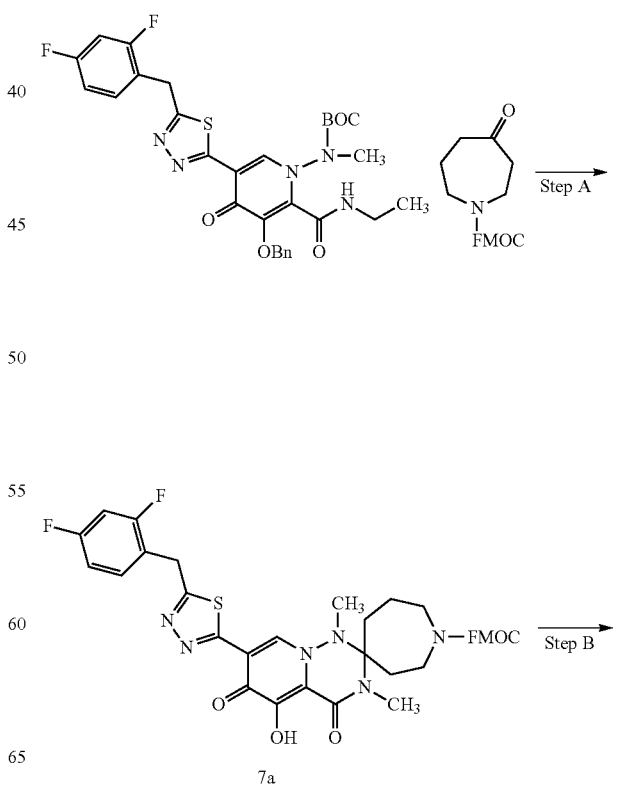

121

-continued

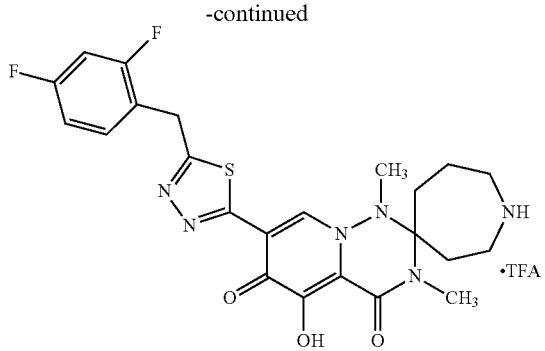

34

Step A—Synthesis of Intermediate Compound 7a

A mixture of tert-butyl (3-(benzyloxy)-5-(5-(2,4-difluorobenzyl)-1,3,4-thiadiazol-2-yl)-2-(methylcarbamoyl)-4-oxopyridin-1(4H)-yl)(methyl)carbamate, prepared in a similar manner to the previous examples, (25 mg, 0.042 mmol) and (9H-fluoren-9-yl)methyl 4-oxoazepane-1-carboxylate (70.2 mg, 0.209 mmol) in dichloroacetic acid (0.25 mL) was heated at 100° C. for 4 hours. The mixture was cooled to room temperature and diluted with DMSO. Direct purification using preparative RP-HPLC provided intermediate compound 7a. LCMS (M+H)=725.

Step B—Synthesis of Compound 34

A solution of intermediate compound 7a (16 mg, 0.022 mmol) in DMF treated at room temperature with piperidine (0.5 mL) and stirred at room temperature for 20 hours. Direct purification using preparative RP-HPLC provided compound 34 as the TFA salt. LCMS (M+H)=503.

Example 8

Preparation of Compounds 35 and 36

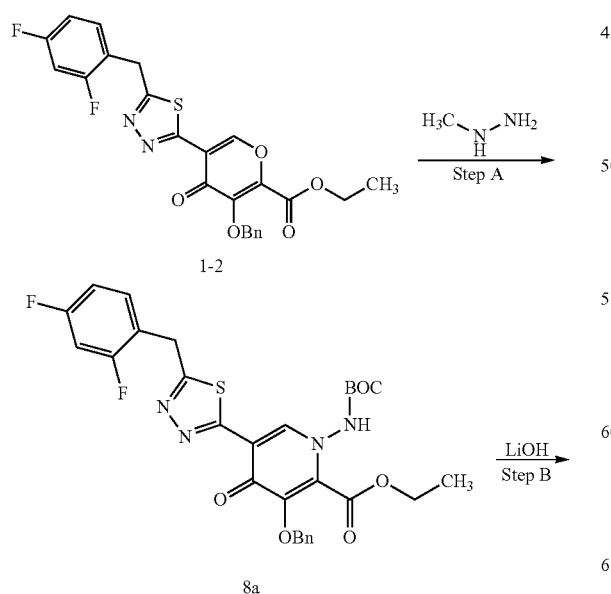

122

-continued

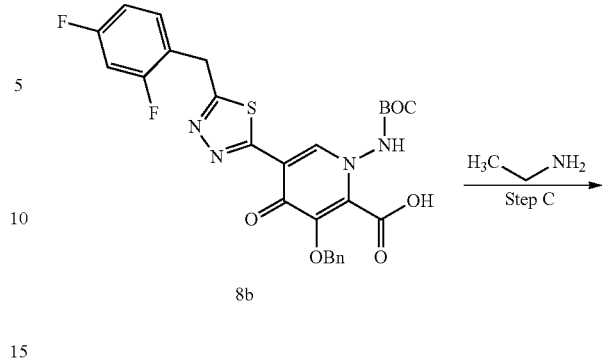

8b

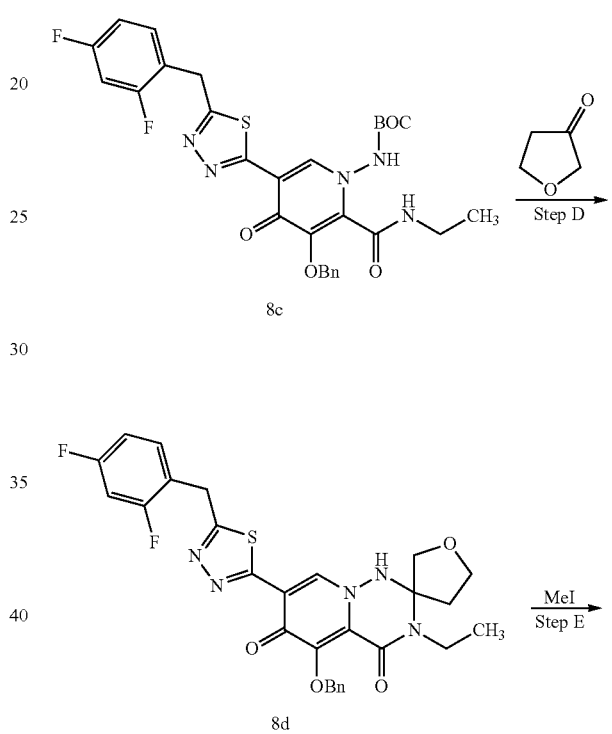

8c

8d

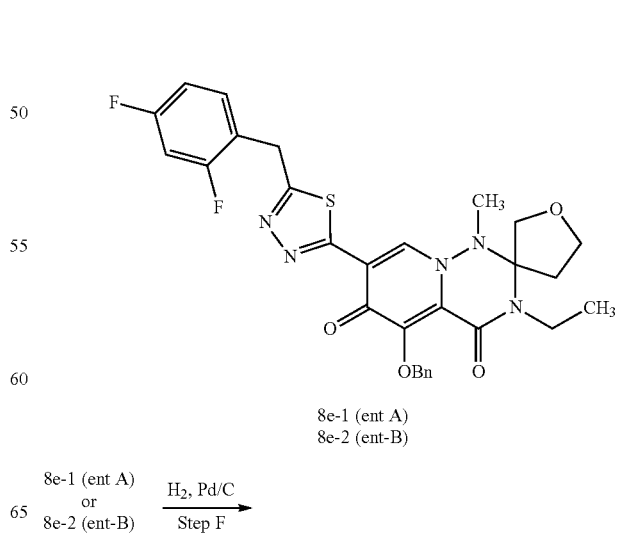

8e-1 (ent A)
8e-2 (ent-B)

8e-1 (ent A) or 8e-2 (ent-B) → H₂, Pd/C, Step F

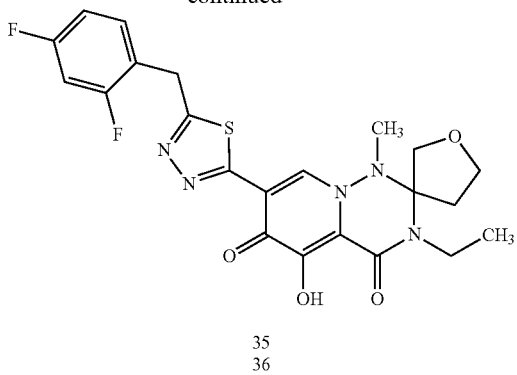

35
36

Step A—Synthesis of Intermediate Compound 8a

A mixture of compound 1-2 (5000 mg, 10.32 mmol) and tert-butyl hydrazinecarboxylate (1364 mg, 10.32 mmol) in N-methylimidazole (20.0 mL) was heated at 60° C. for 14 hours. The mixture was cooled to room temperature, diluted with ethyl acetate (15 mL) and the organic phase was washed with 1 M aq citric acid (3×10 mL) and brine. The organic layer was dried over anhydrous sodium sulfate and filtered and the filtrate was concentrated in vacuo. Purification using column chromatography on silica gel (0 to 100% ethyl acetate/hexanes) provided intermediate compound 8a. LCMS (M+H)=599, $^1$H NMR (500 MHz, DMSO): δ 8.90 (s; 1 H); 7.53-7.58 (m; 1 H); 7.27-7.37 (m; 6 H); 7.12 (td; J=8.54; 2.57 Hz; 1 H); 5.19 (s; 2 H); 4.51 (s; 2 H); 4.26 (q; J=7.1 Hz; 2 H); 1.42 (s; 9 H); 1.20 (t; J=7.1 Hz; 3 H).

Step B—Synthesis of Intermediate Compound 8b

Compound 8a (6.00 g, 10.02 mmol) in ethanol (20 mL) was treated at room temperature with 2 M aq LiOH (50.1 mL, 100 mmol). The mixture was heated at 75° C. for 48 hours, cooled to room temperature and concentrated in vacuo. The resulting residue was neutralized with glacial acetic acid in acetonitrile. Purification using preparative RP-HPLC provided intermediate compound 8b as a powder. LCMS (M+H)=571; $^1$H NMR (500 MHz, DMSO): δ 11.36 (br s; 1 H); 8.83 (s; 1 H); 7.53-7.58 (m; 1 H); 7.26-7.42 (m; 6 H); 7.12 (td; J=8.5; 2.52 Hz; 1 H); 5.16 (s; 2 H); 4.51 (s; 2 H); 1.43 (s; 9 H).

Step C—Synthesis of Intermediate Compound 8c

A solution of compound 8b (1.00 g, 1.753 mmol) in DMF (5.0 mL) was treated at room temperature with PyClock (1.167 g, 2.103 mmol) and ethylamine (2 M in THF) (1.928 mL, 3.86 mmol). The mixture was allowed to stir at room temperature for 16 hours, quenched with water and neutralized with glacial acetic acid. Purification using RP-MPLC provided intermediate compound 8c. LCMS (M+H)=598; $^1$H NMR (500 MHz, DMSO): δ 11.30 (br s; 1 H); 8.77 (s; 1 H); 7.53-7.58 (m; 1 H); 7.28-7.42 (m; 6 H); 7.12 (td; J=8.5; 2.6 Hz; 1 H); 5.17 (s; 2 H); 4.50 (s; 2 H); 3.19 (p; J=6.7 Hz; 2 H); 1.44 (s; 9 H); 1.03 (t; J=7.2 Hz; 3 H)

Step D—Synthesis of Intermediate Compound 8d

Compound 8c (50 mg, 0.084 mmol) and dihydrofuran-3(2H)-one (138 mg, 0.418 mmol) in acetic acid (1.0 mL) heated at 85° C. for 12 hours. The reaction was cooled to room temperature, then diluted with acetonitrile (4 mL). Purification of the resulting acetonitrile solution using preparative mass-guided RP-HPLC provided intermediate compound 8d. LCMS (M+H)=566.

Step E—Synthesis of Intermediate Compound 8e and Intermediate Compound 8f

Compound 8d was dissolved in 5% aq DMF (1 mL) and treated with $K_2CO_3$ (5 equiv) and iodomethane (5 equiv). The mixture was allowed to stir at room temperature for 16 hours and then quenched with the addition of glacial acetic acid. Purification using preparative RP-HPLC provided a mixture of intermediate compounds (±)-8e. ($^1$H NMR spectrum indicates conformational isomers at room temperature). LCMS (M+H)=580; $^1$H NMR (500 MHz, CDCl$_3$): δ 8.82 (d; J=12.4 Hz; 1 H); 7.45-7.50 (m; 2 H); 7.26-7.29 (m; 3 H); 6.86-6.88 (m; 2 H); 5.62 (t; J=10.5 Hz; 1 H); 5.30 (dd; J=10.6; 3.28 Hz; 1 H); 4.52 (s; 2 H); 4.19 (d; J=10.2 Hz; 1 H); 4.04-4.10 (m; 1 H); 3.86-3.95 (m; 2 H); 3.68 (d; J=10.2 Hz; 1 H); 3.47 (d; J=9.3 Hz; 1 H); 3.34 (td; J=14.5; 7.2 Hz; 1 H); 3.11 (d; J=9.6 Hz; 1 H); 2.87 (s; 1 H); 2.77 (s; 2 H); 2.49 (t; J=7.0 Hz; 1 H); 2.26 (d; J=11.9 Hz; 1 H); 2.12 (t; J=6.1 Hz; 1 H); 1.50-1.54 (m; 1 H); 1.28-1.33 (m; 3 H). Resolution to the enantiomers was accomplished by SFC (Chiralcel OD, 21×250 mm, 50% methanol+0.2% DEA, 55 ml/min, 20 mg/ml in methanol) to provide intermediate compound 8e-1 (enantiomer A, earlier eluting) and intermediate compound 8e-2 (enantiomer B, later eluting).

Step F—Synthesis of Compound 35 and Compound 36

A mixture of compound 8e-1 (enantiomer A) (45 mg, 0.078 mmol) and Pd/C (15 mg, 0.141 mmol) in ethyl acetate (3 mL) was sparged with nitrogen. Hydrogen (1 atm) was introduced and the reaction mixture was allowed to stir at room temperature for 16 hours. After filtration and concentration of the filtrate, the resulting residue was purified using preparative RP-HPLC to provide compound 35. ($^1$H NMR spectrum indicates conformational isomers at room temperature) LCMS (M+H)=490; 1H NMR (500 MHz, DMSO): δ 8.71 (s; 1 H); 8.65 (s; 1 H); 7.50-7.55 (m; 2 H); 7.28 (td; J=9.8; 2.5 Hz; 2 H); 7.11 (td; J=8.5; 2.5 Hz; 2 H); 4.50 (s; 4 H); 4.32 (d; J=10.8 Hz; 1 H); 3.99-4.05 (m; 4 H); 3.77-3.88 (m; 4 H); 3.64-3.71 (m; 2 H); 2.86 (s; 3 H); 2.77 (s; 3 H); 2.59 (dt; J=14.1; 6.9 Hz; 1 H); 2.35-2.46 (m; 2 H); 2.13 (dt; J=13.3; 8.1 Hz; 1 H); 1.21-1.26 (m; 6 H).

Compound 36 was prepared using this method by starting with intermediate compound 8e-2 (enantiomer B) as the starting material.

The following compounds of the present invention were made using the methods described in the Example above and substituting the appropriate reactants and reagents.

| Compound | Structure | Exact Mass [M + H]+ |
|---|---|---|
| 37 | 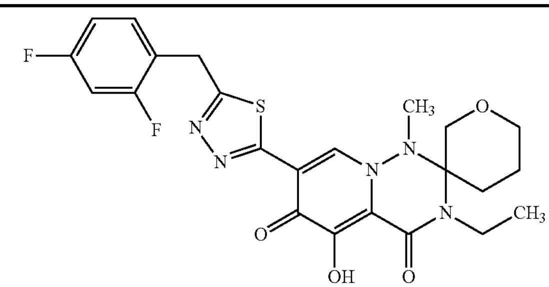 | 504 |
| 38 | 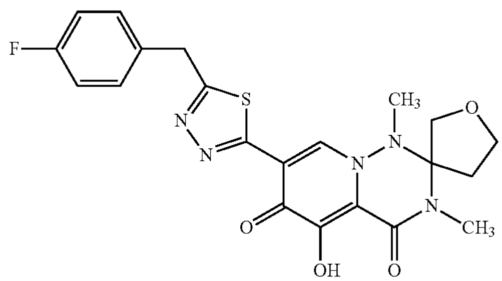 [SMILES: CN1C(=O)c2c(O)c(=O)c(-c3nnc(Cc4ccc(F)cc4)s3)cn2N(C)C12CCOC2] | 458 |
Example 9
Preparation of Compound 39
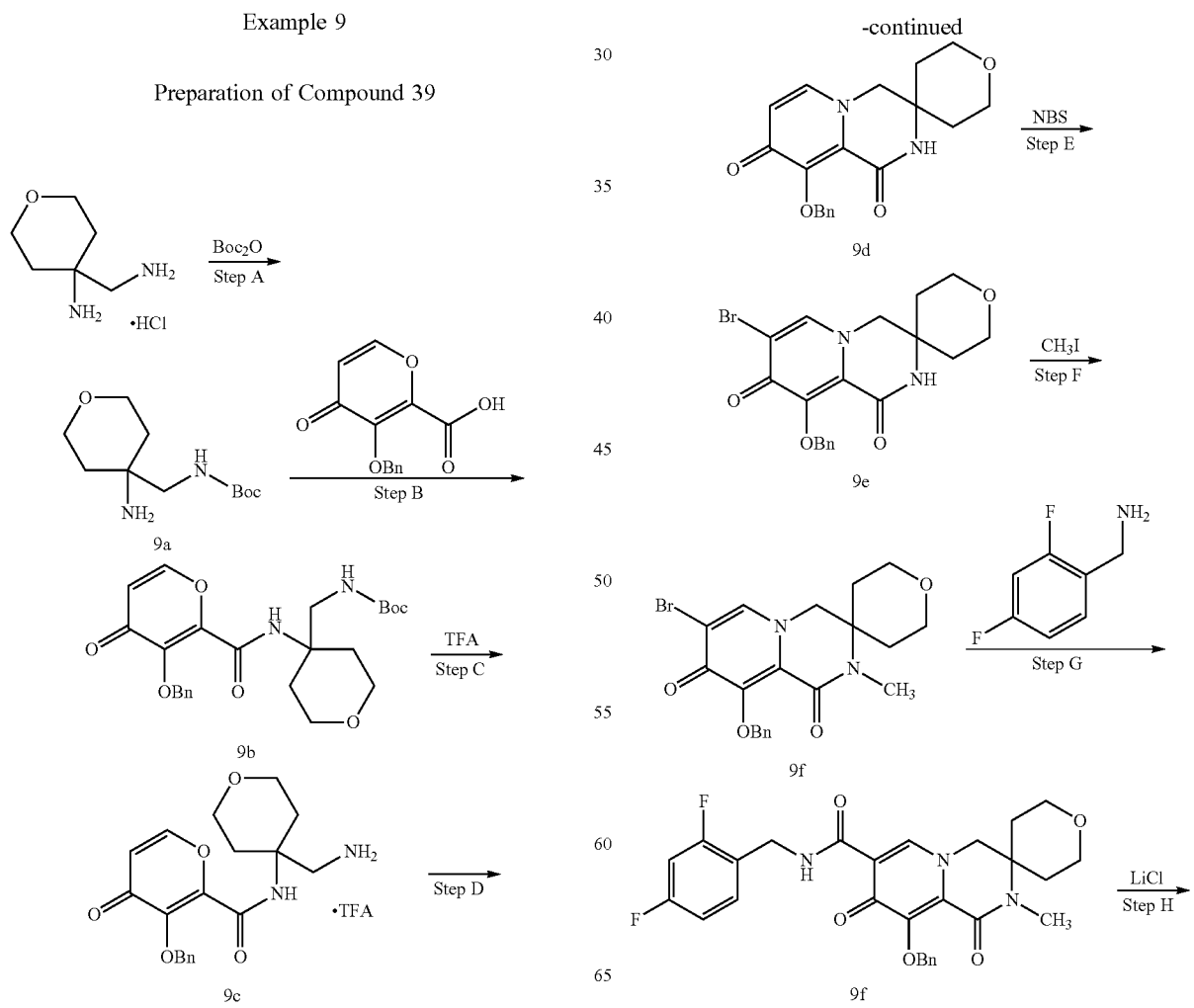

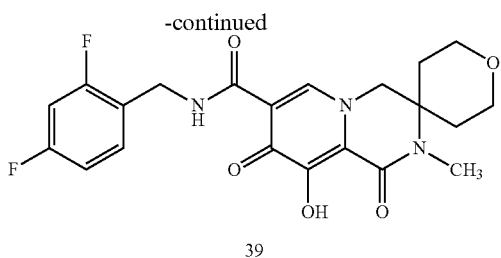

39

Step A—Synthesis of Intermediate Compound 9a

A solution of 4-(aminomethyl)tetrahydro-2H-pyran-4-amine hydrochloride (450 mg, 2.70 mmol) in THF (40 mL) was added triethylamine (1.505 mL, 10.80 mmol), Boc$_2$O (0.627 mL, 2.70 mmol) at room temperature. The mixture was allowed to stir for 12 hours at room temperature and then water (40 mL) was added. The mixture was extracted with dichloromethane (5×30 mL) and the combined organic portion was washed with water (2×30 mL), dried over anhydrous Na$_2$SO$_4$ and concentrated to provide intermediate compound 9a. LRMS (+ESI) m/z: 231.1. $^1$H NMR: (400 MHz, CDCl$_3$) δ 4.96 (br, 1H), 3.73-3.76 (m, 4H), 3.10 (d, J=6.0 Hz, 2H), 1.671-1.67 (m, 2H), 1.45 (s, 9H), 1.34-1.38 (m, 2H).

Step B—Synthesis of Intermediate Compound 9b

To a solution of intermediate compound 9a (1 g, 4.34 mmol) in DMF (20 mL) was added, at room temperature, triethylamine (0.822 g, 8.12 mmol), HATU (1.699 g, 4.47 mmol) and 3-(benzyloxy)-4-oxo-4H-pyran-2-carboxylic acid (0.982 g, 4.26 mmol). The mixture was allowed to stir for 12 hours at room temperature and then treated with water (30 mL). The mixture was extracted with ethyl acetate (5×15 mL) and the combined organic portion was washed with water (2×25 mL) and brine (25 mL), dried over anhydrous Na$_2$SO$_4$ and concentrated, the resulting residue was purified using column chromatography on silica gel (petroleum ether:ethyl acetate=1:1 to 1:10) to provide intermediate compound 9b.

Step C—Synthesis of Intermediate Compound 9c

To a solution of intermediate compound 9b (1.5 g, 3.27 mmol) in CH$_2$Cl$_2$ (35 mL) was added TFA (7 mL). The mixture was allowed to stir at room temperature for 2 hours and then concentrated to provide intermediate compound 9c. LRMS (+ESI) m/z: 359.0. $^1$HNMR: (300 MHz, CD$_3$OD) δ 8.13 (d, J=5.4 Hz, 1H), 7.52-7.55 (m, 2H), 7.41-7.44 (m, 3H), 6.60 (d, J=5.4 Hz, 1H), 5.44 (s, 2H), 3.34-3.85 (m, 6H), 1.58-1.90 (m, 4H).

Step D—Synthesis of Intermediate Compound 9d

A solution of intermediate compound 9c (0.9 g, 1.976 mmol)) in EtOH (15 mL) was heated at reflux for 12 hours and then concentrated and purified using preparative RP-HPLC to provide intermediate compound 9d. LRMS (+ESI) m/z: 359.0. $^1$H NMR: (400 MHz, CD$_3$OD) δ 7.67 (d, J=7.6 Hz, 1H), 7.37-7.40 (m, 2H), 7.26-7.29 (m, 3H), 6.53 (d, J=7.6 Hz, 1H), 5.30 (s, 2H), 4.11 (s, 2H), 3.62-3.71 (m, 4H), 1.52-1.59 (m, 2H), 1.29-1.32 (m, 2H).

Step E—Synthesis of Intermediate Compound 9e

To a solution of intermediate compound 9d (30 mg, 0.088 mmol) in dichloromethane (4 mL) was added N-bromosuccinimide (31.4 mg, 0.176 mmol). The mixture was allowed to stir at room temperature for 2 hours. The mixture was washed with water (2 mL) and brine (2 mL) and the combined organic portion was concentrated and purified using preparative TLC on silica gel (dichloromethane:methanol=10:1) to provide intermediate compound 9e. LRMS (+ESI) m/z: 420.7. $^1$H NMR: (400 MHz, CD$_3$OD) δ 8.23 (s, 1H), 7.37-7.40 (m, 2H), 7.27-7.29 (m, 3H), 5.32 (s, 2H), 4.13 (s, 2H), 3.63-3.71 (m, 4H), 1.54-1.61 (m, 2H), 1.31-1.34 (m, 2H).

Step F—Synthesis of Intermediate Compound 9f

To a solution of intermediate compound 9e (0.02 g, 0.048 mmol) in DMF (2 mL) was added Cs$_2$CO$_3$ (0.062 g, 0.19 mmol) and CH$_3$I (0.068 g, 0.48 mmol), then the mixture was allowed to stir at 80° C. for 3 hours, then water (4 mL) was added, extracted with dichloromethane (2 mL×6), the combined organic portion was dried over anhydrous Na$_2$SO$_4$, filtered and the filtrate was concentrated in vacuo. The resulting residue was purified using preparative TLC on silica gel (dichloromethane:methanol, 10:1) to provide intermediate compound 9f. LRMS (+ESI) m/z: 434.8. $^1$H NMR: (400 MHz, CD$_3$OD) δ 8.30 (s, 1H), 7.36-7.38 (m, 2H), 7.27-7.29 (m, 3H), 5.24 (s, 2H), 4.39 (s, 2H), 3.78-3.82 (m, 2H), 3.51-3.57 (m, 2H), 3.01 (s, 3H), 1.93-2.01 (m, 2H), 1.19-1.23 (m, 2H).

Step G—Synthesis of Intermediate Compound 9g

A solution of intermediate compound 9f (10 mg, 0.023 mmol) in DMSO (2 mL) was treated with (2,4-difluorophenyl)methanamine (33.03 mg, 0.231 mmol), N,N-diisopropylethylamine (14.91 mg, 0.115 mmol) and Pd(PPh$_3$)$_4$ (2.67 mg, 0.0023 mmol) at room temperature under an atmosphere of carbon monoxide. The mixture was allowed to stir at 90° C. under carbon monoxide (1 atm) for 15 hours and then diluted with water (4 mL). The mixture was extracted with ethyl acetate (3 mL×4) and the combined organic portion was washed with water (3 mL×2) and concentrated in vacuo. The resulting residue was purified using preparative TLC on silica gel (dichloromethane:methanol, 20:1) to provide intermediate compound 9g. LRMS (+ESI) m/z: 523.9. $^1$H NMR: (400 MHz, CD$_3$OD) δ 8.57 (s, 1H), 7.30-7.57 (m, 4H), 6.97-7.12 (m, 4H), 5.27 (s, 2H), 4.52 (s, 2H), 4.19 (s, 2H), 3.81-3.83 (m, 2H), 3.58-3.64 (m, 2H), 3.05 (s, 3H), 1.28-1.30 (m, 4H).

Step H—Synthesis of Compound 39

To a solution of intermediate compound 9g (5 mg, 0.010 mmol) in DMF (2 mL) was added LiCl (12.15 mg, 0.287 mmol) at room temperature. The mixture was heated at 95° C. for 2 hours and then directly purified using preparative RP-HPLC to provide compound 39. LRMS (+ESI) m/z: 434. $^1$H NMR: (400 MHz, CD$_3$OD) δ 8.53-8.69 (m, 1H), 7.40-7.43 (m, 1H), 3.77-6.93 (m, 2H), 4.64 (s, 2H), 3.89-3.90 (m, 2H), 3.70-3.71 (m, 2H), 3.16 (s, 3H), 2.24-2.25 (m, 2H), 1.59-1.63 (m, 2H), 1.27-1.28 (m, 2H).

The following compounds of the present invention were made using the methods described in the Example above and substituting the appropriate reactants and reagents.

| Compound | Structure | Exact Mass [M + H]+ |
|---|---|---|
| 40 | 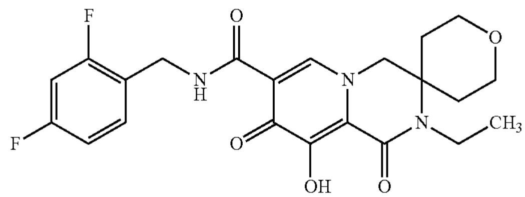 [SMILES: CCN1C(=O)c2c(O)c(=O)c(C(=O)NCc3ccc(F)cc3F)cn2CC12CCOCC2] | Calc'd 448.2, found 448.4 |
| 41 | 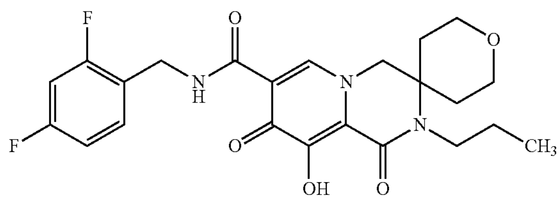 [SMILES: CCCN1C(=O)c2c(O)c(=O)c(C(=O)NCc3ccc(F)cc3F)cn2CC12CCOCC2] | Calc'd 462.2, found 462.2 |
| 42 | 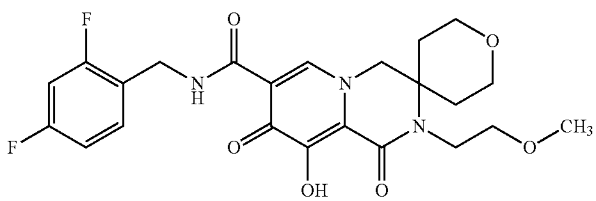 [SMILES: COCCN1C(=O)c2c(O)c(=O)c(C(=O)NCc3ccc(F)cc3F)cn2CC12CCOCC2] | Calc'd 478.2, found 478.0 |
| 43 | 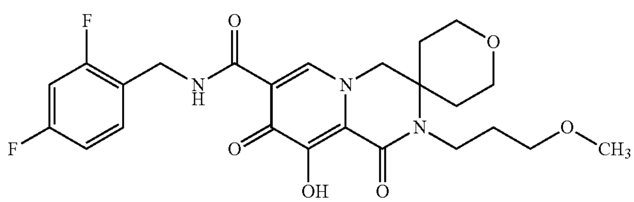 | Calc'd 492.2, found 492.0 |
| 44 | 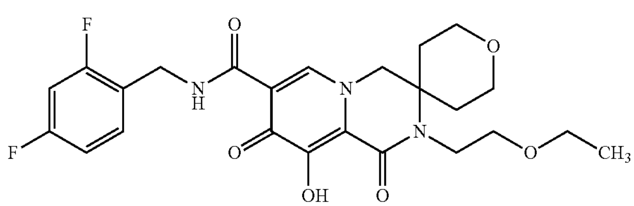 | Calc'd 492.2, found 492.1 |
| 45 | 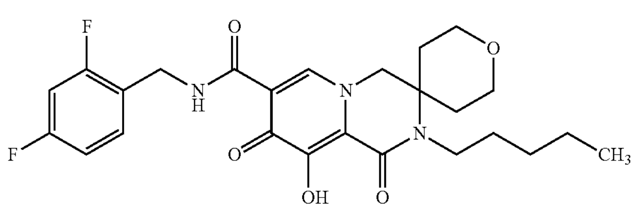 | Calc'd 490.2, found 490.0 |
| 46 | 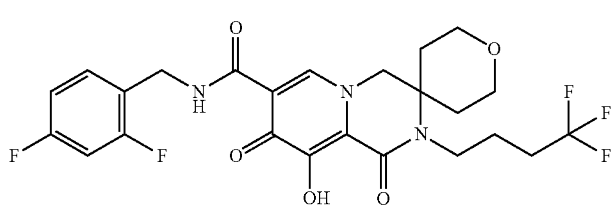 [SMILES: O=C(NCc1ccc(F)cc1F)c1cn2c(c(O)c1=O)C(=O)N(CCCC(F)(F)F)C1(CCOCC1)C2] | Calc'd 530.2, found 530.0 |

-continued
| Compound | Structure | Exact Mass [M + H]+ |
|---|---|---|
| 47 | 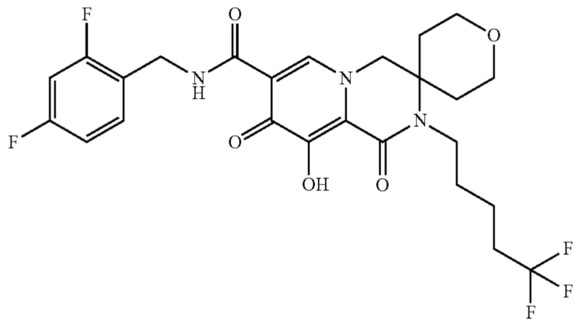 [SMILES: O=C(NCc1ccc(F)cc1F)c1cn2c(c(O)c1=O)C(=O)N(CCCCC(F)(F)F)C1(CCOCC1)C2] | Calc'd 544.2, found 543.9 |
Example 10
Preparation of Compound 48
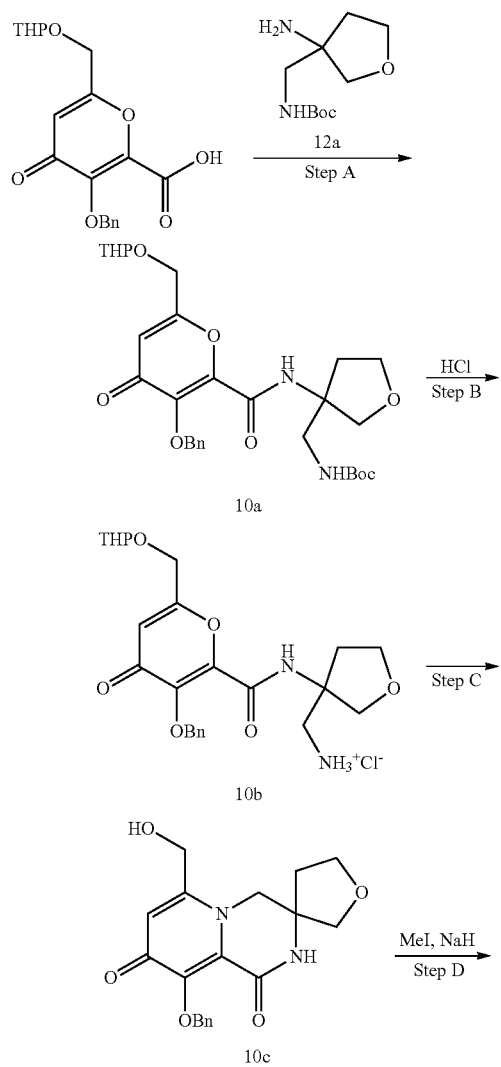
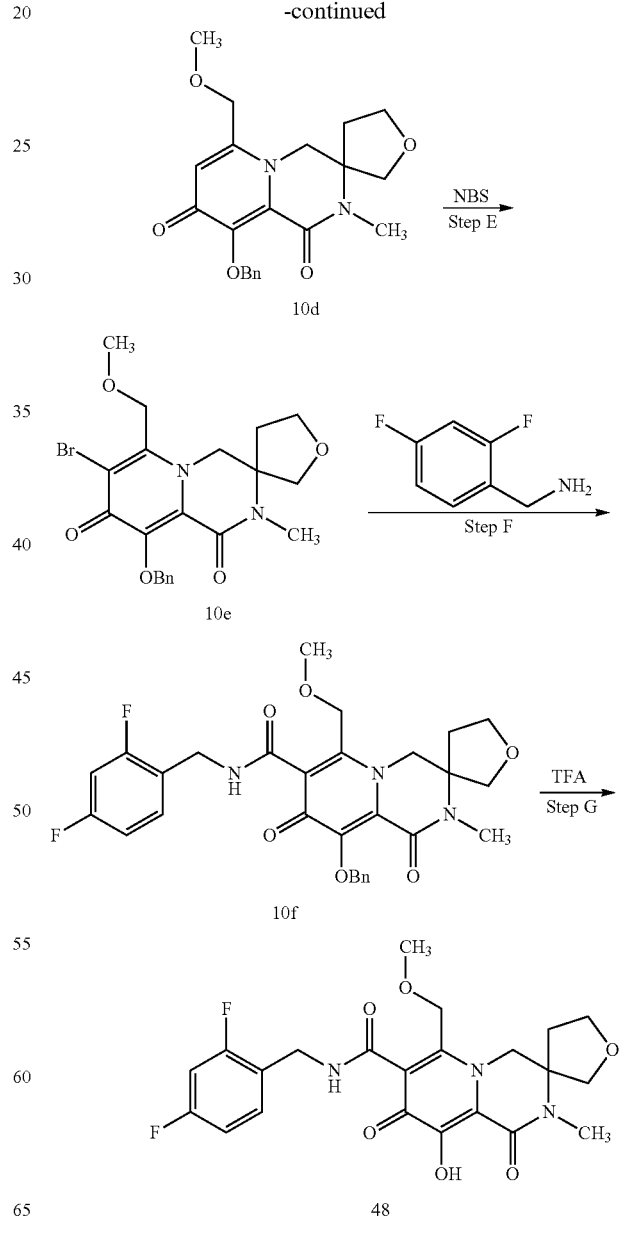

Step A—Synthesis of Intermediate Compound 10a

To a solution of compound 3-(benzyloxy)-4-oxo-6-(((tetrahydro-2H-pyran-2-yl) oxy)methyl)-4H-pyran-2-carboxylic acid (233 mg, 0.648 mmol), intermediate compound 12a (140 mg, 0.648 mmol) and N,N-diisopropylethylamine (167 mg, 1.296 mmol) in DMF (10 mL) was added HATU (492 mg, 1.296 mmol) and HOAT (176 mg, 1.296 mmol). The mixture was allowed to stir at room temperature for 16 hours and then diluted with water (20 mL) and extracted with ethyl acetate (4×20 mL). The combined organic portion was washed with brine (20 mL), dried over anhydrous $Na_2SO_4$, filtered and the filtrate was concentrated in vacuo. The resulting residue was purified using preparative TLC on silica gel (petroleum ether:ethyl acetate, 5:1) to provide intermediate compound 10a. LRMS (+ESI) m/z 559.2.

Step B—Synthesis of Intermediate Compound 10b

To a solution of intermediate compound 10a (160 mg, 0.287 mmol) in ethyl acetate (10 mL) was added a solution of HCl in ethyl acetate (4 M, 4 mL) at room temperature. The mixture was allowed to stir for 2 hours at room temperature and then concentrated in vacuo to provide intermediate compound 10b, which was used without further purification. LRMS (+ESI) m/z 375.1.

Step C—Synthesis of Intermediate Compound 10c

Intermediate compound 10b (150 mg, 0.401 mmol) in EtOH (50 mL) was heated at 100° C. for 54 hours. The mixture was concentrated and the resulting residue was purified using preparative TLC on silica gel (PE:EA=2:1) to provide intermediate compound 10c as an oil. LRMS (+ESI) m/z 357.1.

Step D—Synthesis of Intermediate Compound 10d

A mixture of intermediate compound 10c (20 mg, 0.056 mmol) in DMF (3 mL) was treated at 0° C. with NaH (10 mg, 0.25 mmol) and iodomethane (31 mg, 0.224 mmol) and the mixture was allowed to stir at 0° C. for 2 hours. The mixture was diluted with water (30 mL) and extracted with ethyl acetate (3×25 mL). The combined organic portion was washed with brine (30 mL) and concentrated in vacuo. The resulting residue was purified using preparative TLC on silica gel to provide intermediate compound 12d. LRMS (+ESI) m/z 385.1.

Step E—Synthesis of Intermediate Compound 10e

A solution of intermediate compound 10d (15 mg, 0.039 mmol) in $CH_3CN$ (5 mL) was treated with N-bromosuccinimide (10 mg, 0.058 mmol), stirred at room temperature for 1 hour and then concentrated in vacuo. The resulting residue was purified using preparative TLC on silica gel to provide intermediate compound 10e. LRMS (+ESI) m/z 463.1.

Step F—Synthesis of Intermediate Compound 10f

A solution of 9'-(benzyloxy)-7'-bromo-6'-(methoxymethyl)-2'-methyl-4,5-dihydro-2H-spiro[furan-3,3'-pyrido[1,2-a]pyrazine]-1',8'(2'H,4'H)-dione (20 mg, 0.041 mmol) in DMSO (1 mL) and methanol (3 mL) was treated with (2,4-difluorophenyl)methanamine (60 mg, 0.419 mmol), N,N-diisopropylethylamine (60 mg, 0.465 mmol) and $Pd(PPh_3)_4$ (10 mg, 0.0086 mmol) at room temperature. The mixture was heated at 80° C. under carbon monoxide (1 atm) for 15 hours, cooled to room temperature and diluted with water (4 mL). The mixture was extracted with ethyl acetate (4×3 mL) and the combined organic portion was washed with water (2×3 mL), concentrated and the resulting residue was purified using preparative TLC on silica gel (dichloromethane:methanol=20:1) to provide intermediate compound 10f as a solid. LRMS (+ESI) m/z 554.2.

Step G—Synthesis of Compound 48

A solution of intermediate compound 10f (20 mg, 0.035 mmol) in dichloromethane (1 mL) was treated with TFA (3 mL) at 25° C. The reaction mixture was allowed to stir at 25° C. for 2 hours and then conentrated. The resulting residue was purified using preparative RP-HPLC to provide compound 48. LRMS (+ESI) m/z: 464.1. $^1$H NMR (400 MHz, MeOD) δ 7.85-7.90 (m, 1H), 6.96-7.01 (m, 2H), 4.32-4.60 (m, 6H), 4.04-4.13 (m, 2H), 3.89-3.93 (m, 1H), 3.70-3.72 (m, 1H), 3.34 (s, 3H), 3.20 (s, 3H), 2.20-2.33 (m, 2H).

Example 11

Preparation of Compound 49

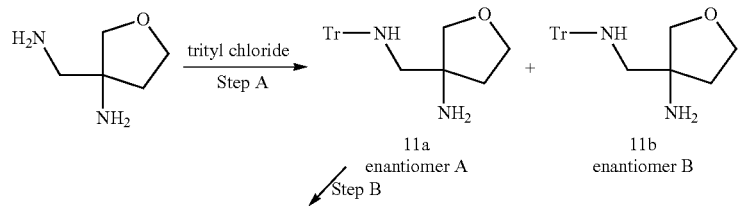

11a
enantiomer A 11b
enantiomer B

Step B

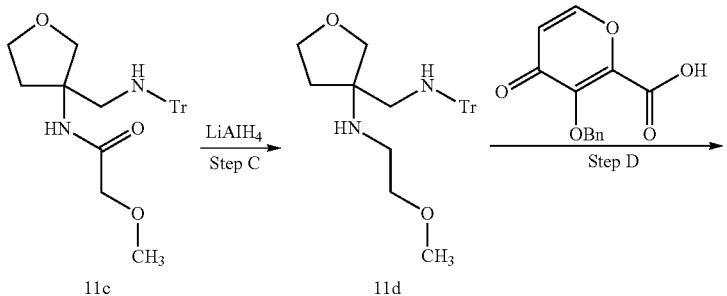

11c

11d

-continued

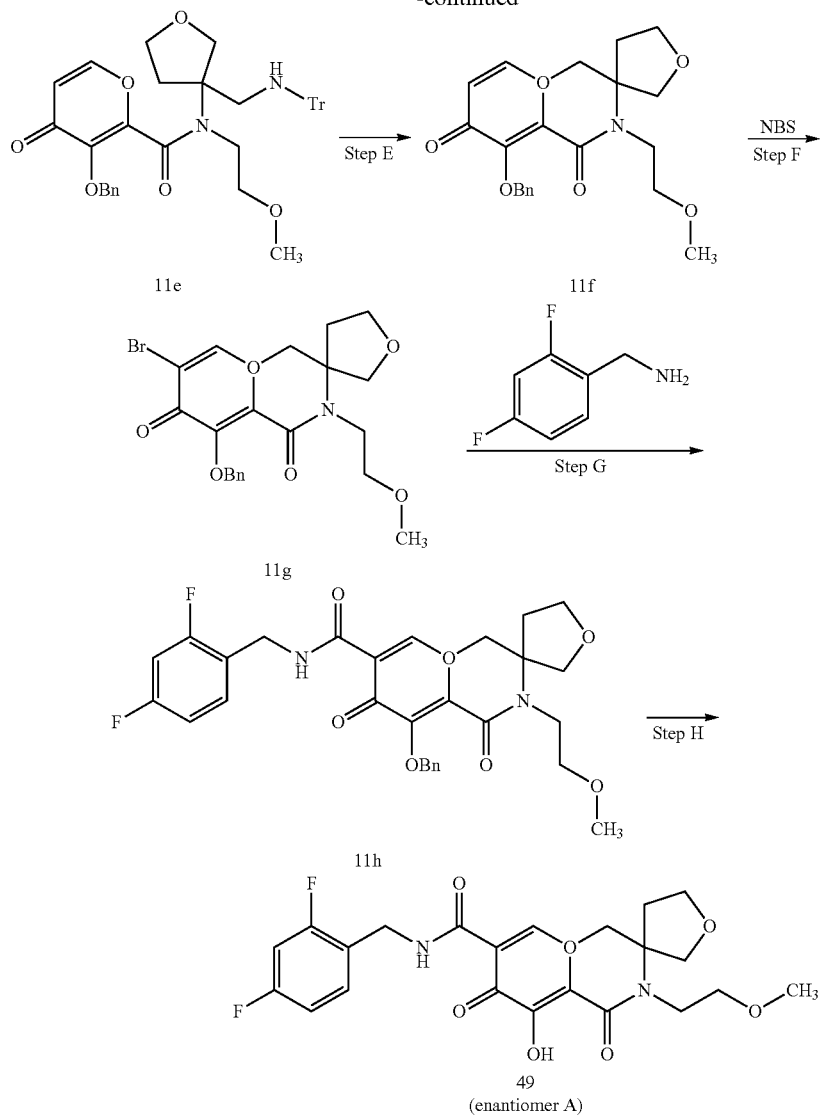

Step A—Synthesis of Intermediate Compound 11a and Intermediate Compound 11b 3-(aminomethyl)tetrahydrofuran-3-amine dihydrochloride salt (10.0 g, 52.9 mmol) and trityl chloride (16.2 g, 58.2 mmol) in dichloromethane (100 mL) was cooled to 0° C. and treated with triethylamine (24.33 mL, 175 mmol). The ice bath was removed and the mixture was allowed to stir at room temperature for 48 hours. The reaction mixture was filtered and the filtrated was directly loaded onto a dry pre-packed silica column. Purification using column chromatography on silica gel (0 to 100% Ethyl acetate/hexanes) provided 3-((tritylamino)methyl)tetrahydrofuran-3-amine LCMS (M+H)=359; $^1$H NMR (500 MHz, CDCl$_3$): δ 7.50 (d; J=7.8 Hz; 6 H); 7.39 (d; J=7.9 Hz; 6 H); 7.18 (t; J=7.3 Hz; 3 H); 4.01 (q; J=8.0 Hz; 1 H); 3.79 (bs; 1 H); 3.68 (d; J=10.0 Hz; 1 H); 3.57 (d; J=9.2 Hz; 1 H); 2.31 (s; 2 H); 1.83 (s; 2 H). Resolution to the enantiomers was accomplished with SFC (OJ-H column, 40% 2-propanol+diethylamine/CO$_2$) to provide 11a as enantiomer A (earlier eluting) and 11b as enantiomer B (later eluting).

Step B—Synthesis of Intermediate Compound 11e

Compound 11a (1.70 g, 4.74 mmol) in dichloromethane (20.0 mL) cooled to 0° C. and treated with triethylamine (1.322 mL, 9.48 mmol) and methoxyacetyl chloride (0.477 mL, 5.22 mmol). Stirred at 0° C. for 1 hour. Directly loaded onto a 120 g silica column with hexanes. Purification using column chromatography on silica gel (0 to 100% ethyl acetate/hexanes; eluted at 90% ethyl acetate) provided intermediate compound 11c. LCMS (M+H)=431; $^1$H NMR (500 MHz, CDCl$_3$): δ 7.50-7.40 (m; 6 H); 7.32-7.23 (m; 6 H); 7.15-7.23 (m; 3 H); 6.97 (s; 1 H); 3.92-4.00 (m; 3 H); 3.83 (s; 3 H); 3.72 (d; J=9.5 Hz; 1 H); 3.45 (s; 3 H); 2.56-2.49 (m; 2 H); 2.35 (bs, 1 H) 1.98-1.86 (m; 1 H).

Step C—Synthesis of Intermediate Compound 11d

Intermediate compound 11c (1.614 g, 3.75 mmol) in tetrahydrofuran (20 mL) was cooled to 0° C. and treated with a slurry of lithium aluminum hydride (0.300 g, 7.90 mmol) in THF (2×5 mL). The resulting mixture was heated under nitrogen at reflux for 4 hours, cooled to 0° C. and sequentially treated with water (0.30 mL), 15% w/w aqueous NaOH (0.30 mL), and water (0.90 mL). The resulting mixture was filtered through a pad of Solka-Floc and the filtrate was concentrated in vacuo. The resulting residue was purified using column chromatography on silica gel (0 to 100% ethyl acetate/hexanes) to provide intermediate compound 11d. LCMS (M+H)=417.

Step D—Synthesis of Intermediate Compound 11e 3-(benzyloxy)-4-oxo-4H-pyran-2-carboxylic acid (520 mg, 2.11 mmol) in THF (6 mL) treated at room temperature with 1-(chloro-1-pyrrolidinylmethylene)pyrrolidinium hexafluorophosphate (843 mg, 2.54 mmol) and N,N-diisopropylethylamine (0.738 mL, 4.23 mmol), stirred at room temperature for 10 minutes and then treated with a solution of intermediate compound 11d (880 mg, 2.113 mmol) in THF (2×2 mL) at room temperature. The mixture was allowed to stir at room temperature for 5 hours. The crude reaction mixture was directly loaded onto a dry silica gel column. Purification using column chromatography on silica gel (0 to 100% ethyl acetate/hexanes) provided intermediate compound 11e. LCMS (M+H)=645;

Step E—Synthesis of Intermediate Compound 11f

Intermediate compound 11e (1.30 g, 2.02 mmol) in $CH_2Cl_2$ (20 mL) was treated dropwise with trifluoroacetic acid (1.55 mL, 20.16 mmol) and the mixture was allowed to stir at room temperature for 16 hours. After concentration, the resulting residue was dissolved in N-methylimidazole (10 mL) and heated at 80° C. for 16 hours. The mixture was cooled to room temperature and neutralized with glacial acetic acid. Purification using preparative RP-HPLC provided intermediate compound 11f. LCMS (M+H)=385.

Step F—Synthesis of Intermediate Compound 11g

Intermediate compound 11f (180.8 mg, 0.470 mmol) in $CH_2Cl_2$ (5 mL) was treated with N-bromosuccinimide (92 mg, 0.517 mmol) at room temperature. The reaction mixture was allowed to stir for 2 hours at room temperature. After concentration, the resulting residue was purified using column chromatography on silica gel (0 to 10% methanol/$CH_2Cl_2$) to provide intermediate compound 11g. LCMS (M+H)=463.

Step G—Synthesis of Intermediate Compound 11h

A mixture of intermediate compound 11g (99 mg, 0.214 mmol), N,N-diisopropylethylamine (0.112 mL, 0.641 mmol), 2,4-difluorobenzylamine (0.058 mL, 0.470 mmol) and tetrakis(triphenylphosphine) palladium (123 mg, 0.107 mmol) in DMSO (2 mL) was sub-surface sparged with nitrogen for 10 minutes and then carbon monoxide for 10 minutes. The reaction solution was heated at 90° C. under carbon monoxide (1 atm) for 8 hours. The mixture was cooled to room temperature, filtered and the filtrate was purified using preparative RP-HPLC to provide intermediate compound 11h. LCMS (M+H)=554.

Step H—Synthesis of Compound 49

Intermediate compound 11h (132 mg, 0.238 mmol) in TFA (1 mL, 12.98 mmol) was allowed to stir at room temperature for 3 hours. The mixture was diluted with aqueous DMSO and purified using preparative RP-HPLC to provide compound 49. LCMS (M+H)=464; $^1$H NMR (500 MHz, DMSO): δ 12.33 (s; 1 H); 10.39 (t; J=6.0 Hz; 1 H); 8.43 (s; 1 H); 7.36-7.41 (m; 1 H); 7.22-7.26 (m; 1 H); 7.04-7.08 (m; 1 H); 4.53 (d; J=5.9 Hz; 2 H); 4.46 (d; J=13.3 Hz; 1 H); 4.35 (d; J=13.3 Hz; 1 H); 4.06 (d; J=10.3 Hz; 1 H); 3.98 (td; J=8.6; 4.7 Hz; 1 H); 3.66-3.76 (m; 2 H); 3.51-3.63 (m; 4 H); 3.27 (s, 3 H) 2.06-2.21 (m; 2 H).

A similar sequence provided compound 50 using intermediate 11b (enantiomer B, later eluting).

The following compounds of the present invention were made using the methods described in the Example above and substituting the appropriate reactants and reagents.

| Compound | Structure | enantiomer | Exact Mass [M + H]+ |
|---|---|---|---|
| 50 | 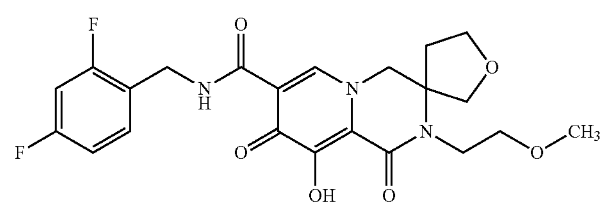 [SMILES: COCCN1C(=O)c2c(O)c(=O)c(C(=O)NCc3ccc(F)cc3F)cn2CC12CCOC2] | B | Calc'd 464.2, found 464.1 |
| 51 | 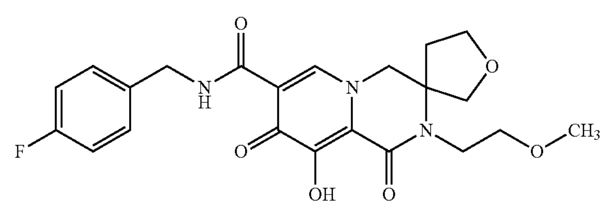 [SMILES: COCCN1C(=O)c2c(O)c(=O)c(C(=O)NCc3ccc(F)cc3)cn2CC12CCOC2] | A | Calc'd 446.2, found 446.0 |
| 52 | 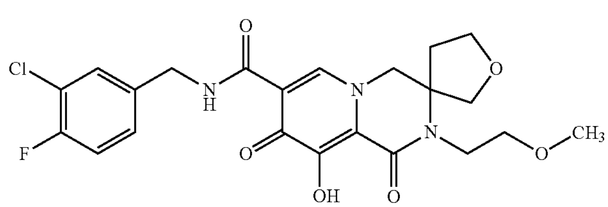 [SMILES: COCCN1C(=O)c2c(O)c(=O)c(C(=O)NCc3ccc(F)c(Cl)c3)cn2CC12CCOC2] | A | Calc'd 480.1, found 480.0 |

-continued

| Compound | Structure | enantiomer | Exact Mass [M + H]+ |
|---|---|---|---|
| 53 | 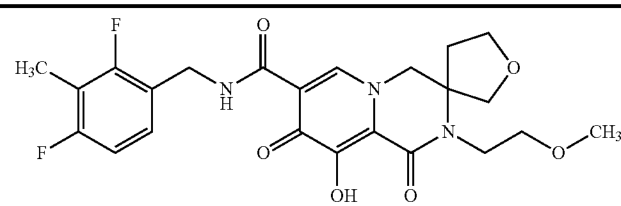 | A | Calc'd 478.2, found 478.0 |
| 54 | 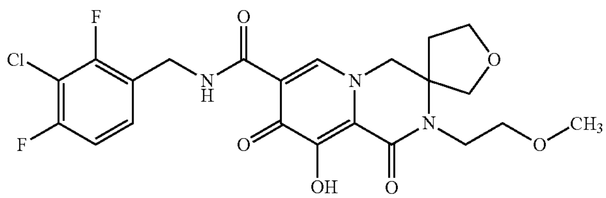 [SMILES: COCCN1C(=O)c2c(O)c(=O)c(C(=O)NCc3ccc(F)c(Cl)c3F)cn2CC12CCOC2] | A | Calc'd 498.1, found 498.1 |

Example 12

Preparation of Compound 55

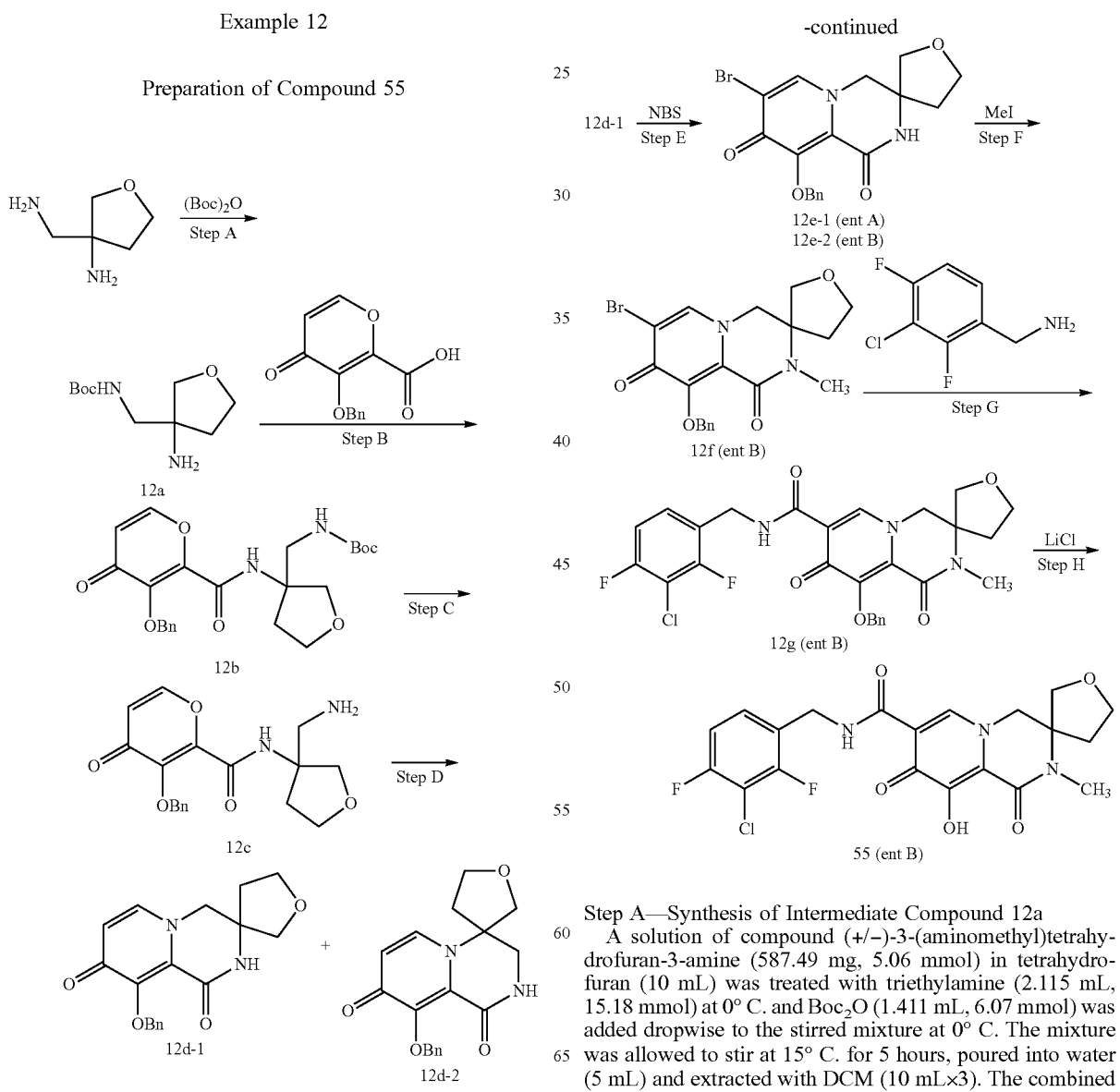

Step A—Synthesis of Intermediate Compound 12a

A solution of compound (+/−)-3-(aminomethyl)tetrahydrofuran-3-amine (587.49 mg, 5.06 mmol) in tetrahydrofuran (10 mL) was treated with triethylamine (2.115 mL, 15.18 mmol) at 0° C. and Boc$_2$O (1.411 mL, 6.07 mmol) was added dropwise to the stirred mixture at 0° C. The mixture was allowed to stir at 15° C. for 5 hours, poured into water (5 mL) and extracted with DCM (10 mL×3). The combined organic portions were washed with brine (5 mL), dried over anhydrous Na₂SO₄, filtered and the filtrate was concentrated to provide 12a that was used without further purification. ¹H NMR (400 MHz, CDCl₃) δ 3.99-4.03 (m, 1H), 3.90-3.92 (m, 1H), 3.48-3.63 (m, 2H), 3.22-3.26 (m, 2H), 1.95-1.98 (m, 1H), 1.70-1.75 (m, 1H), 1.39 (s, 9H).

Step B—Synthesis of Intermediate Compound 12b

A solution of 12a (722 mg, 3.34 mmol) in DMF (10 mL) was treated with N,N-diisopropylethylamine (1.29 g, 10.02 mmol) and HATU (1.904 g, 5.01 mmol), stirred for several minutes and then treated with 3-(benzyloxy)-4-oxo-4H-pyran-2-carboxylic acid (657.55 mg, 2.67 mmol). The mixture was allowed to stir at 15° C. for 3 hours, diluted with water (5 mL) and extracted with ethyl acetate (12 mL×5). The combined organic layers were washed with brine (8 mL), dried over anhydrous Na₂SO₄, filtered, and the filtrate was concentrated. The residue was purified using chromatography on silica gel (petroleum ether:ethyl acetate=5:1-1:1) to provide 12b ¹H NMR (400 MHz, CDCl₃) δ 8.00 (s, 1H), 7.81 (d, J=5.6 Hz, 1H), 7.41 (d, J=10.0 Hz, 5H), 6.48 (d, J=5.2 Hz, 1H), 5.41-5.50 (m, 2H), 3.69-3.81 (m, 3H), 3.55-3.58 (m, 1H), 3.50 (d, J=4.2 Hz, 2H), 1.91 (s, 1H), 1.66 (s, 1H), 1.42 (s, 9H). MS (+ESI) m/z: 445.1.

Step C—Synthesis of Intermediate Compound 12c

A solution of 12b (1.19 g, 2.67 mmol) in dichloromethane (20 mL) was treated with TFA (4 mL) at 0° C. and stirred at 15° C. for 2 hours. The reaction mixture was concentrated to provide 12c. The crude product was used without further purification. ¹H NMR (400 MHz, CDCl₃) δ 8.51 (s, 1H), 7.96 (d, J=5.6 Hz, 1H), 7.71 (s, 2H), 7.44 (s, 5H), 6.81 (d, J=5.6 Hz, 1H), 5.44-5.55 (m, 2H), 3.88-3.93 (m, 1H), 3.70-3.79 (m, 3H), 3.34 (s, 2H), 1.98-2.05 (m, 1H), 1.64-1.70 (m, 1H).

Step D—Synthesis of Intermediate Compound 12d-1 and 12d-2

A solution of 12c (637.7 mg, 1.848 mmol) in EtOH (15 mL) was heated to reflux for 48 hours, cooled to room temperature and concentrated. The residue was purified using preparative TLC on silica gel (dichloromethane:MeOH=10:1) to give 12d-1 as the more polar (lower band) and 12d-2 as the less polar (upper band). 12d-1: ¹H NMR (400 MHz, CDCl₃) δ 7.49-7.53 (m, 2H), 7.27-7.29 (m, 3H), 7.19 (d, J=7.2 Hz, 1H), 6.50 (d, J=7.2 Hz, 1H), 5.33-5.43 (m, 2H), 3.93 (s, 4H), 3.43-3.61 (m, 2H), 1.94 (t, J=8.0 Hz, 2H). 12d-2: ¹H NMR (400 MHz, CDCl₃) δ 7.53-7.60 (m, 2H), 7.34 (s, 1H), 7.25-7.31 (m, 3H), 6.52 (d, J=7.2 Hz, 1H), 5.35-5.41 (m, 2H), 4.11-4.18 (m, 2H), 3.95-3.97 (m, 1H), 3.62-3.64 (m, 1H), 3.48-3.51 (m, 1H), 3.22-3.26 (m, 1H), 2.27 (t, J=7.2 Hz, 2H).

Step E—Synthesis of Intermediate Compound 12e

A solution of compound 12d-1 (88.65 mg, 0.271 mmol) in dichloromethane (5 mL) was treated with N-bromosuccinimide (193.02 mg, 1.08 mmol) at 0° C. The reaction mixture was allowed to stir at 18° C. for 2 hours, quenched with aqueous Na₂SO₃ (1 mL), diluted with water (3 mL) and extracted with dichloromethane (4×6 mL). The combined organic layer was washed with brine (3 mL), dried over Na₂SO₄, filtered, and the filtrate was concentrated. The residue was purified using preparative TLC on silica gel (dichloromethane:MeOH=10:1) to provide (±)-12e. ¹H NMR (400 MHz, CDCl₃) δ 8.25 (s, 1H), 7.41-7.44 (m, 2H), 7.22-7.34 (m, 3H), 5.22-5.31 (m, 2H), 4.21 (s, 2H), 3.88-3.92 (m, 2H), 3.56 (d, J=5.6 Hz, 1H), 3.41 (d, J=9.2 Hz, 1H), 1.95-2.01 (m, 1H), 1.81-1.86 (m, 1H). Resolution to the enantiomers was accomplished with SFC (Chiralpak AS 250×30 mm, 40% MeOH (0.1% NH₃H₂O) in SC—CO₂, 80 mL/min, 220 nm) to provide earlier eluting 12e-1 (ent A) and later eluting 12e-2 (ent B).

Step F—Synthesis of Intermediate Compound 12f

A solution of 12e-2 (ent B) (34.95 mg, 0.087 mmol) in DMF (3 mL) was treated with Cs₂CO₃ (84.61 mg, 0.260 mmol) and iodomethane (37 mg, 0.260 mmol). The mixture was allowed to stir at 25° C. for 1 hour, filtered and the filtrate was concentrated. The residue was purified using column chromatography on silica gel (MeOH:dichloromethane=1:20) to provide 12f. ¹H NMR (400 MHz, MeOD) δ 8.18 (s, 1H), 7.36 (d, J=4.0 Hz, 2H), 7.26 (dd, J=1.6, 4.8 Hz, 3H), 5.15-5.29 (m, 2H), 4.11-4.24 (m, 2H), 3.88-3.97 (m, 1H), 3.72-3.83 (m, 2H), 3.37 (d, J=10.6 Hz, 1H), 3.01 (s, 3H), 1.81-1.96 (m, 2H). MS (+ESI) m/z: 419.1, 421.1.

Step G—Synthesis of Intermediate Compound 12g

A solution of 12f (33.56 mg, 0.080 mmol) in DMSO (3 mL) was treated with (3-chloro-2,4-difluorophenyl)methanamine (142.08 mg, 0.81 mmol), N,N-diisopropylethylamine (0.141 mL, 0.81 mmol), and Pd(Ph₃P)₄ (46.2 mg, 0.04 mmol). The mixture was allowed to stir at 90° C. for 4 hours under CO (1 atm), filtered and the filtrate was diluted with ethyl acetate and washed with 1M aqueous HCl (3 mL, 1M) and brine, dried over anhydrous sodium sulfate, filtered, and the filtrate was concentrated. The crude residue was purified using preparative TLC on silica gel (ethyl acetate) to provide 12g. ¹H NMR (400 MHz, CDCl₃) δ 10.53 (brs, 1H), 8.36 (s, 1H), 7.55 (d, J=6.4 Hz, 2H), 7.29-7.40 (m, 4H), 6.95 (t, J=7.8 Hz, 1H), 5.29-5.38 (m, 2H), 4.61-4.73 (m, 2H), 4.07-4.14 (m, 1H), 3.87-4.05 (m, 3H), 3.75 (d, J=10.2 Hz, 1H), 3.50 (d, J=10.2 Hz, 1H), 3.11 (s, 3H), 2.10 (td, J=7.2, 13.6 Hz, 1H), 1.84-1.97 (m, 1H). MS (+ESI) m/z: 544.1.

Step H—Synthesis of Compound 55

A solution of 12g (22.2 mg, 0.041 mmol) in DMF (3 mL) was treated with lithium chloride (15.59 mg, 0.408 mmol) and heated to 80° C. for 1.5 hours, cooled to room temperature and directly purified using preparative RP-HPLC to provide compound 55. ¹H NMR (400 MHz, CDCl₃) δ 10.45 (brs, 1H), 8.31 (brs, 1H), 6.74-7.04 (m, 1H), 4.66 (d, J=4.8 Hz, 2H), 4.04-4.19 (m, 3H), 3.90-4.01 (m, 2H), 3.66 (d, J=10.2 Hz, 1H), 3.18 (s, 3H), 2.29 (td, J=7.2, 14.0 Hz, 1H), 2.05-2.16 (m, 1H). MS (+ESI) m/z: 454.0.

Compound 56 made using this method and using intermediate 12e-1 (enantiomer A) as the starting material.

The following compound of the present invention was made using the methods described in the Example above and substituting the appropriate reactants and reagents.

| compound | Structure | enantiomer | Exact Mass [M + H]+ |
|---|---|---|---|
| 56 | 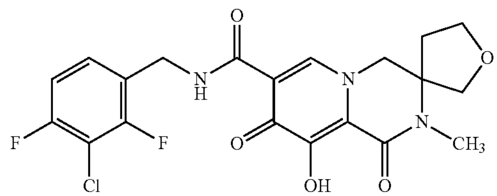 [SMILES: CN1C(=O)c2c(O)c(=O)c(C(=O)NCc3ccc(F)c(Cl)c3F)cn2CC12CCOC2] | A | Calc'd 454.1, found 454.1 |
| 57 | 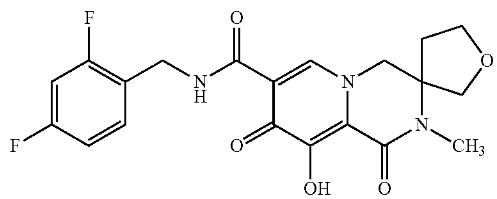 [SMILES: CN1C(=O)c2c(O)c(=O)c(C(=O)NCc3ccc(F)cc3F)cn2CC12CCOC2] | A | Calc'd 420.1, found 420.2 |
| 58 | 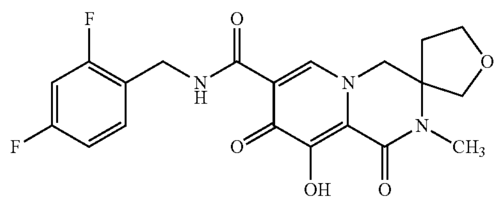 [SMILES: CN1C(=O)c2c(O)c(=O)c(C(=O)NCc3ccc(F)cc3F)cn2CC12CCOC2] | B | Calc'd 420.1, found 420.2 |
| 59 | 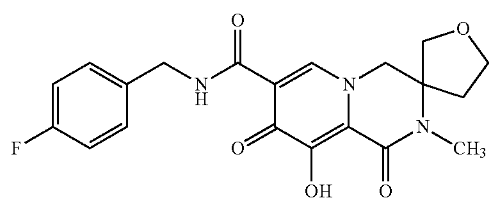 [SMILES: CN1C(=O)c2c(O)c(=O)c(C(=O)NCc3ccc(F)cc3)cn2CC12CCOC2] | A | Calc'd 402.1, found 402.1 |
| 60 | 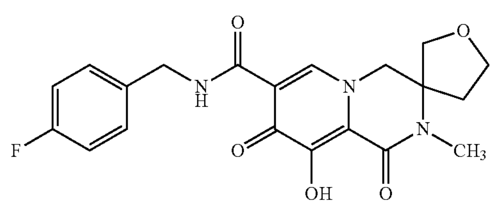 [SMILES: CN1C(=O)c2c(O)c(=O)c(C(=O)NCc3ccc(F)cc3)cn2CC12CCOC2] | B | Calc'd 402.1, found 402.1 |
| 61 | 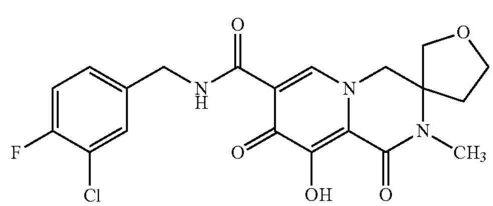 [SMILES: CN1C(=O)c2c(O)c(=O)c(C(=O)NCc3ccc(F)c(Cl)c3)cn2CC12CCOC2] | A | Calc'd 436.1, found 436.1 |
| 62 | 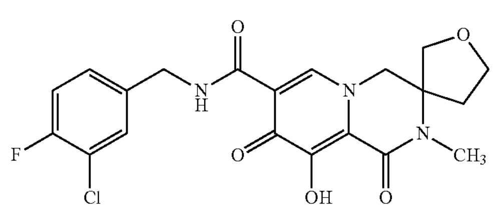 [SMILES: CN1C(=O)c2c(O)c(=O)c(C(=O)NCc3ccc(F)c(Cl)c3)cn2CC12CCOC2] | B | Calc'd 436.1, found 436.1 |

-continued

| compound | Structure | enantiomer | Exact Mass [M + H]+ |
|---|---|---|---|
| 63 | 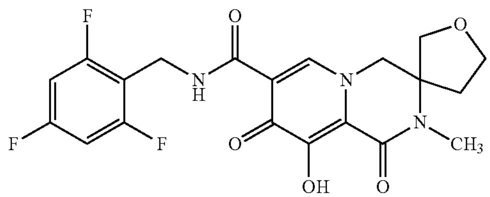 [SMILES: CN1C(=O)c2c(O)c(=O)c(C(=O)NCc3c(F)cc(F)cc3F)cn2CC12CCOC2] | A | Calc'd 438.1, found 438.1 |
| 64 | 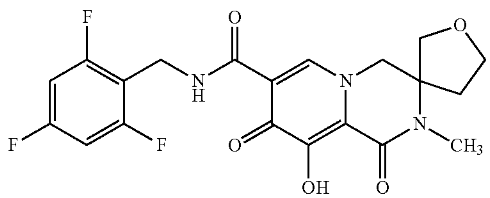 [SMILES: CN1C(=O)c2c(O)c(=O)c(C(=O)NCc3c(F)cc(F)cc3F)cn2CC12CCOC2] | B | Calc'd 438.1, found 438.1 |
| 65 | 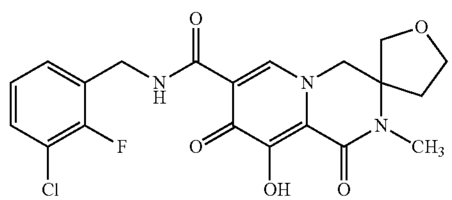 [SMILES: CN1C(=O)c2c(O)c(=O)c(C(=O)NCc3cccc(Cl)c3F)cn2CC12CCOC2] | A | Calc'd 436.1, found 436.1 |
| 66 | 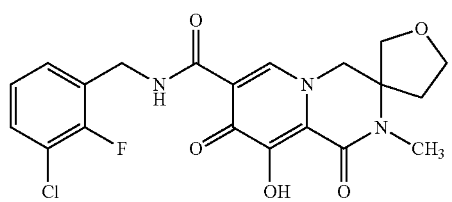 [SMILES: CN1C(=O)c2c(O)c(=O)c(C(=O)NCc3cccc(Cl)c3F)cn2CC12CCOC2] | B | Calc'd 436.1, found 436.1 |
| 67 | 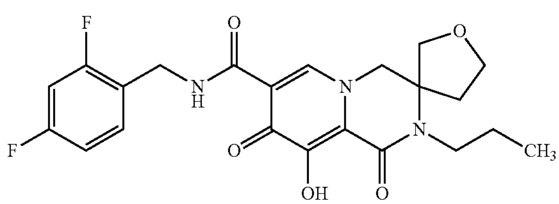 [SMILES: CCCN1C(=O)c2c(O)c(=O)c(C(=O)NCc3ccc(F)cc3F)cn2CC12CCOC2] | (±) | Calc'd 448.2, found 448.2 |
| 68 | 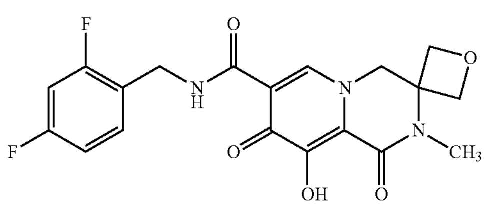 [SMILES: CN1C(=O)c2c(O)c(=O)c(C(=O)NCc3ccc(F)cc3F)cn2CC12COC2] | n/a | Calc'd 406.1, found 406.1 |
| 69 | 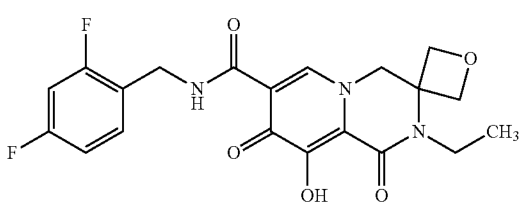 [SMILES: CCN1C(=O)c2c(O)c(=O)c(C(=O)NCc3ccc(F)cc3F)cn2CC12COC2] | n/a | Calc'd 420.1, found 420.1 |

| compound | Structure | enantiomer | Exact Mass [M + H]+ |
|---|---|---|---|
| 70 | 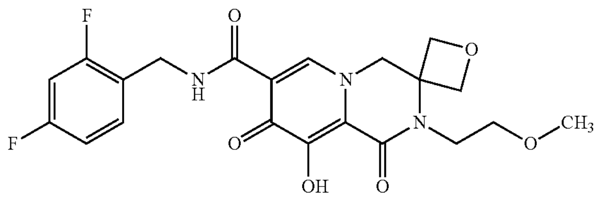 [SMILES: COCCN1C(=O)c2c(O)c(=O)c(C(=O)NCc3ccc(F)cc3F)cn2CC12COC2] | n/a | Calc'd 450.1, found 450.1 |

The following compounds of the present invention were prepared using the appropriate reactants and reagents according to the methods described in Example 12 from (±)-12e with chiral resolution after Step G (carbonylation) using the methods shown below the table.

| compound | Structure | enantiomer[1] | Exact Mass [M + H]+ |
|---|---|---|---|
| 71 | 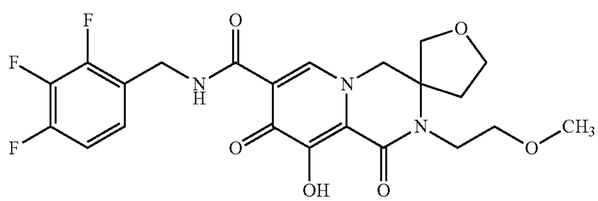 [SMILES: COCCN1C(=O)c2c(O)c(=O)c(C(=O)NCc3ccc(F)c(F)c3F)cn2CC12CCOC2] | A[2] | Calc'd 482.2, found 482.1 |
| 72 | 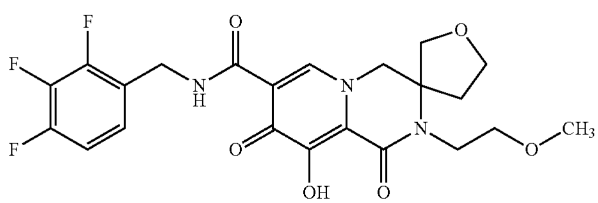 [SMILES: COCCN1C(=O)c2c(O)c(=O)c(C(=O)NCc3ccc(F)c(F)c3F)cn2CC12CCOC2] | B[2] | Calc'd 482.2, found 482.1 |
| 73 | 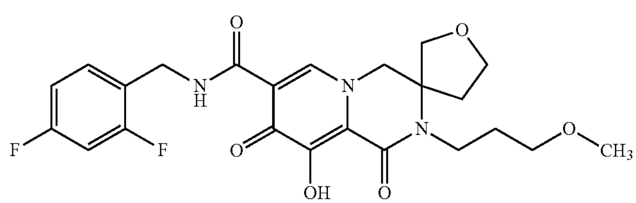 [SMILES: COCCCN1C(=O)c2c(O)c(=O)c(C(=O)NCc3ccc(F)cc3F)cn2CC12CCOC2] | A[2] | Calc'd 478.2, found 478.1 |
| 74 | 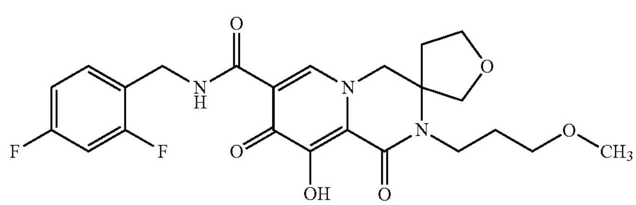 [SMILES: COCCCN1C(=O)c2c(O)c(=O)c(C(=O)NCc3ccc(F)cc3F)cn2CC12CCOC2] | B[2] | Calc'd 478.2, found 478.1 |
| 75 | 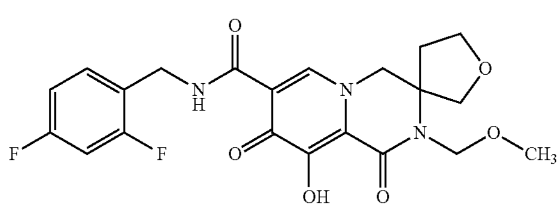 [SMILES: COCN1C(=O)c2c(O)c(=O)c(C(=O)NCc3ccc(F)cc3F)cn2CC12CCOC2] | A[2] | Calc'd 450.1, found 450.1 |

| compound | Structure | enantiomer[1] | Exact Mass [M + H]+ |
|---|---|---|---|
| 76 | 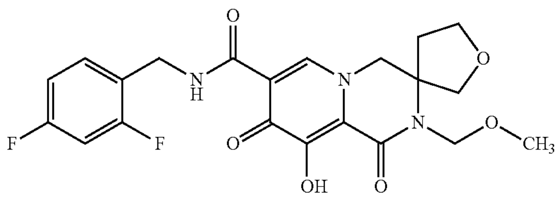 [SMILES: COCN1C(=O)c2c(O)c(=O)c(C(=O)NCc3ccc(F)cc3F)cn2CC12CCOC2] | B[2] | Calc'd 450.1, found 450.1 |
| 77 | 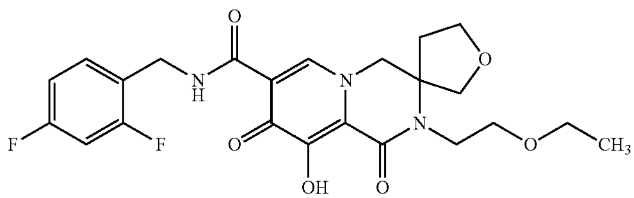 [SMILES: CCOCCN1C(=O)c2c(O)c(=O)c(C(=O)NCc3ccc(F)cc3F)cn2CC12CCOC2] | A[3] | Calc'd 478.2, found 478.2 |
| 78 | 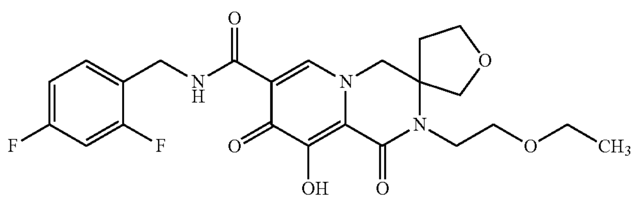 [SMILES: CCOCCN1C(=O)c2c(O)c(=O)c(C(=O)NCc3ccc(F)cc3F)cn2CC12CCOC2] | B[3] | Calc'd 478.2, found 478.2 |
| 79 | 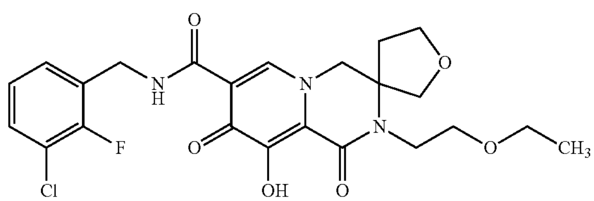 [SMILES: CCOCCN1C(=O)c2c(O)c(=O)c(C(=O)NCc3cccc(Cl)c3F)cn2CC12CCOC2] | A[4] | Calc'd 494.1, found 494.1 |
| 80 | 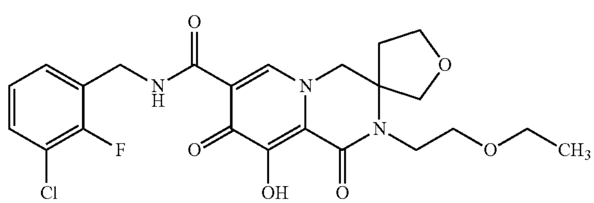 [SMILES: CCOCCN1C(=O)c2c(O)c(=O)c(C(=O)NCc3cccc(Cl)c3F)cn2CC12CCOC2] | B[4] | Calc'd 494.1, found 494.1 |

[1]Enantiomer A is earlier eluting and enantiomer B is later eluting with the specified conditions
[2]OJ 250 × 30 mm, 30% MeOH (0.1% NH$_3$H$_2$O) in SC—CO$_2$, 60 mL/min, 220 nm
[3]Chiralpak AS 250 × 30 mm, 30% MeOH (0.1% NH$_3$H$_2$O) in SC—CO$_2$, 60 mL/min, 220 nm
[4]Chiralpak AS 250 × 30 mm, 20% MeOH (0.1% NH$_3$H$_2$O) in SC—CO$_2$, 60 mL/min, 220 nm

Example 13

Preparation of Compound 81 and 82

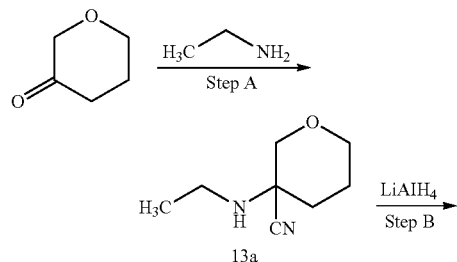

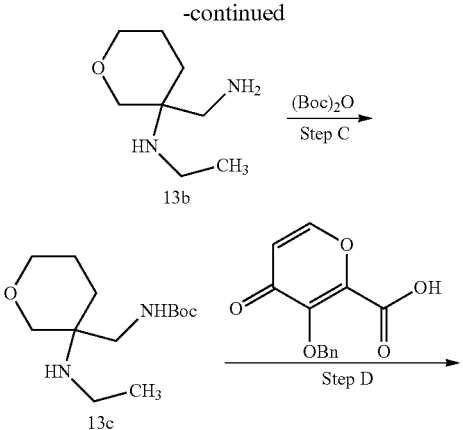

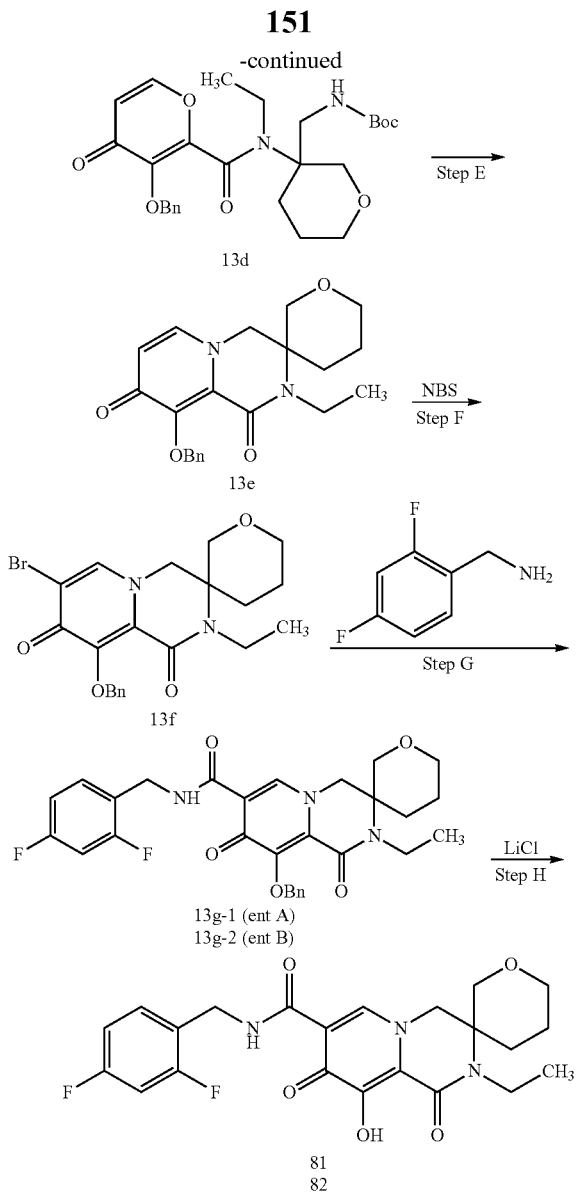

Step A—Synthesis of Intermediate Compound 13a

A mixture of dihydro-2H-pyran-3(4H)-one (2 g, 19.98 mmol) and ethanamine (1.801 g, 40.0 mmol) was allowed to stir at 18° C. for 5 hours and then trimethylsilyl cyanide (2.68 mL, 19.98 mmol) was added dropwise at 0° C. After addition, the mixture was allowed to stir at 18° C. for 16 hours and the residue was diluted with dichloromethane and concentrated. The residue was purified using column chromatography on silica gel (petroleum ether:ethyl acetate=2:1) to provide 13a. $^1$H NMR (400 MHz, CDCl$_3$) δ 3.91-4.01 (m, 2H), 3.43 (t, J=6.0 Hz, 1H), 3.32 (d, J=12.0 Hz, 1H), 2.72-2.82 (m, 2H), 2.14-2.23 (m, 1H), 1.85-1.91 (m, 1H), 1.70-1.75 (m, 2H), 1.14 (t, J=6.8 Hz, 3H).

Step B—Synthesis of Intermediate Compound 13b

A solution of 13a (2.4 g, 15.56 mmol) in THF (40 mL) was treated with LiAlH$_4$ (1.181 g, 31.1 mmol) at 0° C. in portions, the mixture was allowed to stir at 18° C. for 2 hours and treated with saturated aqueous Na$_2$SO$_4$ (0.5 mL) at 0° C. The mixture was filtered, the filtrate was dried over anhydrous Na$_2$SO$_4$, filtered and the filtrate was concentrated to provide 13b that was used without further purification. $^1$H NMR (400 MHz, CDCl$_3$) δ 3.69-3.72 (m, 1H), 3.45-3.55 (m, 2H), 3.31-3.39 (m, 1H), 2.60-2.65 (m, 2H), 2.40-2.53 (m, 2H), 1.52-1.62 (m, 1H), 1.26-1.40 (m, 3H), 1.07-1.10 (m, 3H).

Step C—Synthesis of Intermediate Compound 13c

A solution of 13b (2 g, 12.64 mmol) in dichloromethane (40 mL) was treated with Et$_3$N (5.28 mL, 37.9 mmol) and (Boc)$_2$O (3.23 mL, 13.90 mmol) and the mixture was allowed to stir at 18° C. for 16 hours, washed with aqueous NaHCO$_3$ (40 mL) and extracted with dichloromethane (30 mL×3). The combined organic layers were dried over anhydrous Na$_2$SO$_4$ and concentrated. The residue was purified using column chromatography on silica gel (dichloromethane:ethyl acetate=1:1) to provide 13c. $^1$H NMR (400 MHz, CDCl$_3$) δ 5.05 (br s, 1H), 3.76-3.79 (m, 1H), 3.52-3.55 (m, 1H), 3.42-3.45 (m, 1H), 3.28-3.31 (m, 1H), 3.02-3.04 (m, 1H), 2.41-2.51 (m, 2H), 1.37-1.56 (m, 14H), 1.10 (t, J=6.0 Hz, 3H).

Step D—Synthesis of Intermediate Compound 13d

A solution of 13c (1 g, 4.06 mmol) in THF (25 mL) was treated with PyClu (1.621 g, 4.87 mmol) and N,N-diisopropylethylamine (2.128 mL, 12.18 mmol) at 15° C. The solution was allowed to stir at 15° C. for 40 minutes and then treated with a solution of intermediate tert-butyl ((3-(ethylamino)tetrahydro-2H-pyran-3-yl)methyl)carbamate (1.6 g, 6.09 mmol) in THF (5 mL) at 15° C. The mixture was allowed to stir at 15° C. for 16 hours, diluted with water (30 mL) and extracted with ethyl acetate (30 mL×3). The combined organic phase was dried over Na$_2$SO$_4$, concentrated and purified using column chromatography on silica gel (petroleum ether:ethyl acetate=3:1) to provide 13d. $^1$H NMR (400 MHz, CDCl$_3$) δ 7.70 (d, J=5.2 Hz, 1H), 7.41-7.43 (m, 2H), 7.31-7.34 (m, 3H), 6.44 (d, J=5.2 Hz, 1H), 5.18-5.30 (m, 2H), 4.64 (s, 1H), 3.94-9.97 (m, 1H), 3.70-3.75 (m, 3H), 3.43-3.47 (m, 1H), 3.18-3.37 (m, 2H), 2.67-2.70 (m, 1H), 1.42-1.52 (m, 4H), 1.36 (s, 9H), 1.06-1.10 (m, 3H).

Step E—Synthesis of Intermediate Compound 13e

A solution of 13d (2 g, 4 mmol) in dichloromethane (16 mL) was treated with TFA (4 mL) at 0° C. and stirred at 16° C. for 4 hours. The mixture was concentrated and the residue was dissolved in EtOH (20 mL) and heated at 80° C. for 16 hours. The mixture was concentrated and the residue was purified using RP-HPLC to provide 13e. $^1$H NMR (400 MHz, CDCl$_3$) δ 7.52-7.54 (m, 2H), 7.27-7.31 (m, 3H), 7.17 (d, J=6.4 Hz, 1H), 6.52 (d, J=6.4 Hz, 1H), 5.28-5.43 (m, 2H), 4.19 (d, J=13.2 Hz, 1H), 3.89-3.95 (m, 2H), 3.52-3.57 (m, 2H), 3.33-3.38 (m, 1H), 2.10-2.45 (m, 2H), 1.92-1.95 (m, 1H), 1.71-1.76 (m, 3H), 1.21 (t, J=7.2 Hz, 3H). MS (+ESI) m/z: 369.1.

Step F—Synthesis of Intermediate Compound 13f

A solution of 13e (500 mg, 1.36 mmol) in dichloromethane (10 mL) was treated with N-bromosuccinimide (484 mg, 2.7 mmol) at 18° C. The reaction mixture was allowed to stir for 1 hour at 18° C., washed with aqueous Na$_2$SO$_3$ (10 mL), dried over anhydrous Na$_2$SO$_4$ filtered and the filtrate was concentrated. The residue was purified using preparative TLC on silica gel (dichloromethane:MeOH=10:1) to provide 13f. $^1$H NMR (400 MHz, CDCl$_3$) δ 7.63 (s, 1H), 7.57-7.59 (m, 2H), 7.29-7.32 (m, 3H), 5.28-5.43 (m, 2H), 4.25 (d, J=13.2 Hz, 1H), 3.95 (d, J=13.2 Hz, 1H), 3.54-3.59 (m, 2H), 3.28-3.37 (m, 4H), 1.97-2.02 (m, 1H), 1.75-1.78 (m, 3H), 1.23 (t, J=7.2 Hz, 3H). MS (+ESI) m/z: 447.1, 449.1.

Step G—Synthesis of Intermediate Compound 13g-1 and Intermediate Compound 13g-2

A mixture of 13f (120 mg, 0.268 mmol), N,N-diisopropylethylamine (0.141 mL, 0.805 mmol) and 2,4-difluorophenylmethanamine (192 mg, 1.341 mmol) in DMSO (1 mL) and MeOH (4 mL) was treated with Pd(Ph$_3$P)$_4$ (155 mg, 0.134 mmol). The mixture was allowed to stir at 80° C. for 3 hours under carbon monoxide (1 atm), cooled to room temperature and concentrated. The residue was dissolved in ethyl acetate (5 mL), filtered and the filtrate was washed with 0.5 M HCl (5 mL) and concentrated. The residue was purified preparative TLC on silica gel (ethyl acetate:dichloromethane=1.5:1) to provide (±)-13g. MS (+ESI) m/z: 538.2. Resolution to the enantiomers was accomplished with SFC (Chiral Pak AD, 5 μm, 250×30 mm I.D. 40% EtOH (contained 0.1% NH$_3$H$_2$O) in SC—CO$_2$, 60 mL/min, 220 nm) to provide 13g-1 and 13g-2. 13g-1: $^1$H NMR (400 MHz, CDCl$_3$) δ 10.41 (s, 1H), 8.29 (s, 1H), 7.45-7.47 (m, 2H), 7.20-7.33 (m, 4H), 6.72-6.76 (m, 2H), 5.21-5.30 (m, 2H), 4.57 (d, J=6.0 Hz, 2H), 4.27 (d, J=13.2 Hz, 1H), 3.97 (d, J=13.2 Hz, 1H), 3.85-3.87 (m, 1H), 3.64-3.66 (m, 1H), 3.49-3.53 (m, 2H), 3.28-3.30 (m, 2H), 1.88-1.91 (m, 1H), 1.64-1.71 (m, 3H), 1.15-1.18 (m, 3H). 13g-2. $^1$H NMR (400 MHz, CDCl$_3$) δ 10.42 (t, J=5.6 Hz, 1H), 8.29 (s, 1H), 7.45-7.47 (m, 2H), 7.20-7.33 (m, 4H), 6.72-6.76 (m, 2H), 5.21-5.30 (m, 2H), 4.57 (d, J=6.0 Hz, 2H), 4.27 (d, J=13.2 Hz, 1H), 3.97 (d, J=13.2 Hz, 1H), 3.85-3.87 (m, 1H), 3.64-3.66 (m, 1H), 3.49-3.53 (m, 2H), 3.28-3.30 (m, 2H), 1.88-1.91 (m, 1H), 1.64-1.71 (m, 3H), 1.15-1.18 (m, 3H).

Step H—Synthesis of Compound 81

A solution of 13g-1 (25 mg, 0.047 mmol) and lithium chloride (19.72 mg, 0.465 mmol) in DMF (4 mL) was allowed to stir at 100° C. for 2 hours. The mixture was filtered, and the filtrate was directly purified using RP-HPLC to provide compound 81. $^1$H NMR (400 MHz, CDCl$_3$) δ 10.44 (s, 1H), 8.34 (s, 1H), 7.33-7.39 (m, 1H), 6.77-6.83 (m, 2H), 4.62 (d, J=6.0 Hz, 2H), 4.41 (d, J=13.2 Hz, 1H), 4.12 (d, J=13.2 Hz, 1H), 3.98-4.01 (m, 1H), 3.50-3.69 (m, 5H), 2.11-2.14 (m, 1H), 1.78-1.92 (m, 3H), 1.26 (t, J=6.8 Hz, 3H). MS (+ESI) m/z 448.1.

Step H—Synthesis of Compound 82

A solution of 13g-2 (25 mg, 0.047 mmol) and lithium chloride (19.72 mg, 0.465 mmol) in DMF (4 mL) was allowed to stir at 100° C. for 2 hours. The mixture was filtered, and the filtrate was directly purified using RP-HPLC to provide compound 82. $^1$H NMR 0355117-0139-P2 (400 MHz, CDCl$_3$) δ 10.52 (s, 1H), 8.41 (s, 1H), 7.33-7.39 (m, 1H), 6.77-6.83 (m, 2H), 4.64 (d, J=6.0 Hz, 2H), 4.44 (d, J=13.2 Hz, 1H), 4.13 (d, J=13.2 Hz, 1H), 3.98-4.01 (m, 1H), 3.41-3.71 (m, 5H), 2.11-2.14 (m, 1H), 1.78-1.92 (m, 3H), 1.26 (t, J=6.8 Hz, 3H). MS (+ESI) m/z: 448.1.

The following compounds of the present invention were made using the methods described in the Example above and substituting the appropriate reactants and reagents.

| Compound | Structure | enantiomer[1] | Exact Mass [M + H]+ |
|---|---|---|---|
| 83 | 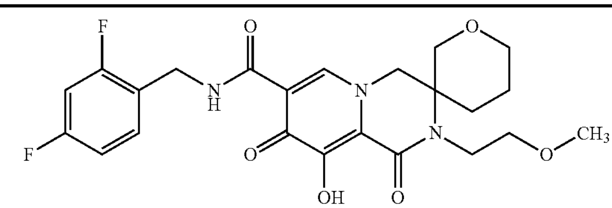 | A[2] | Calc'd 478.2, found 478.1 |
| 84 | 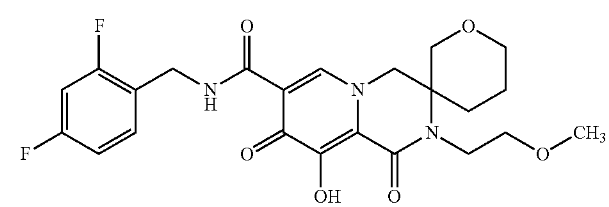 [SMILES: COCCN1C(=O)c2c(O)c(=O)c(C(=O)NCc3ccc(F)cc3F)cn2CC12CCCOC2] | B[2] | Calc'd 478.2, found 478.1 |
| 85 | 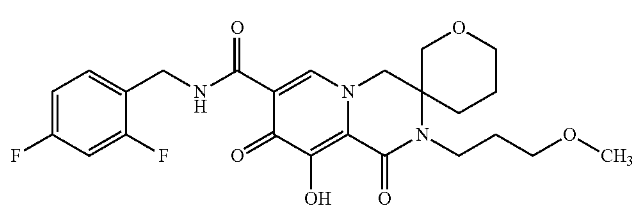 [SMILES: COCCCN1C(=O)c2c(O)c(=O)c(C(=O)NCc3ccc(F)cc3F)cn2CC12CCCOC2] | A[3] | Calc'd 492.2, found 492.1 |
| 86 | 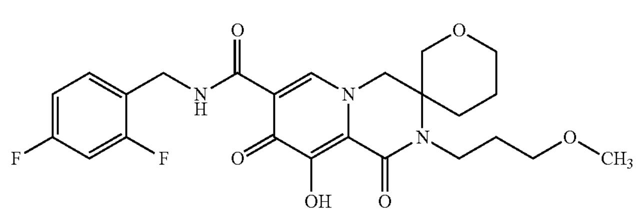 [SMILES: COCCCN1C(=O)c2c(O)c(=O)c(C(=O)NCc3ccc(F)cc3F)cn2CC12CCCOC2] | B[3] | Calc'd 492.2, found 492.0 |

[1]Enantiomer A is earlier eluting and enantiomer B is later eluting with the specified conditions
[2]Chiral Pak AS, 250 × 30 mm, 30% IPA (0.1% NH$_3$H$_2$O) in SC—CO$_2$, 60 mL/min, 220 nm
[3]Chiral Pak AD, 250 × 30 mm 55% EtOH (0.1% NH$_3$H$_2$O) in SC—CO$_2$, 80 mL/min, 220 nm

Example 14

Preparation of Compound 87

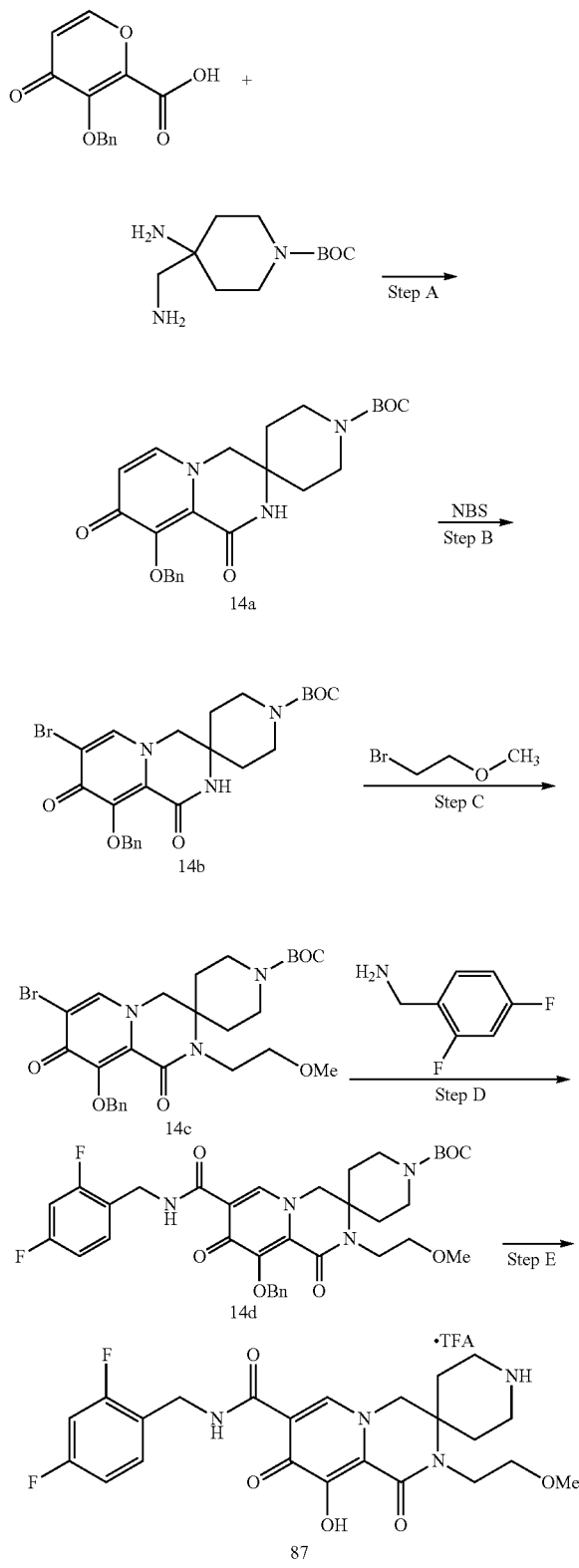

Step A—Synthesis of Intermediate Compound 14a 3-(benzyloxy)-4-oxo-4H-pyran-2-carboxylic acid (1000 mg, 4.06 mmol) and tert-butyl 4-amino-4-(aminomethyl)piperidine-1-carboxylate (1397 mg, 6.09 mmol) were suspended in water and treated with sodium bicarbonate (1024 mg, 12.18 mmol). The mixture was allowed to stir at rt for 30 minutes until effervescence ceased, then capped and heated at 100° C. for 4 h, cooled to room temperature and neutralized with glacial acetic acid. The mixture was filtered and directly purified using RP-MPLC to provide a mixture of open and cyclized products that was treated with excess EDC/HOBT in dichloromethane, stirred at room temperature, concentrated and purified using RP-MPLC to provide 14a. LRMS (+ESI) m/z: 440.1

Step B—Synthesis of Intermediate Compound 14b

A solution of 14a (556 mg, 1.265 mmol) in N,N-dimethylformamide (5.0 mL) was treated at rt with N-bromosuccinimide (270 mg, 1.518 mmol) and stirred at rt for 14 hours. DMSO was added and the mixture was purified using preparative RP-HPLC to provide 14b. LRMS (+ESI) m/z: 517.7, 519.7

Step C—Synthesis of Intermediate Compound 14c

A solution of 14b (100 mg, 0.193 mmol) in DMF (3.0 mL) was treated at rt with tert-butyl 9'-(benzyloxy)-7'-bromo-1', 8'-dioxo-1',2',4',8'-tetrahydrospiro[piperidine-4,3'-pyrido[1,2-a]pyrazine]-1-carboxylate (100 mg, 0.193 mmol) and Cs$_2$CO$_3$ (189 mg, 0.579 mmol), heated at rt for 14 h, cooled to room temperature, filtered and the filtrate was purified using preparative RP-HPLC to provide 14c. LRMS (+ESI) m/z: 576.2, 578.2

Step D—Synthesis of Intermediate Compound 14d

A mixture of 14c (40 mg, 0.069 mmol), 2,4-difluorobenzylamine (0.019 mL, 0.153 mmol), N,N-diisopropylethylamine (0.036 mL, 0.208 mmol) and Pd(PPh$_3$)$_4$ (40.1 mg, 0.035 mmol) was subsurface sparged with nitrogen and then heated at 90° C. under carbon monoxide (1 atm) for 8 hours. The mixture was diluted with water (100 uL), filtered and the filtrate was directly purified using RP-HPLC to provide 14d. LRMS (+ESI) m/z: 667.2

Step E—Synthesis of Compound 87

A solution of 14d (50 mg, 0.075 mmol) in trifluoroacetic acid (1 mL, 12.98 mmol) was allowed to stir for 2 hours at room temperature, diluted in DMSO and directly purified using RP-HPLC to provide compound 87. LRMS (+ESI) m/z: 477.1

The following compounds of the present invention were made using the methods described in the Example above and substituting the appropriate reactants and reagents.

| Compound | Structure | Exact Mass [M + H]+ |
|---|---|---|
| 88 | 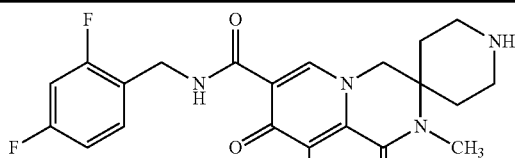 | Calc'd 433.2, found 432.9 |
| 89 | 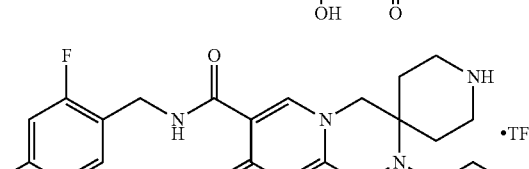 | Calc'd 491.2, found 491.1 |

Example 15

Preparation of Compound 90

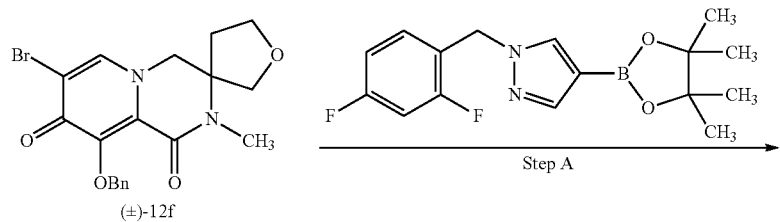

Step A—Synthesis of Intermediate Compound 15a

A mixture of (±)-12f (30 mg, 0.07 mmol) and Cs$_2$CO$_3$ (27.2 mg, 0.083 mmol) in water (0.1 mL) and dioxane (1 mL) was treated with Pd(Ph$_3$P)$_4$ (7.2 mg, 6.3 nmol). The mixture was heated under microwave heating at 130° C. for 1 hour. The mixture was directly purified using preparative TLC on silica gel (dichloromethane:methanol, 8:1) to provide intermediate compound 15a. LRMS (+ESI) m/z: 533.0. $^1$H NMR (400 MHz, CD$_3$OD) δ 8.53 (s, 1H), 8.22 (s, 1H), 8.06 (s, 1H), 7.27-7.38 (m, 6H), 6.97-6.99 (m, 2H), 5.42 (s, 2H), 5.23-5.24 (m, 2H), 4.23 (s, 2H), 3.75-3.94 (m, 3H), 3.40-3.43 (m, 1H), 3.04 (s, 3H), 1.92-1.93 (m, 2H).

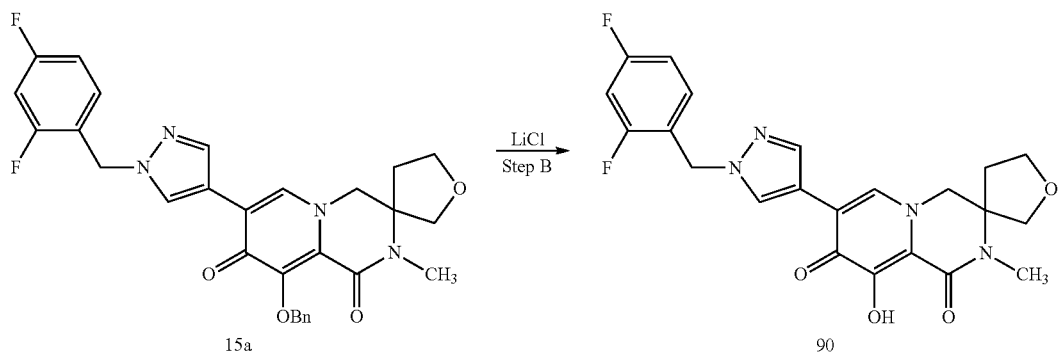

Step B—Synthesis of Compound 90

A mixture of intermediate compound 15a and lithium chloride (25.2 mg, 0.595 mmol) in DMF (3 mL) was heated at 90° C. for 5 hours. The mixture was filtered and the filtrate was directly purified using preparative RP-HPLC to provide compound 90. LRMS (+ESI) m/z: 443; $^1$H NMR: (400 MHz, CD$_3$OD) δ 8.46-8.48 (m, 1H), 7.98-8.02 (m, 2H), 7.28-7.32 (m, 1H), 6.96-7.01 (m, 2H), 5.35-5.39 (m, 2H), 4.25-4.28 (m, 1H), 3.86-4.06 (m, 4H), 3.61-3.06 (m, 1H), 3.14 (s, 3H), 2.14-2.28 (m, 2H).

The following compound of the present invention was made using the methods described in the Example above and substituting the appropriate reactants and reagents.

| Compound | Structure | Exact Mass [M + H]+ |
|---|---|---|
| 91 | 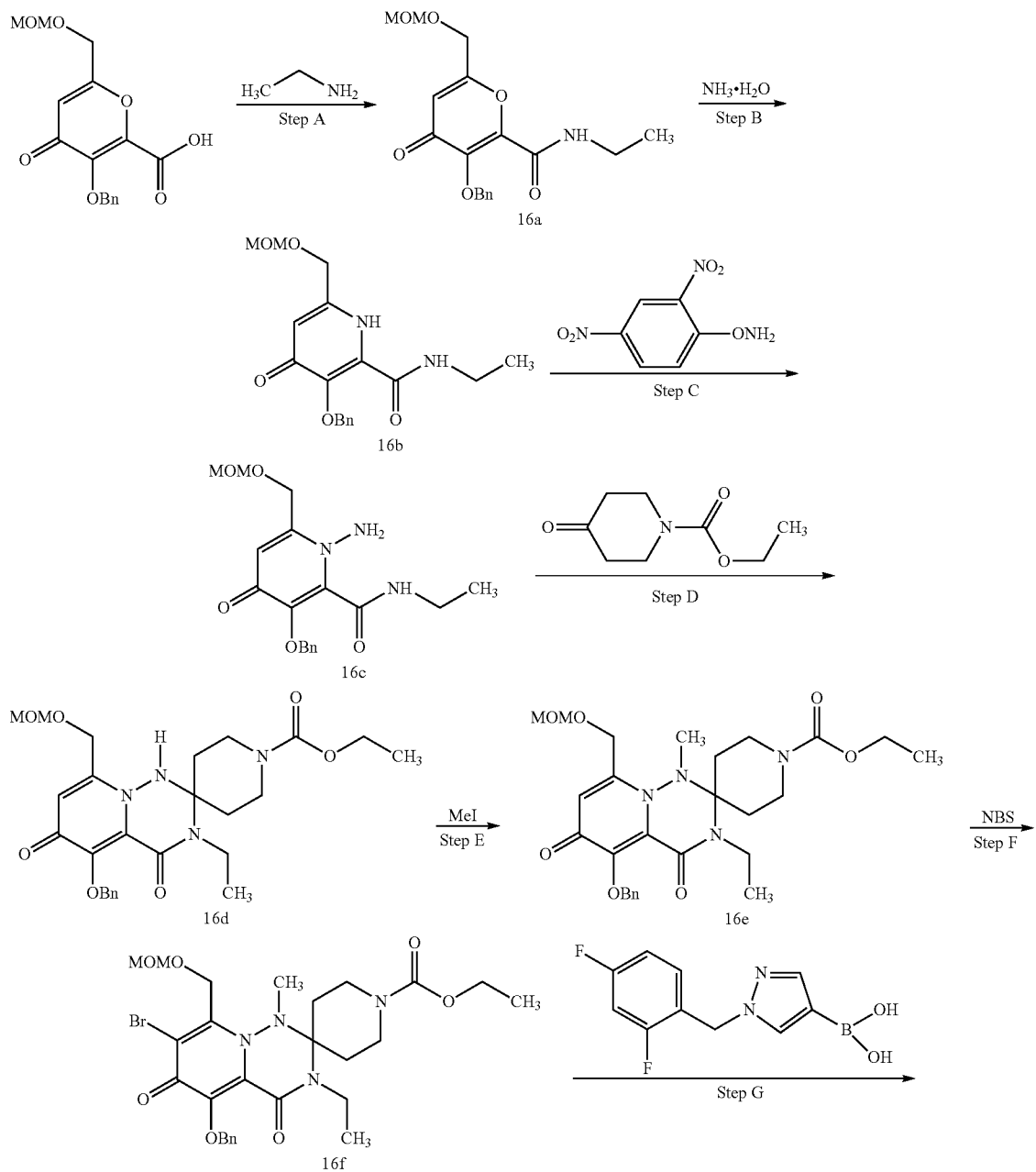 | Calc'd 457.2, found 457.2 |
Example 16
Preparation of Compound 92

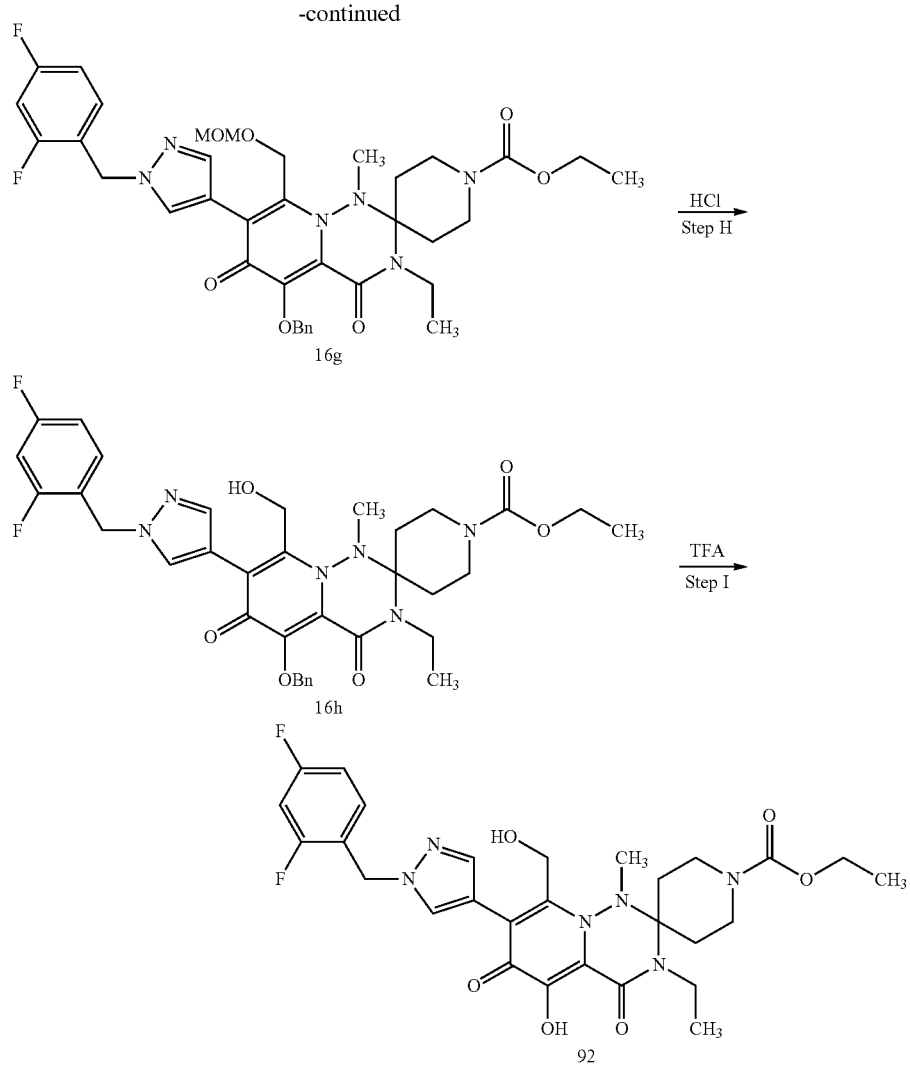

Step A—Synthesis of Intermediate Compound 16a

To a solution of 3-(benzyloxy)-6-((methoxymethoxy)methyl)-4-oxo-4H-pyran-2-carboxylic acid (10.0 g, 32.0 mmol), HATU (24.0 g, 64.0 mmol), HOAt (9.0 g, 64.0 mmol) in DMF (80 mL) was added ethanamine (10.0 mL, 153 mmol). The reaction mixture was allowed to stir in a sealed tube at room temperature overnight. The reaction mixture was diluted with water (40 mL) and extracted with ethyl acetate (2×100 mL). The combined organic portion was washed with brine, dried, filtered and evaporated under reduced pressure to provide a residue that was purified using column chromatography on silica gel (petroleum ether:ethyl acetate, 5:1) to provide intermediate compound 16a. LRMS (+ESI) m/z=348.4. $^1$H NMR (300 MHz, DMSO-d6) δ 8.54-8.58 (m, 1H), 7.34-7.44 (m, 5H), 6.53 (s, 1H), 5.18 (s, 2H), 4.68 (d, J=3.9 Hz, 2H), 4.46 (d, J=15.0 Hz, 2H), 3.30 (s, 3H), 3.17-3.27 (m, 2H), 1.02-1.07 (m, 3H).

Step B—Synthesis of Intermediate Compound 16b

To a solution of compound intermediate compound 16a (7.0 g, 20.0 mmol) in EtOH (90 mL) was added NH$_3$.water (90 mL) at room temperature, and the mixture was allowed to stir at room temperature for 5 hours. The mixture was concentrated in vacuo to provide crude intermediate compound 16b that was used directly for next step without further purification. LRMS (+ESI) m/z=347.2.

Step C—Synthesis of Intermediate Compound 16c

To a solution of crude intermediate compound 16b (6.0 g, 17 mmol) in DMF (60 mL) was added K$_2$CO$_3$ (4.9 g, 36 mmol) and O-(2, 4-dinitrophenyl)hydroxylamine (4.0 g, 20 mmol). The reaction mixture was allowed to stir at room temperature for 16 hours. The mixture was directly purified using preparative RP-HPLC to provide intermediate compound 16c. LRMS (+ESI) m/z=362.2. $^1$H NMR (400 MHz, DMSO-d6) δ 8.52-8.54 (m, 1H), 7.28-7.39 (m, 5H), 6.26 (s, 1H), 5.85 (s, 2H), 5.03 (s, 2H), 4.68 (d, J=4.8 Hz, 2H), 4.58-4.60 (m, 2H), 3.28 (d, J=7.2 Hz, 3H), 3.17-3.23 (m, 2H), 1.01-1.05 (m, 3H).

Step D—Synthesis of Intermediate Compound 16d

To a solution of intermediate compound 16c (200 mg, 0.56 mmol) in THF (8 mL) was added Acetic acid (9 mL) and ethyl 4-oxopiperidine-1-carboxylate (2.6 g, 15 mmol) at room temperature and the reaction mixture was heated to 80° C. under microwave heating for 1 hour. The mixture was concentrated in vacuo and the resulting residue was purified using column chromatography on silica gel (EA:CH$_3$OH=120:1) to provide intermediate compound 16d. LRMS (+ESI) m/z=515.2. $^1$H NMR (400 MHz, CD$_3$OD) δ 7.39-7.41 (m, 2H), 7.28-7.35 (m, 3H), 6.69 (s, 1H), 5.26 (d, J=8.0 Hz, 1H), 5.13 (d, J=12.0 Hz, 1H), 4.66 (s, 2H), 4.38

(d, J=12.0 Hz, 1H), 4.28 (d, J=12.0 Hz, 1H), 4.13-4.19 (m, 2H), 3.90-3.93 (m, 1H), 3.73-3.77 (m, 1H), 3.57 (s, 1H), 3.46 (s, 1H), 3.36 (s, 2H), 3.28-3.32 (m, 1H), 3.22-3.26 (m, 1H), 3.16-3.21 (m, 1H), 2.59-2.66 (m, 2H), 2.24-2.31 (m, 2H), 1.26-1.30 (m, 3H), 1.06-1.10 (m, 3H).

Step E—Synthesis of Intermediate Compound 16e

To a solution of intermediate compound 16d (200 mg, 0.39 mmol) in DMF (2 mL) was added $Cs_2CO_3$ (130 mg, 0.40 mmol) and iodomethane (7 drops). The mixture was allowed to stir for 2 hours at room temperature. The reaction mixture was filtered and extracted with ethyl acetate (2×10 mL). The combined organic extracts were dried over $Na_2SO_4$ and concentrated in vacuo to provide intermediate compound 16e, which was used for the next step without further purification. LRMS (+ESI) m/z=529.3.

Step F—Synthesis of Intermediate Compound 16f

To a solution of intermediate compound 16e (150 mg, 0.28 mmol) in dichloromethane (2.0 mL) was added N-bromosuccinimide (71 mg, 0.40 mmol) and the mixture was allowed to stir at room temperature for 3 hours. The mixture was concentrated in vacuo and the resulting residue was purified using column chromatography on silica gel (petroleum ether:ethyl acetate=3:1 to ethyl acetate) to provide intermediate compound 16f as a solid. LRMS (+ESI) m/z=607.2. $^1$H NMR (400 MHz, Methanol-d4) δ 7.36-7.40 (m, 2H), 7.28-7.32 (m, 3H), 5.47 (d, J=8.0 Hz, 1H), 5.17 (d, J=12.0 Hz, 1H), 5.03 (d, J=12.0 Hz, 1H), 4.95 (d, J=8.0 Hz, 1H), 4.71-4.85 (m, 3H), 4.09-4.17 (m, 4H), 3.65-3.73 (m, 2H), 3.54-3.59 (m, 3H), 3.30-3.32 (m, 1H), 2.82 (s, 3H), 2.15-2.31 (m, 2H), 1.38-1.48 (m, 1H), 1.21-1.27 (m, 7H).

Step G—Synthesis of Intermediate Compound 16g

To a solution of intermediate compound 16f (50 mg, 0.08 mmol) in dioxane (3 mL) was added $Cs_2CO_3$ (54 mg, 0.16 mmol), $Pd(PPh_3)_4$ (20 mg, 0.02 mmol) and 1-(2,4-difluorobenzyl-4-(4,4,5,5-tetramethyl-1,3,2-dioxaborolan-2-yl)-1H-pyrazole (80 mg, 0.25 mmol) at room temperature and the reaction mixture was heated to 130° C. under microwave heating for 1 hour. The mixture was filtered and the filtrate was purified using preparative RP-HPLC to provide intermediate compound 16g. LRMS (+ESI) m/z=721.3.

Step H—Synthesis of Intermediate Compound 16h

To a solution of intermediate compound 16g (16 mg, 0.02 mmol) in ethyl acetate (4 mL) was added a solution of HCl/ethyl acetate (4 mL) at 0° C. The mixture was allowed to stir for 3 hours at room temperature. The mixture was concentrated in vacuo to provide intermediate compound 16h which was used without further purification. LRMS (+ESI) m/z=677.2.

Step I—Synthesis of Compound 92

To a solution of intermediate compound 16h (12 mg, 0.02 mmol) in dichloromethane (8 mL) was added TFA (3 mL) at 0° C. The mixture was allowed to stir for 3 hours at room temperature. The mixture was concentrated in vacuo and the resulting residue was purified using preparative RP-HPLC to provide compound 92. LRMS (+ESI) m/z=587.2. $^1$H NMR (400 MHz, Methanol-d4) 8.06-8.20 (m, 1H), 7.94 (s, 1H), 7.37-7.40 (m, 1H), 6.99-7.06 (m, 2H), 5.37-5.51 (m, 2H), 4.70 (d, J=12.0 Hz, 1H), 4.26 (d, J=12.0 Hz, 1H), 4.13-4.18 (m, 2H), 3.97 (d, J=12.0 Hz, 1H), 3.84-3.89 (m, 1H), 3.56-3.62 (m, 1H), 3.32-3.33 (m, 3H), 2.91 (s, 3H), 2.30-2.42 (m, 2H), 1.80-1.92 (m, 2H), 1.28-1.33 (m, 6H).

Example 17

Preparation of Compound 93

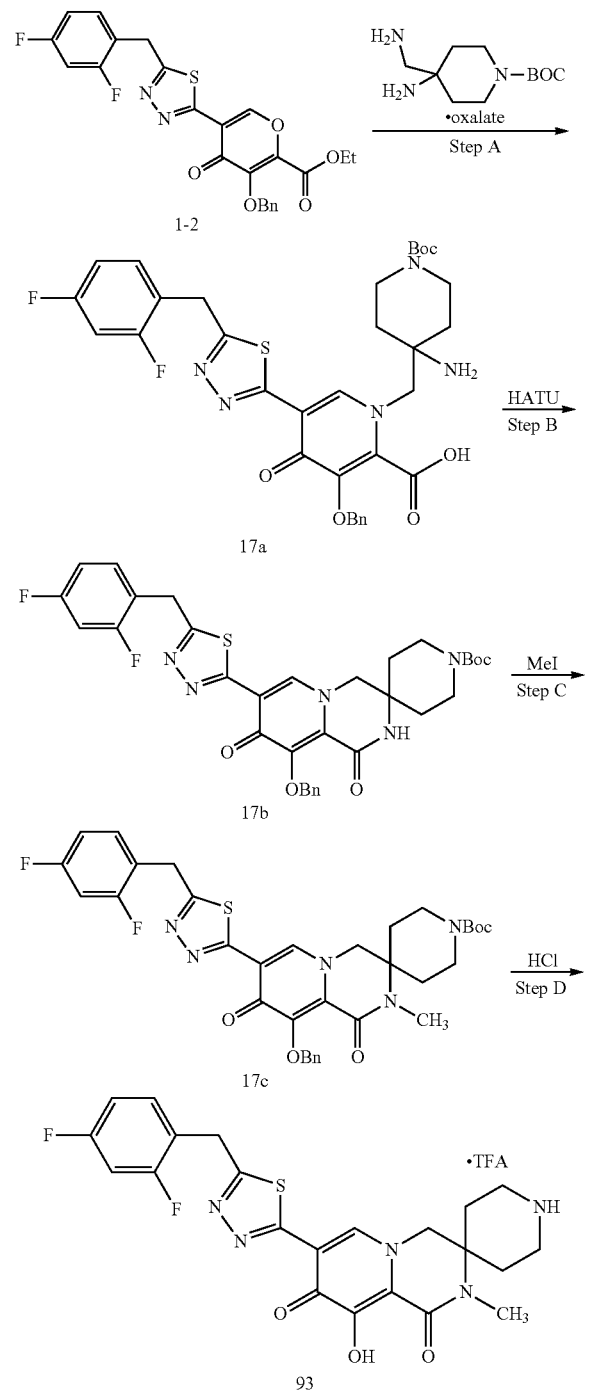

-continued

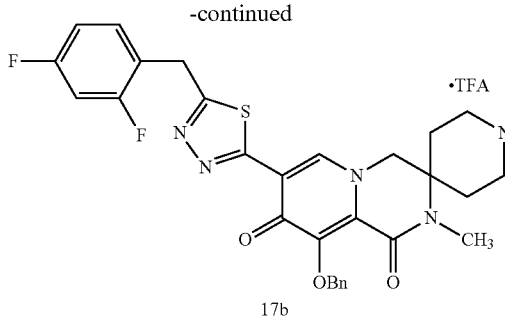

17b

Step A—Synthesis of Intermediate Compound 17a

A mixture of intermediate compound 1-2 (100 mg, 0.206 mmol) and tert-butyl 4-amino-4-(aminomethyl)piperidine-1-carboxylate oxalate (65.9 mg, 0.206 mmol) in N-methylimidazole (2 mL) was allowed to stir at room temperature for 2 hours. The reaction mixture was diluted with water (0.5 mL) and directly purified using RP-MPLC to provide intermediate compound 17a as a solid. LCMS (M+H)=668

Step B—Synthesis of Intermediate Compound 17b

A mixture of intermediate compound 17a (60 mg, 0.090 mmol), HATU (51.2 mg, 0.135 mmol) and diisopropylethylamine (34.8 mg, 0.270 mmol) in DMF (1 mL) was allowed to stir at room temperature for 4 hours. The reaction mixture was diluted with water (0.2 mL) and directly purified using RP-HPLC to provide intermediate compound 17b. LCMS (M+H)=650

Step C—Synthesis of Intermediate Compound 17c

A mixture of intermediate compound 17b (900 mg, 1.385 mmol), iodomethane (590 mg, 4.16 mmol) and cesium carbonate (2257 mg, 6.93 mmol) in DMF (5 mL) was allowed to stir at room temperature for 1 hour. The reaction mixture was diluted with water (3 mL) and directly purified using RP-MPLC to provide intermediate compound 17c. LCMS (M+H)=664

Step D—Synthesis of Intermediate Compound 17d and Compound 93

A solution of intermediate compound 17c (850 mg, 1.281 mmol) in methanol (10 mL) was treated with a solution of HCl in methanol (1.25 M, 10.25 mL, 12.81 mmol) at room temperature. The reaction was heated at 60° C. for 2 hours. The solvent was removed in vacuo. The resulting residue was dissolved in DMSO (5 mL) and purified using RP-MPLC to provide intermediate compound 17d [LCMS (M+H)=564] and compound 93. $^1$H NMR (400 MHz, CD$_3$OD): δ 8.84 (s, 1H), 7.45 (m, 1H), 6.96-7.02 (m, 2H), 4.73 (s, 2H), 4.48 (s, 2H), 3.51-3.53 (m, 2H), 3.35-3.40 (m, 2H), 3.18 (s, 3H), 2.41-2.44 (m, 2H), 2.05-2.07 (m, 2H). LCMS (M+H)=474

Example 18

Preparation of Compound 94

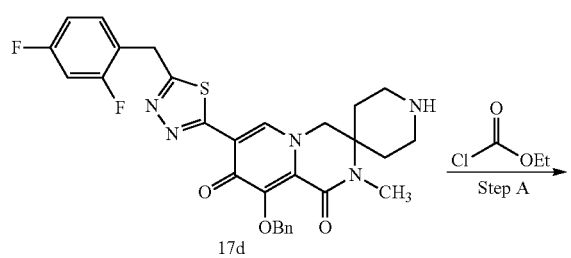

17d

-continued

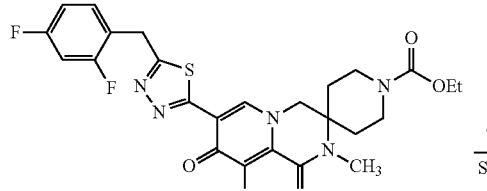

18a

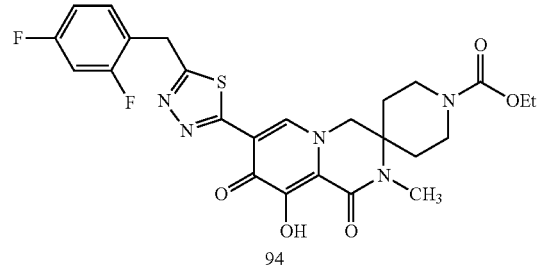

94

Step A—Synthesis of Intermediate Compound 18a

A solution of intermediate compound 17d (380 mg, 0.674 mmol) in THF (7 mL) was cooled at 0° C. and treated with triethylamine (205 mg, 2.023 mmol) and ethyl chloroformate (110 mg, 1.011 mmol). The mixture was allowed to stir at 0° C. for 15 minutes, treated with methanol (3 mL) and stirred at room temperature for 30 minutes. The mixture was concentrated and the resulting residue was purified using chromatography on silica gel (5% methanol/dichloromethane) to provide intermediate compound 18a. LCMS (M+H)=636.

Step B—Synthesis of Compound 94

Intermediate compound 18a (300 mg, 0.472 mmol) in dichloromethane (2 mL) was treated at room temperature with TFA (4 mL). The mixture was allowed to stir at room temperature for 1 hour and then concentrated. The resulting residue was purified using RP-HPLC to provide compound 94. $^1$H NMR (400 MHz, CDCl$_3$): δ 8.66 (s, 1H), 7.33-7.34 (m, 1H), 6.84-6.87 (m, 2H), 4.45 (s, 2H), 4.44 (s, 2H), 4.27 (m, 2H), 4.19 (q, J=5.2 Hz, 2H), 3.09 (s, 3H), 3.06 (m, 2H), 2.09 (m, 2H), 1.74 (m, 2H), 1.30 (t, J=5.2 Hz, 3H). LCMS (M+H)=546

Example 19

Preparation of Compound 95

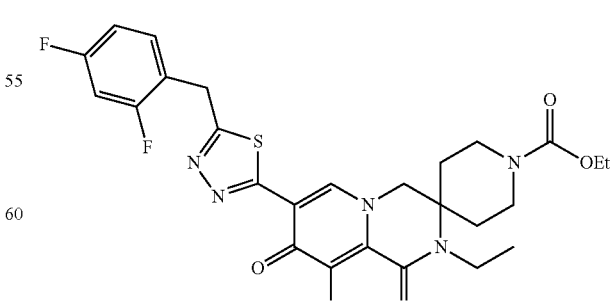

95

Using the methods described in Example 17 and Example 18 and substituting iodethane for iodomethane in Step C, compound 95 was prepared. $^1$H NMR (400 MHz, CDCl$_3$): δ 8.82 (s, 1H), 7.24-7.40 (m, 1H), 6.81-6.92 (m, 2H), 4.16-4.45 (m, 8H), 3.60-3.68 (m, 2H), 2.97-3.09 (m, 2H), 2.02-2.18 (m, 2H), 1.73-1.83 (m, 2H), 1.26-1.40 (m, 6H). LCMS (M+H)=560.1.

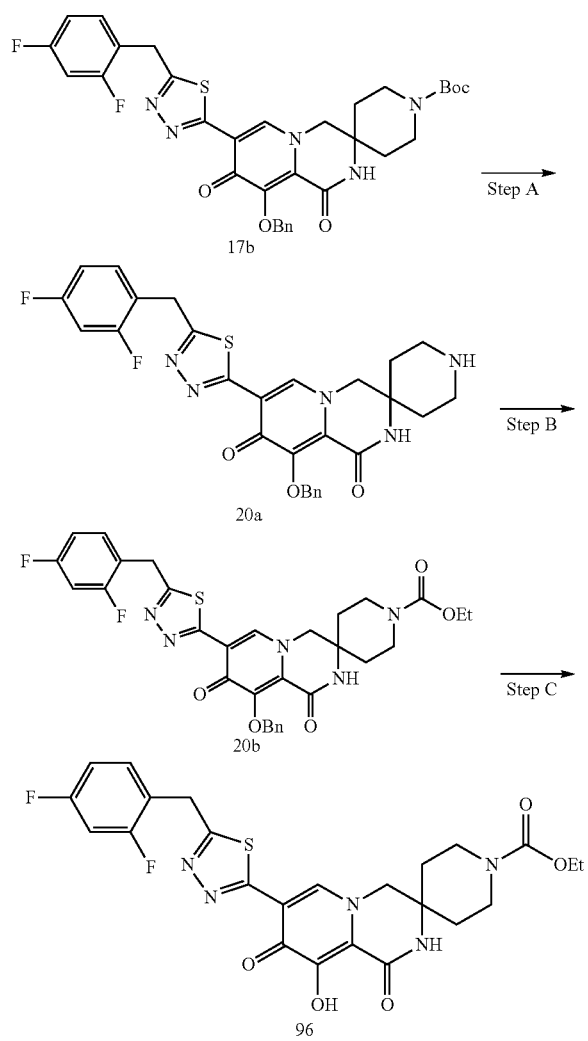

Example 20

Preparation of Compound 96

Step A—Synthesis of Intermediate Compound 20a

A solution of intermediate compound 17b (20 mg, 0.031 mmol) in methanol (1 mL) was treated with a solution of HCl in methanol (1.25 M, 1 mL, 1.250 mmol). The mixture was heated at 60° C. for 2 hours and then concentrated in vacuo. The resulting residue was dissolved in methanol (1 mL), diluted with dichloromethane (10 mL) and treated with saturated aqueous NaHCO$_3$ (2 mL). The mixture was aged at room temperature for 5 minutes, treated with anhydrous Na$_2$SO$_4$, filtered and the filtrate was concentrated to provide intermediate compound 20a. LCMS (M+H)=550.

Step B—Synthesis of Intermediate Compound 20b

A solution of intermediate compound 20a (15 mg, 0.027 mmol) in THF (1 mL) was cooled at 0° C. and treated with triethylamine (7.6 µl, 0.06 mmol) and ethyl chloroformate (2.6 µl, 0.03 mmol). The reaction was allowed to stir at 0° C. for 15 minutes and then concentrated in vacuo. The resulting residue was purified using chromatography on silica gel column (8% methanol/dichloromethane) to provide intermediate compound 20b. LCMS (M+H)=622.

Step C—Synthesis of Compound 96

A solution of intermediate compound 20b (11.5 mg, 0.018 mmol) in dichloromethane (0.5 mL) was treated with TFA (1 mL) and the mixture was allowed to stir at room temperature for 1 hour and then concentrated in vacuo. The resulting residue was purified using a RP-HPLC to provide compound 96. $^1$H NMR (400 MHz, CDCl$_3$): δ 8.70 (s, 1H), 7.55 (s, 1H), 7.31-7.39 (m, 1H), 6.84-6.92 (m, 2H), 4.48 (brs, 2H), 4.24 (brs, 2H), 4.19 (q, J=7.1 Hz, 2H), 3.77-3.85 (m, 2H), 3.50-3.58 (m, 2H), 1.81-1.92 (m, 4H), 1.30 (t, J=7.1 Hz, 3H). LCMS (M+H)=532.1.

Example 21

Preparation of Compound 97

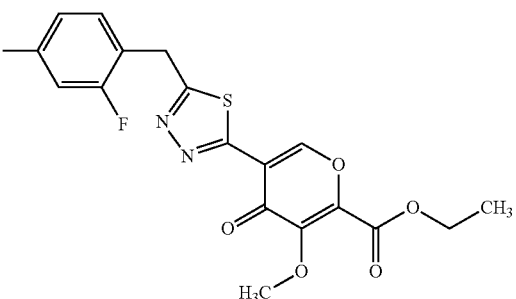

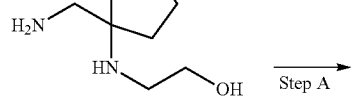

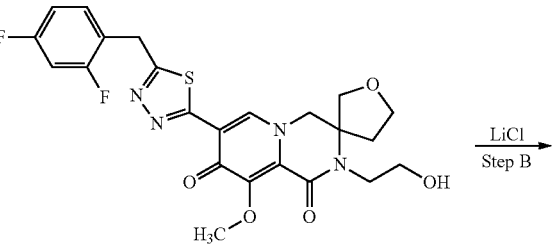

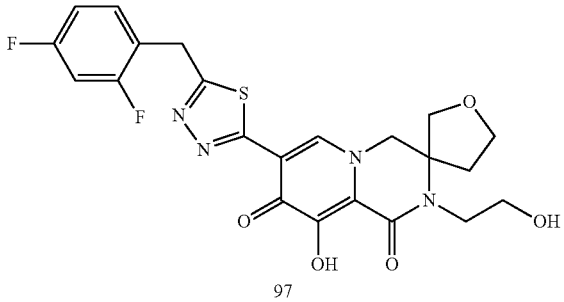

169

Step A—Synthesis of Intermediate Compound 21a

A mixture of compound 3 (100 mg, 0.245 mmol) and 2-((3-(aminomethyl)-tetrahydrofuran-3-yl)amino) ethanol.2TFA (238 mg, 0.612 mmol) in N-methylimidazole (2.0 mL) heated at 100° C. for 14 hours. The mixture was then cooled to room temperature, diluted with acetonitrile (5 mL) and neutralized with acetic acid. Direct purification of the mixture using preparative RP-HPLC provided intermediate compound 21a. LCMS (M+H)=505. $^1$H NMR (500 MHz, CDCl$_3$): δ 8.80 (s; 1 H); 7.30-7.34 (m; 1 H); 6.83-6.88 (m; 2 H); 4.48 (s; 2 H); 4.36 (d; J=11.9 Hz; 1 H); 4.22 (d; J=12.3 Hz; 1 H); 4.16 (d; J=10.1 Hz; 1 H); 4.08 (s; 3 H); 4.03-4.09 (m, 1 H); 3.91-4.01 (m; 3 H); 3.77-3.84 (m; 2 H); 3.65 (d; J=10.5 Hz; 1 H); 2.33 (br s; 1 H); 2.13 (br s; 1 H).

Step B—Synthesis of Compound 97

Intermediate compound 21a (20 mg, 0.04 mmol) was dissolved in DMF (2.0 mL), treated with LiCl (17 mg, 0.40 mmol) and heated at 100° C. for 2 hours. The mixture was cooled to room temperature and directly purified using preparative RP-HPLC to provide compound 97. LCMS (M+H)=491; $^1$H NMR (500 MHz, CDCl$_3$) 8.70 (s; 1 H); 7.36-7.27 (m, 1 H); 6.82-6.92 (m, 2 H); 4.47 (s; 2 H); 4.19-4.31 (m; 3 H); 4.07-4.14 (m; 1 H); 3.88-4.02 (m; 3 H); 3.75-3.79 (m; 2 H); 3.66 (d; J=10.6 Hz; 1 H). 2.32-2.42 (m; 1 H); 2.14-2.24 (m, 1 H)

Example 22

Preparation of Compound 98 and Intermediate Compound 22a

170

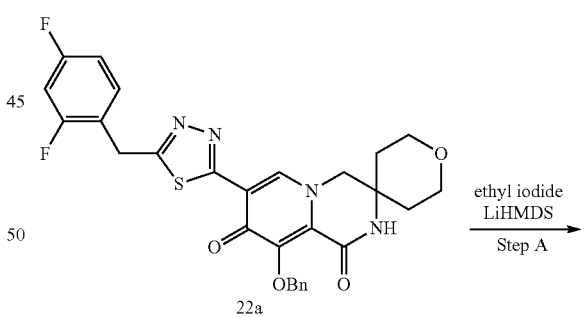

A mixture of 4-(aminomethyl)tetrahydro-2H-pyran-4-amine.2HCl (413 mg, 2.04 mmol) and compound 1-2 (1000 mg, 2.06 mmol) in N-methylimidazole (10 mL) was treated with DBU (0.622 mL, 4.13 mmol). The mixture was heated to 100° C. and stirred for 16 hours. The mixture was cooled to room temperature, diluted with ethyl acetate and washed with water. The organic portion was dried over anhydrous sodium sulfate, filtered, and the filtrate was concentrated in vacuo. The resulting residue was purified using silica gel chromatography (0-5% methanol/dichloromethane) to provide intermediate compound 22a. LCMS (M+H)=551. The aqueous portion was concentrated in vacuo and the resulting residue was purified using RP-HPLC to provide compound 98. LCMS (M+H)=461.

Example 23

Preparation of Compound 99 and Compound 100

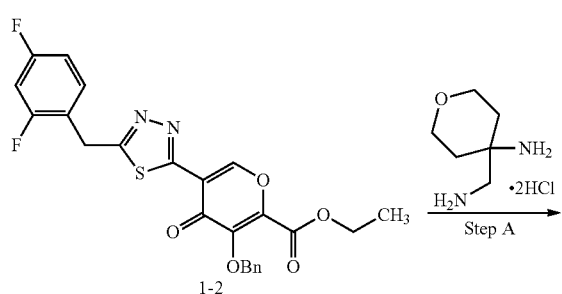

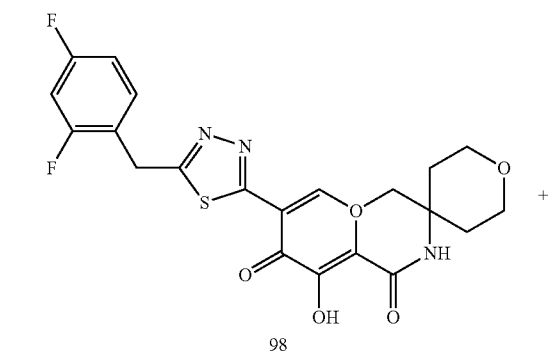

171
-continued

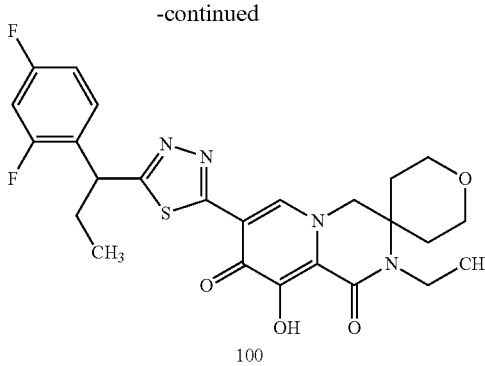
100

Intermediate compound 22a (500 mg, 0.908 mmol) in DMF (4 mL) was cooled to −20° C. and treated dropwise with LiHMDS (1M in THF, 1.82 mL, 1.82 mmol). The mixture was allowed to stir at −20° C. for 20 minutes, treated with EtI (0.11 mL, 1.36 mmol) and aged for 16 hours at −20° C. The mixture was treated with aqueous 1N HCl (0.2 mL) and the resulting mixture was extracted with ethyl acetate and the combined organic portion was dried over anhydrous sodium sulfate, filtered and the filtrate was concentrated in vacuo. The resulting residue was dissolved in TFA (3 mL) and stirred at room temperature for 4 hours and then concentrated in vacuo. The resulting residue was directly purified using RP-HPLC to provide compound 99 LCMS (M+H)=489 and compound 100 LCMS (M+H)=517.

The following compounds of the present invention were prepared using the methods described in the Example above using the appropriate reactants and reagents.

172

Example 24

Preparation of Compound 103 and Compound 104

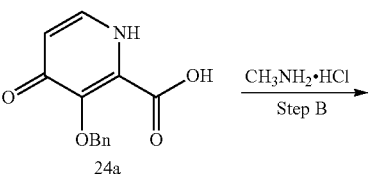

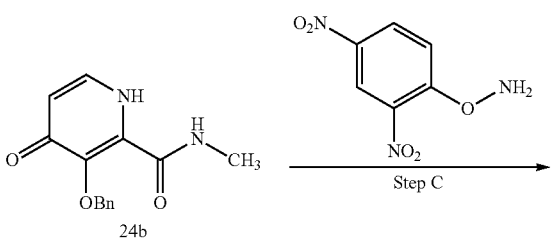

| Compound | Structure | Exact Mass [M + H]+ |
|---|---|---|
| 101 | ![structure] | 461 |
| 102 | ![structure] | 475 |

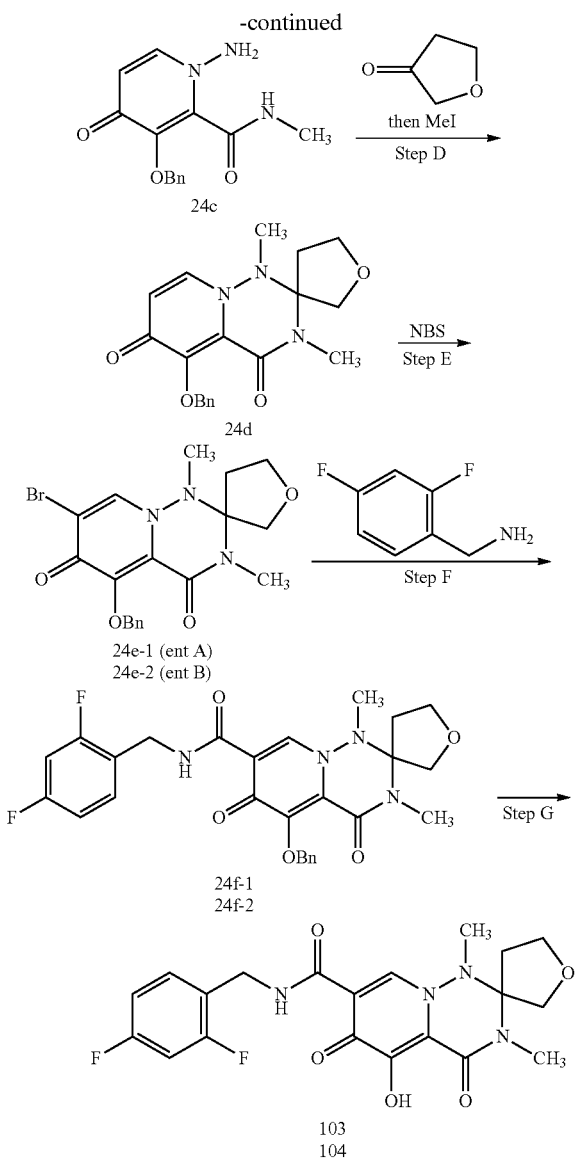

The reaction was allowed to stir for 20 hours while slowly warming to room temperature. The mixture was concentrated to provide a viscous, amber-colored syrup that was dissolved in DMSO (30 mL), neutralized with glacial acetic acid and purified using RP-MPLC to provide 24b.

Exact Mass [M+H]$^+$ Calc'd for 259.1. found 259.1. $^1$H NMR (500 MHz, DMSO) δ 8.40 (s, 1 H), 7.62 (d, J=6.8 Hz, 1 H), 7.30-7.39 (m, 5 H), 6.42 (d, J=6.7 Hz, 1 H), 5.32 (s, 2 H), 2.74 (d, J=4.8 Hz, 3 H).

Step C—Synthesis of Intermediate Compound 24c

A mixture of 24b (18.10 g, 70.1 mmol) and potassium carbonate (29.1 g, 210 mmol) in N,N-dimethylformamide (150 mL) at 0° C. was treated with O-(2,4-dinitrophenyl)hydroxylamine (27.9 g, 140 mmol) and was allowed to warm to room temperature and stir at rt for 48 hours. The mixture was filtered through a pad of celite (acetonitrile rinse) and the filtrate was neutralized with glacial acetic acid. The resulting solution was directly purified using RP-MPLC to provide 24c that was used without further purification. Exact Mass [M+H]$^+$ Calc'd for 274.1. found 274.2. $^1$H NMR (500 MHz, CDCl$_3$): δ 7.61 (bs, 1 H), 7.42 (d, J=7.6 Hz, 1 H), 7.31-7.35 (m, 5 H), 6.24 (d, J=7.6 Hz, 1 H), 5.07 (s, 2 H), 2.64 (d, J=4.9 Hz, 3 H).

Step D—Synthesis of Intermediate Compound 24d

A solution of 24c (11.9 g, 43.5 mmol) in tetrahydrofuran (100 mL) was treated at rt with 3-oxotetrahydrofuran (11.25 g, 131 mmol) and acetic acid (1.0 mL). The mixture was heated at 75° C. for 4 h, cooled to room temperature and directly loaded onto a silica gel column. Gradient elution (0 to 20% methanol/dichloromethane) provided 5'-(benzyloxy)-1',3'-dimethyl-4,5-dihydro-1'H,2H,3'H-spiro[furan-3,2'-pyrido [2,1-f][1,2,4]triazine]-4',6'-dione that was used without further purification. Exact Mass [M+H]$^+$ Calc'd for 342.1. found 341.8. A solution of the intermediate compound in DMSO (20 mL) was treated at rt with iodomethane (5.45 mL, 87 mmol) and finely-powdered potassium hydroxide (4.89 g, 87 mmol). The mixture was allowed to stir at rt for 1 hour and then quenched with glacial acetic acid (10.0 mL). The mixture was directly purified using RP-MPLC to provide 24d. Exact Mass [M+H]$^+$ Calc'd for 356.2. found 355.8.

Step E—Synthesis of Intermediate Compound 24e-1 and 24e-2

A solution of 24d (9.50 g, 26.7 mmol) in N,N-dimethylformamide (50 mL) was cooled to 0° C. and treated with N-bromosuccinimide (7.14 g, 40.1 mmol). The mixture was allowed to slowly warm to room temperature and stir for 2 hours. The mixture was diluted with DMSO (10 mL) and directly purified using RP-MPLC. The fractions were concentrated with a 2-propanol azeotrope to provide a residue that was neutralized (residual TFA from RP-MPLC purification) with triethylamine and further purified using column chromatography on silica gel (10 to 100% [1:3 EtOH/ethyl acetate]/hexanes) to provide (±)-24e. Exact Mass [M+H]$^+$ Calc'd for 434.1, 436.1. found 433.6, 435.6. $^1$H NMR 0362764-0100-1: (400 MHz, CDCl$_3$) δ 7.80-7.82 (m, 1H), 7.53-7.57 (m, 2H), 7.26-7.33 (m, 3H), 5.55-5.57 (m, 1H), 5.20-5.23 (m, 1H), 4.15-4.16 (m, 1H), 3.93-4.03 (m, 2H), 3.61-3.64 (m, 1H), 3.19 (s, 3H), 2.69-2.79 (m, 3H), 2.47-2.53 (m, 1H), 2.09-2.14 (m, 1H). Chiral resolution by SFC (ChiralCel OJ-H, 250×30 mm, 20% ethanol (0.1% NH$_3$H$_2$O) in SC—CO$_2$, 60 mL/min, 220 nM) provided earlier eluting 24e-1 (ent A) [a]$_D$=+27.8 (c 0.91, 24° C., methanol) and later eluting 24e-2 (ent B) [a]$_D$−27.5 (c 0.96, 24° C., methanol).

Step A—Synthesis of Intermediate Compound 24a 3-(benzyloxy)-4-oxo-4H-pyran-2-carboxylic acid (30.00 g, 122 mmol) was dissolved in 28% aqueous ammonium hydroxide (150 mL, 1079 mmol) at rt and the mixture was allowed to stir at rt for 16 hours. The mixture was diluted with water to a total volume of 500 mL and then treated with 36% aqueous HCl until the pH was −4 and additional water (500 mL) was added. The mixture was aged for 12 hours at room temperature. The solids were collected by filtration, washed with water (250 mL) and then dried in vacuo to provide 24a that was used without further purification. Exact Mass [M+H]$^+$ Calc'd for 246.1. found 246.1. $^1$H NMR 0362764-0049-1: (400 MHz, DMSO-d6) δ 7.70 (bs, 1H), 7.43-7.45 (m, 2H), 7.27-7.35 (m, 3H), 6.53 (bs, 1H), 5.07 (s, 2H).

Step B—Synthesis of Intermediate Compound 24b

A mixture of 24a (20 g, 82 mmol) and HOBT (13.74 g, 90 mmol) in dichloromethane (100 mL) was cooled to 0° C. and treated with EDC (17.20 g, 90 mmol) and N-methylmorpholine (26.9 mL, 245 mmol). After 5 minutes of stirring, methanamine hydrochloride (6.06 g, 90 mmol) was added.

Step F—Synthesis of Intermediate Compound 24f-1

The mixture of 24e-1 (1.92 g, 4.42 mmol), 2,4-difluorobenzylamine (1.156 mL, 9.73 mmol), N,N-diisopropylethylamine (2.316 mL, 13.26 mmol) and tetrakis(triphenylphosphine)palladium(0) (2.55 g, 2.211 mmol) in DMSO (20 mL) was sub-surface sparged with nitrogen for 10 minutes and then with carbon monoxide for 30 minutes at room temperature. The mixture was heated at 90° C. under carbon monoxide (1 atm) for 8 hours., cooled to room temperature, treated with water (1 mL), stirred for 5 minutes and filtered. The filtrate was purified using RP-MPLC to provide 24f-1. Exact Mass [M+H]$^+$ Calc'd for 525.2. found 525.1.

Step F—Synthesis of Intermediate Compound 24f-2

The mixture of 24e-2 (5.15 g, 11.86 mmol), 2,4-difluorobenzylamine (3.10 mL, 26.1 mmol), N,N-diisopropylethylamine (6.21 mL, 35.6 mmol) and tetrakis(triphenylphosphine)palladium(0) (6.85 g, 5.93 mmol) in DMSO (50 mL) was sub-surface sparged with nitrogen for 10 minutes and then with carbon monoxide for 30 minutes at room temperature. The mixture was heated at 90° C. under carbon monoxide (1 atm) for 8 hours., cooled to room temperature, treated with water (5 mL), stirred for 5 minutes and filtered. The filtrate was purified using RP-MPLC to provide 24f-2. Exact Mass [M+H]$^+$ Calc'd for 525.2. found 525.2.

Step G—Synthesis of Compound 103

A solution of 24f-1 (1.8 g, 3.43 mmol) in TFA (5 mL) was allowed to stir at room temperature for 2 hours and then concentrated. The residue was purified using RP-MPLC and subsequent recrystallization from acetonitrile provided compound 103. [a]$_D$–0.2 (c 1.0, 20° C., acetonitrile). Exact Mass [M+H]$^+$ Calc'd for 435.1. found 434.8. The $^1$H NMR spectrum exhibits conformational isomers at room temperature; brackets { } indicate groups of signals that are assigned to the same proton and integrations are not representative of any ratio. $^1$H NMR (500 MHz, DMSO) δ {11.75 (s, 1 H), 11.70 (s, 1 H)}, 10.26-10.28 (m, 1 H), {8.33 (s, 1 H), 8.26 (s, 1 H)}, 7.38-7.43 (m, 1 H), 7.21-7.25 (m, 1 H), 7.03-7.07 (m, 1 H), {4.53-4.54 (m, 2 H), 4.40-4.42 (m, 2 H)}, 3.95-4.06 (m, 2 H), 3.74-3.79 (m, 1 H), 3.63-3.69 (m, 1 H), {3.16 (s, 3 H), 3.11 (s, 3 H)}, {2.82 (s, 3 H), 2.72 (s, 3 H)}, 2.27-2.36 (m, 1 H), 2.07-2.13 (m, 1 H).

Step G—Synthesis of Compound 104

A solution of 24f-2 (2.2 g, 4.19 mmol) in TFA (6 mL) was allowed to stir at room temperature for 2 hours and then concentrated. The residue was purified using RP-MPLC and subsequent recrystallization from acetonitrile provided compound 104. [a]$_D$+0.2 (c 1.0, 20° C., acetonitrile). Exact Mass [M+H]$^+$ Calc'd for 435.1. found 435.0. The $^1$H NMR spectrum exhibits conformational isomers at room temperature; brackets { } indicate groups of signals that are assigned to the same proton and integrations are not representative of any ratio. $^1$H NMR (500 MHz, DMSO) δ {11.75 (s, 1 H), 11.70 (s, 1 H)}, 10.26-10.28 (m, 1 H), {8.33 (s, 1 H), 8.26 (s, 1 H)}, 7.38-7.43 (m, 1 H), 7.21-7.25 (m, 1 H), 7.03-7.07 (m, 1 H), {4.53-4.54 (m, 2 H), 4.40-4.42 (m, 2 H)}, 3.95-4.06 (m, 2 H), 3.74-3.79 (m, 1 H), 3.63-3.69 (m, 1 H), {3.16 (s, 3 H), 3.11 (s, 3 H)}, {2.82 (s, 3 H), 2.72 (s, 3 H)}, 2.27-2.36 (m, 1 H), 2.07-2.13 (m, 1 H).

The compounds in the following table were prepared in a similar manner to Example 24 using the intermediate aryl bromides 24e-1 or 24e-2 and appropriate conditions and intermediates. Chiral resolution to the enantiomers was accomplished by resolving the aryl bromide with the SFC conditions noted in the table.

| Compound | Structure | Enantiomer[1] | Exact Mass [M + H]+ |
|---|---|---|---|
| 105 | 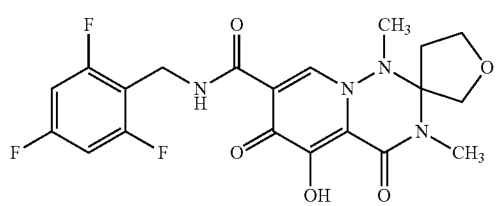 [SMILES: CN1C(=O)c2c(O)c(=O)c(C(=O)NCc3c(F)cc(F)cc3F)cn2N(C)C12CCOC2] | A | Calc'd 453.1, found 453.1 |
| 106 | 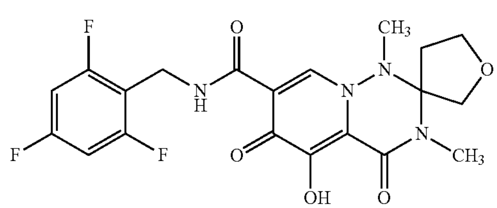 [SMILES: CN1C(=O)c2c(O)c(=O)c(C(=O)NCc3c(F)cc(F)cc3F)cn2N(C)C12CCOC2] | B | Calc'd 453.1, found 453.1 |
| 107 | 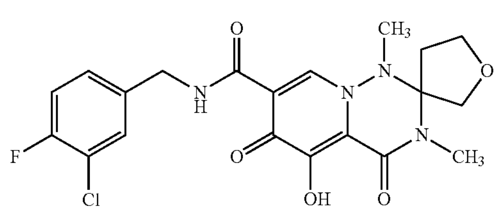 [SMILES: CN1C(=O)c2c(O)c(=O)c(C(=O)NCc3ccc(F)c(Cl)c3)cn2N(C)C12CCOC2] | A | Calc'd 451.1, found 451.1 |

-continued

| Compound | Structure | Enantiomer[1] | Exact Mass [M + H]+ |
|---|---|---|---|
| 108 | 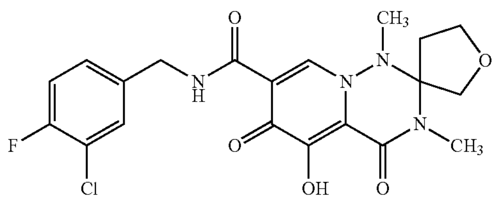 [SMILES: CN1C(=O)c2c(O)c(=O)c(C(=O)NCc3ccc(F)c(Cl)c3)cn2N(C)C12CCOC2] | B | Calc'd 451.1, found 451.1 |
| 109 | 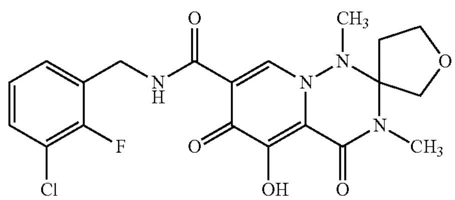 [SMILES: CN1C(=O)c2c(O)c(=O)c(C(=O)NCc3cccc(Cl)c3F)cn2N(C)C12CCOC2] | A | Calc'd 451.1, found 451.1 |
| 110 | 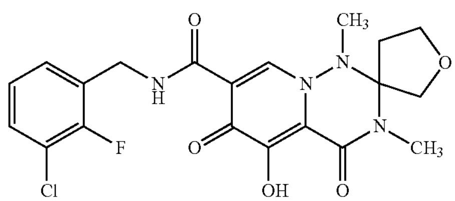 [SMILES: CN1C(=O)c2c(O)c(=O)c(C(=O)NCc3cccc(Cl)c3F)cn2N(C)C12CCOC2] | B | Calc'd 451.1, found 451.1 |
| 111 | 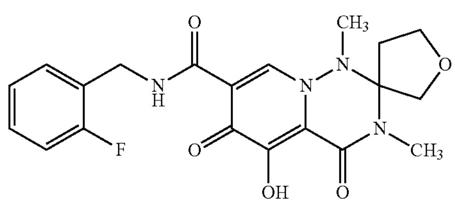 [SMILES: CN1C(=O)c2c(O)c(=O)c(C(=O)NCc3ccccc3F)cn2N(C)C12CCOC2] | A | Calc'd 417.2, found 417.1 |
| 112 | 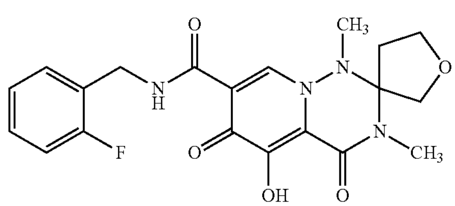 [SMILES: CN1C(=O)c2c(O)c(=O)c(C(=O)NCc3ccccc3F)cn2N(C)C12CCOC2] | B | Calc'd 417.2, found 417.1 |
| 113 | 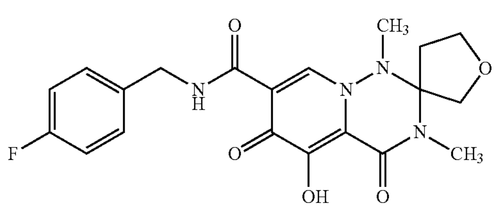 [SMILES: CN1C(=O)c2c(O)c(=O)c(C(=O)NCc3ccc(F)cc3)cn2N(C)C12CCOC2] | A | Calc'd 417.2, found 417.1 |
| 114 | 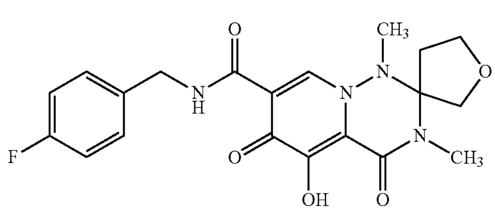 [SMILES: CN1C(=O)c2c(O)c(=O)c(C(=O)NCc3ccc(F)cc3)cn2N(C)C12CCOC2] | B | Calc'd 417.2, found 417.1 |

| Compound | Structure | Enantiomer[1] | Exact Mass [M + H]+ |
|---|---|---|---|
| 115 | 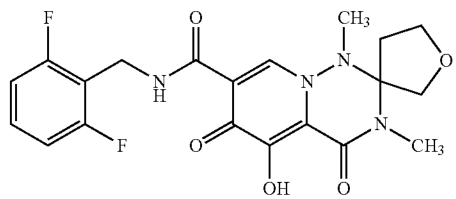 [SMILES: CN1C(=O)c2c(O)c(=O)c(C(=O)NCc3c(F)cccc3F)cn2N(C)C12CCOC2] | A | Calc'd 435.1, found 435.1 |
| 116 | 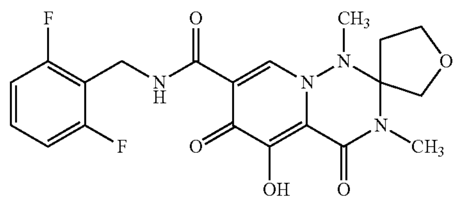 [SMILES: CN1C(=O)c2c(O)c(=O)c(C(=O)NCc3c(F)cccc3F)cn2N(C)C12CCOC2] | B | Calc'd 435.1, found 435.1 |
| 117 | 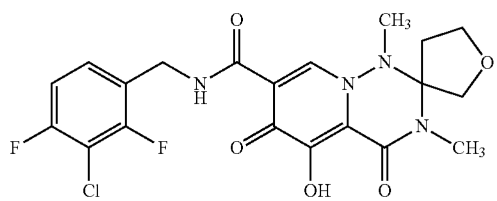 [SMILES: CN1C(=O)c2c(O)c(=O)c(C(=O)NCc3ccc(F)c(Cl)c3F)cn2N(C)C12CCOC2] | A | Calc'd 469.1, found 469.1 |
| 118 | 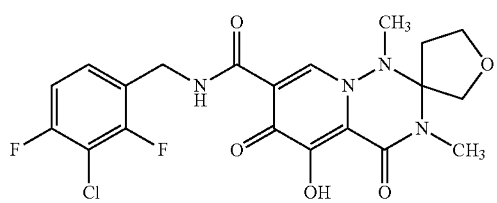 [SMILES: CN1C(=O)c2c(O)c(=O)c(C(=O)NCc3ccc(F)c(Cl)c3F)cn2N(C)C12CCOC2] | B | Calc'd 469.1, found 469.1 |
| 119 | 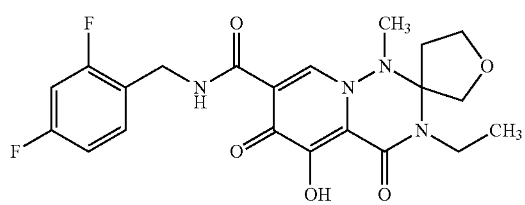 [SMILES: CCN1C(=O)c2c(O)c(=O)c(C(=O)NCc3ccc(F)cc3F)cn2N(C)C12CCOC2] | A[2] | Calc'd 449.2, found 449.0 |
| 120 | 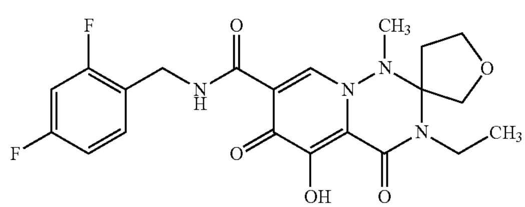 [SMILES: CCN1C(=O)c2c(O)c(=O)c(C(=O)NCc3ccc(F)cc3F)cn2N(C)C12CCOC2] | B[2] | Calc'd 449.2, found 449.0 |
| 121 | 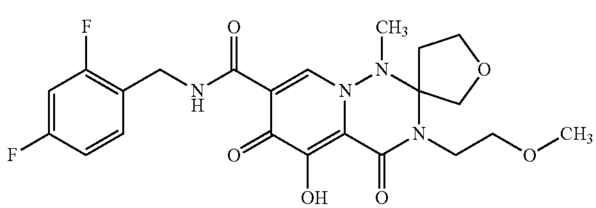 [SMILES: COCCN1C(=O)c2c(O)c(=O)c(C(=O)NCc3ccc(F)cc3F)cn2N(C)C12CCOC2] | A[2] | Calc'd 479.2, found 479.1 |

| Compound | Structure | Enantiomer[1] | Exact Mass [M + H]+ |
|---|---|---|---|
| 122 | 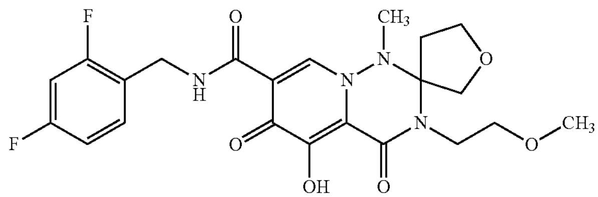 [SMILES: COCCN1C(=O)c2c(O)c(=O)c(C(=O)NCc3ccc(F)cc3F)cn2N(C)C12CCOC2] | B[2] | Calc'd 479.2, found 479.1 |
| 123 | 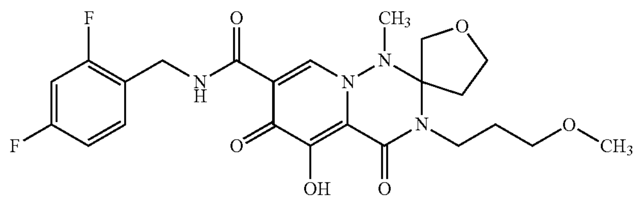 [SMILES: COCCCN1C(=O)c2c(O)c(=O)c(C(=O)NCc3ccc(F)cc3F)cn2N(C)C12CCOC2] | A[3] | Calc'd 493.2, found 492.9 |
| 124 | 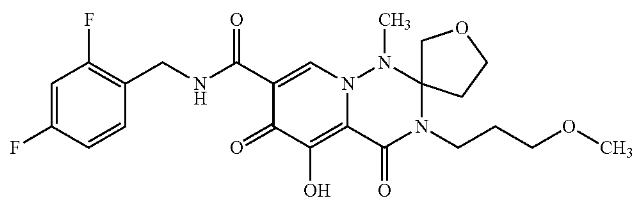 [SMILES: COCCCN1C(=O)c2c(O)c(=O)c(C(=O)NCc3ccc(F)cc3F)cn2N(C)C12CCOC2] | B[3] | Calc'd 493.2, found 492.9 |
| 125 | 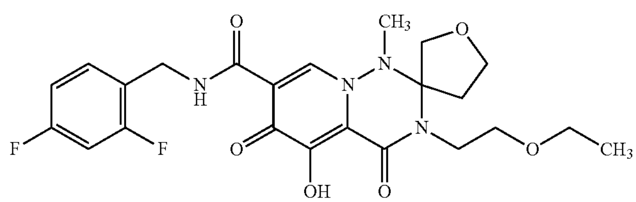 [SMILES: CCOCCN1C(=O)c2c(O)c(=O)c(C(=O)NCc3ccc(F)cc3F)cn2N(C)C12CCOC2] | A[4] | Calc'd 493.2, found 493.1 |
| 126 | 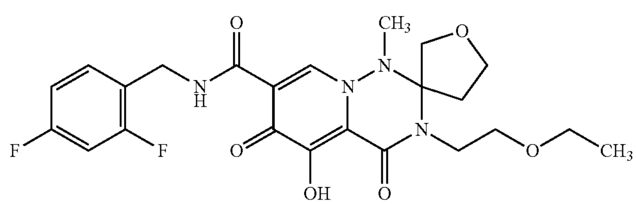 [SMILES: CCOCCN1C(=O)c2c(O)c(=O)c(C(=O)NCc3ccc(F)cc3F)cn2N(C)C12CCOC2] | B[4] | Calc'd 493.2, found 493.1 |
| 127 | 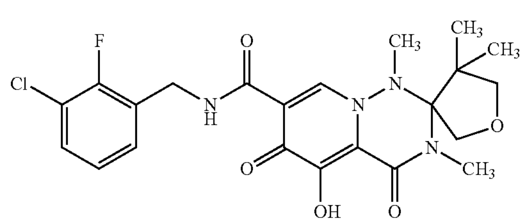 [SMILES: CN1C(=O)c2c(O)c(=O)c(C(=O)NCc3cccc(Cl)c3F)cn2N(C)C12COCC2(C)C] | A[5] | Calc'd 479.1, found 479.0 |
| 128 | 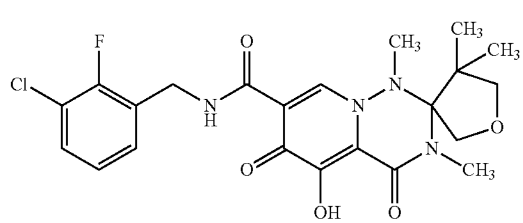 [SMILES: CN1C(=O)c2c(O)c(=O)c(C(=O)NCc3cccc(Cl)c3F)cn2N(C)C12COCC2(C)C] | B[5] | Calc'd 479.1, found 479.2 |

-continued

| Compound | Structure | Enantiomer[1] | Exact Mass [M + H]+ |
|---|---|---|---|
| 129 | 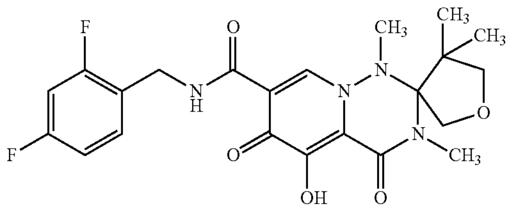 [SMILES: CN1C(=O)c2c(O)c(=O)c(C(=O)NCc3ccc(F)cc3F)cn2N(C)C12COCC2(C)C] | A[5] | Calc'd 463.2, found 463.3 |
| 130 | 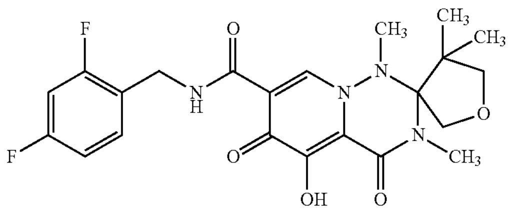 [SMILES: CN1C(=O)c2c(O)c(=O)c(C(=O)NCc3ccc(F)cc3F)cn2N(C)C12COCC2(C)C] | B[5] | Calc'd 463.2, found 463.0 |
| 131 | 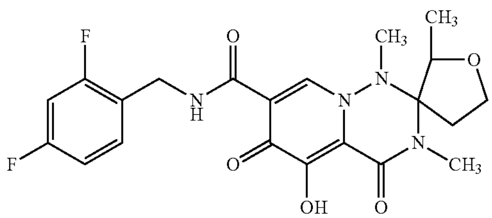 [SMILES: CC1OCCC12N(C)C(=O)c1c(O)c(=O)c(C(=O)NCc3ccc(F)cc3F)cn1N2C] | 1-A[7] | Calc'd 449.2, found 449.0 |
| 132 | 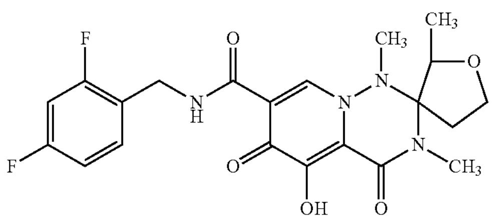 [SMILES: CC1OCCC12N(C)C(=O)c1c(O)c(=O)c(C(=O)NCc3ccc(F)cc3F)cn1N2C] | 1-B[7] | Calc'd 449.2, found 449.0 |
| 133 | 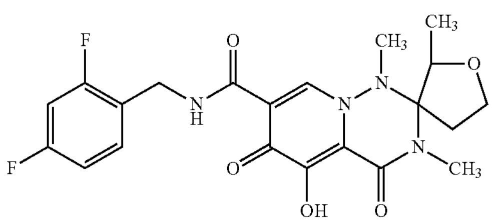 [SMILES: CC1OCCC12N(C)C(=O)c1c(O)c(=O)c(C(=O)NCc3ccc(F)cc3F)cn1N2C] | 2-A[8] | Calc'd 449.2, found 449.1 |
| 134 | 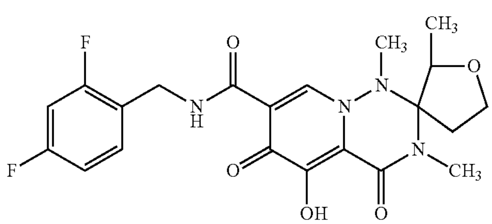 [SMILES: CC1OCCC12N(C)C(=O)c1c(O)c(=O)c(C(=O)NCc3ccc(F)cc3F)cn1N2C] | 2-B[8] | Calc'd 449.2, found 449.1 |
| 135 | 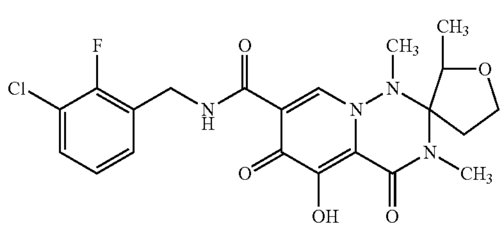 [SMILES: CC1OCCC12N(C)C(=O)c1c(O)c(=O)c(C(=O)NCc3cccc(Cl)c3F)cn1N2C] | 1-A[7] | Calc'd 465.1, found 465.0 |

-continued

| Compound | Structure | Enantiomer[1] | Exact Mass [M + H]+ |
|---|---|---|---|
| 136 | 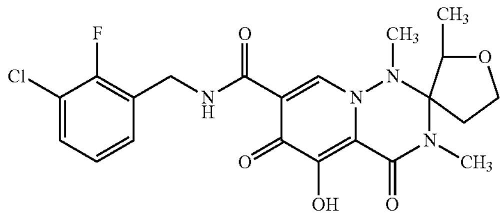 [SMILES: CC1OCCC12N(C)C(=O)c1c(O)c(=O)c(C(=O)NCc3cccc(Cl)c3F)cn1N2C] | 1-B[7] | Calc'd 465.1, found 465.1 |
| 137 | 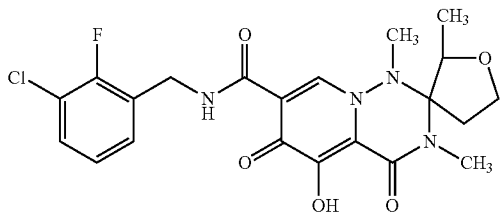 [SMILES: CC1OCCC12N(C)C(=O)c1c(O)c(=O)c(C(=O)NCc3cccc(Cl)c3F)cn1N2C] | 2-A[8] | Calc'd 465.1, found 465.1 |
| 138 | 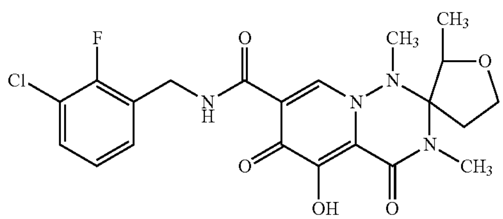 [SMILES: CC1OCCC12N(C)C(=O)c1c(O)c(=O)c(C(=O)NCc3cccc(Cl)c3F)cn1N2C] | 2-B[8] | Calc'd 465.1, found 465.1 |
| 139 | 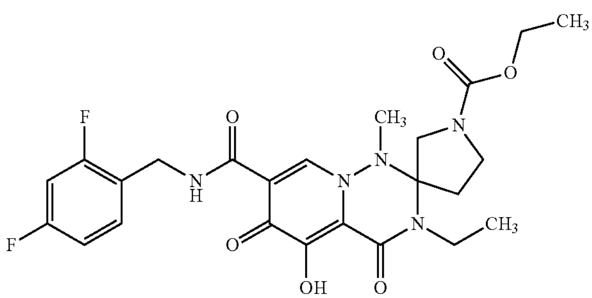 [SMILES: CCOC(=O)N1CCC2(C1)N(CC)C(=O)c1c(O)c(=O)c(C(=O)NCc3ccc(F)cc3F)cn1N2C] | A[6] | Calc'd 520.2, found 520.1 |
| 140 | 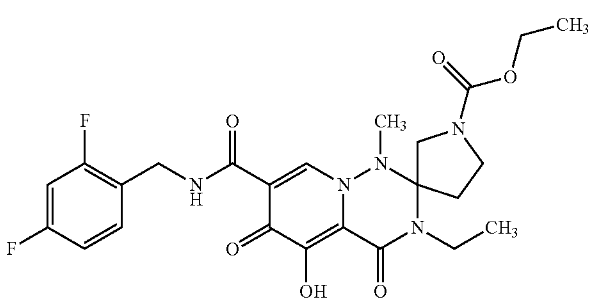 [SMILES: CCOC(=O)N1CCC2(C1)N(CC)C(=O)c1c(O)c(=O)c(C(=O)NCc3ccc(F)cc3F)cn1N2C] | B[6] | Calc'd 520.2, found 520.1 |
| 141 | 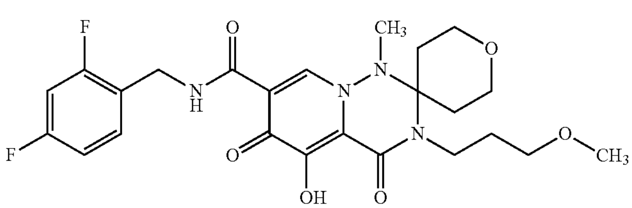 [SMILES: COCCCN1C(=O)c2c(O)c(=O)c(C(=O)NCc3ccc(F)cc3F)cn2N(C)C12CCOCC2] | n/a | Calc'd 507.2, found 506.9 |

| Compound | Structure | Enantiomer[1] | Exact Mass [M + H]+ |
|---|---|---|---|
| 142 | 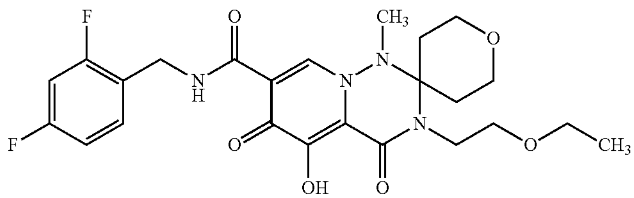 [SMILES: CCOCCN1C(=O)c2c(O)c(=O)c(C(=O)NCc3ccc(F)cc3F)cn2N(C)C12CCOCC2] | n/a | Calc'd 507.2, found 506.9 |
| 143 | 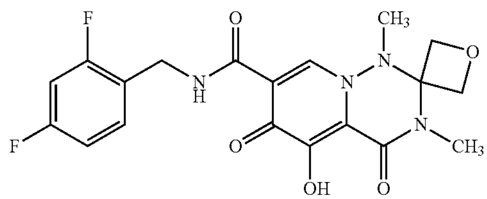 [SMILES: CN1C(=O)c2c(O)c(=O)c(C(=O)NCc3ccc(F)cc3F)cn2N(C)C12COC2] | n/a | Calc'd 421.1, found 420.9 |
| 144 | 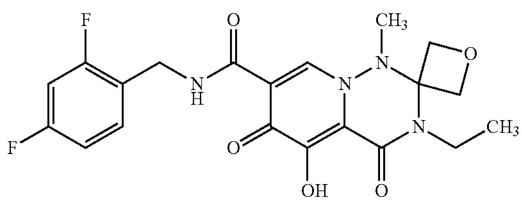 [SMILES: CCN1C(=O)c2c(O)c(=O)c(C(=O)NCc3ccc(F)cc3F)cn2N(C)C12COC2] | n/a | Calc'd 435.1, found 435.0 |
| 145 | 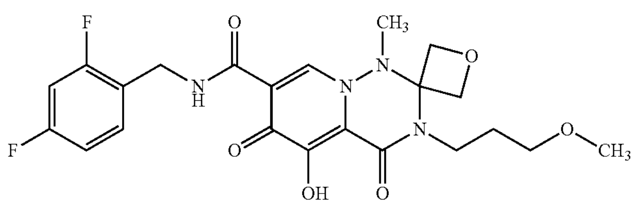 [SMILES: COCCCN1C(=O)c2c(O)c(=O)c(C(=O)NCc3ccc(F)cc3F)cn2N(C)C12COC2] | n/a | Calc'd 479.2, found 478.9 |
| 146 | 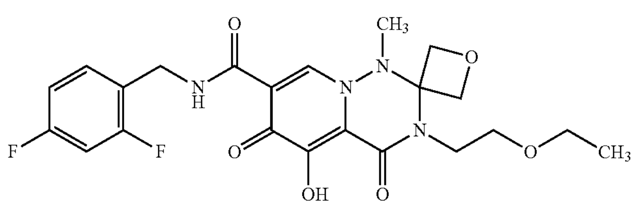 [SMILES: CCOCCN1C(=O)c2c(O)c(=O)c(C(=O)NCc3ccc(F)cc3F)cn2N(C)C12COC2] | n/a | Calc'd 479.2, found 479.0 |

[1]Enantiomer A is earlier eluting and enantiomer B is later eluting with the specified conditions

[2]AS-H (2 × 15 cm), 20% ethanol (0.1% DEA) in SC—$CO_2$, 100 bar, 60 mL/min, 254 nm

[3]AS-H (2 × 25 cm), 20% methanol in SC—$CO_2$, 100 bar, 70 mL/min, 220 nm

[4]AS-H (2 × 25 cm), 30% (2:1) MeCN:EtOH in SC—$CO_2$, 100 bar, 60 mL/min, 220 nm

[5]OD-H (2 × 25 cm), 35% ethanol (0.1% DEA) in SC—$CO_2$, 100 bar, 60 mL/min, 220 nm

[6]IA (2 × 15 cm), 35% methanol in SC—$CO_2$, 100 bar, 60 mL/min, 220 nm

[7]Diastereomeric series 1 corresponds to the earlier eluting diastereomer after Step D by RP-HPLC (C18, acetonitrile/water/0.05% TFA). Chiral resolution after Step E by chiral SFC (AD-H (3 × 25 cm), 25% methanol (0.1% DEA) in SC—$CO_2$, 100 bar, 70 mL/min, 220 nm) provided enantiomers 1-A and 1-B.

[8]Diastereomeric series 2 corresponds to the later eluting diastereomer after Step D by RP-HPLC (C18, acetonitrile/water/0.05% TFA). Chiral resolution after Step E by chiral SFC (AD-H (2 × 15 cm), 20% methanol (0.1% DEA) in SC—$CO_2$, 100 bar, 60 mL/min, 220 nm) provided enantiomers 2-A and 2-B.

Example 25

Preparation of Compound 147 and Compound 148

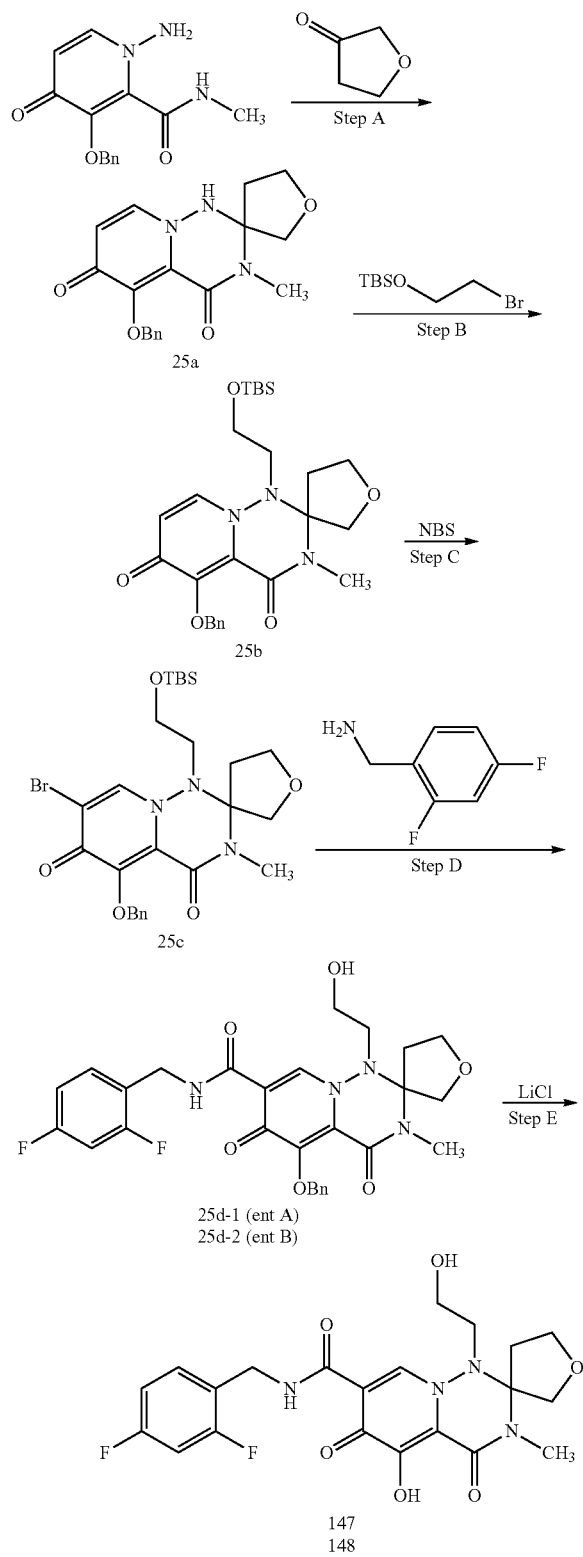

Step A—Synthesis of Intermediate Compound 25a

To a solution of 1-amino-3-(benzyloxy)-N-methyl-4-oxo-1,4-dihydropyridine-2-carboxamide (300 mg, 1.098 mmol) in tetrahydrofuran (6 mL) and acetic acid (0.3 mL) was added dihydrofuran-3(2H)-one (189 mg, 2.195 mmol) and the mixture was heated by microwave irradiation at 90° C. for 3 hours, cooled to room temperature, quenched with water (1 mL) and diluted with dichloromethane (10 mL). The organic layer was dried over anhydrous sodium sulfate, filtered and the filtrate was concentrated. The crude residue was purified using column chromatography to give intermediate compound 25a. $^1$H NMR (400 MHz, CDCl3) δ 7.31-7.35 (m, 5H), 7.03-7.06 (m, 1H), 6.45-6.47 (m, 1H), 6.31 (bs, 1H), 5.23 (s, 2H), 4.32-4.41 (m, 2H), 4.05-4.12 (m, 2H), 2.86-2.89 (m, 1H), 2.71-2.74 (m, 4H).

Step B—Synthesis of Intermediate Compound 25b

To a solution of 25a (350 mg, 1.025 mmol) in DMF (5 mL) was added finely-powdered potassium hydroxide (115 mg, 2.051 mmol) and (2-bromoethoxy)(tert-butyl)dimethylsilane (736 mg, 3.08 mmol). The mixture was allowed to stir at 28° C. for 1 hour, filtered and the filtrate was concentrated. The residue was purified using column chromatography on silica gel (dichloromethane:MeOH=10:1 to 7:1) to give intermediate compound 25b. $^1$H NMR (400 MHz, CDCl$_3$) δ 7.45-7.49 (m, 2H), 7.25-7.36 (m, 4H), 6.28-6.32 (m, 1H), 5.52-5.55 (m, 2H), 3.83-4.15 (m, 2H), 3.08-3.53 (m, 2H), 3.51 (s, 2H), 2.84-2.92 (m, 3H), 2.01-2.63 (m, 2H), 1.33-1.39 (m, 2H), 0.84 (s, 9H), 0.00 (m, 6H). MS (+ESI) m/z: 500.5.

Step C—Synthesis of Intermediate Compound 25c

A solution of 25b (300 mg, 0.540 mmol) in dichloromethane (10 mL) was treated with N-bromosuccinimide (249 mg, 1.401 mmol) at 0° C. The mixture was allowed to stir at 28° C. for 2 hours, filtered and the filtrate was purified using prep-TLC on silica gel (dichloromethane/MeOH=20/1) to provide intermediate compound 25c. $^1$H NMR (400 MHz, CDCl$_3$) δ 7.79-7.91 (m, 1H), 7.27-7.36 (m, 2H), 7.20-7.26 (m, 3H), 5.14-5.53 (m, 2H), 3.85-4.15 (m, 1H), 3.30-3.84 (m, 5H), 3.14 (s, 3H), 2.71-2.86 (m, 2H), 1.97-2.07 (m, 1H), 1.43-1.59 (m, 1H), 0.84 (s, 9H), 0.00 (m, 6H).

Step D—Synthesis of Intermediate Compound 25d-1 and 25d-2

A solution of 25c (150 mg, 0.233 mmol) in DMSO (3 mL) was treated with (2,4-difluorophenyl)methanamine (186 mg, 1.296 mmol), N,N-diisopropylethylamine (0.295 mL, 1.687 mmol) and Pd(Ph$_3$P)$_4$ (150 mg, 0.130 mmol). The mixture was allowed to stir at 90° C. under carbon monoxide (1 atm) for 8 hours. The mixture was filtered and the filtrate was directly purified using preparative RP-HPLC (acidic conditions during purification resulted in loss of the say' ether) to provide intermediate compound (±)-25d. $^1$H NMR (400 MHz, CDCl$_3$) δ 8.58 (s, 1H), 7.43-7.46 (m, 1H), 7.34-7.36 (m, 2H), 7.26-7.32 (m, 3H), 6.92-6.96 (m, 1H), 5.40-5.42 (m, 1H), 5.18-5.24 (m, 1H), 4.62-4.63 (m, 2H), 4.34-4.36 (m, 1H), 3.61-3.97 (m, 4H), 3.50-3.59 (m, 3H), 3.00-3.12 (m, 3H), 2.00-2.06 (m, 1H), 1.19-1.12 (m, 2H), MS (+ESI) m/z: 555.2. Chiral resolution with SFC (Chiralcel AD, 250 mm×30 mm, 5 um, 40% EtOH (0.1% NH$_3$H$_2$O) in SC—CO$_2$, 40 mL/min, 220 nm) provided earlier eluting 25d-1 (ent A) and later eluting 25d-2 (ent B).

Step E—Synthesis of Compound 147

A solution of 25d-1 (30 mg, 0.054 mmol) in DMF (5 mL) was treated with LiCl (22.93 mg, 0.541 mmol) and the mixture was heated at 80° C. for 3 hours, cooled to room temperature and directly purified using preparative RP- HPLC to provide Compound 147. ¹H NMR (400 MHz, CDCl₃) δ 10.52 (s, 1H), 8.63 (s, 1H), 7.31-7.37 (m, 1H), 6.81-6.84 (m, 2H), 4.61-4.64 (m, 2H), 4.30-4.33 (m, 2H), 3.81-4.14 (m, 4H), 3.25 (s, 3H), 2.91-2.99 (m, 2H), 2.44-2.60 (s, 1H), 2.00-2.06 (m, 1H), MS (+ESI) m/z: 465.1.

Step E—Synthesis of Compound 148

Similar conditions were used to convert 25d-2 to Compound 148. ¹H NMR (400 MHz, CDCl₃) δ 10.46 (s, 1H), 8.57 (s, 1H), 7.31-7.37 (m, 1H), 6.78-6.82 (m, 2H), 4.61-4.64 (m, 2H), 4.30-4.33 (m, 2H), 3.81-4.14 (m, 4H), 3.25 (s, 3H), 299-3.25 (m, 2H), 2.42-2.45 (s, 1H), 1.98-2.06 (m, 1H), MS (+ESI) m/z: 465.1.

The following compounds of the present invention were made using the methods described in the Example above and substituting the appropriate reactants and reagents. Chiral resolution to the enantiomers was accomplished after Step D (carbonylation) with SFC according to the notes in the table.

| Compound | Structure | Enantiomer[1] | Exact Mass [M + H]+ |
|---|---|---|---|
| 149 | 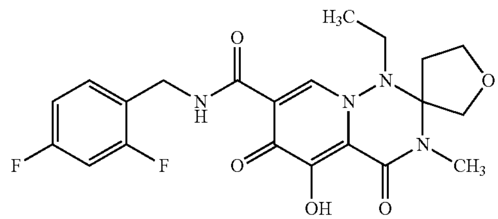 [SMILES: CCN1n2cc(C(=O)NCc3ccc(F)cc3F)c(=O)c(O)c2C(=O)N(C)C12CCOC2] | A[2] | Calc'd 449.2, found 449.1 |
| 150 | 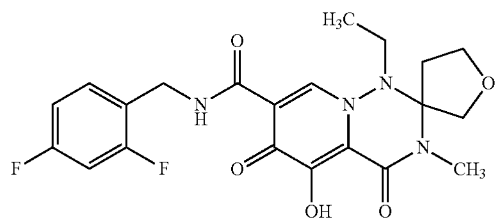 [SMILES: CCN1n2cc(C(=O)NCc3ccc(F)cc3F)c(=O)c(O)c2C(=O)N(C)C12CCOC2] | B[2] | Calc'd 449.2, found 449.1 |
| 151 | 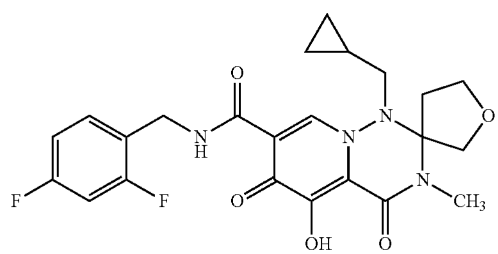 [SMILES: CN1C(=O)c2c(O)c(=O)c(C(=O)NCc3ccc(F)cc3F)cn2N(CC2CC2)C12CCOC2] | A[3] | Calc'd 475.2, found 475.1 |
| 152 | 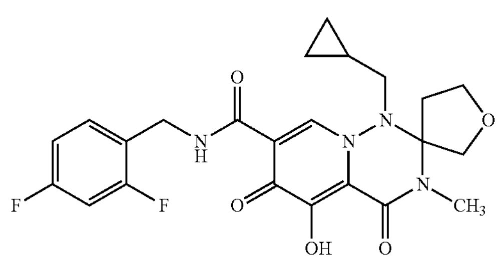 [SMILES: CN1C(=O)c2c(O)c(=O)c(C(=O)NCc3ccc(F)cc3F)cn2N(CC2CC2)C12CCOC2] | B[3] | Calc'd 475.2, found 475.1 |
| 153 | 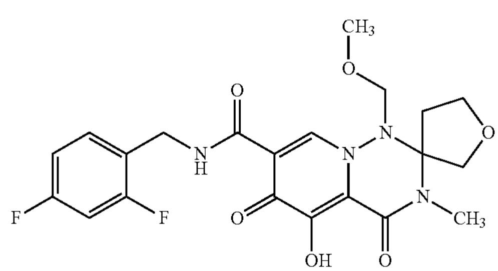 [SMILES: COCN1n2cc(C(=O)NCc3ccc(F)cc3F)c(=O)c(O)c2C(=O)N(C)C12CCOC2] | A[4] | Calc'd 465.2, found 465.2 |

-continued

| Compound | Structure | Enantiomer[1] | Exact Mass [M + H]+ |
|---|---|---|---|
| 154 | 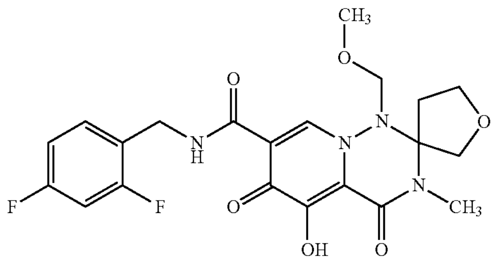 [SMILES: COCN1n2cc(C(=O)NCc3ccc(F)cc3F)c(=O)c(O)c2C(=O)N(C)C12CCOC2] | B[4] | Calc'd 465.2, found 465.2 |
| 155 | 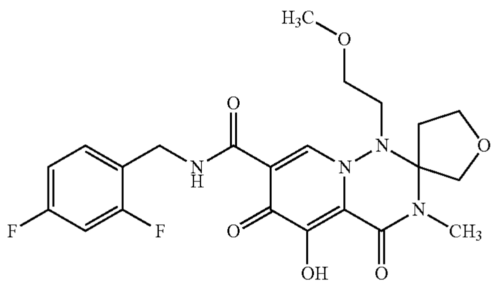 [SMILES: COCCN1n2cc(C(=O)NCc3ccc(F)cc3F)c(=O)c(O)c2C(=O)N(C)C12CCOC2] | A[3] | Calc'd 479.2, found 479.2 |
| 156 | 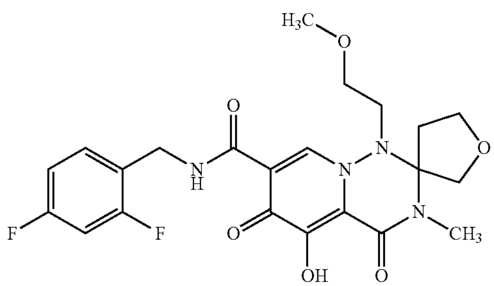 [SMILES: COCCN1n2cc(C(=O)NCc3ccc(F)cc3F)c(=O)c(O)c2C(=O)N(C)C12CCOC2] | B[3] | Calc'd 479.2, found 479.2 |
| 157 | 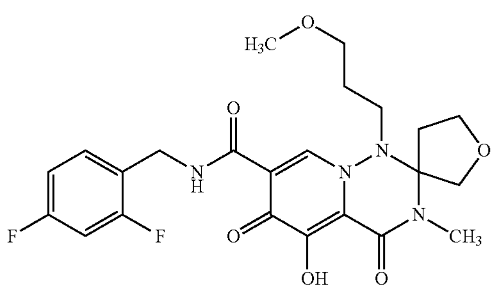 [SMILES: COCCCN1n2cc(C(=O)NCc3ccc(F)cc3F)c(=O)c(O)c2C(=O)N(C)C12CCOC2] | A[5] | Calc'd 493.2, found 493.2 |
| 158 | 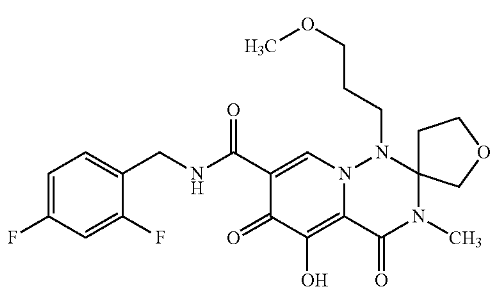 [SMILES: COCCCN1n2cc(C(=O)NCc3ccc(F)cc3F)c(=O)c(O)c2C(=O)N(C)C12CCOC2] | B[5] | Calc'd 493.2, found 493.2 |

[1] Enantiomer A is earlier eluting and enantiomer B is later eluting with the specified conditions
[2] Chiral Pak OJ, 250 × 30 mm, 25% ethanol (0.1% $NH_3H_2O$) in SC—$CO_2$, 50 mL/min, 220 nm
[3] Chiralcel OD, 250 × 30 mm, 35% methanol (0.1% $NH_3H_2O$) in SC—$CO_2$, 80 mL/min, 220 nm
[4] Chiralcel OJ-H, 250 mm × 30 mm, 40% EtOH (0.1% $NH_3H_2O$) in SC—CO2, 60 mL/min, 220 nm
[5] Chiralpak AD, 250 × 30 mm, 5 um, 80% MeOH (0.1% $NH_3•H_2O$) in SC—$CO_2$, 60 mL/min, 220 nm.

The following compounds of the present invention were made using the methods described in the Example above and substituting the appropriate reactants and reagents. Chiral resolution to the enantiomers was accomplished after Example 25, Step C (aryl bromide) with SFC according to the notes in the table.

| Compound | Structure | Enantiomer[1] | Exact Mass [M + H]+ |
|---|---|---|---|
| 159 | 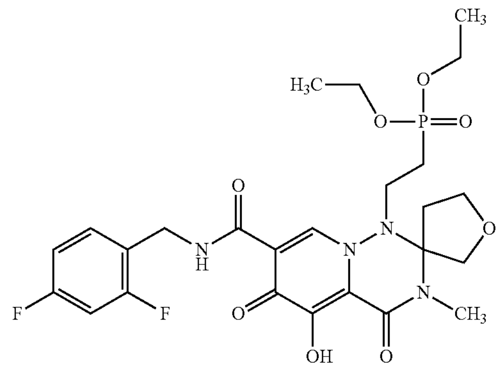 [SMILES: CCOP(=O)(CCN1n2cc(C(=O)NCc3ccc(F)cc3F)c(=O)c(O)c2C(=O)N(C)C12CCOC2)OCC] | A[2] | Calc'd 585.2, found 585.1 |
| 160 | 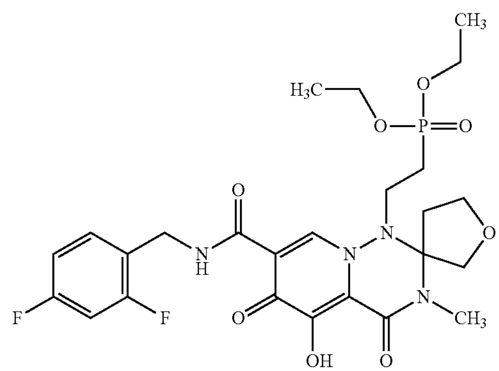 [SMILES: CCOP(=O)(CCN1n2cc(C(=O)NCc3ccc(F)cc3F)c(=O)c(O)c2C(=O)N(C)C12CCOC2)OCC] | B[2] | Calc'd 585.2, found 585.1 |
| 161 | 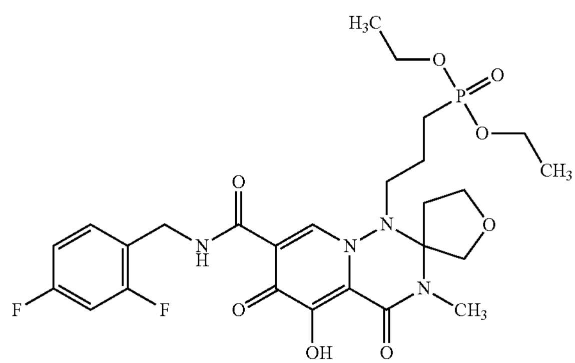 [SMILES: CCOP(=O)(CCCN1n2cc(C(=O)NCc3ccc(F)cc3F)c(=O)c(O)c2C(=O)N(C)C12CCOC2)OCC] | (±) | Calc'd 599.2, found 599.1 |
| 162 | 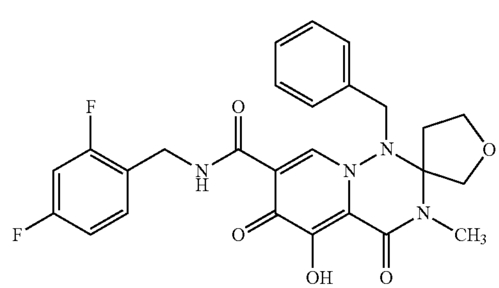 [SMILES: CN1C(=O)c2c(O)c(=O)c(C(=O)NCc3ccc(F)cc3F)cn2N(Cc2ccccc2)C12CCOC2] | A[3] | Calc'd 511.2, found 511.0 |

-continued

| Compound | Structure | Enantiomer[1] | Exact Mass [M + H]+ |
|---|---|---|---|
| 163 | 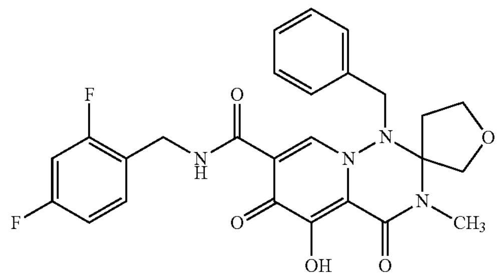 [SMILES: CN1C(=O)c2c(O)c(=O)c(C(=O)NCc3ccc(F)cc3F)cn2N(Cc2ccccc2)C12CCOC2] | B[3] | Calc'd 511.2, found 511.0 |
| 164 | 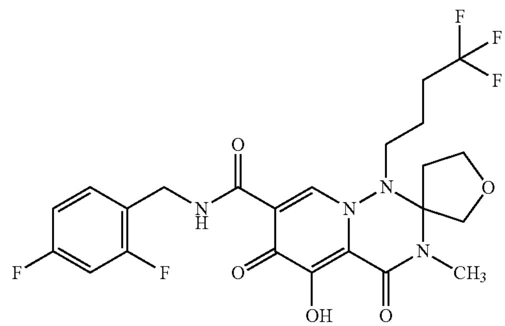 [SMILES: CN1C(=O)c2c(O)c(=O)c(C(=O)NCc3ccc(F)cc3F)cn2N(CCCC(F)(F)F)C12CCOC2] | A[4] | Calc'd 531.2, found 531.0 |
| 165 | 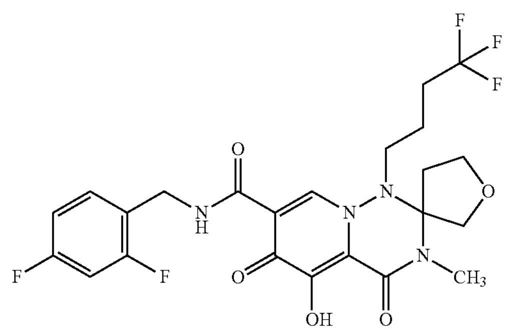 [SMILES: CN1C(=O)c2c(O)c(=O)c(C(=O)NCc3ccc(F)cc3F)cn2N(CCCC(F)(F)F)C12CCOC2] | B[4] | Calc'd 531.2, found 531.0 |
| 166 | 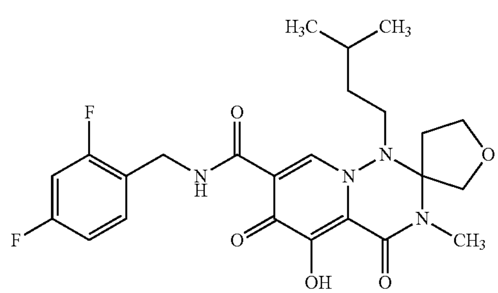 [SMILES: CC(C)CCN1n2cc(C(=O)NCc3ccc(F)cc3F)c(=O)c(O)c2C(=O)N(C)C12CCOC2] | A[5] | Calc'd 491.2, found 491.2 |
| 167 | 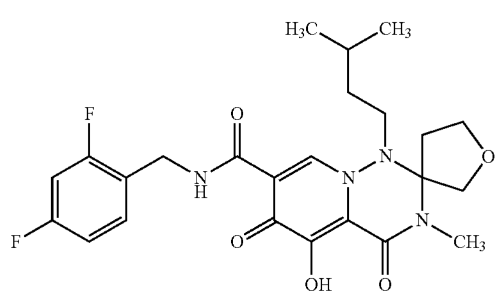 [SMILES: CC(C)CCN1n2cc(C(=O)NCc3ccc(F)cc3F)c(=O)c(O)c2C(=O)N(C)C12CCOC2] | B[5] | Calc'd 491.2, found 491.2 |

| Compound | Structure | Enantiomer[1] | Exact Mass [M + H]+ |
|---|---|---|---|
| 168 | 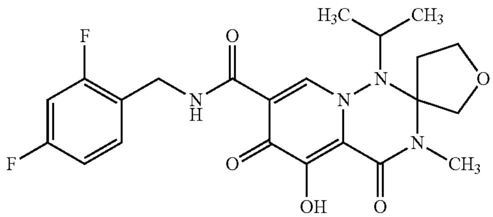 [SMILES: CC(C)N1n2cc(C(=O)NCc3ccc(F)cc3F)c(=O)c(O)c2C(=O)N(C)C12CCOC2] | (±) | Calc'd 463.2, found 463.2 |

[1]Enantiomer A is earlier eluting and enantiomer B is later eluting with the specified conditions
[2]OJ-H (2 × 25 cm), 15% (1:2) acetonitrile:methanol (0.1% NH4OH) in SC—CO2, 60 mL/min, 220 nm
[3]OJ-H (2 × 25 cm), 25% ethanol in SC—CO2, 60 mL/min, 220 nm
[4]OD-H (2 × 25 cm), 20% ethanol in SC—CO2, 70 mL/min, 220 nm
[5]OJ-H (2 × 25 cm), 15% ethanol (0.1% NH4OH) in SC—CO2, 60 mL/min, 220 nm

Example 26

Preparation of Compound 169 and Compound 170

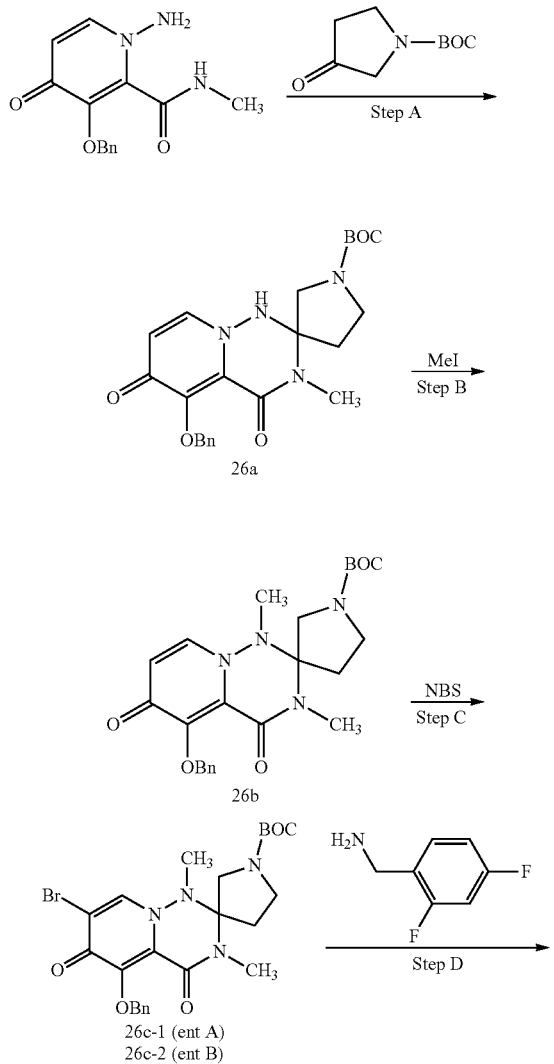

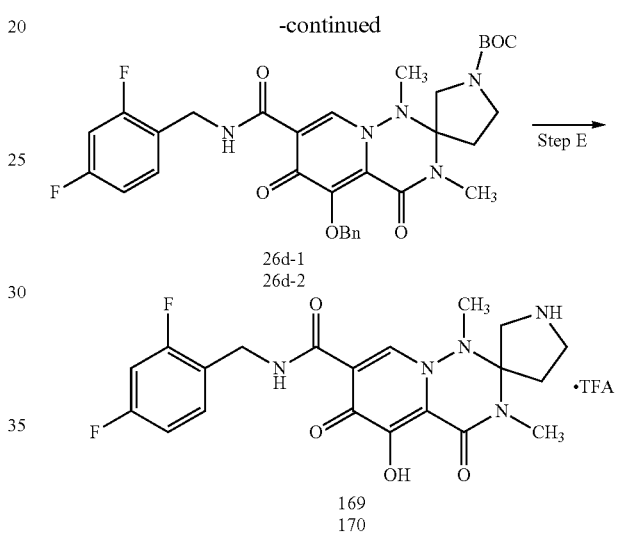

Step A—Synthesis of Intermediate Compound 26a

A suspension of 1-amino-3-(benzyloxy)-N-methyl-4-oxo-1,4-dihydropyridine-2-carboxamide (160 mg, 0.585 mmol) in THF (3.0 mL) was treated at rt with tert-butyl 3-oxopyrrolidine-1-carboxylate (434 mg, 2.342 mmol) and 1 drop of glacial acetic acid. The mixture was capped and heated at 70° C. for 6 h, cooled to room temperature and directly applied to a silica gel column. Purification by column chromatography on silica gel (10 to 20% MeOH/dichloromethane) provided 26a that was used without further purification. MS (+ESI) m/z: 440.8

Step B—Synthesis of Intermediate Compound 26b

A solution of 26a in DMSO (6 mL) was treated at rt with iodomethane (0.146 mL, 2.342 mmol) and finely-powdered potassium hydroxide (131 mg, 2.342 mmol), stirred at rt for 14 hours and then neutralized with glacial acetic acid. The mixture was directly purification by RP-MPLC to provide 26b that was used without further purification. MS (+ESI) m/z: 454.8

Step C—Synthesis of Intermediate Compound 26c

A solution of 26b (160 mg, 0.352 mmol) in DMF (2.0 mL) was treated at rt with N-bromosuccinimide (138 mg, 0.774 mmol) and TFA (1 drop). The mixture was allowed to stir at rt for 4 hours and then diluted with DMSO (2 mL). The mixture was directly purified using preparative RP-HPLC. After lyophilization, further purification by column chromatography on silica gel (10 to 100% [1:3 EtOH/ethyl acetate]/hexanes) provided (±)-26c. MS (+ESI) m/z: 532.7, 534.7. Chiral resolution by SFC (AD column, 30% MeOH (0.2% NH$_4$OH) in SC—CO$_2$, 70 ml/min, 100 bar, 35 mg/ml in MeOH, 220 nM) provided earlier eluting 26c-1 (ent A) and later eluting 26c-2 (ent B).

Step D—Synthesis of Intermediate Compound 26d-1

A mixture of 26c-1 (47 mg, 0.088 mmol), 2,4-difluorobenzylamine (0.023 mL, 0.194 mmol), N,N-diisopropylethylamine (0.046 mL, 0.264 mmol) and tetrakis(triphenylphosphine)palladium (50.9 mg, 0.044 mmol) in DMSO (1 mL) was sub-surface sparged with nitrogen gas for 30 minutes, stirred under carbon monoxide (1 atm) at 90° C. for 8 hours cooled to room temperature, treated with water (100 uL) and filtered. The filtrate was directly purified using RP-HPLC to provide 26d-1. MS (+ESI) m/z: 623.9

Step D—Synthesis of Intermediate Compound 26d-2

A mixture of 26c-2 (49 mg, 0.092 mmol), 2,4-difluorobenzylamine (0.024 mL, 0.202 mmol),N,N-diisopropylethylamine (0.048 mL, 0.276 mmol) and tetrakis(triphenylphosphine)palladium(0) (53.1 mg, 0.046 mmol) in DMSO (1 mL) was sub-surface sparged with nitrogen gas for 30 minutes and then stirred under carbon monoxide (1 atm) at 90° C. for 8 hours. Added water (100 uL) and filtered. The filtrate was purified using RP-HPLC to provide 26d-2. MS (+ESI) m/z: 623.9

Step E—Synthesis of Compound 169

A solution of 26d-1 (55 mg, 0.088 mmol) in TFA (1 mL) was allowed to stir for 2 hours at room temperature, diluted with DMSO and directly purified using RP-HPLC to provide compound 169. MS (+ESI) m/z: 434.0

Step E—Synthesis of Compound 170

A solution of 26d-2 (55 mg, 0.088 mmol) in TFA (1 mL) was allowed to stir for 2 hours at room temperature, diluted with DMSO and directly purified using RP-HPLC to provide compound 170. MS (+ESI) m/z: 434.0

The following compounds of the present invention were made using the methods described in the Example above and substituting the appropriate reactants and reagents.

| Compound | Structure | Enantiomer[1] | Exact Mass [M + H]+ |
|---|---|---|---|
| 171 | (structure shown) ·TFA | A[2] | Calc'd 448.2, found 448.0 |
| 172 | (structure shown) ·TFA | B[2] | Calc'd 448.2, found 448.0 |
| 173 | (structure shown) ·TFA | n/a | Calc'd 462.2, found 462.0 |

[1]Enantiomer A is earlier eluting and enantiomer B is later eluting with the specified conditions
[2]AD-H (2 × 25 cm), 20% isopropanol (0.1% NH$_4$OH) in SC—CO$_2$, 60 mL/min, 254 nm Example 27

Assessing Antiviral Potency in a Multiple Round HIV-1 Infection Assay

HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection.

MT4-GFP cells were maintained at 37° C./5% CO$_2$/90% relative humidity in RPMI 1640 supplemented with 10% fetal bovine serum, 100 Um' penicillin/streptomycin, and 400 μg/ml G418 to maintain the reporter gene. For infections, MT4-GFP cells were placed in the same medium lacking G418 and infected overnight with H9IIIB or NL4-3 virus at an approximate multiplicity of infection of 0.01 in the same incubation conditions. Cells were then washed and resuspended in either RPMI 1640 containing no serum at 1.6×10$^5$ cells/mL (serum free conditions), 10% normal human serum at 1.6×10$^5$ cells/mL (10% NHS conditions) or in 100% normal human serum at 2×10$^5$ cells/mL (100% NHS conditions). Compound plates were prepared by dispensing compounds dissolved in DMSO into wells of 384 well poly D lysine-coated plates (0.2 μl/well) using an ECHO acoustic dispenser. Each compound was tested in a 10 point serial 3-fold dilution (typical final concentrations: 4.2 μM-0.21 nM). Controls included no inhibitor (DMSO only) and a combination of three antiviral agents (efavirenz, indinavir, and an integrase strand transfer inhibitor having the structure:

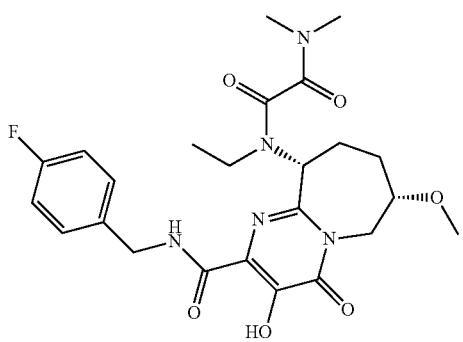 [SMILES: CCN(C(=O)C(=O)N(C)C)[C@@H]1CC[C@H](OC)Cn2c1nc(C(=O)NCc1ccc(F)cc1)c(O)c2=O]

at final concentrations of 4 μM each). Cells were added (50 μL/well) to compound plates and the infected cells were maintained at 37° C./5% $CO_2$/90% relative humidity.

Infected cells were quantified at two time points, 48 hours and 72 hours post-infection, by counting the number of green cells in each well using an Acumen eX3 scanner. The increase in the number of green cells over the 24 hour period between these time points gives the reproductive ratio, $R_0$, which is typically 5-15 and has been shown experimentally to be in logarithmic phase (data not shown). Inhibition of $R_0$ is calculated for each well, and $IC_{50}$s determined by non-linear 4-parameter curve fitting.

| Compound | ViKinG IP (nM) with 0% NHS | ViKinG IP (nM) with 10% NHS | ViKinG IP (nM) with 100% NHS |
|---|---|---|---|
| 5 | 16.4 | 22 | 250 |
| 6 | NA | 13 | 159 |
| 7 | 29.9 | 58 | 148 |
| 8 | 5.5 | NA | 131 |
| 9 | 89.7 | NA | 344 |
| 10 | NA | 57 | 1499 |
| 11 | NA | 31 | 359 |
| 12 | NA | 24 | 126 |
| 13 | 8.6 | 14 | 106 |
| 14 | NA | 41 | NA |
| 15 | 8.0 | 178 | 3135 |
| 16 | 17.3 | 47 | NA |
| 17 | 29.3 | NA | 1518 |
| 18 | NA | 13 | 254 |
| 19 | NA | 9 | 133 |
| 20 | NA | 234 | NA |
| 21 | NA | 141 | NA |
| 22 | NA | 47 | 731 |
| 23 | NA | 100 | NA |
| 24 | 11.9 | 6 | 86 |
| 25 | 5.3 | 17 | 257 |
| 26 | 11.5 | 26 | 161 |
| 27 | 21.2 | 72 | 712 |
| 28 | 53.5 | 122 | 679 |
| 29 | 89.1 | NA | 2075 |
| 30 | 38.5 | NA | 280 |
| 31 | NA | 121 | 2099 |
| 32 | 8.0 | NA | 74 |
| 33 | NA | 49 | 89 |
| 34 | 9.7 | 34 | NA |
| 35 | 1.7 | NA | 133 |
| 36 | 3.8 | NA | 368 |
| 37 | 5.3 | NA | 456 |
| 38 | 3.8 | NA | 132 |
| 39 | 4.2 | NA | 49 |
| 40 | 2.8 | NA | 236 |
| 41 | 11.2 | NA | 7804 |
| 42 | 2.4 | NA | 234 |
| 43 | 3.0 | NA | 39 |
| 44 | 5.8 | NA | 57 |
| 45 | 6.4 | NA | 236 |
| 46 | 3.2 | NA | 110 |
| 47 | 6.6 | NA | 71 |
| 48 | 124.5 | NA | 194 |
| 49 | 2.9 | NA | 123 |
| 50 | 3.1 | NA | 107 |
| 51 | 4.8 | NA | 196 |
| 52 | 4.8 | NA | 2004 |
| 53 | 5.3 | NA | 2566 |
| 54 | 2.3 | NA | 989 |
| 55 | 0.6 | NA | 30 |
| 56 | 1.2 | NA | 100 |
| 57 | 1.6 | NA | 36 |
| 58 | 1.9 | 5 | 27 |
| 59 | 1.9 | NA | 56 |
| 60 | 3.1 | NA | 42 |
| 61 | 2.4 | NA | 119 |
| 62 | 3.1 | NA | 72 |
| 63 | 1.9 | NA | 17 |
| 64 | 3.3 | NA | 26 |
| 65 | 1.5 | NA | 60 |
| 66 | 1.5 | NA | 40 |
| 67 | 6.6 | NA | 3602 |
| 68 | 7.6 | NA | 134 |
| 69 | 3.5 | NA | 452 |
| 70 | 2.5 | NA | 91 |
| 71 | 3.7 | NA | 350 |
| 72 | 4.6 | NA | 290 |
| 73 | 1.8 | NA | 30 |
| 74 | 3.3 | NA | 28 |
| 75 | 1.8 | NA | 559 |
| 76 | 2.4 | NA | 151 |
| 77 | 3.0 | NA | 96 |
| 78 | 2.3 | NA | 55 |
| 79 | 2.3 | NA | 603 |
| 80 | 1.7 | NA | 217 |
| 81 | 4.3 | NA | 323 |
| 82 | 3.1 | NA | 680 |
| 83 | 7.8 | NA | 3047 |
| 84 | 4.5 | NA | 1960 |
| 85 | 5.4 | NA | 78 |
| 86 | 9.3 | NA | 177 |
| 87 | 16.0 | NA | 98 |
| 88 | 10.3 | NA | 97 |
| 89 | 16.1 | NA | 87 |
| 90 | 34.1 | NA | 123 |
| 91 | 59.9 | NA | 181 |
| 92 | 158.9 | NA | 3646 |
| 93 | 73.9 | 114 | NA |
| 94 | 10.6 | NA | 116 |
| 95 | 11.6 | NA | 104 |
| 96 | 69.3 | NA | 2241 |
| 97 | 41.7 | NA | 1051 |
| 98 | 91.6 | NA | 2032 |
| 99 | 40.9 | NA | 870 |
| 100 | 29.2 | NA | 704 |
| 101 | 4.6 | NA | 70 |
| 102 | 6.8 | NA | 85 |
| 103 | 1.7 | 6 | 114 |
| 104 | 0.8 | 4 | 87 |
| 105 | 0.8 | NA | 37 |
| 106 | 0.6 | NA | 27 |
| 107 | 1.2 | NA | 790 |
| 108 | 1.1 | NA | 218 |
| 109 | 0.6 | NA | 229 |
| 110 | 0.5 | NA | 121 |
| 111 | 1.6 | NA | 158 |
| 112 | 0.9 | NA | 231 |
| 113 | 1.5 | NA | 94 |
| 114 | 0.8 | NA | 87 |
| 115 | 1.2 | NA | 54 |
| 116 | 0.7 | NA | 42 |
| 117 | 0.5 | NA | 246 |
| 118 | 0.5 | NA | 101 |
| 119 | 1.2 | 11 | 163 |
| 120 | 2.1 | NA | 266 |
| 121 | 1.8 | 39 | 575 |

-continued

| Compound | ViKinG IP (nM) with 0% NHS | ViKinG IP (nM) with 10% NHS | ViKinG IP (nM) with 100% NHS |
|---|---|---|---|
| 122 | 2.4 | NA | 1991 |
| 123 | 1.2 | 9 | 117 |
| 124 | 1.8 | 22 | 309 |
| 125 | 0.8 | NA | 257 |
| 126 | 1.3 | NA | 455 |
| 127 | 1.0 | NA | 134 |
| 128 | 0.7 | NA | 131 |
| 129 | 0.6 | NA | 73 |
| 130 | 2.3 | NA | 257 |
| 131 | 0.8 | NA | 114 |
| 132 | 0.5 | NA | 77 |
| 133 | 0.5 | NA | 55 |
| 134 | 0.9 | NA | 65 |
| 135 | 0.9 | NA | 486 |
| 136 | 0.5 | NA | 83 |
| 137 | 0.7 | NA | 64 |
| 138 | 0.6 | NA | 134 |
| 139 | 1.5 | NA | 247 |
| 140 | 1.7 | NA | 48 |
| 141 | 2.3 | NA | 71 |
| 142 | 1.3 | 13 | 171 |
| 143 | 1.4 | 7 | 78 |
| 144 | 1.5 | 60 | 591 |
| 145 | 1.4 | NA | 174 |
| 146 | 10.9 | NA | 485 |
| 147 | 1.6 | NA | 74 |
| 148 | 1.2 | NA | 33 |
| 149 | 0.7 | NA | 144 |
| 150 | 0.6 | NA | 71 |
| 151 | 0.7 | NA | 240 |
| 152 | 0.7 | NA | 174 |
| 153 | 1.3 | NA | 275 |
| 154 | 0.7 | NA | 37 |
| 155 | 0.5 | NA | 37 |
| 156 | 1.2 | NA | 106 |
| 157 | 2.5 | NA | 111 |
| 158 | 1.0 | NA | 168 |
| 159 | NA | NA | 71 |
| 160 | NA | NA | 46 |
| 161 | NA | NA | 227 |
| 162 | NA | NA | 72 |
| 163 | NA | NA | 35 |
| 164 | NA | NA | 178 |
| 165 | NA | NA | 146 |
| 166 | NA | NA | NA |
| 167 | NA | NA | NA |
| 168 | NA | NA | NA |
| 169 | 4.4 | NA | 512 |
| 170 | 5.0 | NA | 66 |
| 171 | 1.8 | NA | 88 |
| 172 | 1.6 | NA | 61 |
| 173 | 3.2 | NA | 52 |

NA = not available

What is claimed is:

1. A compound having the formula:

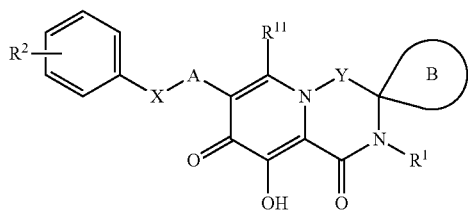

(I)

or a pharmaceutically acceptable salt or prodrug thereof, wherein:
A is —NHC(O)—;
B is a 3 to 8-membered heterocycloalkyl or an 8 to 14 membered bicyclic heterocycloalkyl, each of which can be optionally be substituted with one or more groups, each independently selected from $R^7$;
X is $C_1$-$C_3$ alkylene;
Y is —C($R^3$)$_2$— or —N($R^4$)—;
$R^1$ is selected from H, $C_1$-$C_6$ alkyl, $C_3$-$C_7$ cycloalkyl, —($C_1$-$C_4$ alkylene)-O—($C_1$-$C_6$ alkyl), —($C_1$-$C_4$ alkylene)-S—($C_1$-$C_6$ alkyl), —($C_1$-$C_4$ alkylene)-$SO_2$—($C_1$-$C_6$ alkyl), —($C_1$-$C_4$ alkylene)-N—($C_1$-$C_6$ alkyl)$_2$, —($C_1$-$C_6$ alkylene)$_p$-P(O)(—$OR^{10}$)$_2$, $C_1$-$C_6$ haloalkyl, $C_1$-$C_6$ hydroxyalkyl, phenyl, 3 to 8-membered monocyclic heterocycloalkyl and 5 or 6-membered monocyclic heteroaryl;
$R^2$ represents up to 3 optional substituents, each independently selected from halo, $C_1$-$C_6$ alkyl, —O—($C_1$-$C_6$ alkyl) and $C_1$-$C_6$ haloalkyl;
each occurrence of $R^3$ is independently selected from H, $C_1$-$C_6$ alkyl, $C_1$-$C_6$ haloalkyl, —($C_1$-$C_4$ alkylene)$_p$-(5 or 6-membered monocyclic heteroaryl), —($C_1$-$C_4$ alkylene)$_p$-(phenyl), $C_3$-$C_7$ cycloalkyl, —($C_1$-$C_6$ alkylene)$_p$-P(O)(—$OR^{10}$)$_2$, —($C_1$-$C_4$ alkylene)-S—($C_1$-$C_6$ alkyl), —($C_1$-$C_4$ alkylene)-$SO_2$—($C_1$-$C_6$ alkyl), —N($R^6$)C(O)$R^5$, —($C_1$-$C_4$ alkylene)-N—($C_1$-$C_6$ alkyl)$_2$ and 3 to 8-membered monocyclic heterocycloalkyl;
$R^4$ is selected from H, $C_1$-$C_6$ alkyl, $C_1$-$C_6$ haloalkyl, $C_1$-$C_6$ hydroxyalkyl, —$SO_2R^5$, —C(O)$R^5$, —($C_1$-$C_6$ alkylene)$_p$-C(O)N($R^6$)$_2$, —($C_1$-$C_6$ alkylene)$_p$-P(O)(—$OR^{10}$)$_2$, —N($R^6$)C(O)$R^5$, —($C_2$-$C_4$ alkylene)-O—($C_1$-$C_6$ alkyl), —($C_2$-$C_4$ alkylene)-S—($C_1$-$C_6$ alkyl), —($C_2$-$C_4$ alkylene)-$SO_2$—($C_1$-$C_6$ alkyl), —($C_2$-$C_4$ alkylene)-N—($C_1$-$C_6$ alkyl)$_2$, —($C_1$-$C_6$ alkylene)$_p$-($C_3$-$C_7$ cycloalkyl), —($C_1$-$C_4$ alkylene)$_p$-(5 or 6-membered monocyclic heteroaryl), —($C_1$-$C_4$ alkylene)$_p$-(8 to 10-membered bicyclic heteroaryl), —($C_1$-$C_4$ alkylene)$_p$-(phenyl) and 4 to 8-membered monocyclic heterocycloalkyl;
each occurrence of $R^5$ is independently selected from $C_1$-$C_6$ alkyl, $C_1$-$C_6$ haloalkyl, $C_3$-$C_7$ cycloalkyl, phenyl, 3 to 8-membered monocyclic heterocycloalkyl or 6-membered monocyclic heteroaryl and 8 to 10-membered bicyclic heteroaryl, wherein said $C_3$-$C_7$ cycloalkyl group, said phenyl group, said 5 or 6-membered monocyclic heteroaryl group and said 8 to 10-membered bicyclic heteroaryl group can be optionally substituted with one or more groups, each independently selected from $R^7$;
each occurrence of $R^6$ is independently selected from H, $C_1$-$C_6$ alkyl, $C_3$-$C_7$ cycloalkyl, —($C_1$-$C_6$ alkylene)-N($R^8$)$_2$, $C_1$-$C_6$ haloalkyl, —C(O)O($C_1$-$C_6$ alkyl), —($C_1$-$C_6$ alkylene)$_p$-$R^9$ and —($C_1$-$C_6$ alkylene)-O—($C_1$-$C_6$ alkyl);
each occurrence of $R^7$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, 5 or 6-membered monocyclic heteroaryl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —$NH_2$, —NH($C_1$-$C_6$ alkyl), —N($C_1$-$C_6$ alkyl)$_2$, —S(O)$_2$($C_1$-$C_6$ alkyl), —NHS(O)$_2$—($C_1$-$C_6$ alkyl), —S(O)$_2$NH—($C_1$-$C_6$ alkyl), —S(O)$_2$N($C_1$-$C_6$ alkyl)$_2$, —OC(O)—($C_1$-$C_6$ haloalkyl), —C(O)O-benzyl, —($C_1$-$C_6$ alkylene)$_p$-C(O)O—($C_1$-$C_6$ alkyl), —($C_1$-$C_6$ alkylene)$_p$-C(O)—($C_1$-

$C_6$ alkyl), —($C_1$-$C_6$ alkylene)$_p$-C(O)N($R^8$)$_2$, $C_1$-$C_6$ hydroxyalkyl, —P(O)(O$R^{10}$)$_2$, and —CN;

each occurrence of $R^8$ is independently selected from H, $C_1$-$C_6$ alkyl, $C_3$-$C_7$ cycloalkyl, $C_1$-$C_6$ haloalkyl, —C(O)O($C_1$-$C_6$ alkyl), —($C_1$-$C_6$ alkylene)$_p$-$R^9$ and —($C_1$-$C_6$ alkylene)-O—($C_1$-$C_6$ alkyl);

each occurrence of $R^9$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^{10}$ is independently selected from H and $C_1$-$C_6$ alkyl;

$R^{11}$ is selected from H, $C_1$-$C_6$ alkyl, $C_1$-$C_6$ hydroxyalkyl, —O—($C_1$-$C_6$ alkyl), $C_3$-$C_7$ cycloalkyl and —($C_1$-$C_4$ alkylene)-O—($C_1$-$C_6$ alkyl); and each occurrence of p is independently 0 or 1.

2. The compound of claim 1, wherein X is —CH$_2$—, or a pharmaceutically acceptable salt or prodrug thereof.

3. The compound of claim 1, wherein $R^{11}$ is H or —CH$_2$OCH$_3$—, or a pharmaceutically acceptable salt or prodrug thereof.

4. The compound of claim 1 having the formula:

(Ia)

or a pharmaceutically acceptable salt thereof,
wherein:
A is —NHC(O)—;
B is a 5 or 6-membered heterocycloalkyl;
Y is —CH$_2$— or —N(CH$_3$)—;
$R^1$ is selected from $C_1$-$C_6$ alkyl and —($C_2$-$C_4$ alkylene)-O—($C_1$-$C_6$ alkyl); and
$R^2$ represents up to 3 optional substituents, each independently selected from halo.

5. The compound of claim 1, wherein Y is —CH$_2$— or —N(CH$_3$), or a pharmaceutically acceptable salt or prodrug thereof.

6. A compound
having the formula:

(I)

or a pharmaceutically acceptable salt or prodrug thereof, wherein:
A is

B is a 3 8-membered heterocycloalkyl or an 8 to 14 membered bicyclic heterocycloalkyl, each of which can be optionally be substituted with one or more groups, each independently selected from $R^7$;
X is $C_1$-$C_3$ alkylene;
Y is —N($R^4$)—;
$R^1$ is selected from H, $C_1$-$C_6$ alkyl, $C_3$-$C_7$ cycloalkyl, —($C_1$-$C_4$ alkylene)-O—($C_1$-$C_6$ alkyl), —($C_1$-$C_4$ alkylene)-S—($C_1$-$C_6$ alkyl), —($C_1$-$C_4$ alkylene)-SO$_2$—($C_1$-$C_6$ alkyl), —$C_1$-$C_4$ alkylene)-N—($C_1$-$C_6$ alkyl)$_2$, —($C_1$-$C_6$ alkylene)$_p$-P(O)(—O$R^{10}$)$_2$, $C_1$-$C_6$ haloalkyl, $C_1$-$C_6$ hydroxyalkyl, phenyl, 3 to 8-membered monocyclic heterocycloalkyl and 5 or 6-membered monocyclic heteroaryl;
$R^2$ respresents up to 3 optional subsitutents, each indepenedtly selected from halo, $C_1$-$C_6$ alkyl, —O—($C_1$-$C_6$ alkyl) and $C_1C_6$ haloalkyl;
$R^4$ is selected from H, $C_1$-$C_6$ alkly, $C_1$-$C_6$haloalkyl, $C_1$-$C_6$ hydroxyalkyl, —SO$_2$$R^5$, —C(O)$R^5$, —($C_1$-$C_6$ alkylene)$_p$-C(O)N($R^6$)$_2$, —($C_1$-$C_6$ alkylene)$_p$-P(O)(—O$R^{10}$)$_2$, —N($R^6$)C(O)$R^5$, —($C_2$-$C_4$ alkylene)-O—($C_1$-$C_6$ alkyl), —($C_2$-$C_4$ alkylene)-S—($C_1$-$C_6$ alkyl), —($C_2$$C_4$ alkylene)-SO$_2$—($C_1$-$C_6$ alkyl), —($C_2$-$C_4$ alkylene)-N—($C_1$-$C_6$ alkyl)$_2$, —($C_1$-$C_6$ alkylene)$_p$—($C_3$-$C_7$ cycloalkyl), —($C_1$-$C_4$ alkylene)$_p$-(5 or 6-membered monocyclic heteroaryl), —($C_1$-$C_4$ alkylene)$_p$-(8 to 10-membered bicyclic heteroaryl), —($C_1$-$C_4$ alkylene)$_p$-(phenyl) and 4 to 8 membered monocyclic heterocycloalkyl;
each occurrence of $R^5$ is independently selected from $C_1$-$C_6$ alkyl, $C_1$-$C_6$ haloalkyl, $C_3$-$C_7$ cycloalkyl, phenyl, 3 to 8-membered monocyclic heterocycloalkyl or 6-membered monocyclic heteroaryl and 8 to 10-membered bicyclic heteroaryl, wherein said $C_3$-$C_7$ cycloalkyl group, said phenyl group, said 5 or 6-membered monocyclic heteroaryl group and said 8 to 10-membered bicyclic heteroaryl group can be optionally substituted with one or more groups, each independently selected from $R^7$;
each occurrence of $R^6$ is independently selected from H, $C_1$-$C_6$ alkyl, $C_3$-$C_7$ cycloalkyl, —($C_1$-$C_6$ alkylene)-N($R^8$)$_2$, $C_1$-$C_6$ haloalkyl, —C(O)O($C_1$-$C_6$ alkyl), —($C_1$-$C_6$ alkylene)$_p$-$R^9$ and —($C_1$-$C_6$ alkylene)-O—($C_1$-$C_6$ alkyl);
each occurrence of $R^7$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, 5 or 6-membered monocyclic heteroaryl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —NH$_2$, —NH($C_1$-$C_6$ alkyl), —N($C_1$-$C_6$ alkyl)$_2$, —S(O)$_2$($C_1$-$C_6$ alkyl), —NHS(O)$_2$—($C_1$-$C_6$ alkyl), —S(O)$_2$NH—($C_1$-$C_6$ alkyl), —S(O)$_2$N($C_1$-$C_6$ alkyl)$_2$, —OC(O)—($C_1$-$C_6$ haloalkyl), —C(O)O-benzyl, —($C_1$-$C_6$ alkylene)$_p$-C(O)O—($C_1$-$C_6$ alkyl), —($C_1$-$C_6$ alkylene)$_p$-C(O)—($C_1$-

$C_6$ alkyl), —($C_1$-$C_6$ alkylene)$_p$-C(O)N($R^8$)$_2$, $C_1$-$C_6$ hydroxyalkyl, —P(O)(O$R^{10}$)$_2$, and —CN;

each occurrence of $R^8$ is independently selected from H, $C_1$-$C_6$ alkyl, $C_3$-$C_7$ cycloalkyl, $C_1$-$C_6$ haloalkyl, —C(O)O($C_1$-$C_6$ alkyl), —($C_1$-$C_6$ alkylene)$_p$-$R^9$ and —($C_1$-$C_6$ alkylene)-O—($C_1$-$C_6$ alkyl);

each occurrence of $R^9$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^{10}$ is independently selected from H and $C_1$-$C_6$ alkyl;

$R^{11}$ is selected from H, $C_1$-$C_6$ alkyl, $C_1$-$C_6$ hydroxyalkyl, —O—($C_1$-$C_6$ alkyl), $C_3$-$C_7$ cycloalkyl and —($C_1$-$C_4$ alkylene)-O—($C_1$-$C_6$ alkyl); and each occurrence of p is independently 0 or 1.

7. The compound of claim 1, wherein B is a 5 or 6-membered heterocycloalkyl ring, or a pharmaceutically acceptable salt or prodrug thereof.

8. The compound of claim 7, wherein B is tetrahydrofuranyl or tetrahydropyranyl, or a pharmaceutically acceptable salt or prodrug thereof.

9. The compound of claim 7, wherein B is piperidinyl, optionally substituted on the ring nitrogen atom with —C(O)O$R^5$, —C(O)$R^5$, —S(O)$_2$—($C_1$-$C_6$ alkyl) or —S(O)$_2$NH—($C_1$-$C_6$ alkyl), or a pharmaceutically acceptable salt or prodrug thereof.

10. The compound of claim 1, having the formula (Ib):

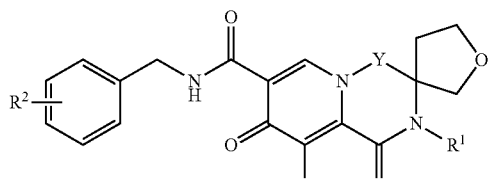

(Ib)

or a pharmaceutically acceptable salt or prodrug thereof, wherein:

Y is —CH$_2$— or —N(CH$_3$)—;

$R^1$ is selected from $C_1$-$C_6$ alkyl and —($C_2$-$C_4$ alkylene)-O—($C_1$-$C_6$ alkyl); and $R^2$ represents up to 3 optional substituents, each independently selected from halo.

11. The compound of claim 1, wherein Y is —N(CH$_3$)—, or a pharmaceutically acceptable salt or prodrug thereof.

12. The compound of claim 1, wherein $R^1$ is selected from methyl, ethyl, n-propyl and —CH$_2$CH$_2$OCH$_3$, or a pharmaceutically acceptable salt or prodrug thereof.

13. The compound of claim 1, wherein $R^2$ represents two fluoro groups, in the ortho and para positions, or a pharmaceutically acceptable salt or prodrug thereof.

14. A compound that is

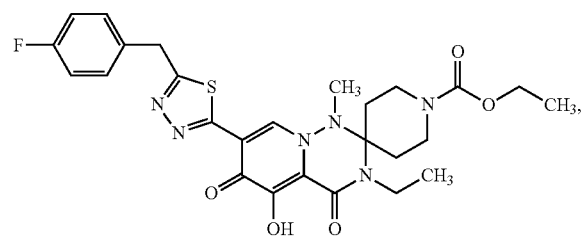

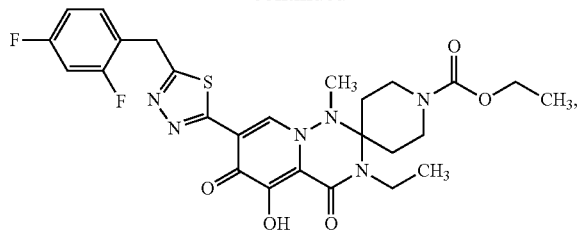

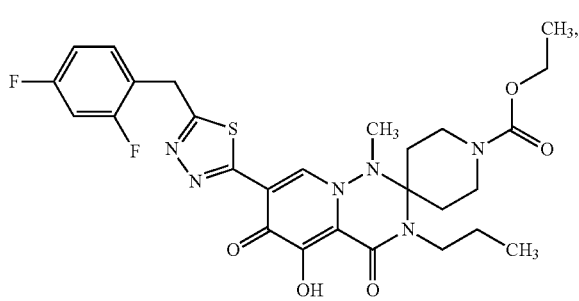

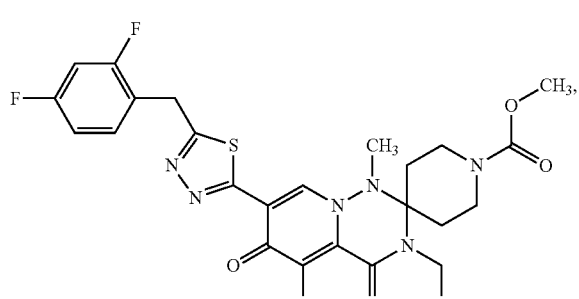

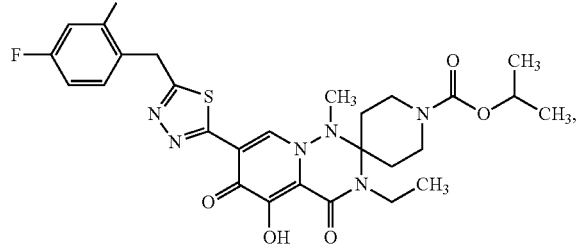

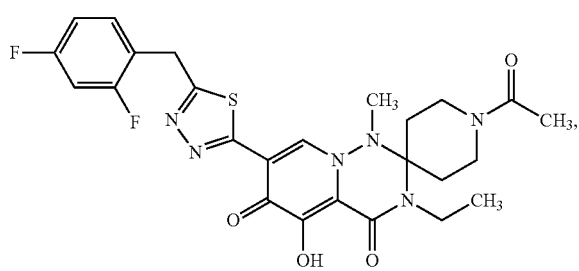

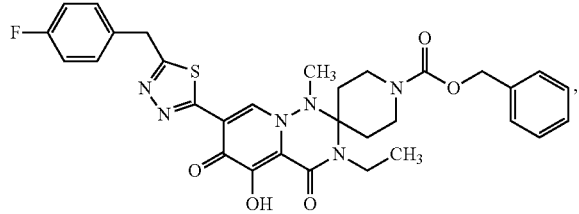

211
-continued
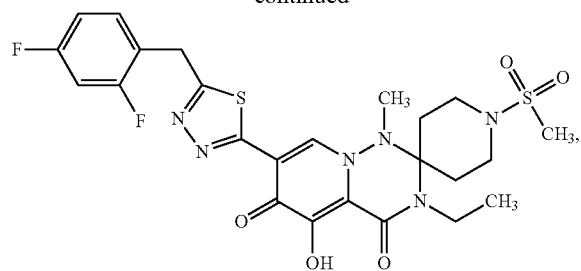
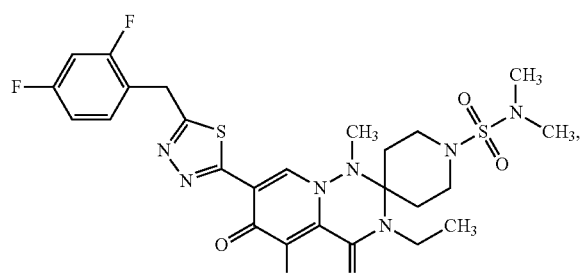
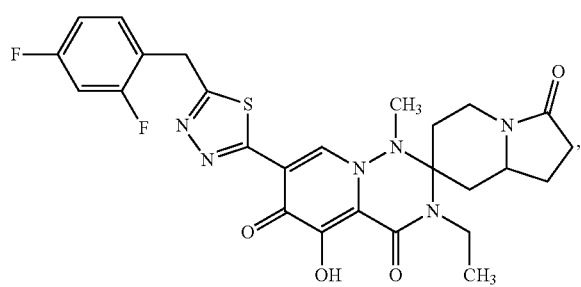
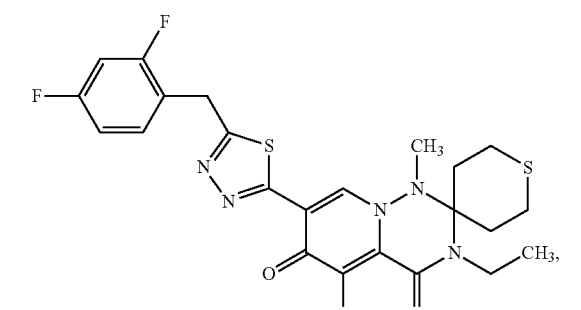
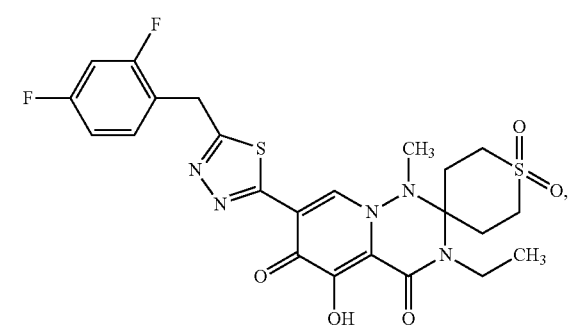
212
-continued
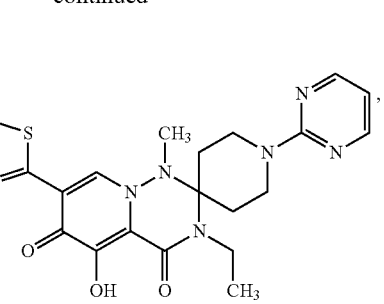
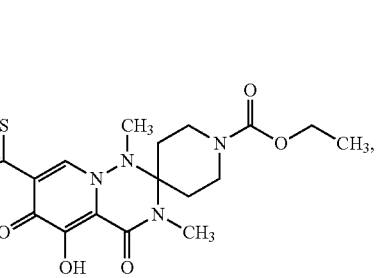
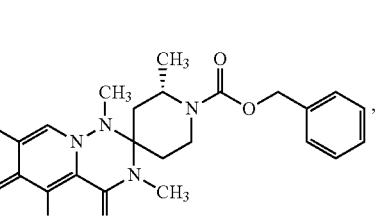
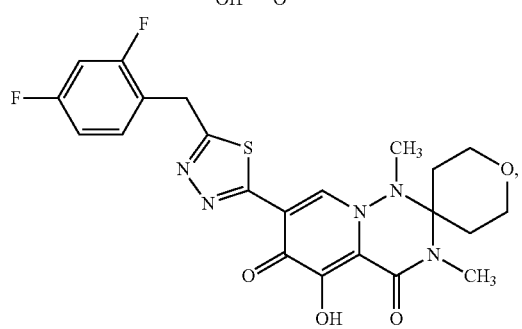

213
-continued
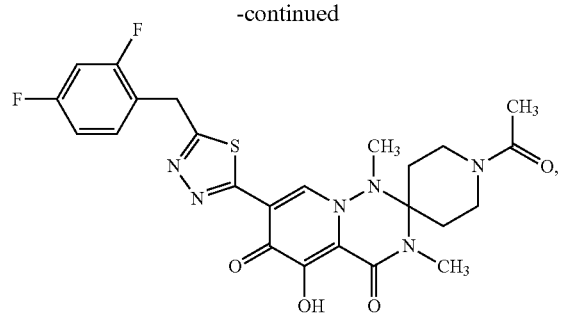
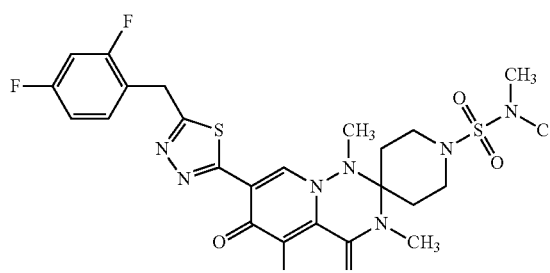
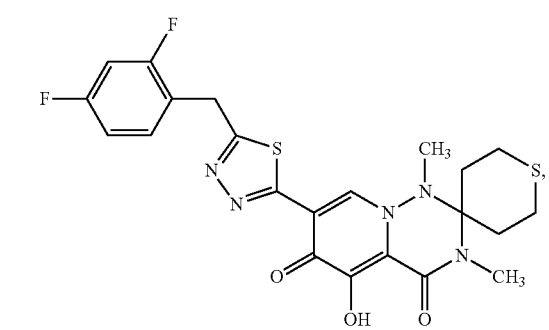
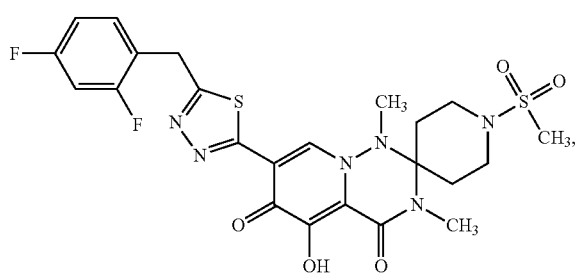
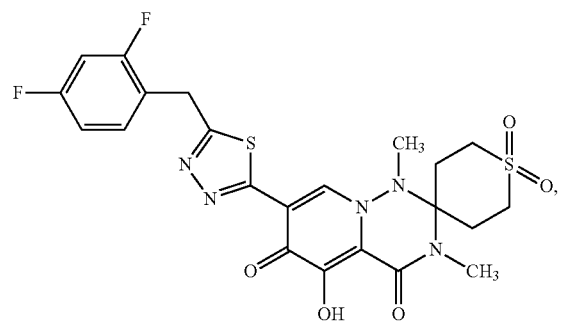
214
-continued
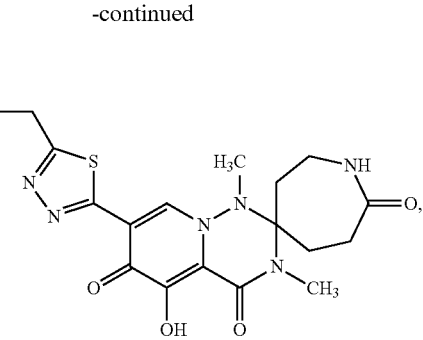
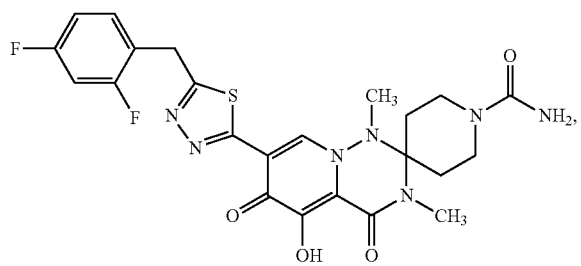
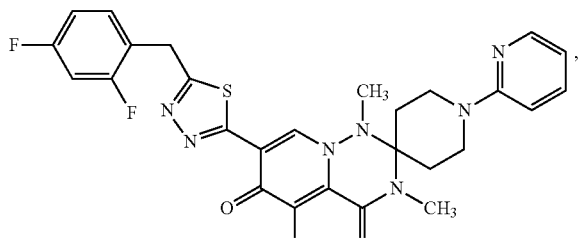
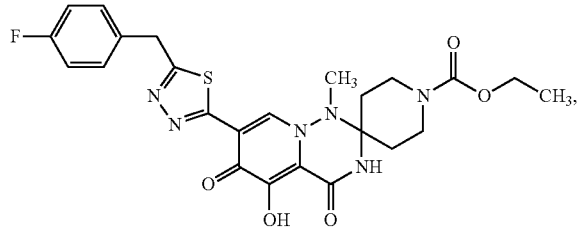
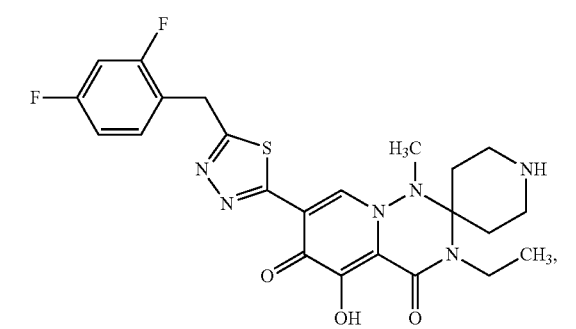
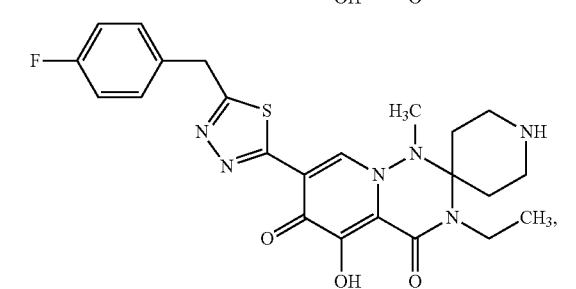

215
-continued
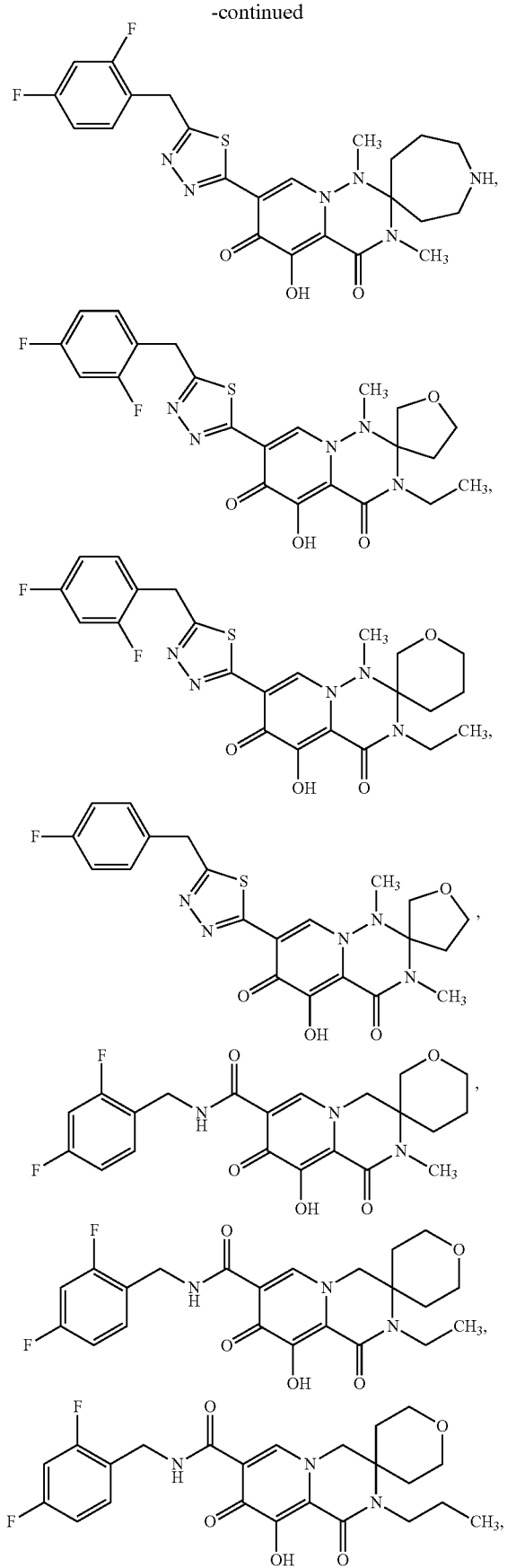
216
-continued
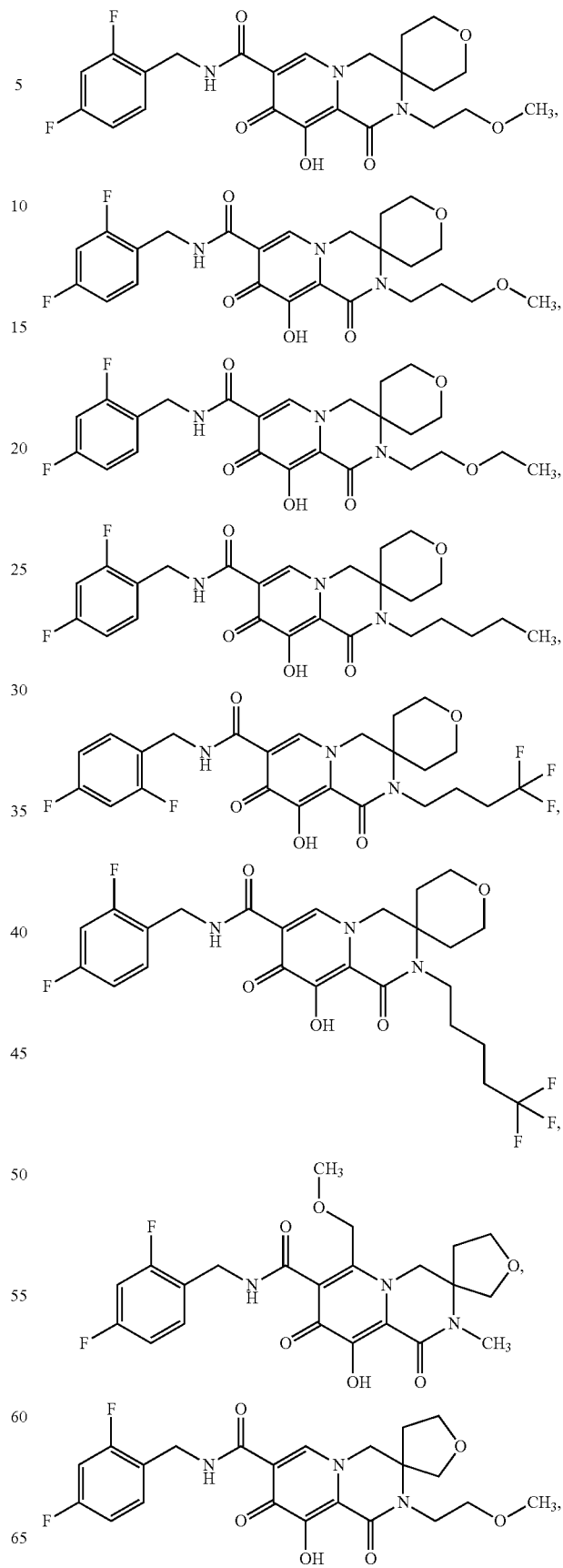

217
-continued
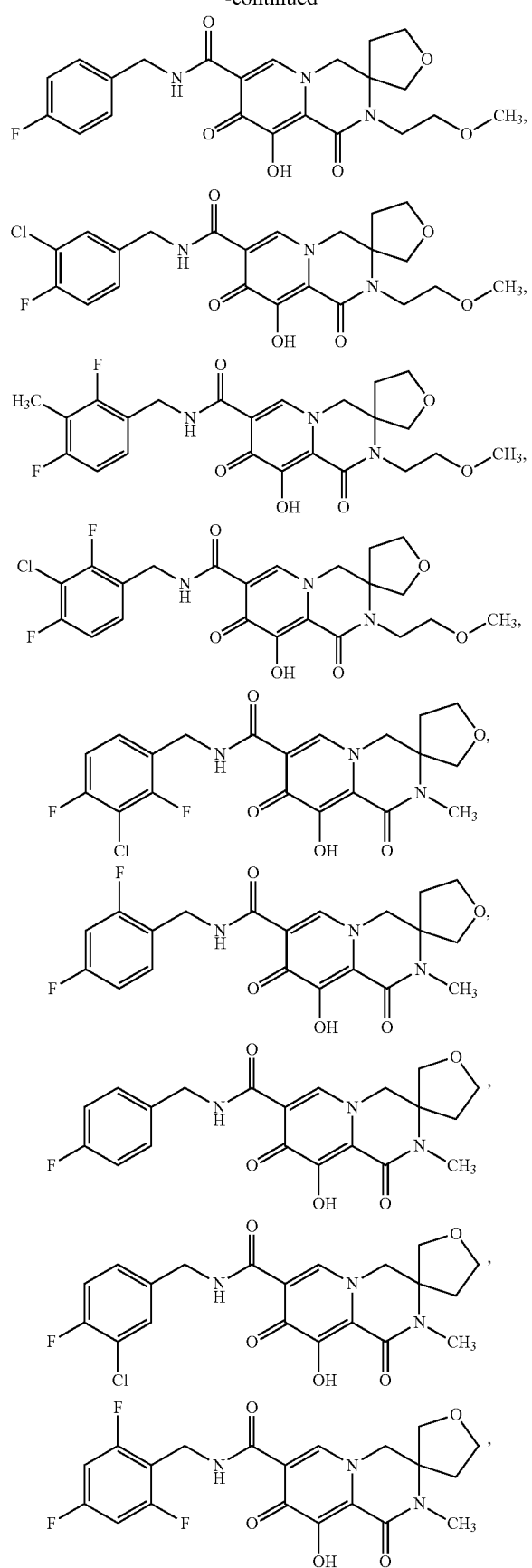
218
-continued
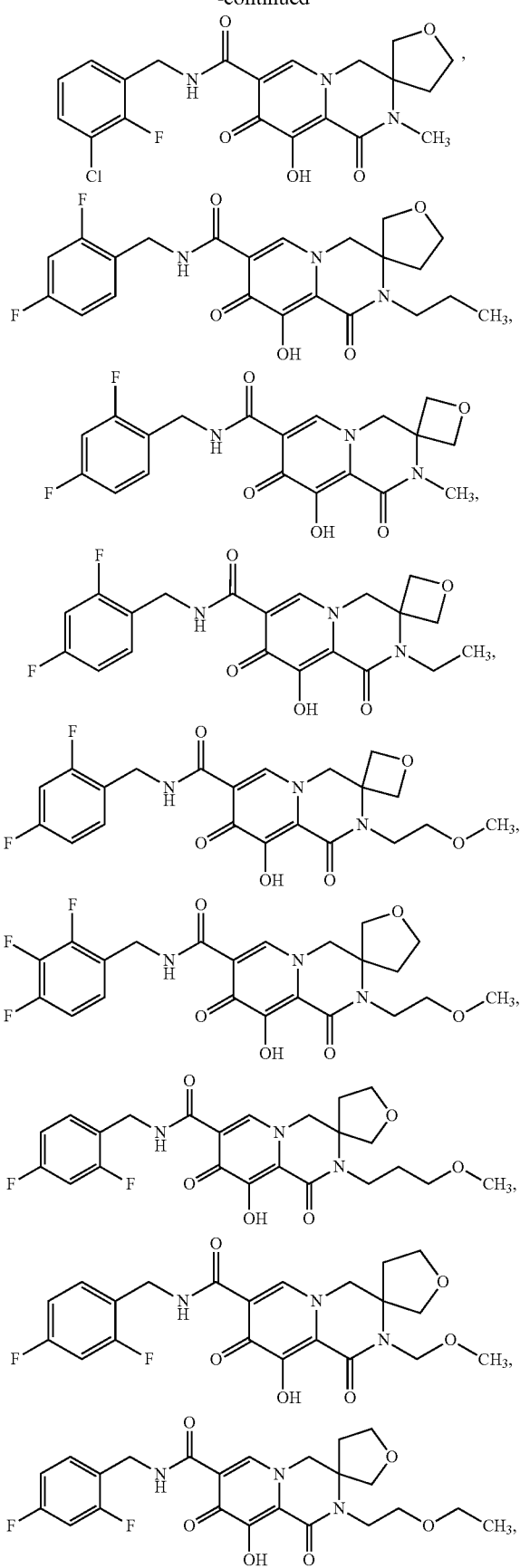

219
-continued
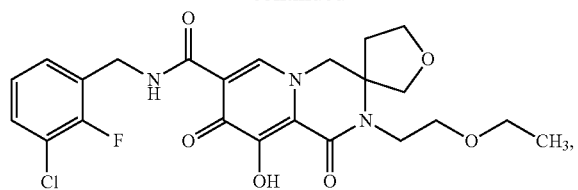
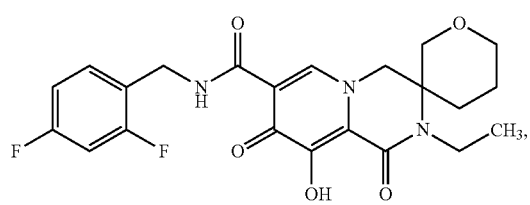
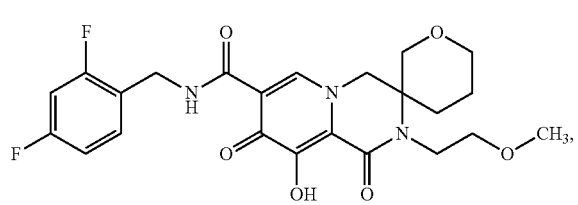
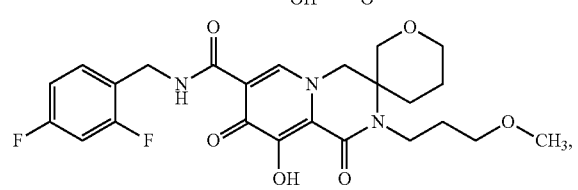
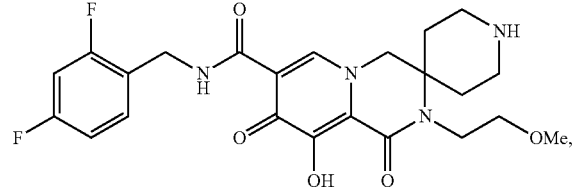
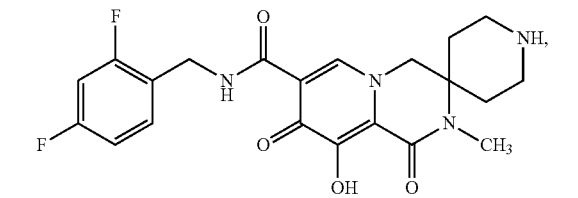
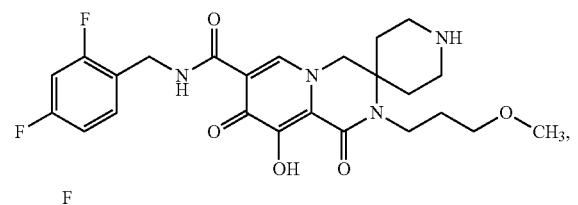
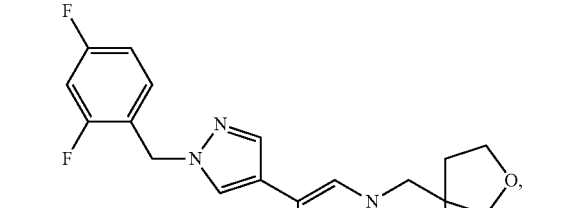
220
-continued
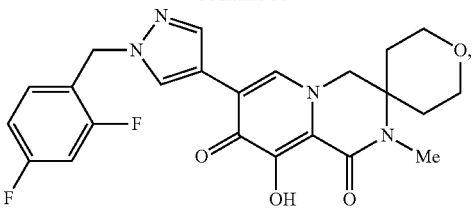
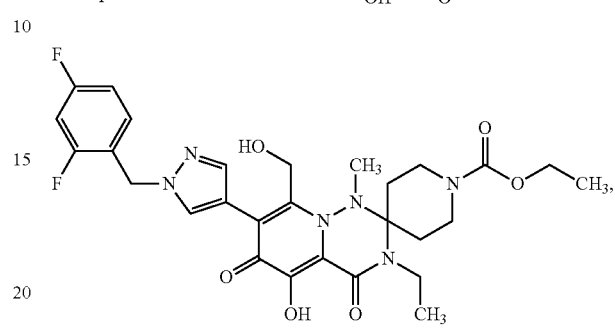
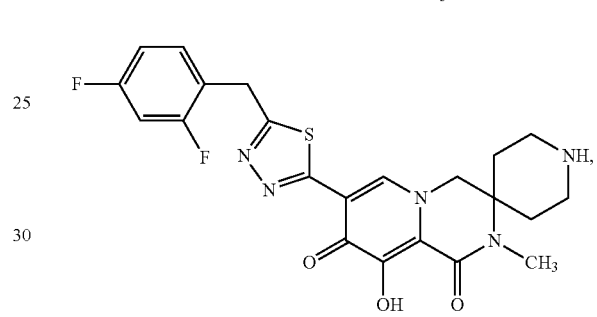
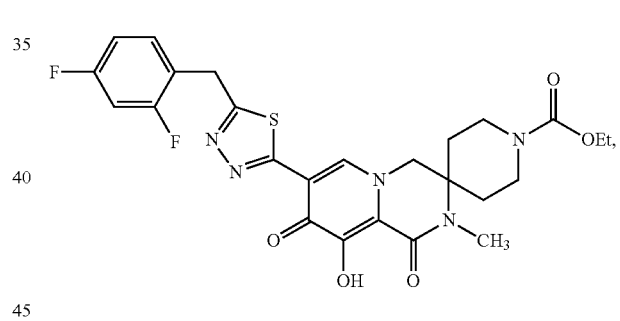
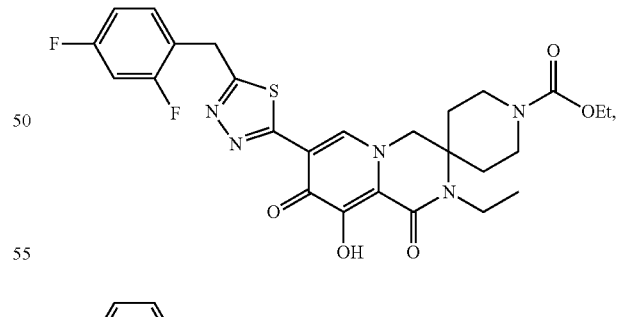
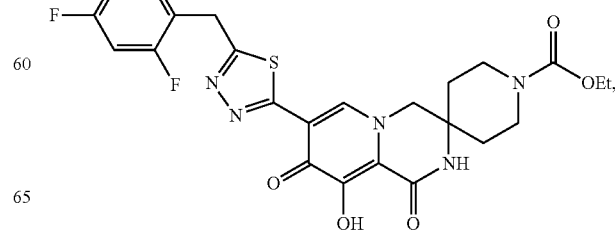

221
-continued
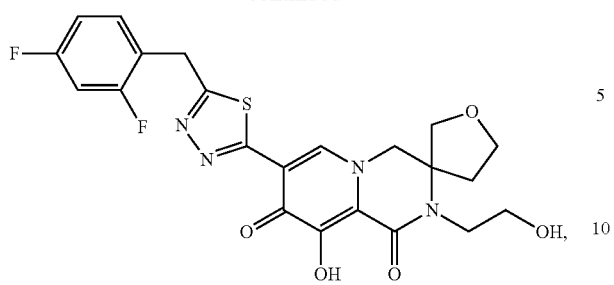
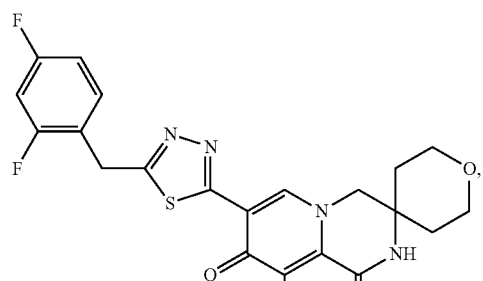
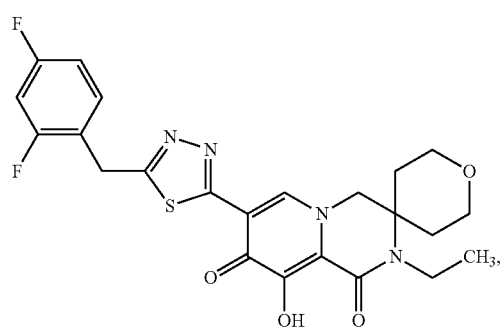
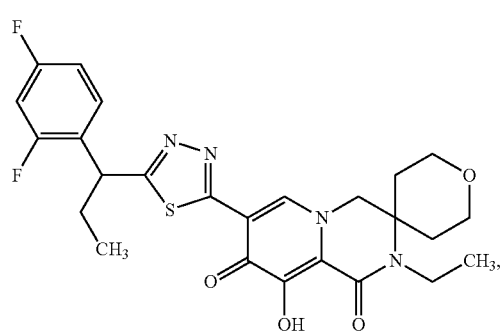
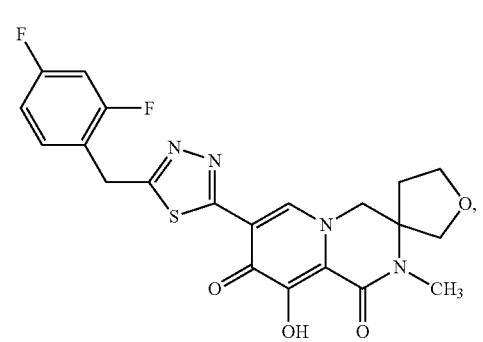
222
-continued
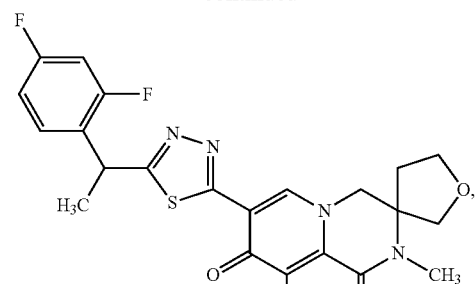
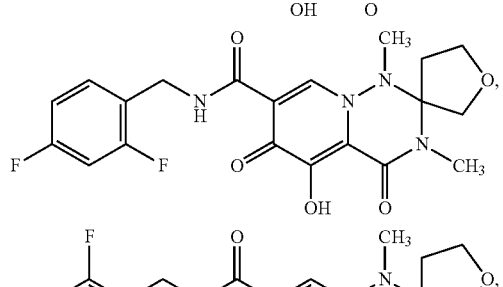
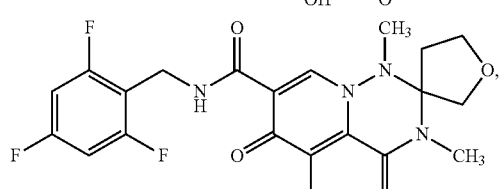
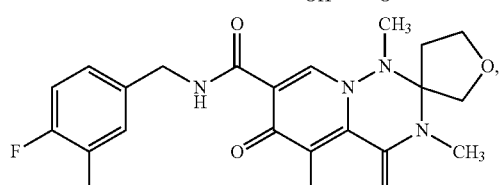
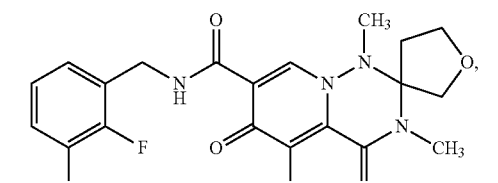
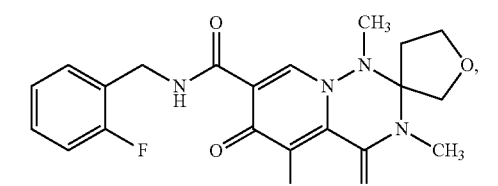
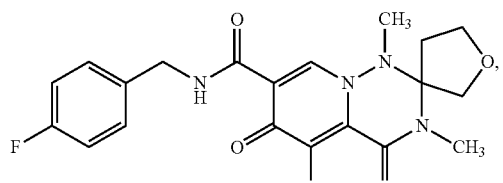
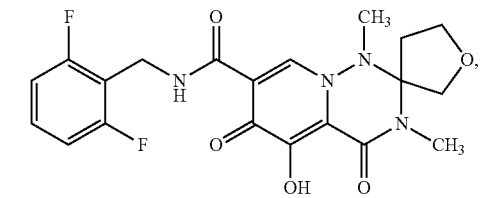

223
-continued
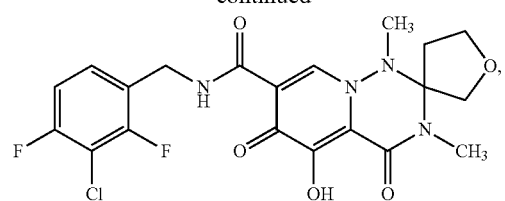
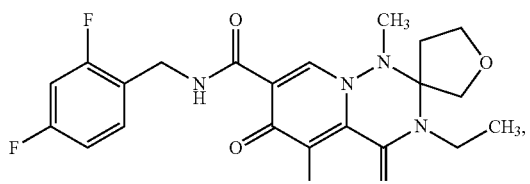
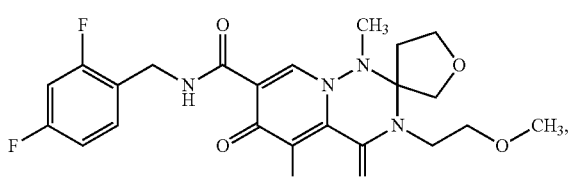
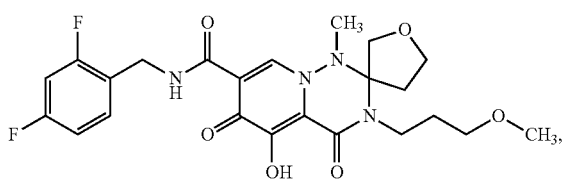
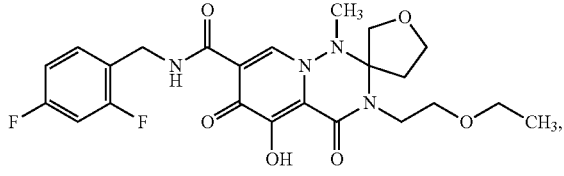
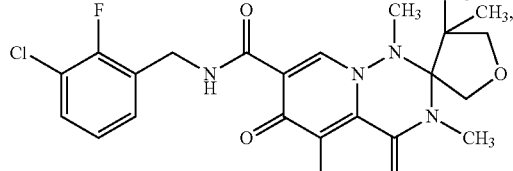
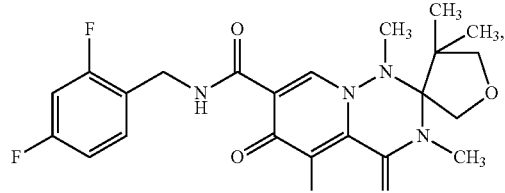
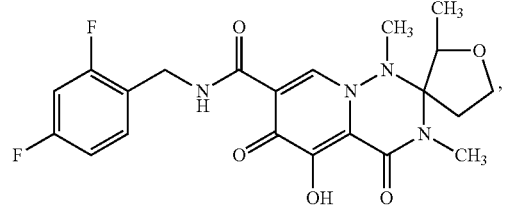
224
-continued
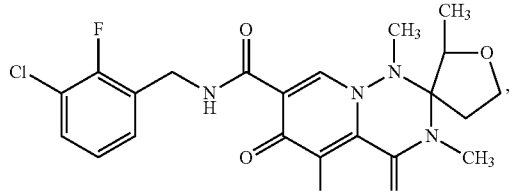
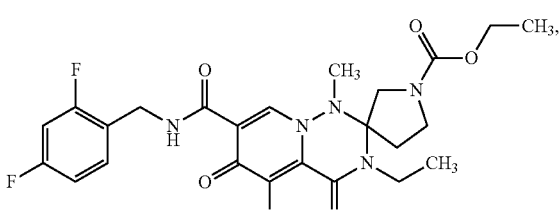
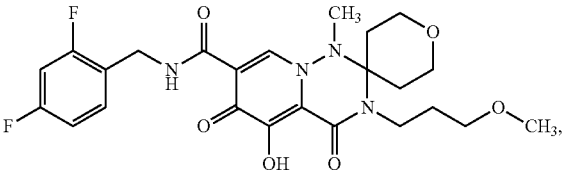
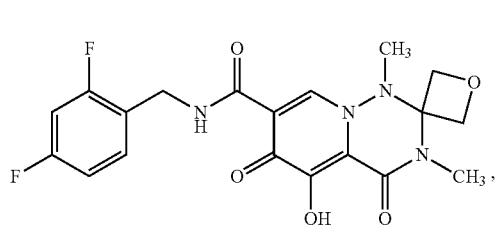
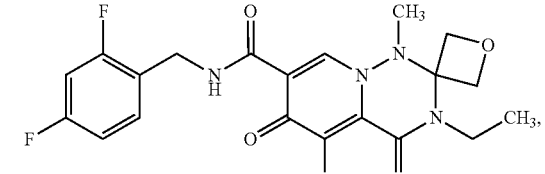
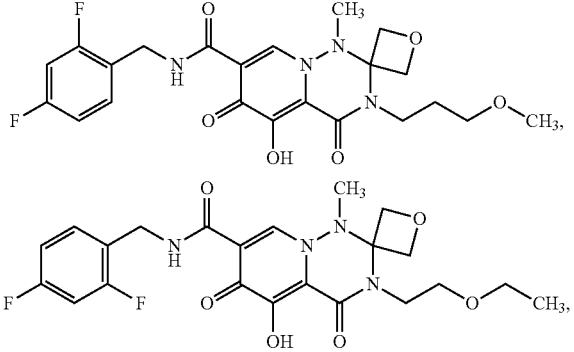

225
-continued
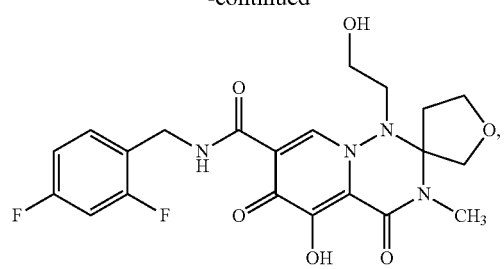
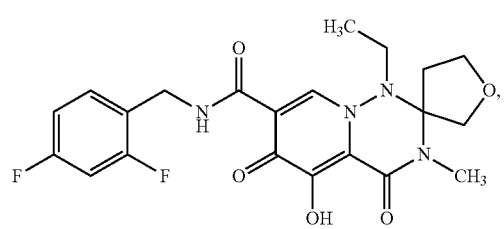
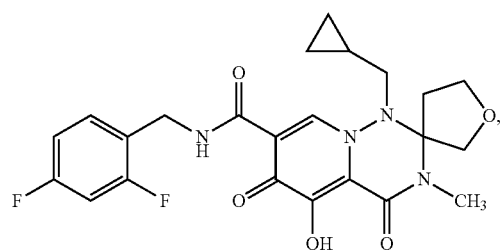
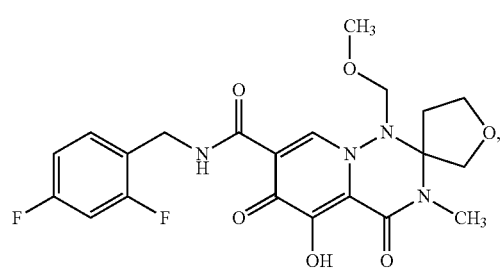
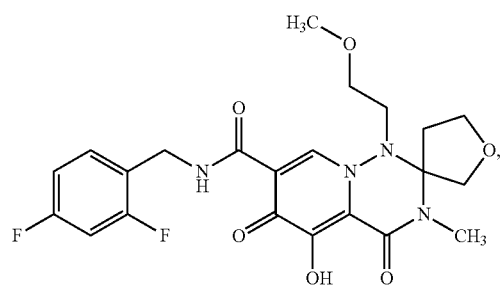
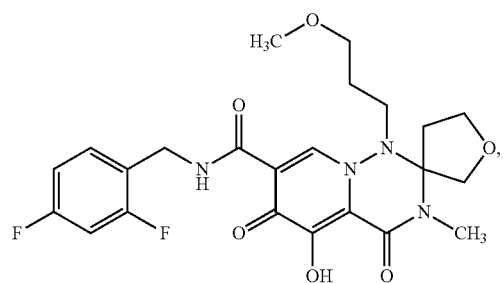
226
-continued
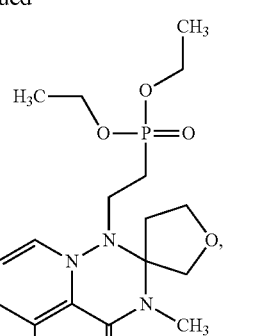
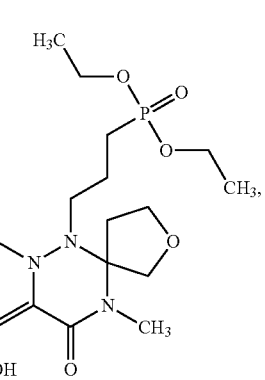
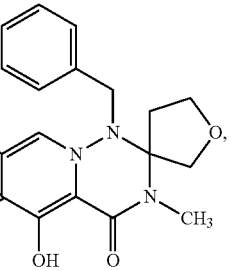
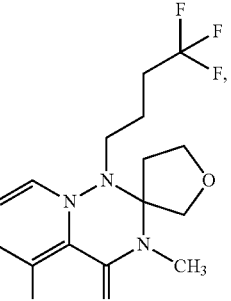
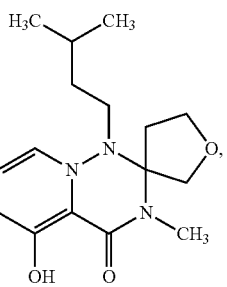

-continued

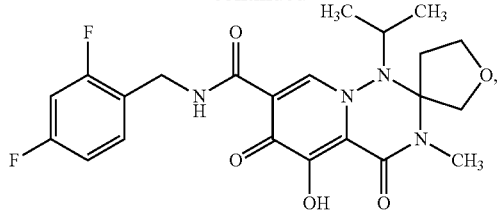

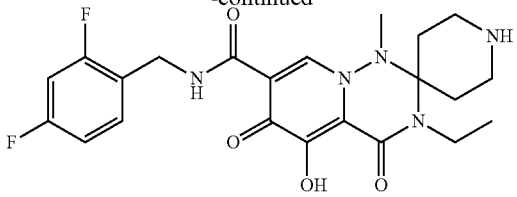

-continued

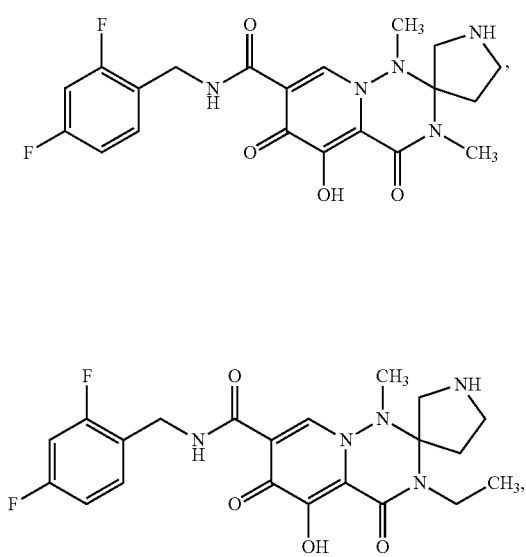

or a pharmaceutically acceptable salt thereof.

15. A pharmaceutical composition comprising an effective amount of a compound according to claim 1, or a pharmaceutically acceptable salt thereof, and a pharmaceutically acceptable carrier.

16. A method for the inhibition of HIV integrase in a subject in need thereof which comprises administering to the subject an effective amount of the compound according to claim 1, or a pharmaceutically acceptable salt thereof.

17. A method for the treatment of infection by HIV or for the treatment, or delay in the onset or progression of AIDS in a subject in need thereof, which comprises administering to the subject an effective amount of the compound according to claim 1, or a pharmaceutically acceptable salt thereof.

18. The pharmaceutical composition of claim 15, further comprising one or more additional therapeutic agents selected from raltegravir, lamivudine, abacavir, ritonavir, dolutegravir, arunavir, atazanavir, emtricitabine, tenofovir, elvitegravir, rilpivirine and lopinavir.

19. The method of claim 17, further comprising administering to the subject one or more additional therapeutic agents selected from raltegravir, abacavir, lamivudine, ritonavir and lopinavir, wherein the amounts administered of the compound of claim 1 and the one or more additional therapeutic agents, are together effective to treat infection by HIV or to treat or delay the onset or progression of AIDS.

* * * * *